(12) United States Patent
Davis et al.

(10) Patent No.: US 10,316,299 B2
(45) Date of Patent: Jun. 11, 2019

(54) KETOACYL ACP SYNTHASE GENES AND USES THEREOF

(71) Applicant: CORBION BIOTECH, INC., South San Francisco, CA (US)

(72) Inventors: David Davis, South San Francisco, CA (US); George N. Rudenko, Mountain View, CA (US); Aravind Somanchi, Redwood City, CA (US); Jason Casolari, Palo Alto, CA (US); Scott Franklin, Woodside, CA (US); Aren Ewing, South San Francisco, CA (US)

(73) Assignee: CORBION BIOTECH, INC., South San Francisco, CA (US)

( * ) Notice: Subject to any disclaimer, the term of this patent is extended or adjusted under 35 U.S.C. 154(b) by 0 days.

(21) Appl. No.: 15/950,048

(22) Filed: Apr. 10, 2018

(65) Prior Publication Data
US 2018/0230442 A1   Aug. 16, 2018

Related U.S. Application Data

(62) Division of application No. 14/796,406, filed on Jul. 10, 2015, now Pat. No. 9,969,990.

(60) Provisional application No. 62/081,143, filed on Nov. 18, 2014, provisional application No. 62/023,112, filed on Jul. 10, 2014.

(51) Int. Cl.
| | | |
|---|---|---|
| *C12N 9/10* | (2006.01) | |
| *C12P 7/64* | (2006.01) | |
| *C12N 15/00* | (2006.01) | |
| *C12N 1/20* | (2006.01) | |
| *C07H 21/04* | (2006.01) | |
| *C12N 15/82* | (2006.01) | |
| *C12P 33/00* | (2006.01) | |

(52) U.S. Cl.
CPC ........... *C12N 9/1029* (2013.01); *C12N 15/82* (2013.01); *C12P 7/64* (2013.01); *C12P 7/6463* (2013.01); *C12P 33/00* (2013.01); *C12Y 203/01041* (2013.01)

(58) Field of Classification Search
None
See application file for complete search history.

(56) References Cited

U.S. PATENT DOCUMENTS

| | | |
|---|---|---|
| 2,235,056 A | 3/1941 | Walmesley |
| 2,383,602 A | 8/1945 | Gerald et al. |
| 2,967,700 A | 1/1961 | Lee et al. |
| 3,142,135 A | 7/1964 | Kathrein |
| 3,280,502 A | 10/1966 | Farrow et al. |
| 3,320,693 A | 5/1967 | Shirota et al. |
| 3,475,274 A | 10/1969 | Harned |
| 3,957,578 A | 5/1976 | Narita et al. |
| 3,962,466 A | 6/1976 | Nakabayashi |
| 3,983,008 A | 9/1976 | Shinozaki et al. |
| 4,005,062 A | 1/1977 | Schnell |
| 4,103,039 A | 7/1978 | Mandai et al. |
| 4,182,777 A | 1/1980 | Saunders |
| 4,273,790 A | 6/1981 | Bosco et al. |
| 4,341,038 A | 7/1982 | Bloch et al. |
| 4,373,434 A | 2/1983 | Alexander et al. |
| 4,390,561 A | 6/1983 | Blair et al. |
| 4,519,845 A | 5/1985 | Ou |
| 4,627,192 A | 12/1986 | Fick |
| 4,673,490 A | 6/1987 | Subramanian et al. |
| 4,755,467 A | 7/1988 | Scopes et al. |
| 4,901,635 A | 2/1990 | Williams |
| 4,992,605 A | 2/1991 | Craig et al. |
| 5,001,059 A | 3/1991 | Skatrud et al. |
| 5,091,116 A | 2/1992 | Krishnamurthy et al. |
| 5,130,242 A | 7/1992 | Barclay |
| 5,212,087 A | 5/1993 | Fournier et al. |
| 5,252,198 A | 10/1993 | Harrison et al. |
| 5,270,175 A | 12/1993 | Moll et al. |
| 5,270,177 A | 12/1993 | Ramos Lazcano et al. |
| 5,304,481 A | 4/1994 | Davies et al. |
| 5,330,913 A | 7/1994 | Nakayama |
| 5,338,673 A | 8/1994 | Thepenier et al. |
| 5,354,878 A | 10/1994 | Connemann et al. |
| 5,360,730 A | 11/1994 | Orndorff et al. |
| 5,391,724 A | 2/1995 | Kindl et al. |
| 5,395,455 A | 3/1995 | Scott et al. |

(Continued)

FOREIGN PATENT DOCUMENTS

| | | |
|---|---|---|
| AU | 2011323288 B2 | 9/2016 |
| CN | 1251108 A | 4/2000 |

(Continued)

OTHER PUBLICATIONS

Dehesh. AF060519.2—GenBank. 2003.*
U.S. Appl. No. 14/184,288, Notice of Allowance dated Feb. 3, 2016.
U.S. Appl. No. 15/173,335, Requirement for Restriction/Election dated Jul. 5, 2017.
U.S. Appl. No. 12/628,140, Final Office Action dated Feb. 2, 2016.
U.S. Appl. No. 12/628,140, Non-Final Office Action dated Nov. 21, 2016.
U.S. Appl. No. 12/628,144, Final Office Action dated Mar. 1, 2016.
U.S. Appl. No. 12/628,144, Notice of Allowance dated Jun. 13, 2016.
U.S. Appl. No. 14/285,354, Notice of Allowance dated Feb. 1, 2016.

(Continued)

*Primary Examiner* — Yong D Pak
(74) *Attorney, Agent, or Firm* — Weaver Austin Villeneuve & Sampson LLP

(57) ABSTRACT

The present invention relates to beta-ketoacyl ACP synthase genes of the KASI/KASIV type and proteins encoded by these genes. The genes can be included in nucleic acid constructs, vectors or host cells. Expression of the gene products can alter the fatty acid profile of host cells. The KAS genes can be combined with a FATA or FATB thioesterase gene to create a cell that produces an increased amount of C8-C16 fatty acids. Suitable host cells include plastidic cells of plants or microalgae. Oleaginous microalga host cells with the new genes are disclosed.

25 Claims, 1 Drawing Sheet
Specification includes a Sequence Listing.

(56) References Cited

U.S. PATENT DOCUMENTS

| | | |
|---|---|---|
| 5,436,394 A | 7/1995 | Willmitzer et al. |
| 5,455,167 A | 10/1995 | Voelker et al. |
| 5,460,870 A | 10/1995 | Arthurs |
| 5,492,938 A | 2/1996 | Kyle et al. |
| 5,518,918 A | 5/1996 | Barclay et al. |
| 5,547,699 A | 8/1996 | Lizuka et al. |
| 5,563,058 A | 10/1996 | Davies et al. |
| 5,595,965 A | 1/1997 | Wiggins |
| 5,597,400 A | 1/1997 | Nonomura et al. |
| 5,680,812 A | 10/1997 | Linsgeseder |
| 5,685,218 A | 11/1997 | Kemper |
| 5,693,507 A | 12/1997 | Daniell et al. |
| 5,711,983 A | 1/1998 | Kyle et al. |
| 5,723,761 A | 3/1998 | Voelker et al. |
| 5,756,135 A | 5/1998 | Seeley |
| 5,826,500 A | 10/1998 | Kemper |
| 5,888,947 A | 3/1999 | Lambert et al. |
| 5,900,370 A | 5/1999 | Running |
| 5,910,630 A | 6/1999 | Davies et al. |
| 5,945,585 A | 8/1999 | Hitz et al. |
| 5,968,791 A | 10/1999 | Davis et al. |
| 6,139,897 A | 10/2000 | Goto et al. |
| 6,166,231 A | 12/2000 | Hoeksema |
| 6,255,505 B1 | 7/2001 | Bijl et al. |
| 6,338,866 B1 | 1/2002 | Criggall et al. |
| 6,344,231 B1 | 2/2002 | Nakajo et al. |
| 6,355,861 B1 | 3/2002 | Thomas |
| 6,372,460 B1 | 4/2002 | Gladue et al. |
| 6,410,281 B1 | 6/2002 | Barclay |
| 6,441,208 B2 | 8/2002 | Bijl et al. |
| 6,534,261 B1 | 3/2003 | Cox, III et al. |
| 6,620,427 B2 | 9/2003 | Lasekan et al. |
| 6,680,426 B2 | 1/2004 | Daniell et al. |
| 6,727,373 B2 | 4/2004 | Bijl et al. |
| 6,750,048 B2 | 6/2004 | Ruecker et al. |
| 6,762,345 B1 | 7/2004 | Cahoon et al. |
| 6,763,345 B1 | 7/2004 | Hempleman et al. |
| 6,867,308 B2 | 3/2005 | Bartok et al. |
| 7,053,267 B2 | 5/2006 | Knauf et al. |
| 7,063,957 B2 | 6/2006 | Chen |
| 7,081,567 B2 | 7/2006 | Xue et al. |
| 7,109,392 B1 | 9/2006 | Broglie et al. |
| 7,135,620 B2 | 11/2006 | Daniell et al. |
| 7,214,297 B2 | 5/2007 | Wang et al. |
| 7,268,276 B2 | 9/2007 | Ruezinsky et al. |
| 7,309,602 B2 | 12/2007 | David |
| 7,351,558 B2 | 4/2008 | Ruecker et al. |
| 7,468,267 B2 | 12/2008 | Monod et al. |
| 7,504,259 B2 | 3/2009 | Yadav et al. |
| 7,588,931 B2 | 9/2009 | Damude et al. |
| 7,622,570 B2 | 11/2009 | Oswald et al. |
| 7,652,156 B2 | 1/2010 | Hillion et al. |
| 7,662,598 B2 | 2/2010 | Ruecker et al. |
| 7,678,931 B2 | 3/2010 | Fichtali et al. |
| 7,781,193 B2 | 8/2010 | Ruecker et al. |
| 7,851,199 B2 | 12/2010 | Bailey et al. |
| 7,879,591 B2 | 2/2011 | Damude et al. |
| 7,883,882 B2 | 2/2011 | Franklin et al. |
| 7,914,832 B2 | 3/2011 | Uchino |
| 7,935,515 B2 | 5/2011 | Franklin et al. |
| 7,939,710 B1 | 5/2011 | Apt et al. |
| 8,003,365 B2 * | 8/2011 | Yoshikuni ............. C12P 5/02 435/252.1 |
| 8,029,579 B2 | 10/2011 | Knuth et al. |
| 8,043,496 B1 | 10/2011 | Schuh et al. |
| 8,088,718 B2 | 1/2012 | Bicerano et al. |
| 8,119,583 B2 | 2/2012 | Day et al. |
| 8,163,675 B2 | 4/2012 | Navarrete et al. |
| 8,187,860 B2 | 5/2012 | Franklin et al. |
| 8,222,010 B2 | 7/2012 | Franklin et al. |
| 8,268,610 B2 | 9/2012 | Franklin et al. |
| 8,278,261 B2 | 10/2012 | Day et al. |
| 8,283,483 B2 | 10/2012 | Williams et al. |
| 8,435,767 B2 | 5/2013 | Franklin et al. |
| 8,450,083 B2 | 5/2013 | Day et al. |
| 8,476,059 B2 | 7/2013 | Trimbur et al. |
| 8,497,116 B2 | 7/2013 | Trimbur et al. |
| 8,512,999 B2 | 8/2013 | Trimbur et al. |
| 8,518,689 B2 | 8/2013 | Trimbur et al. |
| 8,530,207 B2 | 9/2013 | Watts et al. |
| 8,592,188 B2 | 11/2013 | Franklin et al. |
| 8,633,012 B2 | 1/2014 | Franklin et al. |
| 8,647,397 B2 | 2/2014 | Trimbur et al. |
| 8,674,180 B2 | 3/2014 | Franklin et al. |
| 8,697,402 B2 | 4/2014 | Trimbur et al. |
| 8,697,427 B2 | 4/2014 | Franklin et al. |
| 8,765,424 B2 | 7/2014 | Franklin et al. |
| 8,772,575 B2 | 7/2014 | Franklin et al. |
| 8,790,914 B2 | 7/2014 | Trimbur et al. |
| 8,802,422 B2 | 8/2014 | Trimbur et al. |
| 8,822,176 B2 | 9/2014 | Day et al. |
| 8,822,177 B2 | 9/2014 | Day et al. |
| 8,846,352 B2 | 9/2014 | Chua et al. |
| 8,846,375 B2 | 9/2014 | Franklin et al. |
| 8,852,885 B2 | 10/2014 | Franklin et al. |
| 8,889,401 B2 | 11/2014 | Trimbur et al. |
| 8,889,402 B2 | 11/2014 | Trimbur et al. |
| 8,945,908 B2 | 2/2015 | Franklin et al. |
| 8,951,777 B2 | 2/2015 | Franklin et al. |
| 9,062,294 B2 | 6/2015 | Franklin et al. |
| 9,066,527 B2 | 6/2015 | Franklin et al. |
| 9,109,239 B2 | 8/2015 | Franklin et al. |
| 9,068,213 B2 | 10/2015 | Franklin et al. |
| 9,102,973 B2 | 10/2015 | Franklin et al. |
| 9,200,307 B2 | 12/2015 | Franklin et al. |
| 9,249,252 B2 | 2/2016 | Ngantung |
| 9,249,436 B2 | 2/2016 | Franklin et al. |
| 9,249,441 B2 | 2/2016 | Franklin et al. |
| 9,255,282 B2 | 2/2016 | Franklin et al. |
| 9,279,136 B2 | 3/2016 | Franklin et al. |
| 9,353,389 B2 | 5/2016 | Franklin et al. |
| 9,388,435 B2 | 7/2016 | Franklin et al. |
| 9,434,909 B2 | 9/2016 | Trimbur et al. |
| 9,464,304 B2 | 10/2016 | Franklin et al. |
| 9,551,017 B2 | 1/2017 | Franklin et al. |
| 9,593,351 B2 | 3/2017 | Franklin et al. |
| 9,657,299 B2 | 5/2017 | Franklin et al. |
| 9,719,114 B2 | 8/2017 | Franklin et al. |
| 9,909,155 B2 | 3/2018 | Franklin et al. |
| 9,969,990 B2 | 5/2018 | Davis et al. |
| 10,006,034 B2 | 6/2018 | Franklin et al. |
| 10,053,715 B2 | 8/2018 | Franklin et al. |
| 2002/0012979 A1 | 1/2002 | Berry et al. |
| 2002/0059661 A1 | 5/2002 | Dehesh |
| 2002/0122868 A1 | 9/2002 | Floeter et al. |
| 2002/0144455 A1 | 10/2002 | Bertrand et al. |
| 2002/0178467 A1 | 11/2002 | Dehesh |
| 2003/0054524 A1 | 3/2003 | Spener et al. |
| 2003/0079249 A1 | 4/2003 | Shanklin et al. |
| 2003/0082595 A1 | 5/2003 | Jiang et al. |
| 2003/0097686 A1 | 5/2003 | Knauf et al. |
| 2003/0145350 A1 | 7/2003 | Spener et al. |
| 2003/0211594 A1 | 11/2003 | Rosebrook |
| 2003/0229237 A1 | 12/2003 | Haas et al. |
| 2004/0053235 A1 | 3/2004 | Smirnoff et al. |
| 2004/0074760 A1 | 4/2004 | Portnoff et al. |
| 2004/0230085 A1 | 11/2004 | Jakkula et al. |
| 2004/0235123 A1 | 11/2004 | Liao et al. |
| 2004/0033557 A1 | 12/2004 | Scott et al. |
| 2005/0005333 A1 | 1/2005 | Ruezinsky et al. |
| 2005/0102716 A1 | 5/2005 | Venkatramesh et al. |
| 2005/0112735 A1 | 5/2005 | Zappi et al. |
| 2005/0153002 A1 | 7/2005 | Socia Rosales et al. |
| 2005/0170479 A1 | 8/2005 | Weaver et al. |
| 2005/0262588 A1 | 11/2005 | Dehesh et al. |
| 2005/0266537 A1 | 12/2005 | Chen |
| 2005/0272611 A1 | 12/2005 | Lord et al. |
| 2006/0048240 A1 | 3/2006 | Alexandrov et al. |
| 2006/0075522 A1 | 4/2006 | Cleveland et al. |
| 2006/0094088 A1 | 5/2006 | Picataggio et al. |
| 2006/0094089 A1 | 5/2006 | Barclay |
| 2006/0094090 A1 | 5/2006 | Damude et al. |
| 2006/0107346 A1 | 5/2006 | Schneeberger et al. |
| 2006/0122410 A1 | 6/2006 | Fichtali et al. |

(56) References Cited

U.S. PATENT DOCUMENTS

| | | |
|---|---|---|
| 2006/0130182 A1 | 6/2006 | Heim et al. |
| 2006/0153826 A1 | 7/2006 | Arnould et al. |
| 2006/0156436 A1 | 7/2006 | Nakamura et al. |
| 2006/0162006 A9 | 7/2006 | Sherman et al. |
| 2006/0199984 A1 | 9/2006 | Kuechler et al. |
| 2006/0225341 A1 | 10/2006 | Rohr et al. |
| 2006/0286205 A1 | 12/2006 | Fichtali et al. |
| 2007/0004016 A1 | 1/2007 | Picataggio et al. |
| 2007/0009988 A1 | 1/2007 | Monod et al. |
| 2007/0048848 A1 | 3/2007 | Sears |
| 2007/0099280 A1 | 5/2007 | Barclay |
| 2007/0118916 A1 | 5/2007 | Puzio et al. |
| 2007/0167396 A1 | 7/2007 | Dillon et al. |
| 2007/0218183 A1 | 9/2007 | Nakhasi et al. |
| 2007/0248531 A1 | 10/2007 | Debryun et al. |
| 2007/0254354 A1 | 11/2007 | Millis et al. |
| 2007/0261138 A1 | 11/2007 | Graham et al. |
| 2007/0275438 A1 | 11/2007 | David |
| 2008/0014620 A1 | 1/2008 | Op Den Camp et al. |
| 2008/0038804 A1 | 2/2008 | Du et al. |
| 2008/0040822 A1 | 2/2008 | Metz et al. |
| 2008/0107776 A1 | 5/2008 | Prakash et al. |
| 2008/0160593 A1 | 7/2008 | Oyler |
| 2008/0194029 A1 | 8/2008 | Hegemann et al. |
| 2008/0206379 A1 | 8/2008 | Fabritius et al. |
| 2008/0229451 A1 | 9/2008 | Cao et al. |
| 2008/0256666 A1 | 10/2008 | Zhu et al. |
| 2008/0283803 A1 | 11/2008 | Rapp et al. |
| 2009/0004715 A1 | 1/2009 | Trimbur et al. |
| 2009/0011480 A1 | 1/2009 | Trimbur et al. |
| 2009/0018300 A1 | 1/2009 | Bloom et al. |
| 2009/0035842 A1 | 2/2009 | Trimbur et al. |
| 2009/0047721 A1 | 2/2009 | Trimbur et al. |
| 2009/0061493 A1 | 3/2009 | Trimbur et al. |
| 2009/0064567 A1 | 3/2009 | Lippmeier et al. |
| 2009/0099260 A1 | 4/2009 | Namal Senanayake et al. |
| 2009/0117253 A1 | 5/2009 | Hong et al. |
| 2009/0142322 A1 | 6/2009 | Ye |
| 2009/0145392 A1 | 6/2009 | Clark et al. |
| 2009/0148918 A1 | 6/2009 | Trimbur et al. |
| 2009/0176272 A1 | 7/2009 | Champagne et al. |
| 2009/0211150 A1 | 8/2009 | Wu et al. |
| 2009/0234146 A1 | 9/2009 | Cooney et al. |
| 2009/0271892 A1 | 10/2009 | Thomasset et al. |
| 2009/0274736 A1 | 11/2009 | Dillon et al. |
| 2009/0298143 A1 | 12/2009 | Roessler et al. |
| 2009/0298159 A1 | 12/2009 | Wu et al. |
| 2009/0305942 A1 | 12/2009 | Day et al. |
| 2009/0317878 A1 | 12/2009 | Champagne et al. |
| 2010/0010088 A1 | 1/2010 | Chilton et al. |
| 2010/0021912 A1 | 1/2010 | Farese et al. |
| 2010/0035309 A1 | 2/2010 | Havemen et al. |
| 2010/0035320 A1 | 2/2010 | Blanchard et al. |
| 2010/0058651 A1 | 3/2010 | Knuth et al. |
| 2010/0093031 A1 | 4/2010 | Kobayashi et al. |
| 2010/0105955 A1 | 4/2010 | Alibhai et al. |
| 2010/0120643 A1 | 5/2010 | Brown et al. |
| 2010/0137647 A1 | 6/2010 | Bradin |
| 2010/0151112 A1 | 6/2010 | Franklin et al. |
| 2010/0151535 A1 | 6/2010 | Franklin et al. |
| 2010/0151538 A1 | 6/2010 | Franklin et al. |
| 2010/0151539 A1 | 6/2010 | Franklin et al. |
| 2010/0151567 A1 | 6/2010 | Franklin et al. |
| 2010/0154293 A1 | 6/2010 | Hom et al. |
| 2010/0170144 A1 | 7/2010 | Day et al. |
| 2010/0186117 A1 | 7/2010 | Fabijanski et al. |
| 2010/0196575 A1 | 8/2010 | Sanchez et al. |
| 2010/0237279 A1 | 9/2010 | Hulse et al. |
| 2010/0239712 A1 | 9/2010 | Brooks et al. |
| 2010/0248322 A1 | 9/2010 | Pfeiffer et al. |
| 2010/0249260 A1 | 9/2010 | Casati et al. |
| 2010/0297292 A1 | 11/2010 | Brooks et al. |
| 2010/0297295 A1 | 11/2010 | Brooks et al. |
| 2010/0297296 A1 | 11/2010 | Brooks et al. |
| 2010/0297323 A1 | 11/2010 | Brooks et al. |
| 2010/0297325 A1 | 11/2010 | Brooks et al. |
| 2010/0297331 A1 | 11/2010 | Brooks et al. |
| 2010/0303957 A1 | 12/2010 | Brooks et al. |
| 2010/0303961 A1 | 12/2010 | Brooks et al. |
| 2010/0303989 A1 | 12/2010 | Brooks et al. |
| 2010/0303990 A1 | 12/2010 | Brooks et al. |
| 2010/0323413 A1 | 12/2010 | Trimbur et al. |
| 2010/0323414 A1 | 12/2010 | Trimbur et al. |
| 2011/0014665 A1 | 1/2011 | Trimbur et al. |
| 2011/0015417 A1 | 1/2011 | Trimbur et al. |
| 2011/0047863 A1 | 3/2011 | Trimbur et al. |
| 2011/0065821 A1 | 3/2011 | Abraham et al. |
| 2011/0072714 A1 | 3/2011 | Gaertner |
| 2011/0111470 A1 | 5/2011 | Berry et al. |
| 2011/0165634 A1 | 7/2011 | Franklin et al. |
| 2011/0190522 A1 | 8/2011 | Trimbur et al. |
| 2011/0203168 A1 | 8/2011 | Franklin et al. |
| 2011/0250658 A1 | 10/2011 | Franklin et al. |
| 2011/0252696 A1 | 10/2011 | Franklin et al. |
| 2011/0256268 A1 | 10/2011 | Franklin et al. |
| 2011/0256282 A1 | 10/2011 | Piechocki et al. |
| 2011/0270001 A1 | 11/2011 | Ishihara et al. |
| 2011/0284215 A1 | 11/2011 | Pfeiffer et al. |
| 2011/0293785 A1 | 12/2011 | Franklin et al. |
| 2011/0294174 A1 | 12/2011 | Franklin et al. |
| 2012/0009636 A1 | 1/2012 | Berry et al. |
| 2012/0021495 A1 | 1/2012 | Vanzin |
| 2012/0028319 A1 | 2/2012 | Trimbur et al. |
| 2012/0034662 A1 | 2/2012 | Hu et al. |
| 2012/0060242 A1 | 3/2012 | Senger et al. |
| 2012/0119862 A1 | 5/2012 | Franklin et al. |
| 2012/0122192 A1 | 5/2012 | Trimbur et al. |
| 2012/0128851 A1 | 5/2012 | Brooks et al. |
| 2012/0156717 A1 | 6/2012 | Allnutt et al. |
| 2012/0164701 A1 | 6/2012 | Trimbur et al. |
| 2012/0203018 A1 | 8/2012 | Franklin et al. |
| 2012/0277452 A1* | 11/2012 | Franklin ............ C12N 9/0071 554/219 |
| 2012/0277453 A1 | 11/2012 | Franklin et al. |
| 2012/0283460 A1 | 11/2012 | Franklin et al. |
| 2012/0288930 A1 | 11/2012 | Trimbur et al. |
| 2012/0324784 A1 | 12/2012 | Franklin et al. |
| 2012/0329109 A1 | 12/2012 | Chua et al. |
| 2013/0004646 A1 | 1/2013 | Franklin et al. |
| 2013/0006006 A1 | 1/2013 | Day et al. |
| 2013/0031678 A1 | 1/2013 | Zheng et al. |
| 2013/0034887 A1 | 2/2013 | Franklin et al. |
| 2013/0078709 A1 | 3/2013 | Franklin et al. |
| 2013/0089916 A1 | 4/2013 | Franklin et al. |
| 2013/0096211 A1 | 4/2013 | Franklin et al. |
| 2013/0102039 A1 | 4/2013 | Franklin et al. |
| 2013/0116462 A1 | 5/2013 | Durrett et al. |
| 2013/0122180 A1 | 5/2013 | Brooks et al. |
| 2013/0157917 A1 | 6/2013 | Fluck |
| 2013/0165677 A1 | 6/2013 | Franklin et al. |
| 2013/0197247 A1 | 8/2013 | Franklin et al. |
| 2013/0273621 A1 | 10/2013 | Franklin et al. |
| 2013/0295268 A1 | 11/2013 | Day et al. |
| 2013/0296591 A1 | 11/2013 | Day et al. |
| 2013/0316410 A1 | 11/2013 | Franklin et al. |
| 2013/0317240 A1 | 11/2013 | Franklin et al. |
| 2013/0323382 A1 | 12/2013 | Franklin et al. |
| 2013/0323823 A1 | 12/2013 | Franklin et al. |
| 2013/0330790 A1 | 12/2013 | Trimbur et al. |
| 2013/0331584 A1 | 12/2013 | Franklin et al. |
| 2013/0338385 A1 | 12/2013 | Franklin et al. |
| 2014/0170716 A1 | 6/2014 | Trimbur et al. |
| 2014/0249342 A1 | 9/2014 | Franklin et al. |
| 2014/0256024 A1 | 9/2014 | Franklin et al. |
| 2014/0256600 A1 | 9/2014 | Dillon et al. |
| 2014/0305031 A1 | 10/2014 | Day et al. |
| 2014/0315267 A1 | 10/2014 | Franklin et al. |
| 2014/0336100 A1 | 11/2014 | Day et al. |
| 2014/0357746 A1 | 12/2014 | Ngantung et al. |
| 2014/0377847 A1 | 12/2014 | Franklin et al. |
| 2015/0073163 A1 | 3/2015 | Chua et al. |
| 2015/0125914 A1 | 5/2015 | Franklin et al. |
| 2015/0218604 A1 | 8/2015 | Franklin et al. |
| 2015/0275149 A1 | 10/2015 | Dummer et al. |

(56) References Cited

U.S. PATENT DOCUMENTS

| | | |
|---|---|---|
| 2015/0344917 A1 | 12/2015 | Franklin et al. |
| 2016/0010066 A1 | 1/2016 | Davis et al. |
| 2016/0024538 A1 | 1/2016 | Franklin et al. |
| 2016/0032332 A1 | 2/2016 | Davis et al. |
| 2016/0186191 A1 | 6/2016 | Franklin et al. |
| 2016/0186219 A1 | 6/2016 | Franklin et al. |
| 2016/0194672 A1 | 7/2016 | Franklin et al. |
| 2016/0348119 A1 | 12/2016 | Franklin et al. |
| 2016/0376617 A1 | 12/2016 | Franklin et al. |
| 2017/0022436 A1 | 1/2017 | Trimbur et al. |
| 2017/0145450 A1 | 5/2017 | Franklin et al. |
| 2017/0314048 A1 | 11/2017 | Franklin et al. |
| 2018/0142218 A1 | 5/2018 | Moseley et al. |
| 2018/0216144 A1 | 8/2018 | Rakitsky |
| 2018/0237811 A1 | 8/2018 | Franklin et al. |

FOREIGN PATENT DOCUMENTS

| | | |
|---|---|---|
| CN | 1852986 A | 10/2006 |
| CN | 101037639 A | 9/2007 |
| CN | 101092353 A | 12/2007 |
| CN | 101108997 A | 1/2008 |
| CN | 101611125 A | 12/2009 |
| CN | 101765661 A | 6/2010 |
| CN | 101824440 A | 9/2010 |
| DE | 2756977 A1 | 6/1978 |
| EP | 0 562 504 B1 | 11/1995 |
| EP | 1 178 118 A1 | 2/2002 |
| EP | 1 642 959 A1 | 4/2006 |
| EP | 1 681 337 A1 | 7/2006 |
| EP | 1 741 767 A1 | 1/2007 |
| EP | 1 947 189 A2 | 7/2008 |
| EP | 2 327 776 A1 | 6/2011 |
| EP | 2 152 849 B1 | 2/2013 |
| FR | 2924126 A1 | 5/2009 |
| GB | 824151 | 11/1959 |
| JP | 57-150379 | 9/1982 |
| JP | 06-253872 A | 9/1994 |
| JP | 07-008217 | 1/1995 |
| JP | 07-075557 | 3/1995 |
| JP | 09-511650 | 11/1997 |
| JP | 10-46181 | 2/1998 |
| JP | 2000-136199 | 5/2000 |
| JP | 2000-175696 A | 6/2000 |
| JP | 2002-125601 | 5/2002 |
| JP | 2002-523864 A | 7/2002 |
| JP | 2003-102467 A | 4/2003 |
| JP | 2003-325067 A | 11/2003 |
| JP | 2007-314549 A | 12/2007 |
| JP | 2008-081559 | 4/2008 |
| JP | 2008-514221 | 5/2008 |
| JP | 2008-148663 | 7/2008 |
| JP | 2008-178871 | 8/2008 |
| JP | 2010-528627 | 8/2010 |
| JP | 2015-500009 A | 1/2015 |
| JP | 6071904 | 2/2017 |
| KR | 10-2007-00085649 A | 8/2007 |
| KR | 10-2010-0022473 | 3/2010 |
| WO | WO 91/018105 A1 | 11/1991 |
| WO | WO 92/011373 A1 | 7/1992 |
| WO | WO 93/006712 A1 | 4/1993 |
| WO | WO 94/010288 A2 | 5/1994 |
| WO | WO 95/13390 A2 | 5/1995 |
| WO | WO 95/27791 A1 | 10/1995 |
| WO | WO 95/031553 A1 | 11/1995 |
| WO | WO 97/040698 A1 | 11/1997 |
| WO | WO 98/032770 A1 | 7/1998 |
| WO | WO 99/037166 A1 | 7/1999 |
| WO | WO 99/64618 | 11/1999 |
| WO | WO 00/011682 A1 | 3/2000 |
| WO | WO 00/061740 A1 | 10/2000 |
| WO | WO 00/066750 A2 | 11/2000 |
| WO | WO 00/74471 A1 | 12/2000 |
| WO | WO 02/008403 A2 | 1/2002 |
| WO | WO 02/085293 A2 | 10/2002 |
| WO | WO 2004/016282 A1 | 2/2004 |
| WO | WO 04/101753 A2 | 11/2004 |
| WO | WO 2005/003310 A2 | 1/2005 |
| WO | WO 2005/035693 A2 | 4/2005 |
| WO | WO 06/055322 A2 | 5/2006 |
| WO | WO 2006/052807 A2 | 5/2006 |
| WO | WO 2006/122299 A2 | 11/2006 |
| WO | WO 2007/027669 A1 | 3/2007 |
| WO | WO 2007/38566 A2 | 4/2007 |
| WO | WO 07/106903 A2 | 9/2007 |
| WO | WO 07/117511 A2 | 10/2007 |
| WO | WO 07/121100 A2 | 10/2007 |
| WO | WO 07/134294 A2 | 11/2007 |
| WO | WO 2007/141257 A2 | 12/2007 |
| WO | WO 08/002643 A2 | 1/2008 |
| WO | WO 2008/011811 A1 | 1/2008 |
| WO | WO 08/060571 A2 | 5/2008 |
| WO | WO 2008/058664 A1 | 5/2008 |
| WO | WO 08/083352 A1 | 7/2008 |
| WO | WO 08/130372 A2 | 10/2008 |
| WO | WO 2008/134836 A2 | 11/2008 |
| WO | WO 08/151149 A2 | 12/2008 |
| WO | WO 09/076559 A1 | 6/2009 |
| WO | WO 09/105620 A1 | 8/2009 |
| WO | WO 09/126843 A2 | 10/2009 |
| WO | WO 2009/124070 A1 | 10/2009 |
| WO | WO 10/019813 A2 | 2/2010 |
| WO | WO 2010/017346 A2 | 2/2010 |
| WO | WO 10/045368 A2 | 4/2010 |
| WO | WO 2010/037209 A1 | 4/2010 |
| WO | WO 10/063031 A2 | 6/2010 |
| WO | WO 10/063032 A2 | 6/2010 |
| WO | WO 10/111698 A2 | 9/2010 |
| WO | WO 10/120923 A1 | 10/2010 |
| WO | WO 10/120939 A2 | 10/2010 |
| WO | WO 11/026008 A1 | 3/2011 |
| WO | WO 2011/075716 A1 | 6/2011 |
| WO | WO 11/090730 A1 | 7/2011 |
| WO | WO 11/130573 A1 | 10/2011 |
| WO | WO 11/130576 A1 | 10/2011 |
| WO | WO 11/130578 A2 | 10/2011 |
| WO | WO 11/150410 A2 | 12/2011 |
| WO | WO 11/150411 A1 | 12/2011 |
| WO | WO 12/061647 A2 | 5/2012 |
| WO | WO 12/106560 A1 | 8/2012 |
| WO | WO 12/154626 A1 | 11/2012 |
| WO | WO 13/082186 A2 | 6/2013 |
| WO | WO 2013/096891 A1 | 6/2013 |
| WO | WO 13/158938 | 10/2013 |
| WO | WO 14/176515 A2 | 10/2014 |
| WO | WO 15/051319 A2 | 4/2015 |
| WO | WO 2016/007862 A2 | 1/2016 |
| WO | WO 2016/164495 A1 | 10/2016 |
| WO | WO 2017/058802 A1 | 4/2017 |

OTHER PUBLICATIONS

U.S. Appl. No. 13/555,009, Non-Final Office Action dated Sep. 16, 2014.

U.S. Appl. No. 14/626,505, Requirement for Restriction/Election dated Apr. 26, 2016.

U.S. Appl. No. 14/626,505, Non-Final Office Action dated Jul. 19, 2016.

U.S. Appl. No. 13/118,365, Notice of Allowance dated Sep. 20, 2013.

U.S. Appl. No. 14/276,943, Notice of Allowance dated Sep. 22, 2015.

U.S. Appl. No. 14/975,016, Notice of Allowance dated Jan. 10, 2017.

U.S. Appl. No. 14/975,016, Notice of Allowance dated Jan. 31, 2017.

U.S. Appl. No. 14/975,016, Notice of Allowance dated Feb. 24, 2017.

U.S. Appl. No. 13/118,369, Requirement for Restriction/Election dated Dec. 13, 2012.

U.S. Appl. No. 13/118,369, Non-Final Office Action dated Mar. 28, 2013.

(56) References Cited

OTHER PUBLICATIONS

U.S. Appl. No. 13/118,369, Final Office Action dated Mar. 28, 2014.
U.S. Appl. No. 13/630,757, Notice of Allowance dated Oct. 23, 2015.
U.S. Appl. No. 13/630,757, Supplemental Notice of Allowance dated Dec. 3, 2015.
U.S. Appl. No. 13/630,757, Miscellaneous Communication dated Dec. 17, 2015.
U.S. Appl. No. 13/630,757, Notice of Allowance (Supplemental Notice of Allowability) dated Jan. 15, 2016.
U.S. Appl. No. 14/819,117, Requirement for Restriction/Election dated Apr. 11, 2016.
U.S. Appl. No. 14/819,117, Non-Final Office Action dated Nov. 2, 2016.
U.S. Appl. No. 14/819,117, Final Office Action dated Mar. 22, 2017.
U.S. Appl. No. 14/819,117, Notice of Allowance dated Sep. 7, 2017.
U.S. Appl. No. 13/288,815, Requirement for Restriction/Election dated Feb. 11, 2014.
U.S. Appl. No. 14/730,671, Notice of Allowance dated Mar. 21, 2016.
U.S. Appl. No. 13/365,253, Non-Final Office Action dated Mar. 25, 2015.
U.S. Appl. No. 13/365,253, Notice of Allowance dated Sep. 24, 2015.
U.S. Appl. No. 13/365,253, Notice of Allowance (Notice of Allowability) dated Nov. 6, 2015.
U.S. Appl. No. 14/974,983, Requirement for Restriction/Election dated Jul. 28, 2016.
U.S. Appl. No. 14/974,983, Non-Final Office Action dated Dec. 5, 2016.
U.S. Appl. No. 14/974,983, Final Office Action dated Jul. 19, 2017.
U.S. Appl. No. 13/804,185, Final Office Action dated Dec. 11, 2015.
U.S. Appl. No. 13/804,185, Non-Final Office Action dated Jul. 20, 2016.
U.S. Appl. No. 13/804,185, Notice of Allowance dated Jan. 27, 2017.
U.S. Appl. No. 13/941,353, Notice of Allowance dated May 21, 2014.
U.S. Appl. No. 14/474,244, Notice of Allowance dated Sep. 18, 2015.
U.S. Appl. No. 14/975,137, Notice of Allowance dated Sep. 6, 2016.
U.S. Appl. No. 15/369,557, Non-Final Office Action dated Jun. 23, 2017.
U.S. Appl. No. 14/506,491, Requirement for Restriction/Election dated Jan. 19, 2017.
U.S. Appl. No. 14/506,491, Non-Final Office Action dated Jun. 1, 2017.
U.S. Appl. No. 13/087,305, Non-Final Office Action dated Aug. 15, 2012.
U.S. Appl. No. 13/087,305, Final Office Action dated Mar. 18, 2013.
Australian Patent Examination Report No. 1 dated Jan. 23, 2013 issued in AU 2008259834.
Australian Patent Examination Report No. 1 dated May 4, 2015 issued in AU 2013251198.
Canadian Examination Report dated Nov. 30, 2015 issued in Application No. CA 2,689,724.
Chinese First Office Action dated Apr. 23, 2012 issued in Application No. CN 200880100976.9.
Chinese Second Office Action dated Jan. 21, 2013 issued in Application No. CN 200880100976.9.
Chinese Third Office Action dated May 28, 2013 issued in Application No. CN 200880100976.9.
Chinese Fourth Office Action dated Sep. 11, 2013 issued in Application No. CN 200880100976.9.
Chinese Fifth Office Action dated Jan. 23, 2014 issued in Application No. CN 200880100976.9.
Chinese First Office Action dated May 18, 2016 issued in Application No. CN 201410321130.5.
Columbian Opposition dated Sep. 5, 2011 [Brief Communication dated Sep. 5, 2011 re Application No. EP 06 075 479.3, D50-Declaration of Dr. Matthias Staufenbiel; D51-WO-A-2004/016282; D52-Sturchler-Pierrat et al. Proc Natl. Acad. Sci. USA, 94:13287-13292 (1997)].
European Office Action dated Mar. 9, 2012 issued in Application No. EP 08 769 988.0.
Indonesian first Office Action dated Apr. 13, 2016 issued in Application No. W00200903371.
Indonesian second Office Action dated Aug. 4, 2016 issued in Application No. W00200903371.
Indian Examination Report dated Oct. 4, 2016 issued in Application No. IN 8573/DELNP/2009.
Korean Office Action dated Aug. 25, 2014 [no translation] issued in Application No. KR 10-2009-7027618.
Australian Patent Examination Report No. 1 dated Dec. 9, 2014 issued in AU 2009319722.
Canadian Examination Report dated Oct. 3, 2016 issued in Application No. CA 2,745,129.
Chinese First Office Action dated Apr. 26, 2013 issued in CN 200980155465.1.
Chinese Second Office Action dated Jan. 16, 2014 issued in CN 200980155465.1.
Chinese Third Office Action dated Aug. 28, 2014 issued in CN 200980155465.1.
Chinese Rejection Decision dated Mar. 24, 2015 issued in CN 200980155465.1.
Columbian Office Action dated Feb. 13, 2013 issued in CO 11.080.882.
Columbian Office Action dated Nov. 24, 2014 issued in CO 11.080.882.
Columbian Office Action dated Mar. 16, 2015 issued in CO 11.080.882.
Columbian Office Action dated Mar. 1, 2016 issued in CO 11.080.882.
European Extended Search Report dated Sep. 12, 2014 issued in EP 09 829 851.6.
European Office Action dated Jun. 25, 2015 issued in EP 09 829 851.6.
European Partial Search Report dated Sep. 12, 2016 issued in EP 16 16 6059.2.
European Extended Search Report dated Dec. 14, 2016 issued in EP 16 16 6059.2.
Israel Office Action dated Sep. 30, 2013 issued in IL 213157.
Japanese Office Action dated Jul. 1, 2016 issued in JP 2011-538719.
Japanese Office Action dated Oct. 31, 2016 issued in JP 2011-538719.
Japanese Office Action [no translation] dated May 9, 2016 issued in JP 2015-126360.
Japanese Final Office Action [no translation] dated Nov. 24, 2016 issued in JP 2015-126360.
Korean Office Action dated Nov. 14, 2015 issued in KR 10-2011-7014923.
Korean Office Action dated Oct. 5, 2016 issued in KR 10-2011-7014923.
Malaysian Examination Report dated Mar. 31, 2016 issued in MY PI2011002435.
Mexican Office Action dated Sep. 21, 2012 issued in MX/a/2010/011065.
Australian Patent Examination Report No. 1 dated Feb. 25, 2014 issued in AU 2009319721.
Australian Patent Examination Report No. 2 dated Oct. 29, 2015 issued in AU 2009319721.
Canadian Office Action dated Dec. 1, 2015 issued in CA 2,745,040.
Chinese First Office Action dated Dec. 23, 2013 issued in CN 200980155463.2.
Chinese Second Office Action dated Oct. 20, 2014 issued in CN 200980155463.2.
Columbian Office Action dated Mar. 21, 2013 issued in CO 11.080.835.
European Office Action dated Mar. 21, 2016 issued in EP 09 829 850.8.
European Extended Search Report dated May 16, 2016 issued in EP 09 829 850.8.
Israel Office Action dated Apr. 8, 2014 issued in IL 213154.

(56) References Cited

OTHER PUBLICATIONS

Israel Office Action dated Jun. 30, 2015 issued in IL 213154.
Israel Office Action dated Sep. 14, 2016 issued in IL 213154.
Japanese Office Action dated May 13, 2014 issued in JP 2011-538718.
Japanese Office Action dated Jun. 1, 2015 issued in JP 2011-538718.
Japanese Office Action dated Oct. 16, 2016 issued in JP 2014-227718.
Japanese Final Office Action [no translation] dated Jul. 13, 2016 issued in JP 2014-227718.
Korean Office Action dated Jan. 4, 2016 issued in KR 10-2011-7014925.
Korean Office Action dated Jul. 18, 2016 issued in KR 10-2011-7014925.
Korean Office Action dated Feb. 23, 2017 issued in KR 10-2011-7014925.
Mexican Office Action [no translation] dated Dec. 6, 2012 issued in MX/a/2011/005630.
Mexican Office Action [no translation] dated May 14, 2013 issued in MX/a/2011/005630.
Australian Patent Examination Report No. 1 dated Jul. 21, 2016 issued in Application No. AU 2011257982.
Canadian Examination Report dated Feb. 23, 2017 issued in Application No. CA 2,801,057.
Chinese First Office Action dated May 29, 2014 issued in Application No. CN 201180036870.9.
Chinese Second Office Action dated Apr. 15, 2015 issued in Application No. CN 201180036870.9.
Chinese Third Office Action dated Nov. 4, 2015 issued in Application No. CN 201180036870.9.
Chinese Rejection Decision dated Apr. 14, 2016 issued in Application No. CN 201180036870.9.
Chinese Notification of Reexamination dated Jan. 26, 2017 issued in Application No. CN 201180036870.9.
European Extended Search Report dated Jun. 9, 2016 issued in Application No. EP 11 787 551.8.
European Office Action dated Jan. 25, 2017 issued in Application No. EP 11 787 551.8.
Japanese Office Action dated Jul. 7, 2015 issued in Application No. JP 2013-512064.
Japanese Office Action dated Dec. 16, 2016 issued in Application No. JP 2016-001030.
Mexican Office Action dated Aug. 11, 2015 issued in Application No. MX/a/2012/013777.
Mexican Office Action dated Jan. 15, 2016 issued in Application No. MX/a/2012/013777.
Malaysian Examination Report dated Sep. 15, 2015 issued in MY PI 2012005117.
PCT International Search Report dated Nov. 3, 2011 issued in PCT/US2011/038464.
PCT Written Opinion of the International Searching Authority dated Nov. 3, 2011 issued in PCT/US2011/038464.
PCT International Preliminary Report on Patentability dated Jun. 28, 2012 issued in PCT/US2011/038464.
Australian Patent Examination Report No. 1 dated Feb. 26, 2015 issued in Application No. AU 2011257983.
Australian Examination Report dated Feb. 1, 2017 issued in Application No. AU 2016202905.
Canadian Examination Report dated May 17, 2017 issued in Application No. CA 2,801,024.
Chinese First Office Action dated Oct. 29, 2013 issued in Application No. CN 201180036696.8.
Chinese Second Office Action dated Jun. 5, 2014 issued in Application No. CN 201180036696.8.
Chinese Rejection Decision dated Jan. 14, 2015 issued in Application No. CN 201180036696.8.
Chinese Re-examination Decision dated May 26, 2015 issued in Application No. CN 201180036696.8.
Chinese Third Office Action dated Jul. 31, 2015 issued in Application No. CN 201180036696.8.
Chinese Fourth Office Action dated Dec. 30, 2015 issued in Application No. CN 201180036696.8.
European Extended Search Report dated Feb. 19, 2016 issued in Application No. EP 11 787 552.6.
European Office Action dated Oct. 11, 2016 issued in Application No. EP 11 787 552.6.
Japanese Office Action dated Jul. 7, 2015 issued in Application No. JP 2013-512605.
Japanese Final Office Action dated Feb. 29, 2016 issued in Application No. JP 2013-512605.
Japanese Office Action [no translation] dated Jul. 8, 2016 issued in Application No. JP 2013-512605.
Japanese Office Action [no translation] dated Sep. 6, 2016 issued in Application No. JP 2015-199078.
Malaysian Examination Report dated Sep. 15, 2015 issued in Application No. MY PI 2012005120.
Australian Patent Examination Report No. 1 dated Jul. 22, 2015 issued in Application No. AU 2012212079.
Chinese First Office Action dated Apr. 7, 2015 issued in Application No. CN 201280007593.3.
Chinese Second Office Action dated Nov. 17, 2015 issued in Application No. CN 201280007593.3.
Chinese Third Office Action dated Apr. 26, 2016 issued in Application No. CN 201280007593.3.
Chinese Fourth Office Action dated Oct. 17, 2016 issued in Application No. CN 201280007593.3.
Chinese Rejection Decision dated May 26, 2017 issued in Application No. CN 201280007593.3.
European Partial Supplementary Search Report dated May 8, 2015 issued in Application No. EP 12 741 997.6.
European Office Action dated Feb. 6, 2017 issued in Application No. EP 12 741 997.6.
Japanese Office Action dated Jan. 25, 2016 issued in Application No. JP 2013-552645.
Japanese Office Action [no translation] dated Apr. 20, 2016 issued in Application No. JP 2016-145348.
Mexican First Office Action dated Nov. 6, 2015 issued in Application No. MX/a/2013/008651.
Mexican Second Office Action dated Mar. 23, 2016 issued in Application No. MX/a/2013/008651.
Mexican Third Office Action dated Jul. 25, 2016 issued in Application No. MX/a/2013/008651.
Mexican First Office Action dated Apr. 24, 2017 issued in Application No. MX/a/2016/015902.
Malaysia Office Action dated Sep. 30, 2016 issued in Application No. MY PI2013002880.
PCT International Preliminary Report on Patentability dated Oct. 30, 2014 issued in PCT/US2013/037261.
Australian Patent Examination Report No. 1 dated Apr. 20, 2016 issued in Application No. AU 2013249172.
Australian Examination Report No. 2 dated Jan. 25, 2017 issued in Application No. AU 2013249172.
Chinese First Office Action dated Jul. 7, 2016 issued in Application No. CN 201380031877.0.
Chinese Second Office Action dated Mar. 24, 2017 issued in Application No. CN 201380031877.0.
European Supplementary Search Report dated Jan. 25, 2016 issued in Application No. EP 13 778 920.2.
European Examination Report dated Mar. 6, 2017 issued in Application No. EP 13 778 920.2.
Japanese First Office Action dated Mar. 10, 2017 issued in Application No. JP 2015-507197.
Mexican First Office Action dated Jul. 27, 2017 issued in Application No. MX/a/2014/012552.
Singapore Search Report and Written Opinion dated Mar. 24, 2016 issued in Application No. SG 11201406711T.
PCT International Report on Patentability and Written Opinion of the International Searching Authority dated Apr. 5, 2016 issued in PCT/US2014/059161.
Singapore Search Report and Written Opinion dated Aug. 7, 2017 issued in Application No. SG 11201602638S.
PCT Invitation to Pay Additional Fees dated Nov. 20, 2015 issued in PCT/U52015/039951.

(56) References Cited

OTHER PUBLICATIONS

PCT International Search Report and Written Opinion of the International Searching Authority dated Jan. 29, 2016 issued in Application No. PCT/US2015/039951.
PCT International Preliminary Report on Patentability and Written Opinion dated Jan. 10, 2017 issued in PCT/US2015/039951.
PCT International Search Report and Written Opinion of the International Searching Authority dated Jan. 3, 2017 issued in PCT/US2016/053979.
PCT International Search Report and Written Opinion of the International Searching Authority dated Jul. 18, 2016 issued in PCT/US2016/026265.
Geneseq: Database Accession No. AXE01814, "Palmitic acid production-related gene, SEQ:20024," XP002750550, Oct. 14, 2010.
Geneseq: Database Accession No. ADJ49365, "Oil-associated gene related protein #865," XP002750551, Jun. 15, 2007.
Blatti, Jillian L. et al. (Jun. 2013) "Engineering fatty acid biosynthesis in microalgae for sustainable biodiesel," *Current Opinion in Chemical Biology*, 17(3):496-505.
Dehesh et al., (2001) "Overexpression of 3-Ketoacyl-Acyl-Carrier Protein Synthase IIIs in Plants Reduces the Rate of Lipid Synthesis," *Plant Physiology*, 125:1103-1114.
Facciotti et al., (May 1998) "Molecular dissection of the plant acyl-acyl carrier protein thioesterases," *Fett/Lipid, Lipid-Weinheim*, 100(4-5), S.:167-172 [<URL:http://www.researchgate.net/publication/247961590>].
Hsieh et al., (2012) "Accumulation of Lipid Production in *Chlorella minutissima* by Triacylglycerol Biosynthesis-Related Genes Cloned from *Saccharomyces cerevisiae* and *Yarrowia lipolytica*," *The Journal of Microbiology*, 50(3):526-534.
Khozin-Goldberg et al. (2011) "Unravelling algal lipid metabolism: Recent advances in gene identification," *Biochemie*, 93:91-100.
Kosa et al., (Feb. 2011) "Lipids from heterotrophic microbes: advances in metabolism research," *Trends in Biotechnology*, 29(2):53-61.
Leonard et al., (Mar. 1998) A *Cuphea* β-ketoacyl-ACP synthase shifts the synthesis of fatty acids toward shorter chains in *Arabidopsis* seeds expressing *Cuphea* FatB thioesterases, *The Plant Journal*, 13(5):621-628.
Lu et al., (2008) "Overproduction of free fatty acids in *E. coli*: Implications for biodiesel production," *Metabolic Engineering*, 10:333-339.
Pidkowich et al., (Mar. 13, 2007) "Modulating seed β-ketoacyl-acyl carrier protein synthase II level converts the composition of a temperate seed oil to that of a palm-like tropical oil," *PNAS*, 104(11):4742-4747.
Radakovits et al., (2011) "Genetic engineering of fatty acid chain length in *Phaeodactylum tricornutum*," *Metabolic Engineering*, 13:89-95.
Schütt et al., (2002) "β-Ketoacyl-acyl carrier protein synthase IV: a key enzyme for regulation of medium-chain fatty acid synthesis in Cuphea lanceolata seeds," *Planta*, 215:847-854.
U.S. Appl. No. 15/173,335, Non-Final Office Action dated Oct. 12, 2017.
U.S. Appl. No. 14/819,117, Supplemental Notice of Allowance dated Nov. 13, 2017.
U.S. Appl. No. 15/179,253, Requirement for Restriction/Election dated Sep. 28, 2017.
U.S. Appl. No. 14/974,983, Non-Final Office Action dated Oct. 26, 2017.
U.S. Appl. No. 15/369,557, Notice of Allowance dated Oct. 17, 2017.
U.S. Appl. No. 14/506,491, Final Office Action dated Dec. 5, 2017.
U.S. Appl. No. 15/092,538, Requirement for Restriction/Election dated Oct. 6, 2017.
Declaration of Dr. Matthias Staufenbiel, Opposition Document for European Patent No. EP-B-1679080 dated Aug. 2, 2011; Patentee: Janssen Alzheimer Immunotherapy; Opponent: Dr. Alexander Esslinger, 19 pp.
Colombian Office Action dated Jan. 28, 2013 issued in Application No. CO 09149183.
Colombian Office Action dated Jun. 13, 2013 issued in Application No. CO 09149183.
Colombian Office Action dated Sep. 25, 2013 issued in Application No. CO 09149183.
Japanese Notice of Reason for Denial [no translation] dated May 24, 2016 issued in Application No. JP 2016-095504.
Korean Office Action dated Aug. 25, 2014 issued in Application No. KR 10-2009-7027618 .
Mexican Office Action dated Oct. 13, 2011 issued in Application No. MX/a/2009/012850.
Mexican First Office Action dated Sep. 30, 2013 issued in Application No. MX/a/2012/000844.
Mexican Second Office Action dated Jan. 22, 2014 issued in Application No. MX/a/2012/000844.
Mexican Third Office Action dated Oct. 13, 2014 issued in Application No. MX/a/2012/000844.
Mexican Fourth Office Action dated Apr. 1, 2015 issued in Application No. MX/a/2012/000844.
Mexican Office Action dated Feb. 23, 2017 issued in Application No. MX/a/2015/008626.
Malaysian Examination and Search Report dated Dec. 31, 2013 issued in Application No. PI20095102.
Malaysian Examination and Adverse Report dated Dec. 31, 2014 issued in Application No. PI20095102.
Malaysian Examination and Clear Report dated Jul. 15, 2015 issued in Application No. PI20095102.
Malaysian Examination and Search Report dated May 15, 2017 issued in Application No. PI2014000965.
New Zealand First Examination Report dated Oct. 19, 2010 issued in Application No. NZ 581700.
New Zealand Examination Report dated Sep. 22, 2011 issued in Application No. NZ 581700.
New Zealand Examination Report dated Sep. 8, 2011 issued in Application No. NZ 595029.
New Zealand Examination Report dated Dec. 19, 2012 issued in Application No. NZ 595029.
Philippines Examination Report dated Apr. 7, 2014 issued in Application No. PH 1-2009-502294.
Philippines Examination Report dated Nov. 18, 2014 issued in Application No. PH 1-2009-502294.
Singapore Written Opinion and Search Report dated Apr. 29, 2011 issued in Application No. SG 200907978-1.
Thailand Office Action dated Feb. 22, 2011 issued in Application No. TH 0901005340.
Thailand Office Action dated Jul. 26, 2017 issued in Application No. TH 0901005340.
Australian Patent Examination Report No. 1 dated Jul. 20, 2017 issued in Application No. AU 2016250460.
Canadian Examination Report dated Aug. 18, 2015 issued in Application No. CA 2,745,129.
Canadian Examination Report dated Nov. 16, 2017 issued in Application No. CA 2,745,129.
Chinese Reexamination notification dated Nov. 10, 2016 issued in Application No. CN 200980155465.1.
Chinese Reexamination Decision dated Apr. 27, 2017 issued in Application No. CN 200980155465.1.
Chinese Fourth Office Action dated Sep. 25, 2017 issued in Application No. CN 200980155465.1.
Colombian Office Action dated Jun. 18, 2013 issued in Application No. CO 11.080.882.
Indonesia Substantive Examination Report Stage 1 dated Aug. 5, 2015 issued in Application No. ID W-00 2011 02343.
Japanese Office Action dated May 27, 2014 issued in Application No. JP 2011-538719.
Japanese Final Office Action dated Feb. 24, 2015 issued in Application No. JP 2011-538719.
Japanese Pre-Appeal Examination Report dated Aug. 27, 2015 issued in Application No. JP 2011-538719.
PCT International Search Report dated Nov. 5, 2010 issued in PCT/US2009/066141.

(56) References Cited

OTHER PUBLICATIONS

PCT International Preliminary Report on Patentability and Written Opinion dated Oct. 26, 2012 issued in PCT/US2009/066141.
Indonesian Examination Report dated Feb. 22, 2017 issued in Application No. W-00201102342.
Indian Examination Report dated Sep. 1, 2017 issued in Application No. In 4959/DELNP/2011.
Mexican Office Action [no translation] dated Dec. 9, 2013 issued in Application No. MX/a/2011/005630.
Malaysian Examination Report dated Mar. 15, 2017 issued in Application No. MY PI2011002435.
European Consultation by telephone dated May 29, 2017 issued in Application No. EP 11 787 551.8.
European Office Action dated Aug. 23, 2017 issued in Application No. EP 11 787 551.8.
Indonesian Office Action dated Sep. 21, 2017 issued in Application No. W00201205280.
Korean Office Action dated Nov. 29, 2017 issued in Application No. KR 10-2012-7034232.
Australian Examination Report No. 2 dated Aug. 28, 2017 issued in Application No. AU 2016202905.
Korean Office action [no translation] dated Dec. 11, 2017 issued in Application No. KR 10-2012-7034225.
Mexican Office Action dated Sep. 12, 2017 issued in Application No. MX/a/2012/013756.
Australian Patent Examination Report No. 1 dated May 20, 2015 issued in Application No. AU 2011323288.
Australian Patent Examination Report No. 2 dated Mar. 23, 2016 issued in Application No. AU 2011323288.
Australian Patent Examination Report No. 1 dated Aug. 21, 2017 issued in Application No. AU 2016202999.
Canadian Office Action dated Aug. 8, 2017 issued in Application No. CA 2,816,125.
Chinese First Office Action dated Apr. 15, 2014 issued in Application No. CN 201180053258.2.
Chinese Second Office Action dated Feb. 2, 2015 issued in Application No. CN 201180053258.2.
Chinese Third Office Action dated Jul. 3, 2015 issued in Application No. CN 201180053258.2.
Chinese Fourth Office Action dated Dec. 16, 2015 issued in Application No. CN 201180053258.2.
Chinese Fifth Office Action dated Jun. 6, 2016 issued in Application No. CN 201180053258.2.
Chinese Sixth Office Action (Rejection Decision) dated Nov. 2, 2016 issued in Application No. CN 201180053258.2.
Chinese Notification of Reexamination dated Aug. 31, 2017 issued in Application No. CN 201180053258.2.
European Office Action dated Aug. 15, 2014 issued in Application No. EP 11 785 851.4.
European Office Action dated Apr. 11, 2017 issued in Application No. EP 11 785 851.4.
Japanese Office Action dated Oct. 21, 2015 issued in Application No. JP 2013-537836.
Japanese Office Action dated Feb. 12, 2016 issued in Application No. JP 2013-537836.
Japanese Office Action dated Apr. 3, 2017 issued in Application No. JP 2016-009933.
Mexican First Office Action dated Jul. 19, 2016 issued in Application No. MX/a/2013/004631.
Mexican Second Office Action dated Jan. 16, 2017 issued in Application No. MX/a/2013/004631.
Mexican Third Office Action dated May 10, 2017 issued in Application No. MX/a/2013/004631.
Mexican Fourth Office Action dated Jul. 18, 2017 issued in Application No. MX/a/2013/004631.
Malaysian Examination Report dated May 31, 2016 issued in Application No. MY PI2013001587.
Canadian Examination Report dated Nov. 22, 2017 issued in Application No. CA 2,825,691.
European Examination Report dated Oct. 10, 2017 issued in Application No. EP 12 741 997.6.
Japanese Office Action dated Dec. 1, 2017 issued in Application No. JP 2016-145348.
Chinese Rejection Decision dated Oct. 10, 2017 issued in Application No. CN 201380031877.0.
PCT International Preliminary Report on Patentability and Written Opinion of the International Searching Authority dated Oct. 19, 2017 issued in PCT/US2016/026265.
GenBank Accession No. M94159.1 "California Bay Tree thioesterase mRNA, complete cds", (Apr. 27, 1993), 2pp.
GenBank: U31813 "Cinnamomum camphora acyl-ACP thioesterase mRNA, complete cds," Jan. 31, 1996, 2pp.
Abbadi et al., (2000) "Knockout of the regulatory site of 3-ketoacyl-ACP synthase III enhances short- and medium-chain acyl-ACP synthesis," *The Plant Journal*, 24(1):1-9.
Blatti, Jillian L. et al., (Sep. 2012) "Manipulating Fatty Acid Biosynthesis in Microalgae for Biofuel through Protein-Protein Interactions," *PLoS ONE*, 7(9):e42949, 12pp.
Chen et al., (2011) "Structural classification and properties of ketoacyl synthases," *Protein Science*, 20(10):1659-1667.
Gimpel et al., (Dec. 15, 2015) "In Metabolic Engineering of Eukaryotic Microalgae: Potential and Challenges Come with Great Diversity," *Metabolic Engineering of Eukaryotic Microalgae, Frontiers in Microbiology*, 6(Article 1376):14pp.
Snyder et al., (2009) "Acyltransferase action in the modification of seed oil biosynthesis," *New Biotechnology*, 26(1/2): 11-16.
U.S. Appl. No. 15/725,222, filed Oct. 4, 2017, Moseley et al.
"Soybean Oil Innovations, 3rd Edition," United Soybean Board, www.soyconnection.com, 8 pages, (2009). [Available from the Internet on Jan. 15, 2009: <URL: http://www.soyconnection.com/sites/default/files/soy-oil-solutions.pdf>].
"Codex Standard for Named Vegetable Oils," CODEX Alimentarius, CODEX STAN 210-1999, pp.1-16, (1999).
Aggelis et al., "Enhancement of single cell oil production by Yarrowia lipolytica growing in the presence of *Teucrium polium* L. aqueous extract," Biotechnology Letters, 21:747-749, (1999).
Aguirre et al., "Engineering challenges in biodiesel production from microalgae," Critical Reviews in Biotechnology, 33(3): 293-308, (2013).
Altschul et al., "Basic local alignment search tool," J Mol Biol, 215(3):403-410, (1990).
Amaro et al., "Advances and perspectives in using microalgae to produce biodiesel," Applied Energy, 88:3402-3410, (2011).
Andersen, "Biology and Systematics of Heterokont and Haptophyte Algae," American Journal of Botany, 91(10):1508-1522, (2004).
Appel et al., "A multicopy vector system for genetic studies in Mucor circinelloides and other zygomycetes," Molecular Genetics and Genomics, 271(5):595-602, (2004).
Apt et al., "Stable nuclear transformation of the diatom Phaeodactylum tricornutum," Mol Gen Genet, 252(5):572-579, (1996).
Barnes et al., "Contribution of 5'- and 3'-untranslated regions of plastid mRNAs to the expression of *Chlamydomonas reinhardtii* chloroplast genes," Mol Genet Genomics, 274(6):625-636, (2005).
Beale et al., "Chlorophyll Synthesis in Chlorella: Regulation by Degree of Light Limitation of Growth," Plant Physiol., 47:230-235, (1971).
Bhunia et al., "Algal Biodiesel Production: Challenges and Opportunities," Bioenergy and Biofuel from Biowastes and Biomass, American Society of Civil Engineers, pp. 313-345, (2010).
Bigogno et al., "Biosynthesis of arachidonic acid in the oleaginous microalga Parietochloris incisa (Cholorphyceae): Radiolabeling studies," Lipids 37(2):209-216 (2002); Abstract Only.
Bigogno et al., "Lipid and fatty acid composition of the green oleaginous alga Parietochloris incisa, the richest plant source of arachidonic acid," Pytochemistry, 60:497-503, (2002).
Blowers et al., "Studies on Chlamydomonas chloroplast transformation: foreign DNA can be stably maintained in the chromosome," Plant Cell, 1(1):123-132, (1989).
Bohacenko et al., "Detection of Olive Oils Authenticity by Determination of their Sterol Content using LC/GC," Czech J. Food Sci., 19(3):97-103, (2001).

(56) References Cited

OTHER PUBLICATIONS

Bonaventure et al., "Disruption of the FATB Gene in *Arabidopsis* Dethonstrates an Essential Role of Saturated Fatty Acids in Plant Growth," The Plant Cell 15:1020-1033, (2003).
Bordes et al., "A new recombinant protein expression system for high-throughput screening in the yeast Yarrowia lipolytica," Journal of Microbiological Methods, 70(3):493-502, (2007).
Bornscheuer et al. (ed), "Enzymes in Lipid Modification," Wiley-VCH Verlag Gmbh & Co. KGaA, 1st Edition, ISBN: 3-527-30176-3, Sections 1-11, 231 pages, (2000). (part 1 of 2 of book).
Bornscheuer et al. (ed), "Enzymes in Lipid Modification," Wiley-VCH Verlag Gmbh & Co. KGaA, 1st Edition, ISBN: 3-527-30176-3, Sections 12-18, 133 pages, (2000). (part 2 of 2 of book).
Borza et al., "Multiple Metabolic Roles for the Nonphotosynthetic Plastid of the Green Alga Prototheca Wickerhamii," Eukaryotic Cell, 4(2):253-261, (2005).
Boutry et al., "Targeting of bacterial chloramphenicol acetyltransferase to mitochondria in transgenic plants," Nature, 328(6128):340-2, (1987).
Boynton et al., "Chloroplast Transformation in Chlamydomonas with High Velocity Microprojectiles," Science, 240(4858):1534-1538, (1988).
Broun et al., "Accumulation of Ricinoleic, Lesquerolic, and Densipolic Acids in Seeds of Transgenic *Arabidopsis* Plants That Express a Fatty Acyl Hydroxylase cDNA from Castor Bean," Plant Physiol., 113:933-942, (1997).
Broun et al., "Catalytic Plasticity of Fatty Acid Modification Enzymes Underlying Chemical Diversity of Plant Lipids," Science, 282:1315-1317, (1998). [Retrieved from the Internet Feb. 27, 2007: <URL: http://www.sciencemag.org>].
Brown et al., "The amino-acid and sugar composition of 16 species of micralgae used in mariculture," J. Exp. Mar. Biol. Ecol. 145:79-99 abstract (1991).
Burgal et al., "Metabolic engineering of hydroxy fatty acid production in plants: RcDGAT2 drives dramatic increases in ricinoleate levels in seed oil," Plant Biotechnol J., 6(8):819-831, (2008).
Campbell et al., "Codon Usage in Higher Plants, Green Algae, and Cyanobacteria," Plant Physiol., (92):1-11, (1990).
Chasan, "Engineering Fatty Acids—The Long and Short of It," Plant Cell, 7:235-237, (1995).
Chattopadhyay et al., "Effect of single amino acid mutations in the conserved GDNQ motif of L protein of Rinderpest virus on RNA synthesis in vitro and in vivo," Virus Research, 99:139-145, (2004).
Chen et al., "Recognition of prokaryotic transcription terminators by spinach chloroplast RNA polymerase," Nucleic Acids Research, 16(17):8411-8431, (1988).
Chen et al., "Effect of C/N ratio and aeration on the fatty acid composition of heterotrophic Chlorella sorokiniana," Journal of Applied Phycology, 3:203-209, (1991).
Chen et al., "Highly Effective Expression of Rabbit Neutrophil Peptide-1 Gene in Chlorella Ellipsoidea Cells," Current Genetics, 39:365-370, (2001).
Chica et al., "Semi-rational approaches to engineering enzyme activity: combining the benefits of direced evolution and rational design ," Current Opinion in Biotechnology, 16:378-384, (2005).
Chow et al., "Electrotranformation of Chlorella Vulgaris," Plant Cell Reports, 18:778-780, (1999).
Ciferri, "Thiamine-deficiency of Prototheca, a Yeast-like Achloric Alga," Nature, 178:1475-1476, (1956).
Co et al., "Matching the Functionality of Single-Cell Algal Oils with Different Molecular Compositions," J Am Oil Chem Soc, doi: I0.1007/s11746-013-2405-y, 16 pages, (2014).
Cobley et al., "CpeR is an activator required for expression of the phycoerythrin operon (cpeBA) in the cyanobacterium Fremyella diplosiphon and is encoded in the phycoerythrin linker-polypeptide operon (cpeCDESTR)," Molecular Microbiology, 44(6):1517-153.
Cobley et al., Construction of Shuttle Plasmids Which Can Be Efficiently Mobilized From *Escherichia coli* Into the Chromatically Adapting Cyanobacterium, Plasmid, 30:90-105, (1993).
Cohen et al., "The Heterotrophic Connection in a Photoautotrophic Chlorella Vulgaris Dominant in W Astew Ater Oxidation Ponds," War. Sci. Tech., 27(7-8):151-155, (1993).
Comai et al., "Chloroplast Transport of a Ribulose Biphosphate Carboxylase Small Subunit-5-Enolpyruvyl 3-Phosphoshikimate Synthase Chimeric Protein Requires Part of the Mature Small Subunit in Addition to the Transit Peptide," Journal of Biological Chemis.
Cordy et al., "Chlorellasis in a Lamb," Vet. Path., 10:171-176, (1973).
Courchesne et al., "Enhancement of Lipid Production Using Biochemical, Genetic and Transcription Factor Engineering Approaches," J Biotechnol. Epub, 141(1-2):31-41, (2009).
Davies et al.,"Expression of the Arylsulfatase Gene from the Beta 2-Tubulin Promoter in Chlamydomonas reinhardtii," Nucleic Acids Research, 20(12):2959-2965, (1992).
Dawson et al., "Stable Transformation of Chlorella: Rescue of Nitrate Reductase-Deficient Mutants with the Nitrate Reductase Gene," Current Microbiology, 35:356-362, (1997).
Day, Al. et al., "Safety evaluation of a high-lipid algal biomass from Chlorella protorhecoides," Rego!. Toxicol. Pharmacol., doi:10.1016/j.yrtph.2009.06.014, 15 pages, (2009).
De Cock, "Structure development in confectionery products: importance of triacylglycerol composition," Master Thesis, Masters in Bioscience Engineering, Ghent University, 73 pages, (2011).
Debuchy et al., "The argininosuccinate lyase gene of *Chlamydomonas reinhardtii*: an important tool for nuclear transformation and for correlating the genetic and molecular maps of the ARG7 locus," EMBO J., 8(10):2803-2809, (1989).
Dehesh et al., "KAS IV: a 3-ketoacyl-ACP synthase from *Cuphea* sp. is a medium chain specific condensing enzyme," The Plant Journal, 15:383-390, (1998).
Dehesh et al., "Production of high levels of 8:0 and 10:0 fatty acids in transgenic canola by overexpression of Ch FatB2, a thioesterase cDNA from Cuphea hookeriana," The Plant Journal, 9(2):167-172, (1996).
Demirbas et al., "Importance of algae oil as a source of biodiesel," Energy Conversion and Management, 52:163-170, (2011).
Deshnium et al., "Transformation of Synechococcus with a gene for choline oxidase enhances tolerance to salt stress," Plant Mol Biol, 29(5):897-907, (1995).
Desmond et al., "Phylogenomics of Sterol Synthesis: Insights into the Origin, Evolution, and Diversity of a Key Eukaryotic Feature," Genome. Biol. Evol., 1:364-381, (2009).
Devos et al., "Practical Limits of Function Prediction," PROTEINS: Structure, Function, and Genetics, 41:98-107, (2000).
Dormann et al., "Cloning and Expression in *Escherichia coli* of a Novel Thioesterase from *Arabidopsis thaliana* Specific for Long-Chain Acyl-Acyl Carrier Proteins," Archives of Biochemistry and Biophysics, 316(1):612-618, (1995).
Dunahay et al., "Genetic Engineering of Microalgae for Fuel Production," Applied Biochemistry and Biotechnology, 34/35:331-339 (1992).
Dunahay et al., "Manipulation of Microalgal Lipid Production Using Genetic Engineering," Applied Biochemistry and Biotechnology, 57/58:223-231, (1996).
Eccleston et al., "Medium-chain Fatty Acid Biosynthesis and Utilization in *Brassica mapus* Plants Expressing Lauroyl-Acyl Carrier Protein Thioesterase," Planta 198:46-53, (1996).
El-Fadaly et al., "Single Cell Oil Production by an Oleaginous Yeast Strain in a Low Cost Cultivation Medium," Research Journal of Microbiology, 4(8):301-313, (2009).
El-Sheekh, MM., "Stable Transformation with the Intact Cells of Chlorella Kessleri With High Velocity Microprojectiles," Biologia Plantarium 42(2): 209-216, (1999).
EPO Supplementary European Search Report and European Search Opinion for application EP 12782478.7 dated Oct. 22, 2014.
EPO Supplementary European Search Report and European Search Opinion for application EP08769988.0 dated Jul. 1, 2011.
EPO Supplementary European Search Report and European Search Opinion for application EP11158642.6 dated Jul. 1, 2011.
EPO Supplementary European Search Report and European Search Opinion for application EP12741997.6 dated Aug. 31, 2015.

(56) References Cited

OTHER PUBLICATIONS

EPO Supplementary European Search Report and European Search Opinion for application EP 09829850.8 dated May 16, 2014.
Erhan, "Vegetable Oils as Lubricants, Hydraulic Fluids, and Inks," Bailey's Industrial Oil and Fat Products, 6:259-278, (2005).
Evans et al., "A comparison of the oleaginous yeast, Candida curvata, grown on different carbon sources in continuous and batch culture," Lipids, 18(09):623-629, (1983).
Facciotti et al., "Improved stearate phenotype in transgenic canola expressing a modified acyl-acyl carrier protein thioesterase," Nat Biotechnol., 17(6):593-597, (1999).
Falciatore et al., "Transformation of Nonselectable Reporter Genes in Marine Diatoms," Marine Biotechnology; 1:239-251, (1999).
Fall et al., "Bioconversion of Xylan to Triglycerides by By Oil-Rich Yeasts," Applied and Environmental Microbiology, 47(5):1130-1134, (1984).
Fernandez-Reiriz et al., "Biomass Production and Variation in the Biochemical Profile (Total Protein, Carbohydrates, RNA, Lipids and Fatty Acids) of Seven Species of Marine Microalgae," Aquaculture, 83:17-37, (1989).
Ferrentino, "Microalgal oil extraction and in situ transesterification," University of New Hampshire, Pub. No. MT 1447885, 8 pages, (2007).
Ferrentino, et al., "Microalgal Oil Extraction and In-situ Transesterification," AIChE Annual Mtg, San Francisco, CA, Nov. 11-13, 2006. Abstract.
Franklin et al., "Prospects for molecular farming in the green alga Chlamydomonas reinhardtii," Current Opinion in Plant Biology, 7:159-165, (2004).
Franzen et al., "Chloroplast transit peptides from the green alga Chlamydomonas reinhardtii share features with both mitochondrial and higher plant chloroplast presequences," FEBS Letters, 260(2):165-168, (1990).
Frenz et al., "Hydrocarbon recovery by extraction with a biocompatible solvent from free and immobilized cultures of Botryococcus braunii," Enzyme Microb Technol, 11(11):717-724, (1989).
Frohns et al., "Potassium ion channels of Chlorella viruses cause rapid depolarization of host cells during infection," J Virol, 80(5):2437-2444, (2006).
Fromm et al., "Expression of Genes Transferred into Monocot and Dicot Plant Cells by Electroporation," Proc Natl Acad Sci, 82:5824-5828, (1985).
Funes et al., "The typically mitochondrial DNA-encoded ATP6 subunit of the F1F0-ATPase is encoded by a nuclear gene in Chlamydomonas reinhardtii," J Biol Chem, 277(8):6051-6058, (2002).
Gabay et al., "Stigmasterol: a phytosterol with potential anti-osteoarthritic properties," Osteoarthritis and Cartilage,18:106-116, (2010).
GenBank: "Codon Usage Database file for Chlorella vulgaris," Jun. 2007. [Retrieved from the Internet Aug. 26, 2010: <URL: http://www.kazusa.or.jp/codon/cgi-bin/showcodon.cgi?species=3077 >].
GenBank: Accession No. AAC49001.1, May 1995. [Retrieved from the Internet Oct. 14, 2014: <URL: http://www.ncbi.nlrrtnih.gov/protein/595955?sat=13&satkey=6522409>].
Gill et al., "Lipid Accumulation in an Oleaginous Yeast (Candida 107) Growing on Glucose in Single-Stage Continuous Culture," Applied and Environmental Microbiology, 33(02):231-239, (1977).
Gouveia et al., "Microalgae in Novel Food Products," Food Chemistry Research Developments, Chapter 2, Nova Science Publishers, Inc., ISBA 978-1-60456-262-0, 37 pages, (2008).
Graves et al., "Hyaluronan synthesis in virus PBCV-1-infected chlorella-like green algae," Virology, 257(1):15-23, (1999).
Grima et al., "Recovery of microalgal biomass and metabolites: process options and economics," Biotechnology Advances, 20:491-515, (2003).
Gruber et al., "*Escherichia coli*-Anacystis nidulans plasmid shuttle vectors containing the PL promoter from bacteriophage lambda," Current Microbiology, 22(1):15-19, (1991).
Guiry et al., "How Many Species of Algae are There?," J. Phycol., 48:1057-1063, (2012).

Gul et al., "Sterols and the Phytosterol Content in Oilseed Rape (*Brassica napus* L.)," Journal of Cell and Molecular Biology, 5:71-79 (2006).
Gunstone, "Enzymes as biocatalysts in the modification of natural lipids," Journal of the Science of Food and Agriculture, 79:1535-1549, (1999).
Guo-Zhong et al., "The Actin Gene Promoter-driven Bar as a Dominant Selectable Marker for Nuclear Transformation of Dunaliella Salina," Acta Genetica Sinica, 32(4): 424-433, (2005).
Guschina et al., "Lipids and lipid metabolism in eukaryotic algae," Progress in Lipid Research, 45:160-186, (2006).
Hall et al., "Expression of a foreign gene in Chlamydomonas reinhardtii," Gene, 124(1):75-81, (1993).
Hall et al., "Lipid Accumulation in an Oleaginous Yeast (Candida 107) Growing on Glucose Under Various Conditions in a One- and Two-Stage Continuous Culture," Applied and Environmental Microbiology, 33(3):577-584, (1977).
Hallmann et al., "Reporter Genes and Highly Regulated Promoters as Tools for Transformation Experiements in Volvox Carteri," Proc Natl Acad Sci U S A., 91(24):11562-11566, (1994).
Hanley-Bowdoin et al., "Chloroplast promoters," Trends in Biochemical Sciences, 12:67-70, (1987).
Hawkins et al., "Expression of Human Growth Hormone by the Eukaryotic Alga, Chlorella," Current Microbiology, 38:335-341, (1999).
Heifetz, "Genetic Engineering of the Chloroplast," Biochimie, 82:655-666, (2000).
Heise et al., "Factors Controlling Medium-Chain Fatty Acid Synthesis in Plastids From Cuphea Embryos," Prog. Lipid Res., 33(1/2):87-95, (1994).
Henderson et al., "Lipid Composition and Biosynthesis in the Marine Dinoflagellate Crypthecodznzum Cohnii," Phytochem. 27(6):1679-1683 (1988).
Henikoff et al., "Amino Acid Substitution Matrices from Protein Blocks," Proc Natl Acad of Sci, 89(22):10915-10919, (1992).
Heredia et al., "Simultaneous utilization of glucose and xylose by Candida curvata D in continuous culture," Biotechnology Letters, 10(01):25-30, (1988).
Heredia-Arroyo et al., "Oil Accumulation via Heterotrophic/Mixotrophic Chlorella protothecoides," Appl Biochem Biotechnol, 162:1978-1995, (2010).
Hillen et al., "Hydrocracking of the Oils of Botryococcus braunii to Transport Fuels," Biotechnology and Bioengineering, 24(1):193-205, (1982).
Hiramatsu et al., "Expression of a chitinase gene and lysis of the host cell wall during Chlorella virus CVK2 infection," Virology, 260(2):308-315, (1999).
Hitz et al.,"Cloning of a Higher-Plant Plastid Omega-6 Fatty Acid Desaturase cDNA and Its Expression in a Cyanobacterium," Plant Physiology, 105(2):635-641, (1994).
Hu et al., "Microalgal Triacylglycerols as Feedstocks for Biofuel Production: Perspectives and Advances," The Plant Journal 54:621-639, (2008).
Huang et al., "Sterols as ecological indicators," Geochimica et Cosmochimica Acta, 43:739-745, (1979).
Huang et al., "Expression of Mercuric Reductase From Bacillus Megaterium MB1 in Eukaryotic Microalga *Chlorella* sp. DT: An Approach for Mercury Phytoremediation," Appl. Microbiol. Biotechnol., 72:197-205, (2006).
Huss et al., "Deoxyribonucleic acid reassociation in the taxonomy of the genus *Chlorella*," Arch Microbiol, 150:509-511, (1988).
Inoue et al., "Analysis of oil derived from liquefaction of Botryococcus Braunii," Biomass and Bioenergy, 6(4):269-274, (1994).
Itoh et al., "Sterol Compositoin of 19 Vegetable Oils," Journal of the American Oil Chmists' Society, 50:122-125, (1973).
Iturriaga et al. "Heterologous transformation of Mucor circinelloides with the Phycomyces blakesleeanus leu1 gene," Current Genetics, 21(3):215-223, (1992).
Jakobiak et al., "The Bacterial Paromomycin Resistance Gene, aphH, as a Dominant Selectable Marker in Volvox carteri," Protist, 55: 381-393, (2004).

(56) References Cited

OTHER PUBLICATIONS

Jarvis et al. "Transient Expression of Firefly Luciferase in Protoplasts of the Green Alga Chlorella Ellipsoidea," Current Genet., 19: 317-322, (1991).
Jaworski et al., "Industrial oils from transgenic plants," Current Opinion in Plant Biology, 6:178-184, (2003).
Jha et al., "Cloning and functional expression of an acyl-ACP thioesterase FatB type from Diploknema (Madhuca) butyracea seeds in *Escherichia coli*," Plant Physiology and Biochemistry, 44:645-655, (2006).
Jiang et al., "The actin gene promoter-driven bar as a dominant selectable marker for nuclear transformation of Dunaliella salina," Yi Chuan Xue Bao, 32(4):424-433, (2005).
Jones et al., "Palmitoyl-Acyl Carrier Protein (ACP) Thioesterase and the Evolutionary Origin of Plant Acyl-ACP Thioesterases," Plant Cell, 7:359-371, (1995).
Kalscheuer et al., "Establishment of a Gene Transfer System for Rhodococcus Opacus PD630 Based on Electroporation and its Application for Recombinant Biosynthesis of Poly(3-hyroxyalkanoic acids)," Applied Microbiology and Biotechnology, 52(4):508-515, (1999).
Kamiya, "Effects of Blue Light and Ammonia on Nitrogen Metabolism in a Colorless Mutant of Chlorella," Plant Celll Physiol., 30(4):513-521, (1989).
Kamurthy et al., "Antinocieptive Activity of Stigmosterol-3-Glyceryl-2-Linoleiate, Campesterol and Daucosterol Isolated From Aerva Lanata Linn. Aerial Parts," Asian J Pharm Clin Res, 6(1):149-152, (2013).
Kang et al., "Genetic diversity in chlorella viruses flanking kcv, a gene that encodes a potassium ion channel protein," Virology, 326(1):150-159, (2004).
Kang et al., "The regulation activity of Chlorella virus gene 5' upstream sequence in *Escherichia coli* and eucaryotic alage," Institute of Microbiology, Chinese Academy of Sciences, Beijing, 16(4):443-6, (2000). Abstract only.
Karabulut et al., "Determination of changes in some physical and chemical properties of soybean oil during hydrogenation," Food Chemistry, 81:453-456, (2003).
Karlin et al., "Applications and statistics for multiple high-scoring segments in molecular sequences," Proc Natl Acad Sci, 90(12):5873-5877, (1993).
Katayama et al., "Alpha-Linolenate and Photosynethetic Activity in Chlorella Protothecoides," Plant Physiol., 42:308-313, (1967).
Kawasaki et al., "Characterization of Immediate Early Genes Expressed in Chlorovirus Infections," Nucleic Acids Symp Ser, 44:161-162, (2000).
Kawasaki et al., "Immediate Early Genes Expressed in Chlorovirus Infections," Virology, 318(1):214-223, (2004).
Kenyon, "Fatty Acid Composition of Unicellular Strains of Blue-Green Algae," J. Bacteriology 109(2):827-834 (1972).
Kim et al. "Stable Integraion and Functional Expression of Flounder Growth Hormone Gene in Tranformed Microalga, Chlorella Ellipsoidea," Mar. Biotechnol. 4:63-73 (2002).
Kimchi-Sarfaty et al., " a 'Silent' Polymorphism in the MDR1 Gene Changes Substrate Specificity," Science, 315:525-528, (2007). [Retrieved from the Internet Nov. 1, 2007: <URL: http://www.sciencemag.org>].
Kindle, "High-Frequency Nuclear Transformation of Chlamydomonas reinhardtii," Proc Natl Acad Sci, 87(3):1228-1232, (1990).
Kisselev, "Polypeptide Release Factors in Prokaryotes and Eukaryotes: Same Function, Different Structure," Structure, 10:8-9, (2002).
Klein et al., "High-velocity microprojectiles for delivering nucleic acids into living cells," Nature, 327:70-73, (1987).
Klosty et al., "Sterols of Algae. The Occurrence of Ergosterol in Chiorelia pyrarwidosa," J. Am. Chem. Soc., Notes, 74(6):1601-1601, (1952).
Knauf, "The application of genetic engineering to oilseed crops," Trends in Biotechnology, 5(2):40-47, (1987).
Knothe, "'Designer' Biodiesel: Optimizing Fatty Ester Composition to Improve Fuel Properties," Energy & Fuels, 22:1358-1364, (2008).
Knothe, "Analyzing Biodiesel: Standards and Other Methods," JAOCS, 83(10):823-833, (2006).
Kohler et al., "The green fluorescent protein as a marker to visualize plant mitochondria in vivo," Plant J, 11(3):613-621, (1997).
Koksharova, "Genetic Tools for Cyanobacteria," Appl Microbiol Biotechnol, 58(2):123-37, (2002).
Kong et al., "Microbial production of lipids by cofermentation of glucose and xylose with Lipomyces starkeyi 2#," Chinese Journal of Bioprocess Engineering, 05(02):36, (2007). Abstract.
Krebbers et al., "The maize chloroplast genes for the beta and epsilon subunits of the photosynthetic coupling factor CF1 are fused," Nucleic Acids Res, 10(16): 4985-5002, (1982).
Kris-Etherton et al., "Monounsaturated Fatty Acids and Risk of Cardiovascular Disease," Circulation, 100:1253-1258, (1999).
La Scala et al., "The effect of fatty acid composition on the acrylation kinetics of epoxidized triacylglycerols," Journal of the American Oil Chemists' Society, 79(1):59-63, (2002).
Lapidot et al., "Stable Chloroplast Transformation of the Unicellular Red Alga *Porphyridium* Species," Plant Physiol, 129:7-12, (2002).
Larson et al., "Acyl CoA profilesof transgenic plants that accumulate medium-chain fatty acids indicate inefficient storage lipid synthesis in developing oilseeds," The Plant Journal, 32(4):519-527, (2002).
Lawford et al., "Performance Testing of Zymomonas Mobilis Metabolically Engeineered for Confermation of Glucose, Xylose, and Arabinose," Appl Biochem Biotechnol., 98-100:429-48, (2002).
Leema et al., "Heterotrophic Production of Lutein and Biomass by Chlorella Vulgaris with Different Nitrogen Sources," Algae Biofuel, Studium Press (India) Pvt. Ltd., pp. 91-101, (2011).
Leon-Banares et al., "Transgenic microalgae as green cell-factories," TRENDS in Biotechnology, 22(1):45-52, (2004).
Levitan et al., "Dual targeting of the protein disulfide isomerase RB60 to the chloroplast and the endoplasmic reticulum," Proc Natl Acad Sci, 102(17):6225-6230, (2005).
Li et al., "Broad-spectrum oil-producing yeast carbon filter," China Biotechnology, 25(12):39-44 (2005), and machine translation.
Li et al., "High-density cultivation of oleaginous yeast Rhodosporidium toruloides Y4 in fed-batch culture," Enzyme and Microbial Technology, 41:312-317, (2007).
Lindley, "The impact of food processing antioxidants in vegetable oils, fruits, and vegetables," Trends in Food Science & Technology. 9:336-340, (1998).
List et al., "Melting properties of some structured lipids native to high stearic acid soybean oil," Grasas y Aceites, 55(Fasc. 2):135-137, (2004).
Lu, "Biosynthesis and Gene Engineering of Plant Fatty Acids," Chinese Bulletin of Botany, 17(6):481-491, (2000). Abstract only.
Lubitz, "The Protein Quality, Digestibility, and Composition of Algae, Chlorella 71105," J. Food Sci. 28(2):229-232 (1963).
Lumbreras et al., "Efficient Foreign Gene Expression in Chlamydomonas Reinhardtii Mediated by an Endogenous Intron," Plant Journal, 14(4):441-447, (1998).
Madzak et al., "Functional analysis of upstream regulating regions from Yarrowia lipolytica XPR2 promoter," Microbiology, 145:75-87, (1999).
Manuell et al., "Robust expression of a bioactive mammalian protein in Chlamydomonas chloroplast," Plant Biotech J, 5(3):402-412, (2007).
Maruyama et al., "Introduction of Foreign DNA Into Chlorella Saccharophila by Electroporation," Biotechnology Techniques, 8:821-826, (1994).
Mayer et al., "A Structural Model of the Plant Acyl-Acyl Carrier Protein Thioesterase FatB Comprises Two Helix/4-Stranded Sheet Domains, the N-terminal Domain Containing Residues That Affect Specificity and the C-terminal Domain Containing Catalytic Residues," The Journal of Biological Chemistry, 280(5):3621-3627, (2005).
Mayer et al., "Identification of amino acid residues involved in substrate specificity of plant acyl-ACP thioesterases using a bioinformatics-guided approach," BMC Plant Biology, 7(1):1-11, (2007).
Mayfield et al., "Expression and Assembly of a Fully Active Antibody in Algae," Proc Natl Acad Sci, 100(2):438-442, (2003).

(56) References Cited

OTHER PUBLICATIONS

Mayfield et al., "Stable nuclear transformation of Chlamydomonas reinhardtii by using a C. reinhardtii gene as the selectable marker," Proc. Natl. Acad. Sci. USA, Cell Biology, 87:2087-2091, (1990).
Meesters et al., "High-cell-density cultivation of the lipid accumulating yeast Cryptococcus curvatus using glycerol as a carbon source," Applied Microbiology and Biotechnology, 45:575-579, (1996).
Meguro et al., "Original Communication Solubilization of phytosterols in diacylglycerol versus triacylglycerol improves the serum cholesterol-lowering effect," European Journal of Clinical Nutrition, 55:513-517, (2001).
Mekhedov et al., "Toward a Functional Catalog of the Plant Genome. A Survey of Genes for Lipid Biosynthesis," Plant Physiology, 122:389-401, (2000).
Mendes et al., "Supercritical Carbon Dioxide Extraction of Compounds With Pharmaceutical Importance from Microalgae," Inorganica Chimica Acta, 356:328-334, (2003).
Meng et al., "Biodiesel production from oleaginous microorganisms," Renewable Energy, 34:1-5, (2009).
Metzger et al., "Botryococcus braunii: A Rich Source for Hydrocarbons and Related Ether Lipids," Applied Microbiology and Biotechnology, 66(5):486-496, (2005).
Miao et al., "High Yield Bio-Oil Production from Fast Pyrolysis by Metabolic Controlling of Chlorella Protothecoides," J. Biotech., 110:85-93, (2004).
Minowa et al., "Oil Production from Algal Cells of Dunaliella tertiolecta By Direct Thermochemical Liquefaction," Fuel, 74(12):1735-1738, (1995).
Mitra et al., "A Chlorella Virus Gene Promoter Functions as a Strong Promoter Both in Plants and Bacteria," Biochemical and Biophysical Research Communications, 204(1):189-194, (1994).
Mitra et al., "The Chlorella Virus Adenine Methyltransferase Gene Promoter is a Strong Promoter in Plants," Plant Molecular Biology, 26(1):85-93, (1994).
Moreno-Perez et al., "Reduced expression of FatA thioesterases in *Arabidopsis* affects the oil content and fatty acid composition of the seeds," Planta, 235:629-639, (2012).
Morris, "Effect of Growth Temperature on the Cryopreservation of Prototheca," Journal of General Microbiology, 94:395-399, (1976).
Mullet et al., "Multiple transcripts for higher plantrbcL andatpB genes and localization of the transcription initiation site of therbcL gene," Plant Molecular Biology, 4(1):39-54, (1985).
Murakami et al., "Lipid Composition of Commercial Bakers' Yeasts Having Different Freeze- tolerance in Frozen Dough," Biosci. Biotechnol. Biochem., 60(11)1874-1876, (1996).
Murakami et al., "Lipids and Fatty Acid Custipvsi lions of Chlorella," Nihon Yuka gakkai-shi, 46(4):423-427, (1997).
Nackley et al., "Human Catechol-O-Methyltransferase Haplotypes Modulate Protein Expression by Altering mRNA Secondary Structure," Science, 314:1930-1933, (2006).[Retrieved from the Internet Nov. 1, 2007: <URL: http://www.sciencemag.org>].
Nahm, "Quality Characteristics of West African Shea Butter (*Vitellaria paradoxa*) and Approaches to Extend Shelf-Life," Master Thesis, Master of Science in Food Service, Rutgers, The State University of New Jersey, 133 pages, (2011).
Napier et al., "Tailoring plant lipid composition: designer oilseeds come of age," Current Opinion in Plant Biology, 13:330-337, (2010).
Nazaruddin et al., "The Effect of Enzymatic Alcoholysis on the Physicochemical Properties of Commercial Cocoa Butter Substitutes," Pakistan Journal of Nutrition, 10(8):718-723, (2011).
Needleman et al., "A general method applicable to the search for similarities in the amino acid sequence of two proteins," Journal of Molecular Biology, 48(3):443-453, (1970).
Nes et al., "Biosynthesis of Cholesterol and Other Sterols," Chem. Rev., 111:6423-6451, (2011).

Norton et al., "Identification of Ergosta-6(7),8(14),25(27)-trien-3β-ol and Ergosta-5(6),7(8),25(27)-trien-3β-ol, Two New Steroidal Trienes Synthesized by Prototheca wickerhamii," Lipids, 26: 247-249, (1991).
Onai et al., "Natural Tranformation of the Termophillic Cyanbacterium Thermosynechococcus Elongatus BP-1: A Simple and Efficicent Method for Gene Transfer," Mol Genet Genomics, 271(1):50-9, (2004).
Papanikolaou et al., "Single cell oil production by Yarrowia lipolytica growing on an industrial derivative of animal fat in batch cultures," Appl. Microbiol. Biotechnol., 58:308-312, (2002).
Papanikolaou et al., "Lipid production by Yarrowia lipolytica growing on industrial glycerol in a single-stage continuous culture," Bioresource Technology, 82:43-49, (2002).
Park et al., "Isolation and Characterization of Chlorella Virus From Fresh Water in Korea and Application in Chlorella Transformation System," Plant Pathol. J., 21(1):13-20, (2005).
Patil et al., "Fatty acid composition of 12 microalgae for possible use in aquaculture feed," Aquacult Int , 15:1-9, (2007).
Patterson et al., "Sterols of Chlorella. II. The Occurrence of an Unusual Sterol Mixture in Chlorella vulgaris," Plant Physiol., 42:1457-1459, (1967).
Patterson et al., "Sterols of Chlorella-III. Species Containing Ergosterol," Comp. Biochem. Physiol., 31:391-394, (1969).
PCT International Preliminary Report on Patentability (Chapter I) dated May 31, 2011 for application PCT/US09/066142.
PCT International Preliminary Report on Patentability (Chapter I) dated Aug. 13, 2012 for application PCT/US11/38463.
PCT International Preliminary Report on Patentability (Chapter I) dated Dec. 7, 2009 for application PCT/US08/65563.
PCT International Preliminary Report on Patentability for application PCT/US2011/059224 dated May 16, 2013.
PCT International Search Report and Written Opinion of the International Searching Authority for application PCT/US2013/037261 dated Aug. 23, 2013.
PCT International Search Report and Written Opinion of the International Searching Authority for application PCT/US2014/035476 dated Feb. 18, 2015.
PCT International Search Reort and Written Opinion of the International Searching Authority for application PCT/US2014/059161 dated Jun. 1, 2015.
PCT International Search Reort and Written Opinion of the International Searching Authority for application PCT/US2015/023181 dated Jul. 28, 2015.
PCT International Search Report for application PCT/US2011/032582 dated Aug. 9, 2011.
PCT International Search Report for application PCT/US2011/038463 dated Jan. 18, 2012.
PCT International Search Report for application PCT/US2011/059224 dated Jun. 27, 2012.
PCT International Search Report for application PCT/US2012/023696 dated May 23, 2012.
PCT International Search Report for application PCT/US2012/036690 dated Aug. 30, 2012.
PCT International Search Report dated Aug. 20, 2010 for application PCT/US2009/066142.
PCT International Search Report dated Nov. 5, 2010 for application PCT/US2009/066141.
PCT International Search Report dated Nov. 6, 2008 for application PCT/US2008/065563.
PCT Invitation to Pay Additional Fees for application PCT/US2014/059161 dated Mar. 9, 2015.
PCT Invitation to Pay Additional Fees from the International Searching Authority for application PCT/US2014/035476 dated Dec. 1, 2014.
PCT Written Opinion of the International Search Authority dated Aug. 20, 2010 for application PCT/US2009/066142.
PCT Written Opinion of the International Searching Authority for application PCT/US2011/032582 dated Aug. 9, 2011.
PCT Written Opinion of the International Searching Authority for application PCT/US2011/038463 dated Jan. 18, 2012.
PCT Written Opinion of the International Searching Authority for application PCT/US2012/023696 dated May 23, 2012.

(56) References Cited

OTHER PUBLICATIONS

PCT Written Opinion of the International Searching Authority for application PCT/US2012/036690 dated Aug. 30, 2012.
PCT Written Opinion of the International Searching Authority dated Nov. 5, 2010 for application PCT/US2009/066141.
PCT Written Opinion of the International Searching Authority dated Nov. 6, 2008 for application PCT/US2008/065563.
Pearson et al., "Improved tools for biological sequence comparison," Proc Natl Acad Sci, 85(8):2444-2448, (1988).
Petkov et al., "Which are fatty acids of the green alga Chlorella?," Biochemical Systematics and Ecology, 35:281-285, (2007).
Phippen et al., "Total seed oil and fatty acid methyl ester contents of Cuphea accessions," Industrial Crops and Products, 24:52-59, (2006).
Powell et al., "Algae Feeding in Humans," J. Nutrition, 75:7-12, (1961).
Pratoomyot et al., "Fatty acids composition of 10 microalgal species," Songklanakarin J. Sci. Technol., 27(6):1179-1187, (2005).
Proschold et al., "Portrait of a Species: Chlamydomonas reinhardtii," Genetics, 170(4):1601-1610, (2005).
Puglia et al., "In viva spectrophotometric evaluation of skin barrier recovery after topical application of soybean phytosterols," J. Cosmet. Sci., 59:217-224, (2008).
Qingyu et al., "Fine Cell Structure and Biochemical Compositions of Chlorella Prototheocides after Transferring from Autotrophic to Heterotrophic Metabolism," Journal of Nanjing University, Natural Sciences Edition, 29(4):622-630, (1993). Abstract.
Radakovits et al., "Genetic Engineering of Algae for Enhanced Biofuel Production," Eukaryotic Cell, 9(04): 486-501, (2010).
Radmer et al., "Commercial applications of algae: opportunities and constraints," Journal of Applied Phycology, 6:93-98, (1994).
Randolph-Anderson et al., "Further characterization of the respiratory deficient dum-1 mutation of Chlamydomonas reinhardtii and its use as a recipient for mitochondrial transformation," Mol Gen Genet, 236(2-3):235-244, (1993).
Ratledge, "Regulation of lipid accumulation in oleaginous microorganisms," Biochem Soc Trans., 30(Pt 6):1047-1050, (2002).
Rehm et al., "Heterologous expression of the acyl-acyl carrier protein thioesterase gene from the plant Umbellularia californica mediates polyhydroxyalkanoate biosynthesis in recombinant *Escherichia coli*," Appl Microbiol Biotechnol, 55:205-209, (2001).
Rismani-Yazdi et al., "Transcriptome sequencing and annotation of the microalgae Dunaliella tertiolecta: Pathway description and gene discovery for production of next-generation biofuels," BMC Genomics, 12:148, 17 pages; doi:10.1186/1471-2164-12-148, (2011).
Roessler et al., "Genetic Engineering Approaches for Enhanced Production of Biodiesel Fuel from Microalgae," Enzymatic Conversion of Biomass for Fuels Production, Chapter 13, American Chemical Society, doi: 10.1021/bk-1994-0566.ch013, pp. 255-270, (1994).
Rosenberg et al., "A Green Light for Engineered Algae: Redirecting Metabolism to Fuel a Biotechnology Revolution," Current Opinion in Biotechnology. Tissue, Cell and Pathyway Engineering, E-Pub 19:430-436, (2008).
Roy et al., "Production of Intracellular Fat by the Yeast Lipomyces starkeyi," Indian Journal of Experimental Biology, 16(4):511-512, (1978).
Ruiz et al., "Lipids accumulation in Chlorella protothecoides through mixotrophic and heterotrophic cultures for biodiesel production," New Biotechnology, 255:S266-S266, (2009).
Running et al., "Extracellular production of L-ascorbic acid by Chlorella protothecoides, Protothéca species, and mutants of P. moriformis during aerobic culturing at low pH," Journal of Industrial Microbiology & Biotechnology, 29:93-98, (2002).
Saha et al., "Transformation in Aspergillus ochraceus," Current Microbiology, 30(2):83-86, (1995).
Sakuradani, "Studies of Metabolic Engineering of Useful Lipid-producing Microorganisms," NISR Research Grant, (2004).
Sanchez et al., "Mixotrophic culture of Chlorella pyrenoidosa with olive-mill wastewater as the nutrient medium," Journal of Applied Phycology, 13:443-449, (2001).
Sanford, "The biolistic process," Trends in Biotechnology, 6(12):299-302, (1988).
Sauna et al., "Silent Polymorphisms Speak: How They Affect Pharmacogenomics and the Treatment of Cancer," Cancer Res, 67(20):9609-9612 , (2007).
Sawayama et al., "Possibility of renewable energy production and CO2 mitigation by thermochemical liquefaction of microalgae," Biomass and Bioenergy, 17(1):33-39, (1999).
Schreier et al., "The use of nuclear-encoded sequences to direct the light-regulated synthesis and transport of a foreign protein into plant chloroplasts," EMBO J, 4(1):25-32, (1985).
Schultz et al., "A common core of secondary structure of the internal transcribed spacer 2 (ITS2) throughout the Eukaryota," RNA, 11(4):361-364, (2005).
Schütt et al., "The role of acyl carrier protein isoforms from Cuphea lanceolata seeds in the de-novo biosynthesis of medium-chain fatty acids," Publication, Planta, 205:263-268, (1998).
Seffernick et al., "Melamine Deaminase and Atrazine Chlorohdrolase: 98 Percent Identical but Functionally Different," Journal of Bacteriology, 183(8):2405-2410, (2001).
Sen et al., "Developments in Directed Evolution for Improving Enzyme Functions," Appl Biochem Biotechnol, 143:212-223, (2007).
Shao et al., "Cloning and expression of metalothionein mutant α-KKS-α in *Anabaena* sp. PCC 7120," Marine Pollution Bulletine, 45(1012):163-167, (2002).
Shi et al., "High-Yield Production of Lutein by the Green Microalga Chlorella protothecoides in Heterotrophic Fed-Batch Culture," Biotechnol. Prog., 18(4):723-727 (2002).
Shi et al., "Production and rapid extraction of lutein and the other lipid-soluble pigments from Chlorella protothecoides grown under heterotrophic and mixotrophic conditions," Nahrung, 43:109-113, (1999).
Skolnick et al., "From genes to protein structure and function: novel applications of computational approaches in the genomic era," TIBTECH, 18: 34-39, (2000).
Smallwood et al., "Different Substitutions at Conserved Amino Acids in Domains II and III in the Sendai L RNA Polymerase Protein Inactivate Viral RNA Synthesis," Virology, 304:135-145, (2002).
Smith et al., "Comparison of Biosequences," Adv Appl Math, 2(4):482-489, (1981).
Smith et al., "Production of hydroxy fatty acids in the seeds of *Arabidopsis thaliana*," Biochemical Society Transactions, 28(6):947-950, (2000).
Sorger et al., "Triacylglycerol biosynthesis in yeast," AppL Microbiol Biotechnol, 61:289-299, (2003).
Spolaore et al., "Commercial Applications of Microalgae," J. Biosci. Bioeng. 101(2):87-96 (2006).
Stemmer et al., "Single-Step Assembly of a Gene and Entire Plasmid from Large Numbers of Oligodeoxyribonucleotides," Gene, 164:49-53, (1995).
Sud et al., "Lipid Composition and Sensitivity of Prototheca wickerhamii to Membrane-Active Antimicrobial Agents," Antimicrobial Agents and Chemotherapy, 16:486-490, (1979).
Suda, et al., "Evidence for a novel Chlorella virus-encoded alginate lyase," FEMS Microbiology Letters, 180(1):45-53, (1999).
Suh et al., "What limits production of unusual monoenoic fatty acids in transgenic plants?," Planta, 215:584-595, (2002).
Sun et al., "Characterization of two chitinase genes and one chitosanase gene encoded by Chlorella virus PBCV-1," Virology, 263(2):376-387, (1999).
Sung et al., "The research on the lipid content and composition of microalgae and their impact factors," Marine Science, 12(33)122-128, (2009). (English translation of first two pages).
Swern et al. "Fractionation of tallow fatty acids:Preparation of purified oleic acid and an inedible olive oil substitute," Oil & Soap, 22(11):302-304 (1945).
Szabo et al., "Safety evaluation of a high lipid Whole Algalin Flour (WAF) from Chlorella protothecoides," Regulatory Toxicology and Pharmacology, 63:155-165, (2012).

(56) References Cited

OTHER PUBLICATIONS

Szabo et al., "Safety evaluation of Whole Algalin Protein (WAP) from Chlorella protothecoides," Food and Chemical Toxicology, 59:34-45, (2013).
Takaku et al., "Isolation of an Antitumor Compound from Agaricus blazei Murill and Its Mechanism of Action," J. Nutr., 131:1409-1413, (2001). [Retrieved from the Internet May 14, 2013: <URL: http://jn.nutrition.org>].
Takeno et al., "Establishment of an overall transformation system for an oil-producing filamentous fungus, Mortierella alpina 1S-4," Appl Microbiol Biotechnol, 65:419-425, (2004).
Talbot et al., "Formulation and Production of Confectionery Fats," OFI Middle East 2007 Conference and Exhibition, 378 pages, (2007).
Talebi et al., "Genetic manipulation, a feasible tool to enhance unique characteristic of Chlarella vulgaris as a feedstock for biodiesel production," Mol Biol Rep, 40:4421-4428, (2013).
Tan et al., "Establishment of a Micro-Particle Bombardment Transformation System for Dunaliella Salina," J Microbiol.;43(4):361-365, (2005).
Tan et al., "Fatty acid production by heterotrophic Chlorella saccharophila," Hydrobiologia, 215:13-19, (1991).
Tang et al., "Insertion mutagenesis of Chlamydomonas reinhardtii by electroporation and heterologous DNA," Biochem Mol Biol Int, 36(5):1025-1035, (1995).
Tomasinsig et al., "The Cathelicidins—Structure, Function and Evolution," Current Protein and Peptide Science, 6: 23-34, (2005).
Tornabene et al., "Lipid composition of the nitrogen starved green alga Neochloris oleoabundans," Enzyme Microb. Technol., 5:435-440, (1983).
U.S. Appl. No. 12/131,766, Advisory Action dated Oct. 13, 2011.
U.S. Appl. No. 12/131,766, Non-Final Office Action dated Aug. 1, 2011.
U.S. Appl. No. 12/131,766, Non-Final Office Action dated Nov. 23, 2010.
U.S. Appl. No. 12/131,766, Non-Final Office Action dated Dec. 10, 2009.
U.S. Appl. No. 12/131,766, Requirement for Restriction/Election dated Aug. 5, 2009.
U.S. Appl. No. 12/131,766, Requirement for Restriction/Election dated Aug. 17, 2010.
U.S. Appl. No. 12/131,773, Advisory Action dated Jan. 27, 2014.
U.S. Appl. No. 12/131,773, Final Office Action dated Mar. 21, 2011.
U.S. Appl. No. 12/131,773, Final Office Action dated Oct. 15, 2013.
U.S. Appl. No. 12/131,773, Non-Final Office Action dated Jun. 5, 2013.
U.S. Appl. No. 12/131,773, Non-Final Office Action dated Jun. 25, 2010.
U.S. Appl. No. 12/131,773, Non-Final Office Action dated Dec. 15, 2009.
U.S. Appl. No. 12/131,773, Notice of Allowance and Examiner Initiated Interview Summary dated Apr. 1, 2014.
U.S. Appl. No. 12/131,773, Requirement for Restriction/Election dated Aug. 6, 2009.
U.S. Appl. No. 12/131,783, Final Office Action dated Jan. 12, 2012.
U.S. Appl. No. 12/131,783, Final Office Action dated Dec. 13, 2013.
U.S. Appl. No. 12/131,783, Non-Final Office Action dated Jun. 6, 2011.
U.S. Appl. No. 12/131,783, Non-Final Office Action dated Jul. 18, 2013.
U.S. Appl. No. 12/131,783, Notice of Allowance and Examiner Initiated Interview Summary dated Mar. 24, 2014.
U.S. Appl. No. 12/131,783, Requirement for Restriction/Election dated Apr. 19, 2011.
U.S. Appl. No. 12/131,793, Final Office Action dated Mar. 30, 2010.
U.S. Appl. No. 12/131,793, Non-Final Office Action dated Jun. 21, 2012.
U.S. Appl. No. 12/131,793, Non-Final Office Action dated Sep. 16, 2009.
U.S. Appl. No. 12/131,793, Non-Final Office Action dated Nov. 13, 2012.
U.S. Appl. No. 12/131,793, Notice of Allowance dated Apr. 3, 2013.
U.S. Appl. No. 12/131,793, Requirement for Restriction/Election dated Aug. 6, 2009.
U.S. Appl. No. 12/131,804, Final Office Action dated Feb. 2, 2011.
U.S. Appl. No. 12/131,804, Non-Final Office Action dated Oct. 26, 2012.
U.S. Appl. No. 12/131,804, Non-Final Office Action dated Mar. 3, 2010.
U.S. Appl. No. 12/131,804, Non-Final Office Action dated Jun. 7, 2012.
U.S. Appl. No. 12/131,804, Requirement for Restriction/Election dated Sep. 17, 2009.
U.S. Appl. No. 12/131,804, Requirement for Restriction/Election dated Nov. 18, 2009.
U.S. Appl. No. 12/194,389, Final Office Action dated Jan. 5, 2011.
U.S. Appl. No. 12/194,389, Non-Final Office Action dated Feb. 4, 2010.
U.S. Appl. No. 12/194,389, Notice of Allowance dated Jan. 15, 2014.
U.S. Appl. No. 12/194,389, Requirement for Restriction/Election dated Oct. 5, 2010.
U.S. Appl. No. 12/194,389, Requirement for Restriction/Election dated Nov. 2, 2009.
U.S. Appl. No. 12/628,140, Final Office Action dated Mar. 15, 2013.
U.S. Appl. No. 12/628,140, Final Office Action dated May 22, 2014.
U.S. Appl. No. 12/628,140, Final Office Action dated Sep. 12, 2013.
U.S. Appl. No. 12/628,140, Final Office Action dated Oct. 8, 2014.
U.S. Appl. No. 12/628,140, Non-Final Office Action dated Jul. 17, 2015.
U.S. Appl. No. 12/628,140, Non-Final Office Action dated Oct. 30, 2012.
U.S. Appl. No. 12/628,144, Final Office Action dated Nov. 16, 2010.
U.S. Appl. No. 12/628,144, Final Office Action dated Dec. 5, 2011.
U.S. Appl. No. 12/628,144, Final Office Action dated Dec. 12, 2014.
U.S. Appl. No. 12/628,144, Non-Final Office Action dated May 16, 2014.
U.S. Appl. No. 12/628,144, Non-Final Office Action dated Jun. 7, 2011.
U.S. Appl. No. 12/628,144, Non-Final Office Action dated Jul. 8, 2010.
U.S. Appl. No. 12/628,144, Requirement for Restriction/Election and Examiner Initiated Interiew Summary dated Oct. 7, 2014.
U.S. Appl. No. 12/628,147, Examiner Interview Summary Record dated Mar. 3, 2011.
U.S. Appl. No. 12/628,147, Final Office Action dated Jul. 12, 2012.
U.S. Appl. No. 12/628,147, Final Office Action dated Oct. 1, 2010.
U.S. Appl. No. 12/628,147, Non-Final Office Action dated May 25, 2010.
U.S. Appl. No. 12/628,147, Non-Final Office Action dated Oct. 25, 2011.
U.S. Appl. No. 12/628,147, Notice of Allowance and Examiner Initiated Interview Summary dated Aug. 7, 2012.
U.S. Appl. No. 12/628,149, Non-Final Office Action dated Jun. 25, 2010.
U.S. Appl. No. 12/628,149, Non-Final Office Action dated Sep. 16, 2010.
U.S. Appl. No. 12/628,149, Notice of Allowance dated Dec. 15, 2010.
U.S. Appl. No. 12/628,150, Non-Final Office Action dated Apr. 29, 2010.
U.S. Appl. No. 12/628,150, Non-Final Office Action dated Oct. 13, 2010.
U.S. Appl. No. 12/628,150, Notice of Allowance dated Mar. 21, 2011.
U.S. Appl. No. 12/772,163, Non-Final Office Action dated May 25, 2012.
U.S. Appl. No. 12/772,163, Non-Final Office Action dated Dec. 12, 2012.
U.S. Appl. No. 12/772,163, Notice of Allowance dated May 28, 2013.

(56) References Cited

OTHER PUBLICATIONS

U.S. Appl. No. 12/772,163, Requirement for Restriction/Election dated Jun. 24, 2011.
U.S. Appl. No. 12/772,164, Final Office Action dated May 24, 2012.
U.S. Appl. No. 12/772,164, Non-Final Office Action dated Oct. 12, 2011.
U.S. Appl. No. 12/772,164, Requirement for Restriction/Election dated Jul. 20, 2011.
U.S. Appl. No. 12/772,170, Final Office Action dated Feb. 21, 2012.
U.S. Appl. No. 12/772,170, Non-Final Office Action dated Sep. 13, 2011.
U.S. Appl. No. 12/772,170, Non-Final Office Action dated Dec. 17, 2013.
U.S. Appl. No. 12/772,170, Notice of Allowance and Examiner-Initiated Interview Summary dated Jul. 11, 2014.
U.S. Appl. No. 12/772,170, Requirement for Restriction/Election dated Jul. 13, 2011.
U.S. Appl. No. 12/772,173, Final Office Action dated May 7, 2012.
U.S. Appl. No. 12/772,173, Non-Final Office Action dated Dec. 16, 2011.
U.S. Appl. No. 12/772,173, Notice of Allowance dated Mar. 29, 2013.
U.S. Appl. No. 12/772,173, Notice of Allowance dated Jul. 10, 2013.
U.S. Appl. No. 12/772,173, Requirement for Restriction/Election dated Oct. 26, 2011.
U.S. Appl. No. 12/772,174, Non-Final Office Action dated Nov. 29, 2011.
U.S. Appl. No. 12/772,174, Requirement for Restriction/Election dated Aug. 10, 2011.
U.S. Appl. No. 12/960,388, Notice of Allowance dated May 28, 2013.
U.S. Appl. No. 12/960,388, Requirement for Restriction/Election dated Apr. 1, 2013.
U.S. Appl. No. 12/981,409, Non-Final Office Action dated Jan. 6, 2012.
U.S. Appl. No. 12/981,409, Notice of Allowance dated May 29, 2012.
U.S. Appl. No. 12/981,409, Requirement for Restriction/Election dated Apr. 19, 2012.
U.S. Appl. No. 12/981,409, Requirement for Restriction/Election dated Oct. 28, 2011.
U.S. Appl. No. 13/029,061, Requirement for Restriction/Election dated Nov. 29, 2011.
U.S. Appl. No. 13/045,500, Non-Final Office Action dated Mar. 9, 2012.
U.S. Appl. No. 13/045,500, Non-Final Office Action dated Jun. 5, 2014.
U.S. Appl. No. 13/045,500, Final Office Action dated Sep. 26, 2012.
U.S. Appl. No. 13/073,757, Non-Final Office Action dated Aug. 15, 2011.
U.S. Appl. No. 13/073,757, Non-Final Office Action dated Dec. 29, 2011.
U.S. Appl. No. 13/073,757, Notice of Allowance dated Apr. 17, 2012.
U.S. Appl. No. 13/087,311, Final Office Action dated Dec. 16, 2013.
U.S. Appl. No. 13/087,311, Non-Final Office Action dated Apr. 23, 2013.
U.S. Appl. No. 13/087,311, Non-Final Office Action dated Jun. 24, 2014.
U.S. Appl. No. 13/118,365, Final Office Action dated Jul. 22, 2013.
U.S. Appl. No. 13/118,365, Non-Final Office Action dated Feb. 11, 2013.
U.S. Appl. No. 13/118,365, Requirement for Restriction/Election dated Oct. 11, 2012.
U.S. Appl. No. 13/273,179, Non-Final Office Action dated Jan. 28, 2014.
U.S. Appl. No. 13/273,179, Notice of Allowance dated Jul. 11, 2014.
U.S. Appl. No. 13/273,179, Requirement for Restriction/Election dated Nov. 14, 2013.
U.S. Appl. No. 13/288,815, Final Office Action dated Oct. 22, 2014.
U.S. Appl. No. 13/288,815, Non-Final Office Action dated Jun. 18, 2014.
U.S. Appl. No. 13/288,815, Notice of Allowance dated Feb. 26, 2015.
U.S. Appl. No. 13/288,815, Requirement for Restriction/Election dated Jan. 30, 2014.
U.S. Appl. No. 13/365,253, Requirement for Restriction/Election dated Dec. 16, 2014.
U.S. Appl. No. 13/406,417, Non-Final Office Action dated Nov. 5, 2012.
U.S. Appl. No. 13/406,417, Requirement for Restriction/Election dated Apr. 30, 2012.
U.S. Appl. No. 13/464,948, Final Office Action dated Feb. 13, 2014.
U.S. Appl. No. 13/464,948, Non-Final Office Action dated Oct. 9, 2013.
U.S. Appl. No. 13/464,948, Notice of Allowance dated May 25, 2014.
U.S. Appl. No. 13/464,948, Requirement for Restriction/Election dated Aug. 21, 2013.
U.S. Appl. No. 13/479,194, Non-Final Office Action dated Mar. 26, 2014.
U.S. Appl. No. 13/479,200, Non-Final Office Action dated Apr. 10, 2013.
U.S. Appl. No. 13/479,200, Non-Final Office Action dated Sep. 9, 2013.
U.S. Appl. No. 13/479,200, Notice of Allowance dated Nov. 25, 2013.
U.S. Appl. No. 13/479,200, Requirement for Restriction/Election dated Jan. 15, 2013.
U.S. Appl. No. 13/527,480, Final Office Action dated Jan. 16, 2014.
U.S. Appl. No. 13/527,480, Non-Final Office Action dated Jun. 26, 2013.
U.S. Appl. No. 13/527,480, Requirement for Restriction/Election dated May 3, 2013.
U.S. Appl. No. 13/543,666, Non-Final Office Action dated Sep. 5, 2013.
U.S. Appl. No. 13/543,666, Notice of Allowance dated Feb. 10, 2014.
U.S. Appl. No. 13/543,666, Requirement for Restriction/Election dated Jan. 3, 2013.
U.S. Appl. No. 13/547,457, Final Office Action dated Mar. 20, 2014.
U.S. Appl. No. 13/547,457, Non-Final Office Action dated Jul. 8, 2013.
U.S. Appl. No. 13/547,457, Notice of Allowance and Examiner-Initiated Interview Summary dated May 29, 2014.
U.S. Appl. No. 13/550,412, Non-Final Office Action dated Oct. 29, 2012.
U.S. Appl. No. 13/550,412, Notice of Allowance dated Feb. 21, 2013.
U.S. Appl. No. 13/555,009, Notice of Allowance dated Jan. 9, 2015.
U.S. Appl. No. 13/555,009, Requirement for Restriction/Election dated Jun. 16, 2014.
U.S. Appl. No. 13/558,252, Final Office Action dated Jul. 9, 2013.
U.S. Appl. No. 13/558,252, Non-Final Office Action dated Jan. 18, 2013.
U.S. Appl. No. 13/558,252, Notice of Allowance dated Oct. 23, 2013.
U.S. Appl. No. 13/601,928, Non-Final Office Action dated Jan. 31, 2013.
U.S. Appl. No. 13/601,928, Notice of Allowance dated Feb. 26, 2013.
U.S. Appl. No. 13/621,722, Requirement for Restriction/Election dated Jan. 31, 2013.
U.S. Appl. No. 13/621,722, Final Office Action dated Oct. 25, 2013.
U.S. Appl. No. 13/621,722, Non-Final Office Action dated May 9, 2013.
U.S. Appl. No. 13/621,722, Notice of Allowance and Examiner Initiated Interview Summary dated Jan. 10, 2014.
U.S. Appl. No. 13/628,039, Non-Final Office Action dated Jun. 4, 2013.

(56) References Cited

OTHER PUBLICATIONS

U.S. Appl. No. 13/628,039, Notice of Allowance and Examiner-Initiated Interview Summary dated Feb. 20, 2014.
U.S. Appl. No. 13/628,039, Requirement for Restriction/Election dated Mar. 7, 2013.
U.S. Appl. No. 13/630,757, Non-Final Office Action dated Apr. 23, 2015.
U.S. Appl. No. 13/630,757, Non-Final Office Action dated Oct. 27, 2014.
U.S. Appl. No. 13/630,757, Requirement for Restriction/Election dated Jun. 12, 2014.
U.S. Appl. No. 13/650,018, Non-Final Office Action dated Dec. 23, 2013.
U.S. Appl. No. 13/650,018, Notice of Allowance dated Apr. 1, 2015.
U.S. Appl. No. 13/650,018, Notice of Allowance dated Apr. 10, 2015.
U.S. Appl. No. 13/650,018, Notice of Allowance dated Aug. 14, 2014.
U.S. Appl. No. 13/650,018, Requirement for Restriction/Election dated Aug. 22, 2013.
U.S. Appl. No. 13/650,024, Non-Final Office Action dated Jul. 2, 2013.
U.S. Appl. No. 13/650,024, Notice of Allowance dated Oct. 17, 2013.
U.S. Appl. No. 13/804,185, Non-Final Office Action dated Jun. 1, 2015.
U.S. Appl. No. 13/804,185, Requirement for Restriction/Election dated Mar. 16, 2015.
U.S. Appl. No. 13/849,330, Requirement for Restriction/Election dated Jan. 21, 2015.
U.S. Appl. No. 13/852,116, Final Office Action dated Aug. 18, 2014.
U.S. Appl. No. 13/852,116, Non-Final Office Action dated Mar. 26, 2014.
U.S. Appl. No. 13/852,116, Notice of Allowance dated Nov. 7, 2014.
U.S. Appl. No. 13/865,974, Non-Final Office Action dated May 2, 2014.
U.S. Appl. No. 13/865,974, Notice of Allowance dated Oct. 22, 2014.
U.S. Appl. No. 13/865,974, Requirement for Restriction/Election dated Jan. 29, 2014.
U.S. Appl. No. 13/889,214, Non-Final Office Action dated Sep. 18, 2013.
U.S. Appl. No. 13/889,214, Notice of Allowance dated Apr. 28, 2014.
U.S. Appl. No. 13/889,221, Non-Final Office Action dated Sep. 6, 2013.
U.S. Appl. No. 13/889,221, Notice of Allowance dated Apr. 24, 2014.
U.S. Appl. No. 13/941,342, Notice of Allowance dated Jul. 24, 2015.
U.S. Appl. No. 13/941,342, Requirement for Restriction/Election dated Apr. 13, 2015.
U.S. Appl. No. 13/941,346, Final Office Action dated Jun. 26, 2014.
U.S. Appl. No. 13/941,346, Non-Final Office Action dated Jan. 21, 2014.
U.S. Appl. No. 13/941,346, Non-Final Office Action dated Nov. 3, 2014.
U.S. Appl. No. 13/941,346, Notice of Allowance dated Feb. 23, 2015.
U.S. Appl. No. 13/941,353, Requirement for Restriction/Election dated Jan. 16, 2014.
U.S. Appl. No. 13/941,357, Final Office Action dated Nov. 6, 2014.
U.S. Appl. No. 13/941,357, Non-Final Office Action dated Jun. 3, 2014.
U.S. Appl. No. 13/941,357, Notice of Allowance dated Mar. 30, 2015.
U.S. Appl. No. 13/941,357, Requirement for Restriction/Election dated Jan. 7, 2014.
U.S. Appl. No. 14/184,288, Non-Final Office Action dated Sep. 11, 2015.
U.S. Appl. No. 14/184,288, Requirement for Restriction/Election dated Jun. 9, 2015.
U.S. Appl. No. 14/262,070, Non-Final Office Action dated Jul. 10, 2015.
U.S. Appl. No. 14/276,943, Requirement for Restriction/Election dated Jun. 4, 2015.
U.S. Appl. No. 14/285,354, Requirement for Restriction/Election dated Jul. 20, 2015.
U.S. Appl. No. 14/474,244, Final Office Action dated Jul. 30, 2015.
U.S. Appl. No. 14/474,244, Non-Final Office Action dated Apr. 24, 2015.
Ueno et al., "Optimization of heterotrophic culture conditions for n-alkane utilization and phylogenetic position based on the 18S rDNA sequence of a thermotolerant Prototheca zopfii strain," J Biosci Bioeng, 94(2):160-165, (2002). Abstract. [Retrieved from the Internet Dec. 1,.2014: <URL: http://www.ncbi.nlm.nih.gov/pubmed/16233286>].
Urano, et al., "Effect of Osmotic Stabilizers on Protoplast Generation of Chlorella ellipsoidea Yellow/White Color Mutants," Journal of Bioscience and Bioengineering, 90(5):567-569, (2000).
Van Etten et al., "Giant viruses infecting algae," Annu Rev Microbiol, 53:447-494, (1999).
Vazquez-Bermudez et al., "Carbon Supply and 2-Oxoglutarate Effects on Expression of Nitrate Reductase and Nitrogen-Regulated Genes in *Synechococcus* sp. strain PCC 7942," FEMS Microbiology Letters, 221(2):155-159, (2003).
Vazquez-Bermudez et al., "Uptake of 2-Oxoglutarat in Synechococcus Strains Transformed with the *Escherichia coli* kgtP Gene," Journal of Bacteriology, 182(1):211-215, (2000).
Voelker et al., "Alteration of the Specificity and Regulation of Fatty Acid Synthesis of *Escherichia coli* by Expression of a Plant Medium Chain Acyl-Acyl Carrier Protein Thioesterase," Journal of Bacteriology, 176(23):7320-7327, (1994).
Voelker et al., "Broad-Range and Binary-Range Acyl-Acyl-Carrier-Protein Thioesterases Suggest an Alternative Mechanism for Medium-Chain Production in Seeds," Plant Physiol., 114:669-677, (1997).
Voetz et al., "Three Different cDNAs Encoding Acyl Carrier Proteins from Cuphea lanceolata'," Plant Physiol., 106:785-786, (1994).
Volkman et al., "Sterols in microorganisms," Appl Microbial Biotechnol, 60:495-506, (2003).
Walker et al., "Characrization of the Dunaliella tertiolecta RbcS Genes and Their Promoter Activity in Chlamydomonates reinhardtii," Plant Cell Rep, 23(10-11):727-735, (2005).
Wang et al., "Rapid isolation and functional analysis of promoter sequences of the nitrate reductase gene from Chlorella ellipsoidea," J. Appl. Phycol., 16:11-16, (2004).
Warner et al., "Analysis of Tocopherols and Phytosterols in Vegetable Oils by HPLC with Evaporative Light-Scattering Detection," JAOCS, 67(11):827-831 (1990).
Westphal, et al., "Vipp1 Deletion Mutant of Synechocystis: A Connection Between Bacterial Phage Shock and Thylakoid Biogenesis," Proc Natl Acad Sci U S A., 98(7):4243-4248, (2001).
Whisstock et al., "Prediction of protein function from protein sequence and structure," Quarterly Reviews of Biophysics, 36(3):307-340, (2003).
Wiberg et al., "The distribution of caprylate, caprate and laurate in lipids from developing and mature seeds of transgenic *Brassica napus* L.," Planta, 212:33-40, (2000).
Wirth et al., "Transforamtion of Various Species of Gram-Negitive Bacteria Belonging to 11 Difference Genera by Electroporation," Mol Gen Genet.; 216(1):175-177, (1989).
Wishart et al., "A Single Mutation Converts a Novel Phosphotyrosine Binding Domain into a Dual-specificity Phosphatase," The Journal of Biological Chemistry, 270(45):26782-26785, (1995).
Witkowski et al., "Conversion of a β-Ketoacyl Synthase to a Malonyl Decarboxylase by Replacement of the Active-Site Cysteine with Glutame," Biochemistry, 38:11643-11650, (1999).
Wolk et al., "Construction of Shuttle Vectors Capable of Conjugative Transfer From *Escherichia coli* to Nitrogen-Fixing Filamentous Cyanobacteria," Proc Natl Acad Sci U S A., 81(5):1561-1565, (1984).

(56) References Cited

OTHER PUBLICATIONS

Wong et al., "*Arabidopsis thaliana* small subunit leader and transit peptide enhance the expression of Bacillus thuringiensis proteins in transgenic plants," Plant Mol Biol, 20(1):81-93, (1992).
Wu et al., "A Comparative Study of Gases Generated from Simulant Thermal Degradation of Autotrophic and Heterotrophic Chlorella," Progress in Natural Science, 2(4):311-318, (1992).
Wu et al., "Comparative study on Liposoluble Compounds in Autotrophic and Heterotrophic Chlorella Protothecoides," Acta Botanica Sinica, 35(11):849-858, (1992).
Wu et al., "New Discoveries in Study on Hydrocarbons From Thermal Degradation of Heterotrophically Yellowing Algae," Science in China, 37(3):326-35, (1994).
Xiong et al., "High-density fermentation of microalga Chlorella protothecoides in bioreactor for microbio-diesel production," Appl. Microbiol. Biotechnol., 78:29-36, (2008).
Yamada et al., "Alternative expression of a chitosanase gene produces two different proteins in cells infected with Chlorella virus CVK2," Virology, 230(2):361-368, (1997).
Yamada et al., "Chlorella viruses," Adv Virus Res, 66:293-336, (2006).
Yu et al., "Modifications of the metabolic pathways of lipid and tracylglycerol production in microalgae," Microbial Cell Factories, 10:91, (2011). [Retrieved from the Internet Jul. 24, 2012: <URL: http://www.microbialcellfactories.com/content/10/1/91>].
Yuan et al., "Modification of the substate specificity of an acyl-acyl carrier protein thioesterase by protein engineering," Proc. NatL Acad. Sci. USA, Biochemistry, 92:10639-10643, (1995).
Yaidul et al., "Supercritical carbon dioxide (SC-0O2) extraction and fractionation of palm kernel oil from palm kernel as cocoa butter replacers blend," Journal of Food Engineering, 73:210-216, (2006).
Zhang et al., "Malic enzyme: the controlling activity for lipid production? Overexpression of malic enzyme in Mucor circinelloides leads to a 2.5-fold increase in lipid accumulation," Microbiology, 153(7):2013-2025, (2007).
Zhang et al., Geneseq Database, Accession No. AED66345, CN1618976, May 25, 2005.
Zhao et al., "Medium optimization for lipid production through co-fermentation of glucose and xylose by the oleaginous yeast Lipomyces starkeyi," Eur. J. Lipid Sci. Technol., 110:405-412, (2008).
Zurawski et al., "Nucleotide sequence of the gene for the Mr 32,000 thylakoid membrane protein from Spinacia oleracea and Nicotiana debneyi predicts a totally conserved primary translation product of Mr 38,950," Proc Natl Acad Sci, 79(24):7699-7703, (1982).
U.S. Appl. No. 15/173,335, Final Office Action dated Apr. 9, 2018.
U.S. Appl. No. 15/173,335, Notice of Allowance dated Jul. 26, 2018.
U.S. Appl. No. 15/443,209, Requirement for Restriction/Election dated Jul. 3, 2018.
U.S. Appl. No. 14/819,117, Notice of Allowance dated Jan. 16, 2018.
U.S. Appl. No. 14/819,117, Notice of Allowance dated Feb. 9, 2018.
U.S. Appl. No. 15/179,253, Non-Final Rejection dated Feb. 14, 2018.
U.S. Appl. No. 15/179,253, Notice of Allowance dated Aug. 10, 2018.
U.S. Appl. No. 14/974,983, Notice of Allowance dated Jun. 8, 2018.
U.S. Appl. No. 14/974,983, Corrected Notice of Allowability dated Jun. 20, 2018.
U.S. Appl. No. 15/875,984, Non-Final Office Action dated Aug. 27, 2018.
U.S. Appl. No. 14/506,491, Notice of Allowance dated Apr. 9, 2018.
U.S. Appl. No. 14/796,406, Requirement for Restriction/Election dated Oct. 5, 2016.
U.S. Appl. No. 14/796,406, Non-Final Office Action dated Jan. 25, 2017.
U.S. Appl. No. 14/796,406, Notice of Allowance dated Jun. 15, 2017.
U.S. Appl. No. 14/796,406, Notice of Allowance dated Oct. 3, 2017.
U.S. Appl. No. 14/796,406, Notice of Allowance dated Jan. 11, 2018.
U.S. Appl. No. 15/092,538, Non-Final Office Action dated Jan. 8, 2018.
U.S. Appl. No. 15/092,538, Final Office Action dated Jul. 25, 2018.
First Examination Report, dated Nov. 23, 2017, issued in Inidina Patent Aplication No. 4960-DELNP-2011.
Japanese Office Action [no translation] dated Oct. 27, 2017 issued in Application No. JP 2017-015080.
Japanese Office Action [no translation] dated Jul. 4, 2018 issued in Application No. JP 2017-015080.
Korean Office Action dated Nov. 15, 2017 issued in Application No. KR 10-2017-7021034, with English translation.
Korean Office Action dated Jan. 4, 2018, issued in Application No. KR 10-2017-7026170.
Japanese Office Action dated Dec. 19, 2017 issued in Application No. JP 2017-48186, in Japanese Only.
Canadian Notice of Allowance dated Apr. 27, 2018, issued in Application No. CA 2,816,125.
Chinese Decision on the Reexamination dated Mar. 2, 2018 issued in Application No. CN 201180053258.2.
Japanese Office Action dated Dec. 14, 2017 issued in Application No. JP 2016-009933.
Mexican Notice of Allowance dated Dec. 13, 2017 issued in Application No. MX/a/2013/004631.
Australian Patent Examination Report No. 1 dated Oct. 19, 2017, issued in Application No. AU 2016247159.
Australian Patent Examination Report No. 2 dated Jun. 1, 2018, issued in Application No. AU 2016247159.
Korean Office action [with English translation] dated Jun. 18, 2018 issued in Application No. KR 10-2013-7023181.
Mexican First Office Action dated May 14, 2018 issued in Application No. MX/a/2017/072309, with English Translation.
First Office Action, Substantice Examination Report—Stage I, for Indomesian Patent Application No. W00201302051, dated Apr. 5, 2018, with English translation.
Japanese Office Action dated Jun. 13, 2018, for Japanese Patent Application No. 2016-009933.
Second Office Action for Malaysian Patent Application No. PI 2013001587, dated Jun. 14, 2018.
Notice to File a Response for Korean Patent Application No. 10-2013-7013979, dated Jun. 18, 2018.
Second Office Action for EPO Application No. 11 785 851.4, dated Jun. 28, 2018.
First Office Action for Indian Patent Application No. 4315/DELNP/2013, dated Jul. 31, 2018.
First Communication from the examining division, dated Dec. 7, 2017 issued in European Patent Application No. 15747630.0.
Second Communication from the examining division, dated Jul. 27, 2018 issued in European Patent Application No. 15747630.0.
Geneseq: Database Accession No. AWK61076, "Nucleotide sequence SEQ ID 134280," retrieved from EBI accession No. GSB:AWK61076, Oct. 29, 2009.
Geneseq: Database Accession No. BAN54762, "Plasmid pSZ1491 DNA contract, SEQ ID 232," retrieved from EBI accession No. GSB:BAN54762, Jun. 20, 2013.
Liu et al., (2013) "Lipid metabolism in microalgae distinguishes itself," *Current Opinion in Biotechnology*, 24:300-309.
Wang et al., (Jun. 1998) Principle and Technology of Plant Genetic Engineering, Beijing: Science Press, pp. 34-35 [19pp].

\* cited by examiner

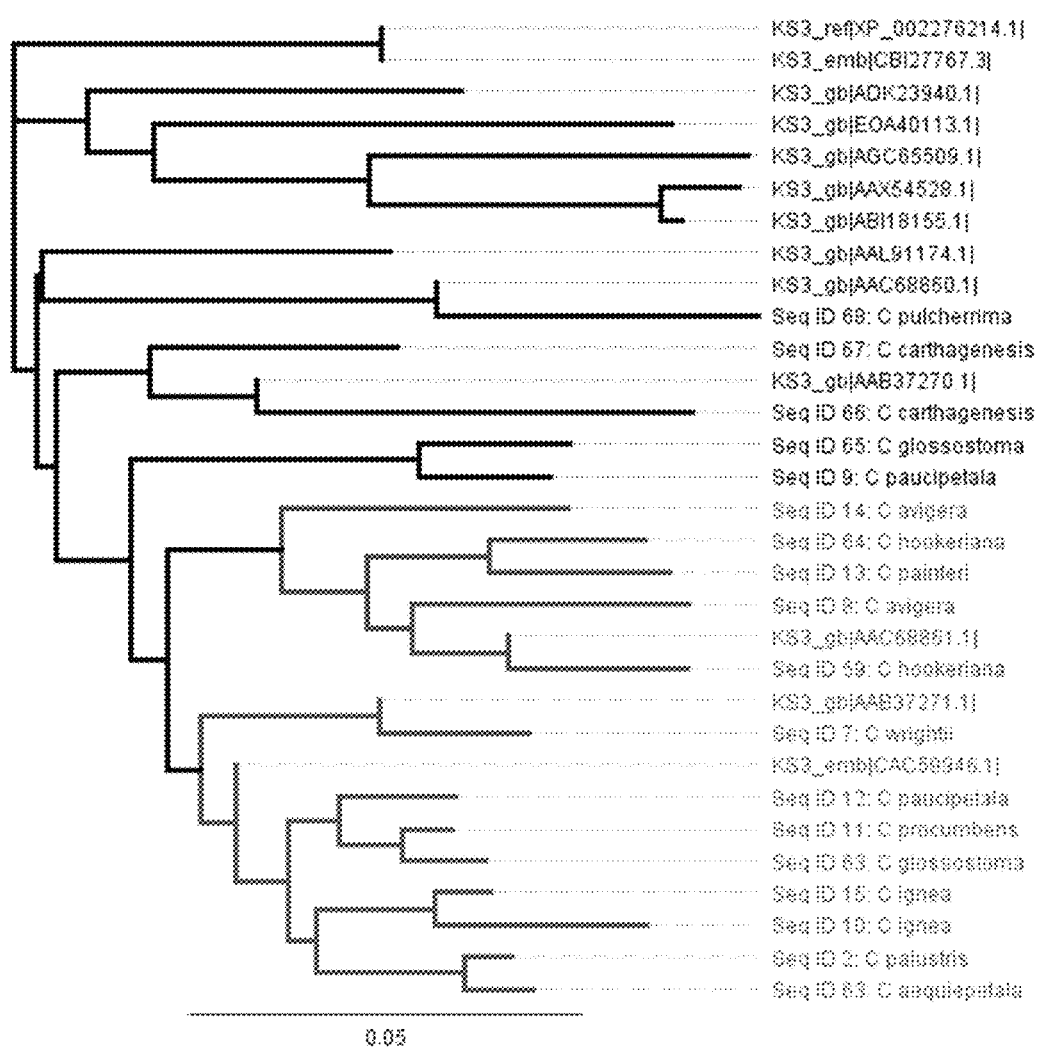

SEQUENCE LISTING

<160> NUMBER OF SEQ ID NOS: 72

<210> SEQ ID NO 1
<211> LENGTH: 411
<212> TYPE: PRT
<213> ORGANISM: Cuphea palustris
<220> FEATURE:
<221> NAME/KEY: MISC_FEATURE
<223> OTHER INFORMATION: FATB2

<400> SEQUENCE: 1

Met Val Ala Ala Ala Ser Ala Ala Phe Phe Ser Val Ala Thr Pro
1               5                   10                  15

Arg Thr Asn Ile Ser Pro Ser Ser Leu Ser Val Pro Phe Lys Pro Lys
            20                  25                  30

Ser Asn His Asn Gly Gly Phe Gln Val Lys Ala Asn Ala Ser Ala His
        35                  40                  45

Pro Lys Ala Asn Gly Ser Ala Val Ser Leu Lys Ser Gly Ser Leu Glu
    50                  55                  60

Thr Gln Glu Asp Lys Thr Ser Ser Ser Pro Pro Arg Thr Phe
65                  70                  75                  80

Ile Asn Gln Leu Pro Val Trp Ser Met Leu Leu Ser Ala Val Thr Thr
                85                  90                  95

Val Phe Gly Val Ala Glu Lys Gln Trp Pro Met Leu Asp Arg Lys Ser
            100                 105                 110

Lys Arg Pro Asp Met Leu Val Glu Pro Leu Gly Val Asp Arg Ile Val
        115                 120                 125

Tyr Asp Gly Val Ser Phe Arg Gln Ser Phe Ser Ile Arg Ser Tyr Glu
    130                 135                 140

Ile Gly Ala Asp Arg Thr Ala Ser Ile Glu Thr Leu Met Asn Met Phe
145                 150                 155                 160

Gln Glu Thr Ser Leu Asn His Cys Lys Ile Ile Gly Leu Leu Asn Asp
                165                 170                 175

Gly Phe Gly Arg Thr Pro Glu Met Cys Lys Arg Asp Leu Ile Trp Val
            180                 185                 190

Val Thr Lys Met Gln Ile Glu Val Asn Arg Tyr Pro Thr Trp Gly Asp
        195                 200                 205

Thr Ile Glu Val Asn Thr Trp Val Ser Ala Ser Gly Lys His Gly Met
    210                 215                 220

Gly Arg Asp Trp Leu Ile Ser Asp Cys His Thr Gly Glu Ile Leu Ile
225                 230                 235                 240

```
Arg Ala Thr Ser Val Trp Ala Met Met Asn Gln Lys Thr Arg Arg Leu
                245                 250                 255

Ser Lys Ile Pro Tyr Glu Val Arg Gln Glu Ile Glu Pro Gln Phe Val
            260                 265                 270

Asp Ser Ala Pro Val Ile Val Asp Arg Lys Phe His Lys Leu Asp
            275                 280                 285

Leu Lys Thr Gly Asp Ser Ile Cys Asn Gly Leu Thr Pro Arg Trp Thr
            290                 295                 300

Asp Leu Asp Val Asn Gln His Val Asn Asn Val Lys Tyr Ile Gly Trp
305                 310                 315                 320

Ile Leu Gln Ser Val Pro Thr Glu Val Phe Glu Thr Gln Glu Leu Cys
                325                 330                 335

Gly Leu Thr Leu Glu Tyr Arg Arg Glu Cys Gly Arg Asp Ser Val Leu
                340                 345                 350

Glu Ser Val Thr Ala Met Asp Pro Ser Lys Glu Gly Asp Arg Ser Leu
                355                 360                 365

Tyr Gln His Leu Leu Arg Leu Glu Asp Gly Ala Asp Ile Val Lys Gly
                370                 375                 380

Arg Thr Glu Trp Arg Pro Lys Asn Ala Gly Ala Lys Gly Ala Ile Leu
385                 390                 395                 400

Thr Gly Lys Thr Ser Asn Gly Asn Ser Ile Ser
                405                 410

<210> SEQ ID NO 2
<211> LENGTH: 525
<212> TYPE: PRT
<213> ORGANISM: Cuphea palustris
<220> FEATURE:
<221> NAME/KEY: MISC_FEATURE
<223> OTHER INFORMATION: KASIV

<400> SEQUENCE: 2

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Leu Val Thr Ser Tyr Ile Asp Pro Cys
        35                  40                  45

Asn Gln Phe Ser Ser Ser Ala Ser Leu Ser Phe Leu Gly Asp Asn Gly
    50                  55                  60

Phe Ala Ser Leu Phe Gly Ser Lys Pro Phe Arg Ser Asn Arg Gly His
65                  70                  75                  80

Arg Arg Leu Gly Arg Ala Ser His Ser Gly Glu Ala Met Ala Val Ala
                85                  90                  95

Leu Glu Pro Ala Gln Glu Val Ala Thr Lys Lys Lys Pro Leu Val Lys
            100                 105                 110

Gln Arg Arg Val Val Val Thr Gly Met Gly Val Thr Pro Leu Gly
        115                 120                 125

His Glu Pro Asp Val Tyr Tyr Asn Asn Leu Leu Asp Gly Val Ser Gly
    130                 135                 140

Ile Ser Glu Ile Glu Ala Phe Asp Cys Thr Gln Phe Pro Thr Arg Ile
145                 150                 155                 160

Ala Gly Glu Ile Lys Ser Phe Ser Thr Asp Gly Trp Val Ala Pro Lys
                165                 170                 175

Leu Ser Lys Arg Met Asp Lys Phe Met Leu Tyr Leu Leu Thr Ala Gly
            180                 185                 190
```

```
Lys Lys Ala Leu Ala Asp Gly Gly Ile Thr Asp Val Met Lys Glu
            195                 200                 205

Leu Asp Lys Arg Lys Cys Gly Val Leu Ile Gly Ser Gly Leu Gly
    210                 215                 220

Met Lys Leu Phe Ser Asp Ser Ile Glu Ala Leu Arg Ile Ser Tyr Lys
225                 230                 235                 240

Lys Met Asn Pro Phe Cys Val Pro Phe Ala Thr Thr Asn Met Gly Ser
                245                 250                 255

Ala Met Leu Ala Met Asp Leu Gly Trp Met Gly Pro Asn Tyr Ser Ile
            260                 265                 270

Ser Thr Ala Cys Ala Thr Ser Asn Phe Cys Ile Leu Asn Ser Ala Asn
        275                 280                 285

His Ile Val Arg Gly Glu Ala Asp Met Met Leu Cys Gly Gly Ser Asp
    290                 295                 300

Ala Val Ile Ile Pro Ile Gly Leu Gly Gly Phe Val Ala Cys Arg Ala
305                 310                 315                 320

Leu Ser Gln Arg Asn Asn Asp Pro Thr Lys Ala Ser Arg Pro Trp Asp
                325                 330                 335

Ser Asn Arg Asp Gly Phe Val Met Gly Glu Gly Ala Gly Val Leu Leu
            340                 345                 350

Leu Glu Glu Leu Glu His Ala Lys Lys Arg Gly Ala Thr Ile Tyr Ala
        355                 360                 365

Glu Phe Leu Gly Gly Ser Phe Thr Cys Asp Ala Tyr His Met Thr Glu
    370                 375                 380

Pro His Pro Glu Gly Ala Gly Val Ile Leu Cys Ile Glu Lys Ala Leu
385                 390                 395                 400

Ala Gln Ala Gly Val Ser Arg Glu Asp Val Asn Tyr Ile Asn Ala His
                405                 410                 415

Ala Thr Ser Thr Pro Ala Gly Asp Ile Lys Glu Tyr Gln Ala Leu Ala
            420                 425                 430

His Cys Phe Gly Gln Asn Ser Glu Leu Arg Val Asn Ser Thr Lys Ser
        435                 440                 445

Met Ile Gly His Leu Ile Gly Ala Ala Gly Gly Val Glu Ala Val Thr
    450                 455                 460

Val Val Gln Ala Ile Arg Thr Gly Trp Ile His Pro Asn Leu Asn Leu
465                 470                 475                 480

Glu Asp Pro Asp Lys Ala Val Asp Ala Lys Val Leu Val Gly Pro Lys
                485                 490                 495

Lys Glu Arg Leu Asn Val Lys Val Gly Leu Ser Asn Ser Phe Gly Phe
            500                 505                 510

Gly Gly His Asn Ser Ser Ile Leu Phe Ala Pro Tyr Asn
        515                 520                 525

<210> SEQ ID NO 3
<211> LENGTH: 492
<212> TYPE: PRT
<213> ORGANISM: Cinnamonum camphora
<220> FEATURE:
<221> NAME/KEY: MISC_FEATURE
<223> OTHER INFORMATION: KASIV

<400> SEQUENCE: 3

Met Ala Met Met Ala Gly Ser Cys Ser Asn Leu Val Ile Gly Asn Arg
1               5                   10                  15

Glu Leu Gly Gly Asn Gly Pro Ser Leu Leu His Tyr Asn Gly Leu Arg
```

-continued

```
                20                  25                  30
Pro Leu Glu Asn Ile Gln Thr Ala Ser Ala Val Lys Lys Pro Asn Gly
            35                  40                  45
Leu Phe Ala Ser Ser Thr Ala Arg Lys Ser Lys Ala Val Arg Ala Met
        50                  55                  60
Val Leu Pro Thr Val Thr Ala Pro Lys Arg Glu Lys Asp Pro Lys Lys
65                  70                  75                  80
Arg Ile Val Ile Thr Gly Met Gly Leu Val Ser Val Phe Gly Asn Asp
                85                  90                  95
Ile Asp Thr Phe Tyr Ser Lys Leu Leu Glu Gly Glu Ser Gly Ile Gly
            100                 105                 110
Pro Ile Asp Arg Phe Asp Ala Ser Ser Phe Ser Val Arg Phe Ala Gly
        115                 120                 125
Gln Ile His Asn Phe Ser Ser Lys Gly Tyr Ile Asp Gly Lys Asn Asp
    130                 135                 140
Arg Arg Leu Asp Asp Cys Trp Arg Tyr Cys Leu Val Ala Gly Arg Arg
145                 150                 155                 160
Ala Leu Glu Asp Ala Asn Leu Gly Pro Glu Val Leu Glu Lys Met Asp
                165                 170                 175
Arg Ser Arg Ile Gly Val Leu Ile Gly Thr Gly Met Gly Gly Leu Ser
            180                 185                 190
Ala Phe Ser Asn Gly Val Glu Ser Leu Ile Gln Lys Gly Tyr Lys Lys
        195                 200                 205
Ile Thr Pro Phe Phe Ile Pro Tyr Ser Ile Thr Asn Met Gly Ser Ala
    210                 215                 220
Leu Leu Ala Ile Asp Thr Gly Val Met Gly Pro Asn Tyr Ser Ile Ser
225                 230                 235                 240
Thr Ala Cys Ala Thr Ala Asn Tyr Cys Phe His Ala Ala Ala Asn His
                245                 250                 255
Ile Arg Arg Gly Glu Ala Glu Ile Met Val Thr Gly Gly Thr Glu Ala
            260                 265                 270
Ala Val Ser Ala Thr Gly Val Gly Gly Phe Ile Ala Cys Arg Ala Leu
        275                 280                 285
Ser His Arg Asn Asp Glu Pro Gln Thr Ala Ser Arg Pro Trp Asp Lys
    290                 295                 300
Asp Arg Asp Gly Phe Val Met Gly Glu Gly Ala Gly Val Leu Val Met
305                 310                 315                 320
Glu Ser Leu His His Ala Arg Lys Arg Gly Ala Asn Ile Ile Ala Glu
                325                 330                 335
Tyr Leu Gly Gly Ala Val Thr Cys Asp Ala His His Met Thr Asp Pro
            340                 345                 350
Arg Ala Asp Gly Leu Gly Val Ser Ser Cys Ile Thr Lys Ser Leu Glu
        355                 360                 365
Asp Ala Gly Val Ser Pro Glu Glu Val Asn Tyr Val Asn Ala His Ala
    370                 375                 380
Thr Ser Thr Leu Ala Gly Asp Leu Ala Glu Val Asn Ala Ile Lys Lys
385                 390                 395                 400
Val Phe Lys Asp Thr Ser Glu Met Lys Met Asn Gly Thr Lys Ser Met
                405                 410                 415
Ile Gly His Cys Leu Gly Ala Ala Gly Gly Leu Glu Ala Ile Ala Thr
            420                 425                 430
Ile Lys Ala Ile Asn Thr Gly Trp Leu His Pro Thr Ile Asn Gln Phe
        435                 440                 445
```

Asn Ile Glu Pro Ala Val Thr Ile Asp Thr Val Pro Asn Val Lys Lys
            450                 455                 460

Lys His Asp Ile His Val Gly Ile Ser Asn Ser Phe Gly Phe Gly Gly
465                 470                 475                 480

His Asn Ser Val Val Phe Ala Pro Phe Met Pro
                485                 490

<210> SEQ ID NO 4
<211> LENGTH: 482
<212> TYPE: PRT
<213> ORGANISM: Cinnamonum camphora
<220> FEATURE:
<221> NAME/KEY: MISC_FEATURE
<223> OTHER INFORMATION: KASI

<400> SEQUENCE: 4

Met Gln Ile Leu Gln Thr Pro Ser Ser Ser Ser Ser Leu Arg Met
1               5                   10                  15

Ser Ser Met Glu Ser Leu Ser Leu Thr Pro Lys Ser Leu Pro Leu Lys
            20                  25                  30

Thr Leu Leu Pro Leu Arg Pro Arg Pro Lys Asn Leu Ser Arg Arg Lys
            35                  40                  45

Ser Gln Asn Pro Arg Pro Ile Ser Ser Ser Ser Pro Glu Arg Glu
50                  55                  60

Thr Asp Pro Lys Lys Arg Val Val Ile Thr Gly Met Gly Leu Val Ser
65                  70                  75                  80

Val Phe Gly Asn Asp Val Asp Ala Tyr Tyr Asp Arg Leu Leu Ser Gly
                85                  90                  95

Glu Ser Gly Ile Ala Pro Ile Asp Arg Phe Asp Ala Ser Lys Phe Pro
            100                 105                 110

Thr Arg Phe Ala Gly Gln Ile Arg Gly Phe Thr Ser Asp Gly Tyr Ile
        115                 120                 125

Asp Gly Lys Asn Asp Arg Arg Leu Asp Asp Cys Leu Arg Tyr Cys Ile
130                 135                 140

Val Ser Gly Lys Lys Ala Leu Glu Asn Ala Gly Leu Gly Pro His Leu
145                 150                 155                 160

Met Asp Gly Lys Ile Asp Lys Glu Arg Ala Gly Val Leu Val Gly Thr
                165                 170                 175

Gly Met Gly Gly Leu Thr Val Phe Ser Asn Gly Val Gln Thr Leu His
            180                 185                 190

Glu Lys Gly Tyr Arg Lys Met Thr Pro Phe Phe Ile Pro Tyr Ala Ile
        195                 200                 205

Thr Asn Met Gly Ser Ala Leu Leu Ala Ile Glu Leu Gly Phe Met Gly
210                 215                 220

Pro Asn Tyr Ser Ile Ser Thr Ala Cys Ala Thr Ser Asn Tyr Cys Phe
225                 230                 235                 240

Tyr Ala Ala Ala Asn His Ile Arg Arg Gly Glu Ala Asp Leu Met Leu
                245                 250                 255

Ala Gly Gly Thr Glu Ala Ala Ile Ile Pro Ile Gly Leu Gly Gly Phe
            260                 265                 270

Val Ala Cys Arg Ala Leu Ser Gln Arg Asn Asp Asp Pro Gln Thr Ala
        275                 280                 285

Ser Arg Pro Trp Asp Lys Asp Arg Asp Gly Phe Val Met Gly Glu Gly
290                 295                 300

Ala Gly Val Leu Val Met Glu Ser Leu Glu His Ala Met Lys Arg Asp

```
            305                 310                 315                 320
        Ala Pro Ile Ile Ala Glu Tyr Leu Gly Gly Ala Val Asn Cys Asp Ala
                        325                 330                 335

Tyr His Met Thr Asp Pro Arg Ala Asp Gly Leu Gly Val Ser Thr Cys
                        340                 345                 350

Ile Glu Arg Ser Leu Glu Asp Ala Gly Val Ala Pro Glu Glu Val Asn
                        355                 360                 365

Tyr Ile Asn Ala His Ala Thr Ser Thr Leu Ala Gly Asp Leu Ala Glu
                        370                 375                 380

Val Asn Ala Ile Lys Lys Val Phe Thr Asn Thr Ser Glu Ile Lys Ile
        385                 390                 395                 400

Asn Ala Thr Lys Ser Met Ile Gly His Cys Leu Gly Ala Ala Gly Gly
                        405                 410                 415

Leu Glu Ala Ile Ala Thr Ile Lys Ala Ile Asn Thr Gly Trp Leu His
                        420                 425                 430

Pro Ser Ile Asn Gln Phe Asn Pro Glu Pro Ser Val Glu Phe Asp Thr
                        435                 440                 445

Val Ala Asn Lys Lys Gln Gln His Glu Val Asn Val Ala Ile Ser Asn
                        450                 455                 460

Ser Phe Gly Phe Gly Gly His Asn Ser Val Val Val Phe Ser Ala Phe
        465                 470                 475                 480

Lys Pro

<210> SEQ ID NO 5
<211> LENGTH: 464
<212> TYPE: PRT
<213> ORGANISM: Umbellularia californica
<220> FEATURE:
<221> NAME/KEY: MISC_FEATURE
<223> OTHER INFORMATION: KASI

<400> SEQUENCE: 5

Met Glu Ser Leu Ser Leu Thr Pro Lys Ser Leu Pro Leu Lys Thr Leu
        1               5                   10                  15

Leu Pro Phe Arg Pro Arg Pro Lys Asn Leu Ser Arg Arg Lys Ser Gln
                        20                  25                  30

Asn Pro Lys Pro Ile Ser Ser Ser Ser Pro Glu Arg Glu Thr Asp
                        35                  40                  45

Pro Lys Lys Arg Val Val Ile Thr Gly Met Gly Leu Val Ser Val Phe
        50                  55                  60

Gly Asn Asp Val Asp Ala Tyr Tyr Asp Arg Leu Leu Ser Gly Glu Ser
        65                  70                  75                  80

Gly Ile Ala Pro Ile Asp Arg Phe Asp Ala Ser Lys Phe Pro Thr Arg
                        85                  90                  95

Phe Ala Gly Gln Ile Arg Gly Phe Thr Ser Asp Gly Tyr Ile Asp Gly
                        100                 105                 110

Lys Asn Asp Arg Arg Leu Asp Asp Cys Leu Arg Tyr Cys Ile Val Ser
                        115                 120                 125

Gly Lys Lys Ala Leu Glu Asn Ala Gly Leu Gly Pro Asp Leu Met Asp
                        130                 135                 140

Gly Lys Ile Asp Lys Glu Arg Ala Gly Val Leu Val Gly Thr Gly Met
        145                 150                 155                 160

Gly Gly Leu Thr Val Phe Ser Asn Gly Val Gln Thr Leu His Glu Lys
                        165                 170                 175

Gly Tyr Arg Lys Met Thr Pro Phe Phe Ile Pro Tyr Ala Ile Thr Asn
```

```
            180                 185                 190
Met Gly Ser Ala Leu Leu Ala Ile Asp Leu Gly Phe Met Gly Pro Asn
            195                 200                 205

Tyr Ser Ile Ser Thr Ala Cys Ala Thr Ser Asn Tyr Cys Phe Tyr Ala
        210                 215                 220

Ala Ala Asn His Ile Arg Arg Gly Glu Ala Asp Val Met Leu Ala Gly
225                 230                 235                 240

Gly Thr Glu Ala Ala Ile Ile Pro Ile Gly Leu Gly Gly Phe Val Ala
                245                 250                 255

Cys Arg Ala Leu Ser Gln Arg Asn Asp Asp Pro Gln Thr Ala Ser Arg
            260                 265                 270

Pro Trp Asp Lys Asp Arg Asp Gly Phe Val Met Gly Glu Gly Ala Gly
        275                 280                 285

Val Leu Val Met Glu Ser Leu Glu His Ala Met Lys Arg Asp Ala Pro
    290                 295                 300

Ile Ile Ala Glu Tyr Leu Gly Gly Ala Val Asn Cys Asp Ala Tyr His
305                 310                 315                 320

Met Thr Asp Pro Arg Ala Asp Gly Leu Gly Val Ser Thr Cys Ile Glu
                325                 330                 335

Arg Ser Leu Glu Asp Ala Gly Val Ala Pro Glu Val Asn Tyr Ile
            340                 345                 350

Asn Ala His Ala Thr Ser Thr Leu Ala Gly Asp Leu Ala Glu Val Asn
        355                 360                 365

Ala Ile Lys Lys Val Phe Thr Asn Thr Ser Glu Ile Lys Ile Asn Ala
    370                 375                 380

Thr Lys Ser Met Ile Gly His Cys Leu Gly Ala Ala Gly Gly Leu Glu
385                 390                 395                 400

Ala Ile Ala Thr Ile Lys Ala Ile Asn Thr Gly Trp Leu His Pro Ser
                405                 410                 415

Ile Asn Gln Phe Asn Pro Glu Pro Ser Val Glu Phe Asp Thr Val Ala
            420                 425                 430

Asn Lys Lys Gln Gln His Glu Val Asn Val Ala Ile Ser Asn Ser Phe
        435                 440                 445

Gly Phe Gly Gly His Asn Ser Val Val Val Phe Ser Ala Phe Lys Pro
    450                 455                 460

<210> SEQ ID NO 6
<211> LENGTH: 472
<212> TYPE: PRT
<213> ORGANISM: Umbellularia californica
<220> FEATURE:
<221> NAME/KEY: MISC_FEATURE
<223> OTHER INFORMATION: KASIV

<400> SEQUENCE: 6

Met Thr Gln Thr Leu Ile Cys Pro Ser Met Glu Thr Leu Ser Leu
1               5                   10                  15

Thr Lys Gln Ser His Phe Arg Leu Arg Leu Pro Thr Pro Pro His Ile
            20                  25                  30

Arg Arg Gly Gly Gly His Arg His Pro Pro Phe Ile Ser Ala Ser
        35                  40                  45

Ala Ala Pro Arg Arg Glu Thr Asp Pro Lys Lys Arg Val Val Ile Thr
    50                  55                  60

Gly Met Gly Leu Val Ser Val Phe Gly Thr Asn Val Asp Val Tyr Tyr
65                  70                  75                  80
```

-continued

```
Asp Arg Leu Leu Ala Gly Glu Ser Gly Val Gly Thr Ile Asp Arg Phe
             85                  90                  95

Asp Ala Ser Met Phe Pro Thr Arg Phe Gly Gln Ile Arg Arg Phe
        100                 105                 110

Thr Ser Glu Gly Tyr Ile Asp Gly Lys Asn Asp Arg Arg Leu Asp Asp
            115                 120                 125

Tyr Leu Arg Tyr Cys Leu Val Ser Gly Lys Lys Ala Ile Glu Ser Ala
130                 135                 140

Gly Phe Asp Leu His Asn Ile Thr Asn Lys Ile Asp Lys Glu Arg Ala
145                 150                 155                 160

Gly Ile Leu Val Gly Ser Gly Met Gly Gly Leu Lys Val Phe Ser Asp
                165                 170                 175

Gly Val Glu Ser Leu Ile Glu Lys Gly Tyr Arg Lys Ile Ser Pro Phe
            180                 185                 190

Phe Ile Pro Tyr Met Ile Pro Asn Met Gly Ser Ala Leu Leu Gly Ile
        195                 200                 205

Asp Leu Gly Phe Met Gly Pro Asn Tyr Ser Ile Ser Thr Ala Cys Ala
    210                 215                 220

Thr Ser Asn Tyr Cys Ile Tyr Ala Ala Ala Asn His Ile Arg Gln Gly
225                 230                 235                 240

Asp Ala Asp Leu Met Val Ala Gly Gly Thr Glu Ala Pro Ile Ile Pro
                245                 250                 255

Ile Gly Leu Gly Gly Phe Val Ala Cys Arg Ala Leu Ser Thr Arg Asn
            260                 265                 270

Asp Asp Pro Gln Thr Ala Ser Arg Pro Trp Asp Ile Asp Arg Asp Gly
        275                 280                 285

Phe Val Met Gly Glu Gly Ala Gly Ile Leu Val Leu Glu Ser Leu Glu
    290                 295                 300

His Ala Met Lys Arg Asp Ala Pro Ile Leu Ala Glu Tyr Leu Gly Gly
305                 310                 315                 320

Ala Val Asn Cys Asp Ala His His Met Thr Asp Pro Arg Ala Asp Gly
                325                 330                 335

Leu Gly Val Ser Thr Cys Ile Glu Ser Ser Leu Glu Asp Ala Gly Val
            340                 345                 350

Ala Ala Glu Glu Val Asn Tyr Ile Asn Ala His Ala Thr Ser Thr Pro
        355                 360                 365

Thr Gly Asp Leu Ala Glu Met Lys Ala Ile Lys Asn Val Phe Arg Asn
    370                 375                 380

Thr Ser Glu Ile Lys Ile Asn Ala Thr Lys Ser Met Ile Gly His Cys
385                 390                 395                 400

Leu Gly Ala Ser Gly Gly Leu Glu Ala Ile Ala Thr Leu Lys Ala Ile
                405                 410                 415

Thr Thr Gly Trp Leu His Pro Thr Ile Asn Gln Phe Asn Pro Glu Pro
            420                 425                 430

Ser Val Asp Phe Asp Thr Val Ala Lys Lys Lys Gln His Glu Val
        435                 440                 445

Asn Val Ala Ile Ser Asn Ser Phe Gly Phe Gly Gly His Asn Ser Val
    450                 455                 460

Leu Val Phe Ser Ala Phe Lys Pro
465                 470

<210> SEQ ID NO 7
<211> LENGTH: 525
<212> TYPE: PRT
```

```
<213> ORGANISM: Cuphea wrightii
<220> FEATURE:
<221> NAME/KEY: MISC_FEATURE
<223> OTHER INFORMATION: KASAI

<400> SEQUENCE: 7
```

| Met | Ala | Ser | Ala | Ala | Phe | Thr | Met | Ser | Ala | Cys | Pro | Ala | Met | Thr | Gly |
|---|---|---|---|---|---|---|---|---|---|---|---|---|---|---|---|
| 1 | | | | 5 | | | | | 10 | | | | | 15 | |

| Arg | Ala | Pro | Gly | Ala | Arg | Arg | Ser | Gly | Arg | Pro | Val | Ala | Thr | Arg | Leu |
|---|---|---|---|---|---|---|---|---|---|---|---|---|---|---|---|
| | | | 20 | | | | | 25 | | | | | 30 | | |

| Arg | Tyr | Val | Phe | Gln | Cys | Leu | Val | Ala | Ser | Cys | Ile | Asp | Pro | Cys | Asp |
|---|---|---|---|---|---|---|---|---|---|---|---|---|---|---|---|
| | | 35 | | | | | 40 | | | | | 45 | | | |

| Gln | Tyr | Arg | Ser | Ser | Ala | Ser | Leu | Ser | Phe | Leu | Gly | Asp | Asn | Gly | Phe |
|---|---|---|---|---|---|---|---|---|---|---|---|---|---|---|---|
| | 50 | | | | | 55 | | | | | 60 | | | | |

| Ala | Ser | Leu | Phe | Gly | Ser | Lys | Pro | Phe | Met | Ser | Asn | Arg | Gly | His | Arg |
|---|---|---|---|---|---|---|---|---|---|---|---|---|---|---|---|
| 65 | | | | | 70 | | | | | 75 | | | | | 80 |

| Arg | Leu | Arg | Arg | Ala | Ser | His | Ser | Gly | Glu | Ala | Met | Ala | Val | Ala | Leu |
|---|---|---|---|---|---|---|---|---|---|---|---|---|---|---|---|
| | | | | 85 | | | | | 90 | | | | | 95 | |

| Gln | Pro | Ala | Gln | Glu | Ala | Gly | Thr | Lys | Lys | Pro | Val | Ile | Lys | Gln |
|---|---|---|---|---|---|---|---|---|---|---|---|---|---|---|
| | | | 100 | | | | | 105 | | | | | 110 | |

| Arg | Arg | Val | Val | Val | Thr | Gly | Met | Gly | Val | Val | Thr | Pro | Leu | Gly | His |
|---|---|---|---|---|---|---|---|---|---|---|---|---|---|---|---|
| | | 115 | | | | | 120 | | | | | 125 | | | |

| Glu | Pro | Asp | Val | Phe | Tyr | Asn | Asn | Leu | Leu | Asp | Gly | Val | Ser | Gly | Ile |
|---|---|---|---|---|---|---|---|---|---|---|---|---|---|---|---|
| 130 | | | | | 135 | | | | | 140 | | | | | |

| Ser | Glu | Ile | Glu | Thr | Phe | Asp | Cys | Thr | Gln | Phe | Pro | Thr | Arg | Ile | Ala |
|---|---|---|---|---|---|---|---|---|---|---|---|---|---|---|---|
| 145 | | | | | 150 | | | | | 155 | | | | | 160 |

| Gly | Glu | Ile | Lys | Ser | Phe | Ser | Thr | Asp | Gly | Trp | Val | Ala | Pro | Lys | Leu |
|---|---|---|---|---|---|---|---|---|---|---|---|---|---|---|---|
| | | | | 165 | | | | | 170 | | | | | 175 | |

| Ser | Lys | Arg | Met | Asp | Lys | Phe | Met | Leu | Tyr | Leu | Leu | Thr | Ala | Gly | Lys |
|---|---|---|---|---|---|---|---|---|---|---|---|---|---|---|---|
| | | | 180 | | | | | 185 | | | | | 190 | | |

| Lys | Ala | Leu | Ala | Asp | Gly | Gly | Ile | Thr | Asp | Glu | Val | Met | Lys | Glu | Leu |
|---|---|---|---|---|---|---|---|---|---|---|---|---|---|---|---|
| | | 195 | | | | | 200 | | | | | 205 | | | |

| Asp | Lys | Arg | Lys | Cys | Gly | Val | Leu | Ile | Gly | Ser | Gly | Met | Gly | Gly | Met |
|---|---|---|---|---|---|---|---|---|---|---|---|---|---|---|---|
| 210 | | | | | 215 | | | | | 220 | | | | | |

| Lys | Val | Phe | Asn | Asp | Ala | Ile | Glu | Ala | Leu | Arg | Val | Ser | Tyr | Lys | Lys |
|---|---|---|---|---|---|---|---|---|---|---|---|---|---|---|---|
| 225 | | | | 230 | | | | | 235 | | | | | | 240 |

| Met | Asn | Pro | Phe | Cys | Val | Pro | Phe | Ala | Thr | Thr | Asn | Met | Gly | Ser | Ala |
|---|---|---|---|---|---|---|---|---|---|---|---|---|---|---|---|
| | | | | 245 | | | | | 250 | | | | | 255 | |

| Met | Leu | Ala | Met | Asp | Leu | Gly | Trp | Met | Gly | Pro | Asn | Tyr | Ser | Ile | Ser |
|---|---|---|---|---|---|---|---|---|---|---|---|---|---|---|---|
| | | | 260 | | | | | 265 | | | | | 270 | | |

| Thr | Ala | Cys | Ala | Thr | Ser | Asn | Phe | Cys | Ile | Leu | Asn | Ala | Ala | Asn | His |
|---|---|---|---|---|---|---|---|---|---|---|---|---|---|---|---|
| | | 275 | | | | | 280 | | | | | 285 | | | |

| Ile | Ile | Arg | Gly | Glu | Ala | Asp | Met | Met | Leu | Cys | Gly | Gly | Ser | Asp | Ala |
|---|---|---|---|---|---|---|---|---|---|---|---|---|---|---|---|
| | 290 | | | | | 295 | | | | | 300 | | | | |

| Val | Ile | Ile | Pro | Ile | Gly | Leu | Gly | Gly | Phe | Val | Ala | Cys | Arg | Ala | Leu |
|---|---|---|---|---|---|---|---|---|---|---|---|---|---|---|---|
| 305 | | | | | 310 | | | | | 315 | | | | | 320 |

| Ser | Gln | Arg | Asn | Ser | Asp | Pro | Thr | Lys | Ala | Ser | Arg | Pro | Trp | Asp | Ser |
|---|---|---|---|---|---|---|---|---|---|---|---|---|---|---|---|
| | | | | 325 | | | | | 330 | | | | | 335 | |

| Asn | Arg | Asp | Gly | Phe | Val | Met | Gly | Glu | Gly | Ala | Gly | Val | Leu | Leu | Leu |
|---|---|---|---|---|---|---|---|---|---|---|---|---|---|---|---|
| | | | 340 | | | | | 345 | | | | | 350 | | |

| Glu | Glu | Leu | Glu | His | Ala | Lys | Lys | Arg | Gly | Ala | Thr | Ile | Tyr | Ala | Glu |
|---|---|---|---|---|---|---|---|---|---|---|---|---|---|---|---|
| | | 355 | | | | | 360 | | | | | 365 | | | |

| Phe | Leu | Gly | Gly | Ser | Phe | Thr | Cys | Asp | Ala | Tyr | His | Met | Thr | Glu | Pro |
|---|---|---|---|---|---|---|---|---|---|---|---|---|---|---|---|
| 370 | | | | | 375 | | | | | 380 | | | | | |

```
His Pro Glu Gly Ala Gly Val Ile Leu Cys Ile Lys Ala Leu Ala
385                 390                 395                 400

Gln Ala Gly Val Ser Lys Glu Asp Val Asn Tyr Ile Asn Ala His Ala
            405                 410                 415

Thr Ser Thr Ser Ala Gly Asp Ile Lys Glu Tyr Gln Ala Leu Ala Arg
            420                 425                 430

Cys Phe Gly Gln Asn Ser Glu Leu Arg Val Asn Ser Thr Lys Ser Met
            435                 440                 445

Ile Gly His Leu Leu Gly Ala Ala Gly Val Glu Ala Val Thr Val
        450                 455                 460

Val Gln Ala Ile Arg Thr Gly Trp Ile His Pro Asn Leu Asn Leu Glu
465                 470                 475                 480

Asp Pro Asp Lys Ala Val Asp Ala Lys Leu Leu Val Gly Pro Lys Lys
            485                 490                 495

Glu Arg Leu Asn Val Lys Val Gly Leu Ser Asn Ser Phe Gly Phe Gly
            500                 505                 510

Gly His Asn Ser Ser Ile Leu Phe Ala Pro Cys Asn Val
            515                 520                 525

<210> SEQ ID NO 8
<211> LENGTH: 502
<212> TYPE: PRT
<213> ORGANISM: Cuphea avigera
<220> FEATURE:
<221> NAME/KEY: MISC_FEATURE
<223> OTHER INFORMATION: KASIVb

<400> SEQUENCE: 8

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Tyr Ile Gly Asp Asn Gly Phe Gly Ser
        35                  40                  45

Lys Pro Pro Arg Ser Asn Arg Gly His Leu Arg Leu Gly Arg Thr Ser
50                  55                  60

His Ser Gly Glu Val Met Ala Val Ala Met Gln Ser Ala Gln Glu Val
65                  70                  75                  80

Ser Thr Lys Glu Lys Pro Ala Thr Lys Gln Arg Arg Val Val Val Thr
            85                  90                  95

Gly Met Gly Val Val Thr Ala Leu Gly His Asp Pro Asp Val Tyr Tyr
            100                 105                 110

Asn Asn Leu Leu Asp Gly Val Ser Gly Ile Ser Glu Ile Glu Asn Phe
        115                 120                 125

Asp Cys Ser Gln Leu Pro Thr Arg Ile Ala Gly Glu Ile Lys Ser Phe
130                 135                 140

Ser Ala Asp Gly Trp Val Ala Pro Lys Phe Ser Arg Arg Met Asp Lys
145                 150                 155                 160

Phe Met Leu Tyr Ile Leu Thr Ala Gly Lys Lys Ala Leu Val Asp Gly
                165                 170                 175

Gly Ile Thr Glu Asp Val Met Lys Glu Leu Asp Lys Arg Lys Cys Gly
            180                 185                 190

Val Leu Ile Gly Ser Gly Leu Gly Gly Met Lys Val Phe Ser Glu Ser
        195                 200                 205

Ile Glu Ala Leu Arg Thr Ser Tyr Lys Lys Ile Ser Pro Phe Cys Val
210                 215                 220
```

```
Pro Phe Ser Thr Thr Asn Met Gly Ser Ala Ile Leu Ala Met Asp Leu
225                 230                 235                 240

Gly Trp Met Gly Pro Asn Tyr Ser Ile Ser Thr Ala Cys Ala Thr Ser
            245                 250                 255

Asn Phe Cys Ile Leu Asn Ala Ala Asn His Ile Thr Lys Gly Glu Ala
            260                 265                 270

Asp Met Met Leu Cys Gly Gly Ser Asp Ser Val Ile Leu Pro Ile Gly
            275                 280                 285

Met Gly Gly Phe Val Ala Cys Arg Ala Leu Ser Gln Arg Asn Asn Asp
            290                 295                 300

Pro Thr Lys Ala Ser Arg Pro Trp Asp Ser Asn Arg Asp Gly Phe Val
305                 310                 315                 320

Met Gly Glu Gly Ala Gly Val Leu Leu Leu Glu Glu Leu Glu His Ala
            325                 330                 335

Lys Lys Arg Gly Ala Thr Ile Tyr Ala Glu Phe Leu Gly Ser Phe
            340                 345                 350

Thr Cys Asp Ala Tyr His Met Thr Glu Pro His Pro Glu Gly Ala Gly
            355                 360                 365

Val Ile Leu Cys Ile Glu Lys Ala Leu Ala Gln Ser Gly Val Ser Arg
370                 375                 380

Glu Asp Val Asn Tyr Ile Asn Ala His Ala Thr Ser Thr Pro Ala Gly
385                 390                 395                 400

Asp Ile Lys Glu Tyr Gln Ala Leu Ala His Cys Phe Gly Gln Asn Ser
            405                 410                 415

Glu Leu Arg Val Asn Ser Thr Lys Ser Met Ile Gly His Leu Leu Gly
            420                 425                 430

Gly Ala Gly Gly Val Glu Ala Val Thr Val Val Gln Ala Ile Arg Thr
            435                 440                 445

Gly Trp Ile His Pro Asn Ile Asn Leu Asp Asp Pro Asp Glu Gly Val
            450                 455                 460

Asp Ala Lys Leu Leu Val Gly Pro Lys Lys Glu Lys Leu Lys Val Lys
465                 470                 475                 480

Val Gly Leu Ser Asn Ser Phe Gly Phe Gly Gly His Asn Ser Ser Ile
            485                 490                 495

Leu Phe Ala Pro Cys Asn
            500

<210> SEQ ID NO 9
<211> LENGTH: 505
<212> TYPE: PRT
<213> ORGANISM: Cuphea paucipetala
<220> FEATURE:
<221> NAME/KEY: MISC_FEATURE
<223> OTHER INFORMATION: KASIVb

<400> SEQUENCE: 9

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Leu Gly Asp Ile Gly Phe Ala Ser Leu
            35                  40                  45

Ile Gly Ser Lys Pro Pro Arg Ser Asn Arg Asn His Arg Arg Leu Gly
50                  55                  60

Arg Thr Ser His Ser Gly Glu Val Met Ala Val Ala Met Gln Pro Ala
```

```
                65                  70                  75                  80
           His Glu Ala Ser Thr Lys Asn Lys Pro Val Thr Lys Gln Arg Arg Val
                            85                  90                  95

Val Val Thr Gly Met Gly Val Ala Thr Pro Leu Gly His Asp Pro Asp
                           100                 105                 110

Val Tyr Tyr Asn Asn Leu Leu Asp Gly Val Ser Gly Ile Ser Gln Ile
                           115                 120                 125

Glu Asn Phe Asp Cys Thr Gln Phe Pro Thr Arg Ile Ala Gly Glu Ile
               130                 135                 140

Lys Ser Phe Ser Thr Glu Gly Tyr Val Ile Pro Lys Phe Ala Lys Arg
           145                 150                 155                 160

Met Asp Lys Phe Met Leu Tyr Leu Leu Thr Ala Gly Lys Lys Ala Leu
                           165                 170                 175

Glu Asp Gly Gly Ile Thr Glu Asp Val Met Lys Glu Leu Asp Lys Arg
                           180                 185                 190

Lys Cys Gly Val Leu Ile Gly Ser Gly Met Gly Gly Met Lys Ile Ile
                           195                 200                 205

Asn Asp Ser Ile Ala Ala Leu Asn Val Ser Tyr Lys Lys Met Thr Pro
               210                 215                 220

Phe Cys Val Pro Phe Ser Thr Thr Asn Met Gly Ser Ala Met Leu Ala
           225                 230                 235                 240

Ile Asp Leu Gly Trp Met Gly Pro Asn Tyr Ser Ile Ser Thr Ala Cys
                           245                 250                 255

Ala Thr Ser Asn Tyr Cys Ile Leu Asn Ala Ala Asn His Ile Val Arg
                           260                 265                 270

Gly Glu Ala Asp Met Met Leu Cys Gly Gly Ser Asp Ala Val Ile Ile
                           275                 280                 285

Pro Val Gly Leu Gly Gly Phe Val Ala Cys Arg Ala Leu Ser Gln Arg
               290                 295                 300

Asn Asn Asp Pro Thr Lys Ala Ser Arg Pro Trp Asp Ser Asn Arg Asp
           305                 310                 315                 320

Gly Phe Val Met Gly Glu Gly Ala Gly Val Leu Leu Leu Glu Glu Leu
                           325                 330                 335

Glu His Ala Lys Lys Arg Gly Ala Thr Ile Tyr Ala Glu Phe Leu Gly
                           340                 345                 350

Gly Ser Phe Thr Cys Asp Ala Tyr His Met Thr Glu Pro His Pro Asp
                           355                 360                 365

Gly Ala Gly Val Ile Leu Cys Ile Glu Lys Ala Leu Ala Gln Ser Gly
               370                 375                 380

Val Ser Arg Glu Asp Val Asn Tyr Ile Asn Ala His Ala Thr Ser Thr
           385                 390                 395                 400

Pro Ala Gly Asp Ile Lys Glu Tyr Gln Ala Leu Ala His Cys Phe Gly
                           405                 410                 415

Gln Asn Ser Glu Leu Arg Val Asn Ser Thr Lys Ser Met Ile Gly His
                           420                 425                 430

Leu Leu Gly Ala Ala Gly Gly Val Glu Ala Val Thr Val Val Gln Ala
                           435                 440                 445

Ile Arg Thr Gly Trp Ile His Pro Asn Ile Asn Leu Glu Asn Pro Asp
               450                 455                 460

Glu Ala Val Asp Ala Lys Leu Leu Val Gly Pro Lys Lys Glu Lys Leu
           465                 470                 475                 480

Lys Val Lys Val Gly Leu Ser Asn Ser Phe Gly Phe Gly Gly His Asn
                           485                 490                 495
```

Ser Ser Ile Leu Phe Ala Pro Tyr Asn
            500                 505

<210> SEQ ID NO 10
<211> LENGTH: 525
<212> TYPE: PRT
<213> ORGANISM: Cuphea ignea
<220> FEATURE:
<221> NAME/KEY: MISC_FEATURE
<223> OTHER INFORMATION: KASIVb

<400> SEQUENCE: 10

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Ser Gln Cys Leu Val Thr Ser Tyr Ile Asp Pro Cys
        35                  40                  45

Asn Lys Tyr Cys Ser Ser Ala Ser Leu Ser Phe Leu Gly Asp Asn Gly
    50                  55                  60

Phe Ala Ser Leu Phe Gly Ser Lys Pro Phe Arg Ser Asn Arg Gly His
65                  70                  75                  80

Arg Arg Leu Gly Arg Ala Ser His Ser Gly Glu Ala Met Ala Val Ala
                85                  90                  95

Leu Gln Pro Ala Gln Glu Val Thr Thr Lys Lys Pro Val Ile Lys
            100                 105                 110

Gln Arg Arg Val Val Val Thr Gly Met Gly Val Val Thr Pro Leu Gly
        115                 120                 125

His Glu Pro Asp Val Tyr Tyr Asn Asn Leu Leu Asp Gly Val Ser Gly
    130                 135                 140

Ile Ser Glu Ile Glu Thr Phe Asp Cys Thr Gln Phe Pro Thr Arg Ile
145                 150                 155                 160

Ala Gly Glu Ile Lys Ser Phe Ser Thr Asp Gly Trp Val Ala Pro Lys
                165                 170                 175

Leu Ser Lys Arg Met Asp Lys Phe Met Leu Tyr Leu Leu Thr Ala Gly
            180                 185                 190

Lys Lys Ala Leu Ala Asp Gly Gly Ile Thr Asp Asp Val Met Lys Glu
        195                 200                 205

Leu Asp Lys Arg Lys Cys Gly Val Leu Ile Gly Ser Gly Met Gly Gly
    210                 215                 220

Met Lys Leu Phe Asn Asp Ser Ile Glu Ala Leu Arg Ile Ser Tyr Lys
225                 230                 235                 240

Lys Met Asn Pro Phe Cys Val Pro Phe Ala Thr Thr Asn Met Gly Ser
                245                 250                 255

Ala Met Leu Ala Met Asp Leu Gly Trp Met Gly Pro Asn Tyr Ser Ile
            260                 265                 270

Ser Thr Ala Cys Ala Thr Ser Asn Phe Cys Ile Leu Asn Ala Ser Asn
        275                 280                 285

His Ile Val Arg Gly Glu Ala Asp Met Met Leu Cys Gly Gly Ser Asp
    290                 295                 300

Ser Val Thr Val Pro Leu Gly Val Gly Phe Val Ala Cys Arg Ala
305                 310                 315                 320

Leu Ser Gln Arg Asn Asn Asp Pro Thr Lys Ala Ser Arg Pro Trp Asp
            325                 330                 335

Ser Asn Arg Asp Gly Phe Val Met Gly Glu Gly Ala Gly Val Leu Leu

```
                    340                 345                 350
Leu Glu Glu Leu Glu His Ala Lys Lys Arg Gly Ala Thr Ile Tyr Ala
                355                 360                 365

Glu Phe Leu Gly Gly Ser Phe Thr Ser Asp Ala Tyr His Met Thr Glu
            370                 375                 380

Pro His Pro Glu Gly Ala Gly Val Ile Leu Cys Ile Glu Lys Ala Leu
385                 390                 395                 400

Ala Gln Ser Gly Val Ser Arg Glu Asp Val Asn Tyr Ile Asn Ala His
                405                 410                 415

Ala Thr Ser Thr Pro Ala Gly Asp Ile Lys Glu Tyr Gln Ala Leu Ala
            420                 425                 430

Arg Cys Phe Gly Gln Asn Ser Glu Leu Arg Val Asn Ser Thr Lys Ser
                435                 440                 445

Met Ile Gly His Leu Leu Gly Ala Ala Gly Gly Val Glu Ala Val Ala
            450                 455                 460

Val Ile Gln Ala Ile Arg Thr Gly Trp Ile His Pro Asn Ile Asn Leu
465                 470                 475                 480

Glu Asp Pro Asp Glu Ala Val Asp Pro Lys Leu Leu Val Gly Pro Lys
                485                 490                 495

Lys Glu Lys Leu Lys Val Lys Val Ala Leu Ser Asn Ser Phe Gly Phe
            500                 505                 510

Gly Gly His Asn Ser Ser Ile Leu Phe Ala Pro Cys Asn
                515                 520                 525

<210> SEQ ID NO 11
<211> LENGTH: 521
<212> TYPE: PRT
<213> ORGANISM: Cuphea procumbens
<220> FEATURE:
<221> NAME/KEY: MISC_FEATURE
<223> OTHER INFORMATION: KASIV

<400> SEQUENCE: 11

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
                20                  25                  30

Arg Gly Ser Thr Phe Gln Cys Leu Val Thr Ser His Asn Asp Pro Cys
            35                  40                  45

Asn Gln Tyr Cys Ser Ser Ala Ser Leu Ser Phe Leu Gly Asp Asn Gly
        50                  55                  60

Phe Gly Ser Lys Pro Phe Arg Ser Asn Arg Gly His Arg Arg Leu Gly
65                  70                  75                  80

Arg Ala Ser His Ser Gly Glu Ala Met Ala Val Ala Leu Gln Pro Ala
                85                  90                  95

Gln Glu Val Ala Thr Lys Lys Pro Ala Met Lys Gln Arg Arg Val
            100                 105                 110

Val Val Thr Gly Met Gly Val Val Thr Pro Leu Gly His Glu Pro Asp
            115                 120                 125

Val Tyr Tyr Asn Asn Leu Leu Asp Gly Val Ser Gly Ile Ser Glu Ile
        130                 135                 140

Glu Thr Phe Asp Cys Thr Gln Phe Pro Thr Arg Ile Ala Gly Glu Ile
145                 150                 155                 160

Lys Ser Phe Ser Thr Asp Gly Trp Val Ala Pro Lys Leu Ser Lys Arg
                165                 170                 175
```

Met Asp Lys Phe Met Leu Tyr Leu Leu Thr Ala Gly Lys Lys Ala Leu
                180                 185                 190

Ala Asp Gly Gly Ile Thr Asp Asp Val Met Lys Glu Leu Asp Lys Arg
            195                 200                 205

Lys Cys Gly Val Leu Ile Gly Ser Gly Met Gly Gly Met Lys Leu Phe
        210                 215                 220

Asn Asp Ser Ile Glu Ala Leu Arg Val Ser Tyr Lys Lys Met Asn Pro
225                 230                 235                 240

Phe Cys Val Pro Phe Ala Thr Thr Asn Met Gly Ser Ala Met Leu Ala
                245                 250                 255

Met Asp Leu Gly Trp Met Gly Pro Asn Tyr Ser Ile Ser Thr Ala Cys
            260                 265                 270

Ala Thr Ser Asn Phe Cys Ile Leu Asn Ala Ala Asn His Ile Val Arg
        275                 280                 285

Gly Glu Ala Asp Met Met Leu Cys Gly Gly Ser Asp Ala Val Ile Ile
        290                 295                 300

Pro Ile Gly Leu Gly Gly Phe Val Ala Cys Arg Ala Leu Ser Gln Arg
305                 310                 315                 320

Asn Asn Asp Pro Thr Lys Ala Ser Arg Pro Trp Asp Ser Asn Arg Asp
                325                 330                 335

Gly Phe Val Met Gly Glu Gly Ala Gly Val Leu Leu Leu Glu Glu Leu
            340                 345                 350

Glu His Ala Lys Lys Arg Gly Ala Thr Ile Tyr Ala Glu Phe Leu Gly
        355                 360                 365

Gly Ser Phe Thr Cys Asp Ala Tyr His Met Thr Glu Pro His Pro Glu
        370                 375                 380

Gly Ala Gly Val Ile Leu Cys Ile Glu Lys Ala Leu Ala Gln Ser Gly
385                 390                 395                 400

Val Ser Arg Glu Asp Val Asn Tyr Ile Asn Ala His Ala Thr Ser Thr
                405                 410                 415

Pro Ala Gly Asp Ile Lys Glu Tyr Gln Ala Leu Ala His Cys Phe Gly
            420                 425                 430

Gln Asn Ser Glu Leu Arg Val Asn Ser Thr Lys Ser Met Ile Gly His
        435                 440                 445

Leu Leu Gly Ala Ala Gly Gly Val Glu Ala Val Thr Val Ile Gln Ala
450                 455                 460

Ile Arg Thr Gly Trp Ile His Pro Asn Leu Asn Leu Glu Asp Pro Asp
465                 470                 475                 480

Lys Ala Val Asp Ala Lys Phe Leu Val Gly Pro Lys Lys Glu Arg Leu
                485                 490                 495

Asn Val Lys Val Gly Leu Ser Asn Ser Phe Gly Phe Gly Gly His Asn
            500                 505                 510

Ser Ser Ile Leu Phe Ala Pro Cys Asn
        515                 520

<210> SEQ ID NO 12
<211> LENGTH: 521
<212> TYPE: PRT
<213> ORGANISM: Cuphea paucipetala
<220> FEATURE:
<221> NAME/KEY: MISC_FEATURE
<223> OTHER INFORMATION: KASIVa

<400> SEQUENCE: 12

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Leu Val Asn Ser His Ile Asp Pro Cys
        35                  40                  45

Asn Gln Asn Val Ser Ser Ala Ser Leu Ser Phe Leu Gly Asp Asn Gly
50                  55                  60

Phe Gly Ser Asn Pro Phe Arg Ser Asn Arg Gly His Arg Arg Leu Gly
65                  70                  75                  80

Arg Ala Ser His Ser Gly Glu Ala Met Ala Val Ala Leu Gln Pro Ala
            85                  90                  95

Gln Glu Val Ala Thr Lys Lys Pro Ala Ile Lys Gln Arg Arg Val
            100                 105                 110

Val Val Thr Gly Met Gly Val Val Thr Pro Leu Gly His Glu Pro Asp
            115                 120                 125

Val Phe Tyr Asn Asn Leu Leu Asp Gly Val Ser Gly Ile Ser Glu Ile
    130                 135                 140

Glu Thr Phe Asp Cys Thr Gln Phe Pro Thr Arg Ile Ala Gly Glu Ile
145                 150                 155                 160

Lys Ser Phe Ser Thr Asp Gly Trp Val Ala Pro Lys Leu Ser Lys Arg
                165                 170                 175

Met Asp Lys Phe Met Leu Tyr Leu Leu Thr Ala Gly Lys Lys Ala Leu
            180                 185                 190

Ala Asp Ala Gly Ile Thr Glu Asp Val Met Lys Glu Leu Asp Lys Arg
            195                 200                 205

Lys Cys Gly Val Leu Ile Gly Ser Gly Met Gly Met Lys Leu Phe
210                 215                 220

Asn Asp Ser Ile Glu Ala Leu Arg Val Ser Tyr Lys Lys Met Asn Pro
225                 230                 235                 240

Phe Cys Val Pro Phe Ala Thr Thr Asn Met Gly Ser Ala Met Leu Ala
                245                 250                 255

Met Asp Leu Gly Trp Met Gly Pro Asn Tyr Ser Ile Ser Thr Ala Cys
            260                 265                 270

Ala Thr Ser Asn Phe Cys Ile Leu Asn Ala Ala Asn His Ile Ile Arg
            275                 280                 285

Gly Glu Ala Asp Met Met Leu Cys Gly Gly Ser Asp Ala Val Ile Ile
            290                 295                 300

Pro Ile Gly Leu Gly Gly Phe Val Ala Cys Arg Ala Leu Ser Gln Arg
305                 310                 315                 320

Asn Ser Asp Pro Thr Lys Ala Ser Arg Pro Trp Asp Ser Asn Arg Asp
                325                 330                 335

Gly Phe Val Met Gly Glu Gly Ala Gly Val Leu Leu Leu Glu Glu Leu
            340                 345                 350

Glu His Ala Lys Lys Arg Gly Ala Thr Ile Tyr Ala Glu Phe Leu Gly
            355                 360                 365

Gly Ser Phe Thr Cys Asp Ala Tyr His Met Thr Glu Pro His Pro Asp
            370                 375                 380

Gly Ala Gly Val Ile Leu Cys Ile Glu Lys Ala Leu Ala Gln Ser Gly
385                 390                 395                 400

Val Ser Arg Glu Asp Val Asn Tyr Ile Asn Ala His Ala Thr Ser Thr
                405                 410                 415

Pro Ala Gly Asp Ile Lys Glu Tyr Gln Ala Leu Ala His Cys Phe Gly
            420                 425                 430

Gln Asn Ser Glu Leu Arg Val Asn Ser Thr Lys Ser Met Ile Gly His
    435                 440                 445

Leu Leu Gly Ala Ala Gly Val Glu Ala Val Thr Val Ile Gln Ala
450                 455                 460

Ile Arg Thr Gly Trp Ile His Pro Asn Leu Asn Leu Glu Asp Pro Asp
465                 470                 475                 480

Glu Ala Val Asp Ala Lys Phe Leu Val Gly Pro Lys Lys Glu Arg Leu
                485                 490                 495

Asn Val Lys Val Gly Leu Ser Asn Ser Phe Gly Phe Gly Gly His Asn
            500                 505                 510

Ser Ser Ile Leu Phe Ala Pro Tyr Asn
        515                 520

<210> SEQ ID NO 13
<211> LENGTH: 510
<212> TYPE: PRT
<213> ORGANISM: Cuphea painteri
<220> FEATURE:
<221> NAME/KEY: MISC_FEATURE
<223> OTHER INFORMATION: KASIV

<400> SEQUENCE: 13

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Pro Gln Cys Leu Asp Pro Cys Asn Gln His Cys Phe
        35                  40                  45

Leu Gly Asp Asn Gly Phe Ala Ser Leu Ile Gly Ser Lys Pro Pro Arg
50                  55                  60

Ser Asn Leu Gly His Leu Arg Leu Gly Arg Thr Ser His Ser Gly Glu
65                  70                  75                  80

Val Met Ala Val Ala Gln Glu Val Ser Thr Asn Lys Lys His Ala Thr
                85                  90                  95

Lys Gln Arg Arg Val Val Val Thr Gly Met Gly Val Val Thr Pro Leu
            100                 105                 110

Gly His Asp Pro Asp Val Tyr Tyr Asn Asn Leu Leu Glu Gly Val Ser
        115                 120                 125

Gly Ile Ser Glu Ile Glu Asn Phe Asp Cys Ser Gln Leu Pro Thr Arg
130                 135                 140

Ile Ala Gly Glu Ile Lys Ser Phe Ser Thr Asp Gly Leu Val Ala Pro
145                 150                 155                 160

Lys Leu Ser Lys Arg Met Asp Lys Phe Met Leu Tyr Ile Leu Thr Ala
                165                 170                 175

Gly Lys Lys Ala Leu Ala Asp Gly Gly Ile Thr Glu Asp Val Met Lys
            180                 185                 190

Glu Leu Asp Lys Arg Lys Cys Gly Val Leu Ile Gly Ser Gly Leu Gly
        195                 200                 205

Gly Met Lys Val Phe Ser Asp Ser Val Glu Ala Leu Arg Ile Ser Tyr
210                 215                 220

Lys Lys Ile Ser Pro Phe Cys Val Pro Phe Ser Thr Thr Asn Met Gly
225                 230                 235                 240

Ser Ala Met Leu Ala Met Asp Leu Gly Trp Met Gly Pro Asn Tyr Ser
                245                 250                 255

Ile Ser Thr Ala Cys Ala Thr Ser Asn Phe Cys Ile Leu Asn Ala Ala
            260                 265                 270

Asn His Ile Thr Lys Gly Glu Ala Asp Met Met Leu Cys Gly Gly Ser
            275                 280                 285

Asp Ala Ala Ile Leu Pro Ile Gly Met Gly Gly Phe Val Ala Cys Arg
    290                 295                 300

Ala Leu Ser Gln Arg Asn Asn Asp Pro Thr Lys Ala Ser Arg Pro Trp
305                 310                 315                 320

Asp Ser Asn Arg Asp Gly Phe Val Met Gly Glu Gly Ala Gly Val Leu
                325                 330                 335

Leu Leu Glu Glu Leu Glu His Ala Lys Lys Arg Gly Ala Thr Ile Tyr
            340                 345                 350

Ala Glu Phe Leu Gly Gly Ser Phe Thr Cys Asp Ala Tyr His Met Thr
        355                 360                 365

Glu Pro His Pro Asp Gly Ala Gly Val Ile Leu Cys Ile Glu Lys Ala
    370                 375                 380

Leu Ala Gln Ser Gly Val Ser Arg Glu Glu Val Asn Tyr Ile Asn Ala
385                 390                 395                 400

His Ala Thr Ser Thr Pro Ala Gly Asp Ile Lys Glu Tyr Gln Ala Leu
                405                 410                 415

Ala His Cys Phe Gly Gln Asn Ser Glu Leu Arg Val Asn Ser Thr Lys
            420                 425                 430

Ser Met Ile Gly His Leu Leu Gly Ala Gly Gly Val Glu Ala Val
        435                 440                 445

Thr Val Val Gln Ala Ile Arg Thr Gly Trp Ile His Pro Asn Ile Asn
    450                 455                 460

Leu Glu Asp Pro Asp Lys Gly Val Asp Ala Lys Leu Leu Val Gly Pro
465                 470                 475                 480

Lys Lys Glu Lys Leu Lys Val Lys Val Gly Leu Ser Asn Ser Phe Gly
                485                 490                 495

Phe Gly Gly His Asn Ser Ser Ile Leu Phe Ala Pro Cys Asn
            500                 505                 510

<210> SEQ ID NO 14
<211> LENGTH: 525
<212> TYPE: PRT
<213> ORGANISM: Cuphea avigera
<220> FEATURE:
<221> NAME/KEY: MISC_FEATURE
<223> OTHER INFORMATION: KASIVa

<400> SEQUENCE: 14

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Leu Val Thr Ser Tyr Asn Asp Pro Cys
        35                  40                  45

Glu Gln Tyr Arg Ser Ser Ala Ser Leu Ser Phe Leu Gly Asp Asn Gly
    50                  55                  60

Phe Ala Ser Leu Phe Gly Ser Lys Pro Phe Arg Ser Asn Arg Gly His
65                  70                  75                  80

Arg Arg Leu Gly Arg Ala Ser His Ser Gly Glu Ala Met Ala Val Ala
                85                  90                  95

Leu Gln Pro Ala Gln Glu Val Gly Thr Lys Lys Pro Val Ile Lys
            100                 105                 110

Gln Arg Arg Val Val Val Thr Gly Met Gly Val Val Thr Pro Leu Gly

```
            115                 120                 125
His Glu Pro Asp Val Tyr Tyr Asn Asn Leu Leu Asp Gly Val Ser Gly
    130                 135                 140

Ile Ser Glu Ile Glu Thr Phe Asp Cys Thr Gln Phe Pro Thr Arg Ile
145                 150                 155                 160

Ala Gly Glu Ile Lys Ser Phe Ser Thr Asp Gly Trp Val Ala Pro Lys
                165                 170                 175

Leu Ser Lys Arg Met Asp Lys Phe Met Leu Tyr Leu Thr Ala Gly
            180                 185                 190

Lys Lys Ala Leu Ala Asp Gly Gly Ile Thr Asp Val Met Lys Glu
            195                 200                 205

Leu Asp Lys Arg Lys Cys Gly Val Leu Ile Gly Ser Gly Leu Gly Gly
    210                 215                 220

Met Lys Val Phe Ser Glu Ser Ile Glu Ala Leu Arg Thr Ser Tyr Lys
225                 230                 235                 240

Lys Ile Ser Pro Phe Cys Val Pro Phe Ser Thr Thr Asn Met Gly Ser
                245                 250                 255

Ala Ile Leu Ala Met Asp Leu Gly Trp Met Gly Pro Asn Tyr Ser Ile
                260                 265                 270

Ser Thr Ala Cys Ala Thr Ser Asn Phe Cys Ile Leu Asn Ala Ala Asn
            275                 280                 285

His Ile Thr Lys Gly Glu Ala Asp Met Met Leu Cys Gly Gly Ser Asp
    290                 295                 300

Ser Val Ile Leu Pro Ile Gly Met Gly Gly Phe Val Ala Cys Arg Ala
305                 310                 315                 320

Leu Ser Gln Arg Asn Asn Asp Pro Thr Lys Ala Ser Arg Pro Trp Asp
                325                 330                 335

Ser Asn Arg Asp Gly Phe Val Met Gly Glu Gly Ala Gly Val Leu Leu
            340                 345                 350

Leu Glu Glu Leu Glu His Ala Lys Lys Arg Gly Ala Thr Ile Tyr Ala
        355                 360                 365

Glu Phe Leu Gly Gly Ser Phe Thr Cys Asp Ala Tyr His Met Thr Glu
    370                 375                 380

Pro His Pro Glu Gly Ala Gly Val Ile Leu Cys Ile Glu Lys Ala Leu
385                 390                 395                 400

Ala Gln Ser Gly Val Ser Arg Glu Asp Val Asn Tyr Ile Asn Ala His
                405                 410                 415

Ala Thr Ser Thr Pro Ala Gly Asp Ile Lys Glu Tyr Gln Ala Leu Ala
                420                 425                 430

His Cys Phe Gly Gln Asn Ser Glu Leu Arg Val Asn Ser Thr Lys Ser
            435                 440                 445

Met Ile Gly His Leu Leu Gly Gly Ala Gly Gly Val Glu Ala Val Thr
        450                 455                 460

Val Val Gln Ala Ile Arg Thr Gly Trp Ile His Pro Asn Ile Asn Leu
465                 470                 475                 480

Asp Asp Pro Asp Glu Gly Val Asp Ala Lys Leu Leu Val Gly Pro Lys
                485                 490                 495

Lys Glu Lys Leu Lys Val Lys Val Gly Leu Ser Asn Ser Phe Gly Phe
            500                 505                 510

Gly Gly His Asn Ser Ser Ile Leu Phe Ala Pro Cys Asn
        515                 520                 525

<210> SEQ ID NO 15
```

```
<211> LENGTH: 525
<212> TYPE: PRT
<213> ORGANISM: Cuphea ignea
<220> FEATURE:
<221> NAME/KEY: MISC_FEATURE
<223> OTHER INFORMATION: KASIVa

<400> SEQUENCE: 15
```

| | | | | | | | | | | | | | | |
|---|---|---|---|---|---|---|---|---|---|---|---|---|---|---|
|Met|Ala|Ser|Ala|Ala|Phe|Thr|Met|Ser|Ala|Cys|Pro|Ala|Met|Thr|Gly|
|1| | | |5| | | | |10| | | | |15|
|Arg|Ala|Pro|Gly|Ala|Arg|Arg|Ser|Gly|Arg|Pro|Val|Ala|Thr|Arg|Leu|
| | | |20| | | | |25| | | | |30| | |
|Arg|Gly|Ser|Thr|Ser|Gln|Cys|Leu|Val|Thr|Ser|Tyr|Ile|Asp|Pro|Cys|
| | | | |35| | | | |40| | | | |45| |
|Asn|Lys|Tyr|Cys|Ser|Ser|Ala|Ser|Leu|Ser|Phe|Leu|Gly|Asp|Asn|Gly|
| |50| | | | |55| | | | |60| | | | |
|Phe|Ala|Ser|Leu|Phe|Gly|Ser|Lys|Pro|Phe|Arg|Ser|Asn|Arg|Gly|His|
|65| | | | |70| | | | |75| | | | |80|
|Arg|Arg|Leu|Gly|Arg|Ala|Ser|His|Ser|Gly|Glu|Ala|Met|Ala|Val|Ala|
| | | | |85| | | | |90| | | | |95| |
|Leu|Gln|Pro|Ala|Gln|Glu|Val|Thr|Thr|Lys|Lys|Pro|Val|Ile|Lys|
| | | |100| | | | |105| | | | |110| | |
|Gln|Arg|Arg|Val|Val|Val|Thr|Gly|Met|Gly|Val|Val|Thr|Pro|Leu|Gly|
| | |115| | | | |120| | | | |125| | | |
|His|Glu|Pro|Asp|Val|Tyr|Tyr|Asn|Asn|Leu|Leu|Asp|Gly|Val|Ser|Gly|
| | |130| | | | |135| | | | |140| | | |
|Ile|Ser|Glu|Ile|Glu|Thr|Phe|Asp|Cys|Thr|Gln|Phe|Pro|Thr|Arg|Ile|
|145| | | | |150| | | | |155| | | | |160|
|Ala|Gly|Glu|Ile|Lys|Ser|Phe|Ser|Thr|Asp|Gly|Trp|Val|Ala|Pro|Lys|
| | | | |165| | | | |170| | | | |175| |
|Leu|Ser|Lys|Arg|Met|Asp|Lys|Phe|Met|Leu|Tyr|Leu|Leu|Thr|Ala|Gly|
| | | |180| | | | |185| | | | |190| | |
|Lys|Lys|Ala|Leu|Ala|Asp|Gly|Gly|Ile|Thr|Asp|Val|Met|Lys|Glu|
| | | |195| | | | |200| | | | |205| | |
|Leu|Asp|Lys|Arg|Lys|Cys|Gly|Val|Leu|Ile|Gly|Ser|Gly|Met|Gly|Gly|
| | |210| | | | |215| | | | |220| | | |
|Met|Lys|Leu|Phe|Asn|Asp|Ser|Ile|Glu|Ala|Leu|Arg|Ile|Ser|Tyr|Lys|
|225| | | | |230| | | | |235| | | | |240|
|Lys|Met|Asn|Pro|Phe|Cys|Val|Pro|Phe|Ala|Thr|Thr|Asn|Met|Gly|Ser|
| | | |245| | | | |250| | | | |255| | |
|Ala|Met|Leu|Ala|Met|Asp|Leu|Gly|Trp|Met|Gly|Pro|Asn|Tyr|Ser|Ile|
| | |260| | | | |265| | | | |270| | | |
|Ser|Thr|Ala|Cys|Ala|Thr|Ser|Asn|Phe|Cys|Ile|Leu|Asn|Ala|Ser|Asn|
| |275| | | | |280| | | | |285| | | | |
|His|Ile|Val|Arg|Gly|Glu|Ala|Asp|Met|Met|Leu|Cys|Gly|Gly|Ser|Asp|
| |290| | | | |295| | | | |300| | | | |
|Ala|Val|Ile|Ile|Pro|Ile|Gly|Leu|Gly|Gly|Phe|Val|Ala|Cys|Arg|Ala|
|305| | | | |310| | | | |315| | | | |320|
|Leu|Ser|Gln|Arg|Asn|Asn|Asp|Pro|Thr|Lys|Ala|Ser|Arg|Pro|Trp|Asp|
| | | |325| | | | |330| | | | |335| | |
|Ser|Asn|Arg|Asp|Gly|Phe|Val|Met|Gly|Glu|Gly|Ala|Gly|Val|Leu|Leu|
| | |340| | | | |345| | | | |350| | | |
|Leu|Glu|Glu|Leu|Glu|His|Ala|Lys|Lys|Arg|Gly|Ala|Thr|Ile|Tyr|Ala|
| |355| | | | |360| | | | |365| | | | |
|Glu|Phe|Leu|Gly|Gly|Ser|Phe|Thr|Cys|Asp|Ala|Tyr|His|Met|Thr|Glu|

```
                    370                 375                 380
Pro His Pro Glu Gly Ala Gly Val Ile Leu Cys Ile Glu Lys Ala Leu
385                 390                 395                 400

Ala Gln Ala Gly Val Ser Lys Glu Asp Val Asn Tyr Ile Asn Ala His
                405                 410                 415

Ala Thr Ser Thr Pro Ala Gly Asp Ile Lys Glu Tyr Gln Ala Leu Ala
                420                 425                 430

Gln Cys Phe Gly Gln Asn Ser Glu Leu Arg Val Asn Ser Thr Lys Ser
                435                 440                 445

Met Ile Gly His Leu Leu Gly Ala Ala Gly Val Glu Ala Val Thr
            450                 455                 460

Val Val Gln Ala Ile Arg Thr Gly Trp Ile His Pro Asn Leu Asn Leu
465                 470                 475                 480

Glu Asp Pro Asp Lys Ala Val Asp Ala Lys Leu Leu Val Gly Pro Lys
                485                 490                 495

Lys Glu Arg Leu Asn Val Lys Val Gly Leu Ser Asn Ser Phe Gly Phe
                500                 505                 510

Gly Gly His Asn Ser Ser Ile Leu Phe Ala Pro Tyr Asn
            515                 520                 525

<210> SEQ ID NO 16
<211> LENGTH: 473
<212> TYPE: PRT
<213> ORGANISM: Cuphea avigera
<220> FEATURE:
<221> NAME/KEY: MISC_FEATURE
<223> OTHER INFORMATION: KASIa

<400> SEQUENCE: 16

Met Gln Ser Leu His Ser Pro Ala Leu Arg Ala Ser Pro Leu Asp Pro
1               5                   10                  15

Leu Arg Leu Lys Ser Ser Ala Asn Gly Pro Ser Ser Thr Ala Ala Phe
            20                  25                  30

Arg Pro Leu Arg Arg Ala Thr Leu Pro Asn Ile Arg Ala Ala Ser Pro
        35                  40                  45

Thr Val Ser Ala Pro Lys Arg Glu Thr Asp Pro Lys Lys Arg Val Val
    50                  55                  60

Ile Thr Gly Met Gly Leu Val Ser Val Phe Gly Ser Asp Val Asp Ala
65                  70                  75                  80

Tyr Tyr Glu Lys Leu Leu Ser Gly Glu Ser Gly Ile Ser Leu Ile Asp
                85                  90                  95

Arg Phe Asp Ala Ser Lys Phe Pro Thr Arg Phe Gly Gly Gln Ile Arg
            100                 105                 110

Gly Phe Asn Ala Thr Gly Tyr Ile Asp Gly Lys Asn Asp Arg Arg Leu
        115                 120                 125

Asp Asp Cys Leu Arg Tyr Cys Ile Val Ala Gly Lys Lys Ala Leu Glu
130                 135                 140

Asn Ser Asp Leu Gly Gly Asp Ser Leu Ser Lys Ile Asp Lys Glu Arg
145                 150                 155                 160

Ala Gly Val Leu Val Gly Thr Gly Met Gly Gly Leu Thr Val Phe Ser
                165                 170                 175

Asp Gly Val Gln Asn Leu Ile Glu Lys Gly His Arg Lys Ile Ser Pro
            180                 185                 190

Phe Phe Ile Pro Tyr Ala Ile Thr Asn Met Gly Ser Ala Leu Leu Ala
        195                 200                 205
```

-continued

```
Ile Asp Leu Gly Leu Met Gly Pro Asn Tyr Ser Ile Ser Thr Ala Cys
    210                 215                 220
Ala Thr Ser Asn Tyr Cys Phe Tyr Ala Ala Asn His Ile Arg Arg
225                 230                 235                 240
Gly Glu Ala Asp Leu Met Ile Ala Gly Thr Glu Ala Ala Ile Ile
                245                 250                 255
Pro Ile Gly Leu Gly Gly Phe Val Ala Cys Arg Ala Leu Ser Gln Arg
            260                 265                 270
Asn Asp Asp Pro Gln Thr Ala Ser Arg Pro Trp Asp Lys Asp Arg Asp
                275                 280                 285
Gly Phe Val Met Gly Glu Gly Ala Gly Val Leu Val Met Glu Ser Leu
290                 295                 300
Glu His Ala Met Lys Arg Gly Ala Pro Ile Ile Ala Glu Tyr Leu Gly
305                 310                 315                 320
Gly Ala Val Asn Cys Asp Ala Tyr His Met Thr Asp Pro Arg Ala Asp
                325                 330                 335
Gly Leu Gly Val Ser Ser Cys Ile Glu Ser Ser Leu Glu Asp Ala Gly
            340                 345                 350
Val Ser Pro Glu Glu Val Asn Tyr Ile Asn Ala His Ala Thr Ser Thr
        355                 360                 365
Leu Ala Gly Asp Leu Ala Glu Ile Asn Ala Ile Lys Lys Val Phe Lys
370                 375                 380
Asn Thr Lys Asp Ile Lys Ile Asn Ala Thr Lys Ser Met Ile Gly His
385                 390                 395                 400
Cys Leu Gly Ala Ser Gly Gly Leu Glu Ala Ile Ala Thr Ile Lys Gly
                405                 410                 415
Ile Thr Thr Gly Trp Leu His Pro Ser Ile Asn Gln Phe Asn Pro Glu
            420                 425                 430
Pro Ser Val Glu Phe Asp Thr Val Ala Asn Lys Lys Gln Gln His Glu
        435                 440                 445
Val Asn Val Ala Ile Ser Asn Ser Phe Gly Phe Gly Gly His Asn Ser
    450                 455                 460
Val Val Ala Phe Ser Ala Phe Lys Pro
465                 470

<210> SEQ ID NO 17
<211> LENGTH: 465
<212> TYPE: PRT
<213> ORGANISM: Cuphea pulcherima
<220> FEATURE:
<221> NAME/KEY: MISC_FEATURE
<223> OTHER INFORMATION: KASI

<400> SEQUENCE: 17

Met His Ser Leu Gln Ser Pro Ser Leu Arg Ala Ser Pro Leu Asp Pro
1               5                   10                  15
Phe Arg Pro Lys Ser Ser Thr Val Arg Pro Leu His Arg Ala Ser Ile
            20                  25                  30
Pro Asn Val Arg Ala Ala Ser Pro Thr Val Ser Ala Pro Lys Arg Glu
        35                  40                  45
Thr Asp Pro Lys Lys Arg Val Val Ile Thr Gly Met Gly Leu Val Ser
    50                  55                  60
Val Phe Gly Ser Asp Val Asp Ala Tyr Tyr Asp Lys Leu Leu Ser Gly
65                  70                  75                  80
Glu Ser Gly Ile Gly Pro Ile Asp Arg Phe Asp Ala Ser Lys Phe Pro
                85                  90                  95
```

Thr Arg Phe Gly Gly Gln Ile Arg Gly Phe Asn Ser Met Gly Tyr Ile
            100                 105                 110

Asp Gly Lys Asn Asp Arg Arg Leu Asp Asp Cys Leu Arg Tyr Cys Ile
        115                 120                 125

Val Ala Gly Lys Lys Ser Leu Glu Asp Ala Asp Leu Gly Ala Asp Arg
130                 135                 140

Leu Ser Lys Ile Asp Lys Glu Arg Ala Gly Val Leu Gly Thr Gly
145                 150                 155                 160

Met Gly Gly Leu Thr Val Phe Ser Asp Gly Val Gln Ser Leu Ile Glu
                165                 170                 175

Lys Gly His Arg Lys Ile Thr Pro Phe Phe Ile Pro Tyr Ala Ile Thr
            180                 185                 190

Asn Met Gly Ser Ala Leu Leu Ala Ile Glu Leu Gly Leu Met Gly Pro
        195                 200                 205

Asn Tyr Ser Ile Ser Thr Ala Cys Ala Thr Ser Asn Tyr Cys Phe His
    210                 215                 220

Ala Ala Ala Asn His Ile Arg Arg Gly Glu Ala Asp Leu Met Ile Ala
225                 230                 235                 240

Gly Gly Thr Glu Ala Ala Ile Ile Pro Ile Gly Leu Gly Gly Phe Val
                245                 250                 255

Ala Cys Arg Ala Leu Ser Gln Arg Asn Asp Asp Pro Gln Thr Ala Ser
            260                 265                 270

Arg Pro Trp Asp Lys Asp Arg Asp Gly Phe Val Met Gly Glu Gly Ala
        275                 280                 285

Gly Val Leu Val Leu Glu Ser Leu Glu His Ala Met Lys Arg Gly Ala
    290                 295                 300

Pro Ile Ile Ala Glu Tyr Leu Gly Gly Ala Ile Asn Cys Asp Ala Tyr
305                 310                 315                 320

His Met Thr Asp Pro Arg Ala Asp Gly Leu Gly Val Ser Ser Cys Ile
                325                 330                 335

Glu Ser Ser Leu Glu Asp Ala Gly Val Ser Pro Glu Glu Val Asn Tyr
            340                 345                 350

Ile Asn Ala His Ala Thr Ser Thr Leu Ala Gly Asp Leu Ala Glu Ile
        355                 360                 365

Asn Ala Ile Lys Lys Val Phe Lys Asn Thr Lys Asp Ile Lys Ile Asn
    370                 375                 380

Ala Thr Lys Ser Met Ile Gly His Cys Leu Gly Ala Ser Gly Gly Leu
385                 390                 395                 400

Glu Ala Ile Ala Thr Ile Lys Gly Ile Asn Thr Gly Trp Leu His Pro
                405                 410                 415

Ser Ile Asn Gln Phe Asn Pro Glu Pro Ser Val Glu Phe Asp Thr Val
            420                 425                 430

Ala Asn Lys Lys Gln Gln His Glu Val Asn Val Ala Ile Ser Asn Ser
        435                 440                 445

Phe Gly Phe Gly Gly His Asn Ser Val Val Ala Phe Ser Ala Phe Lys
    450                 455                 460

Pro
465

<210> SEQ ID NO 18
<211> LENGTH: 466
<212> TYPE: PRT
<213> ORGANISM: Cuphea avigera
<220> FEATURE:

<221> NAME/KEY: MISC_FEATURE
<223> OTHER INFORMATION: mitochondrial KAS

<400> SEQUENCE: 18

```
Met Val Phe Leu Pro Trp Arg Lys Met Leu Cys Pro Ser Gln Tyr Arg
1               5                   10                  15

Phe Leu Arg Pro Leu Ser Ser Ser Thr Thr Phe Asp Pro Arg Arg Val
                20                  25                  30

Val Val Thr Gly Leu Gly Met Val Thr Pro Leu Gly Cys Gly Val Asn
            35                  40                  45

Thr Thr Trp Lys Gln Leu Ile Glu Gly Lys Cys Gly Ile Arg Ala Ile
        50                  55                  60

Ser Leu Glu Asp Leu Lys Met Asp Ala Phe Asp Ile Asp Thr Gln Ala
65                  70                  75                  80

Tyr Val Phe Asp Gln Leu Thr Ser Lys Val Ala Thr Val Pro Thr
                85                  90                  95

Gly Val Asn Pro Gly Glu Phe Asn Glu Asp Leu Trp Phe Asn Gln Lys
                100                 105                 110

Glu His Arg Ala Ile Ala Arg Phe Ile Ala Tyr Ala Leu Cys Ala Ala
            115                 120                 125

Asp Glu Ala Leu Lys Asp Ala Asn Trp Glu Pro Thr Glu Pro Glu Glu
130                 135                 140

Arg Glu Met Thr Gly Val Ser Ile Gly Gly Thr Gly Ser Ile Ser
145                 150                 155                 160

Asp Val Leu Asp Ala Gly Arg Met Ile Cys Glu Lys Lys Leu Arg Arg
                165                 170                 175

Leu Ser Pro Phe Phe Ile Pro Arg Ile Leu Ile Asn Met Ala Ser Gly
            180                 185                 190

His Val Ser Met Lys Tyr Gly Phe Gln Gly Pro Asn His Ala Ala Val
        195                 200                 205

Thr Ala Cys Ala Thr Gly Ala His Ser Ile Gly Asp Ala Ala Arg Met
210                 215                 220

Ile Gln Phe Gly Asp Ala Asp Val Met Val Ala Gly Gly Thr Glu Ser
225                 230                 235                 240

Ser Ile Asp Ala Leu Ser Ile Ala Gly Phe Cys Arg Ser Arg Ala Leu
                245                 250                 255

Thr Thr Lys Tyr Asn Ser Cys Pro Gln Glu Ala Ser Arg Pro Phe Asp
            260                 265                 270

Thr Asp Arg Asp Gly Phe Val Ile Gly Glu Gly Ser Gly Val Leu Val
        275                 280                 285

Leu Glu Glu Leu Asp His Ala Arg Lys Arg Gly Ala Lys Met Tyr Ala
290                 295                 300

Glu Phe Cys Gly Tyr Gly Met Ser Gly Asp Ala His His Ile Thr Gln
305                 310                 315                 320

Pro His Ser Asp Gly Arg Gly Ala Ile Leu Ala Met Thr Arg Ala Leu
                325                 330                 335

Lys Gln Ser Asn Leu His Pro Asp Gln Val Asp Tyr Val Asn Ala His
            340                 345                 350

Ala Thr Ser Thr Ser Leu Gly Asp Ala Ile Glu Ala Lys Ala Ile Lys
        355                 360                 365

Thr Val Phe Ser Asp His Ala Met Ser Gly Ser Leu Ala Leu Ser Ser
370                 375                 380

Thr Lys Gly Ala Ile Gly His Leu Leu Gly Ala Ala Gly Ala Val Glu
385                 390                 395                 400
```

```
Ala Ile Phe Ser Ile Leu Ala Ile Lys Asn Gly Leu Ala Pro Leu Thr
                405                 410                 415

Leu Asn Val Ala Arg Pro Asp Pro Val Phe Thr Glu Arg Phe Val Pro
            420                 425                 430

Leu Thr Ala Ser Lys Glu Met His Val Arg Ala Ala Leu Ser Asn Ser
        435                 440                 445

Phe Gly Phe Gly Gly Thr Asn Thr Thr Leu Leu Phe Thr Ser Pro Pro
    450                 455                 460

Gln Asn
465

<210> SEQ ID NO 19
<211> LENGTH: 402
<212> TYPE: PRT
<213> ORGANISM: Cuphea avigera
<220> FEATURE:
<221> NAME/KEY: MISC_FEATURE
<223> OTHER INFORMATION: KASIII

<400> SEQUENCE: 19

Met Ala Asn Ala Tyr Gly Phe Val Gly Ser Ser Val Pro Thr Val Gly
1               5                   10                  15

Arg Ala Ala Gln Phe Gln Gln Met Gly Ser Gly Phe Cys Ser Val Asp
            20                  25                  30

Phe Ile Ser Lys Arg Val Phe Cys Cys Ser Ala Val Gln Gly Ala Asp
        35                  40                  45

Lys Pro Ala Ser Gly Asp Ser Arg Ala Glu Tyr Arg Thr Pro Arg Leu
    50                  55                  60

Val Ser Arg Gly Cys Lys Leu Ile Gly Ser Gly Ser Ala Ile Pro Thr
65                  70                  75                  80

Leu Gln Val Ser Asn Asp Asp Leu Ala Lys Ile Val Asp Thr Asn Asp
                85                  90                  95

Glu Trp Ile Ser Val Arg Thr Gly Ile Arg Asn Arg Arg Val Leu Thr
            100                 105                 110

Gly Lys Asp Ser Leu Thr Asn Leu Ala Thr Glu Ala Ala Arg Lys Ala
        115                 120                 125

Leu Glu Met Ala Gln Val Asp Ala Glu Asp Val Asp Met Val Leu Met
    130                 135                 140

Cys Thr Ser Thr Pro Glu Asp Leu Phe Gly Ser Ala Pro Gln Ile Gln
145                 150                 155                 160

Lys Ala Leu Gly Cys Lys Lys Asn Pro Leu Ser Tyr Asp Ile Thr Ala
                165                 170                 175

Ala Cys Ser Gly Phe Val Leu Gly Leu Val Ser Ala Ala Cys His Ile
            180                 185                 190

Arg Gly Gly Gly Phe Asn Asn Val Leu Val Ile Gly Ala Asp Ser Leu
        195                 200                 205

Ser Arg Tyr Val Asp Trp Thr Asp Arg Gly Thr Cys Ile Leu Phe Gly
    210                 215                 220

Asp Ala Ala Gly Ala Val Leu Val Gln Ser Cys Asp Ala Glu Glu Asp
225                 230                 235                 240

Gly Leu Phe Ala Phe Asp Leu His Ser Asp Gly Asp Gly Gln Arg His
                245                 250                 255

Leu Arg Ala Val Ile Thr Glu Asn Glu Thr Asp His Ala Val Gly Thr
            260                 265                 270

Asn Gly Ser Val Ser Asp Phe Pro Pro Arg Arg Ser Ser Tyr Ser Cys
```

```
              275                 280                 285
Ile Gln Met Asn Gly Lys Glu Val Phe Arg Phe Ala Cys Arg Ser Val
        290                 295                 300
Pro Gln Ser Ile Glu Leu Ala Leu Gly Lys Ala Gly Leu Asn Gly Ser
305                 310                 315                 320
Asn Ile Asp Trp Leu Leu His Gln Ala Asn Gln Arg Ile Ile Asp
                325                 330                 335
Ala Val Ala Thr Arg Leu Glu Val Pro Gln Glu Arg Val Ile Ser Asn
            340                 345                 350
Leu Ala Asn Tyr Gly Asn Thr Ser Ala Ala Ser Ile Pro Leu Ala Leu
                355                 360                 365
Asp Glu Ala Val Arg Gly Gly Lys Val Lys Pro Gly His Leu Ile Ala
        370                 375                 380
Thr Ala Gly Phe Gly Ala Gly Leu Thr Trp Gly Ser Ala Ile Val Arg
385                 390                 395                 400
Trp Gly
```

<210> SEQ ID NO 20
<211> LENGTH: 11
<212> TYPE: PRT
<213> ORGANISM: Artificial Sequence
<220> FEATURE:
<223> OTHER INFORMATION: HA Epitope TAG

<400> SEQUENCE: 20

```
Thr Met Tyr Pro Tyr Asp Val Pro Asp Tyr Ala
1               5                   10
```

<210> SEQ ID NO 21
<211> LENGTH: 1632
<212> TYPE: DNA
<213> ORGANISM: Cuphea palustris
<220> FEATURE:
<221> NAME/KEY: misc_feature
<223> OTHER INFORMATION: KASIV

<400> SEQUENCE: 21

```
atggcggccg ccgcttccat ggttgcgtcc ccactctgta cgtggctcgt agccgcttgc     60
atgtccactt ccttcgacaa cgacccacgt tccccgtcca tcaagcgtct ccccgccgg    120
aggaggactc tctcccaatc ctccctccgc ggcggatcca ccttccaatg cctcgtcacc    180
tcatacatcg acccttgcaa tcagttctcc tcctccgcct cccttagctt cctcggggat    240
aacggattcg catcccttt cggatccaag cctttccggt ccaatcgcgg ccaccggagg    300
ctcggccgtg cttcccattc cggggaggcc atggccgtgg ctttggaacc tgcacaggaa    360
gtcgccacga agaagaaacc tcttgtcaag caaaggcgag tagttgttac aggaatgggc    420
gtggtgactc ctctaggcca tgaacctgat gtttactaca caatctcct agatggagta    480
agcggcataa gtgagataga ggccttcgac tgcactcagt ttcccacgag aattgccgga    540
gagatcaagt cttttccac agatggatgg gtggcccaa agctctccaa gaggatggac    600
aagttcatgc tttacttgtt gactgctggc aagaaagcat tagcggatgg tggaatcacc    660
gatgatgtga tgaaagagct tgataaaaga agtgtggag ttctcattgg ctccggattg    720
ggcggcatga agctgttcag tgattccatt gaagctctga ggatttcata taagaagatg    780
aatcccttt gtgtaccttt tgctactaca aatatgggat cagctatgct tgcaatggac    840
ttgggatgga tgggtcctaa ctactcgata tcaactgcct gtgctacaag taatttctgt    900
```

| atactgaatt ctgcaaatca catagtcaga ggcgaagctg acatgatgct tgtggtggc | 960 |
| tcggatgcgg tcattatacc tattggtttg ggaggttttg tggcgtgccg agctttgtca | 1020 |
| cagaggaata atgaccctac caaagcttcg agaccatggg acagtaatcg tgatggattt | 1080 |
| gtaatgggcg aaggagctgg agtgttactt ctcgaggagt tagagcatgc aaagaaaaga | 1140 |
| ggtgccacca tttatgcgga attttaggg ggcagtttca cttgcgatgc ctaccatatg | 1200 |
| accgagcctc accctgaagg tgctggagtg atcctctgca tagagaaggc cttggctcag | 1260 |
| gccggagtct ctagagaaga cgtaaattac ataaatgcgc atgcaacttc cactcctgct | 1320 |
| ggagatatca aggaatacca agctctcgca cactgcttcg gccaaaacag tgagctgaga | 1380 |
| gtgaattcca ctaaatcgat gatcggtcat cttattggag cagctggtgg tgtagaagca | 1440 |
| gttaccgtag ttcaggcgat aaggactggg tggatccatc caaatcttaa tttggaggac | 1500 |
| ccggacaaag ccgtggatgc aaaagtgctc gtaggaccta agaaggagag actaaatgtc | 1560 |
| aaggtcggtt tgtccaattc atttgggttc ggtggtcata actcgtccat actcttcgcc | 1620 |
| ccttacaatt ag | 1632 |

<210> SEQ ID NO 22
<211> LENGTH: 1479
<212> TYPE: DNA
<213> ORGANISM: Cinnamomum camphora
<220> FEATURE:
<221> NAME/KEY: misc_feature
<223> OTHER INFORMATION: KASIV

<400> SEQUENCE: 22

| atggcaatga tggcaggttc ttgttccaat ttggtgattg gaaacagaga attgggtggg | 60 |
| aatgggcctt ctttgcttca ctacaatggc ctcagaccat ggaaaatat tcaaacagcc | 120 |
| tcagctgtga aaaagccaaa tgggttattt gcatcttcta cagctcgaaa atccaaagct | 180 |
| gtcagagcca tggtattgcc cactgtaaca gctccaaaac gcgaaaaaga tcccaagaag | 240 |
| cggattgtaa taacaggaat gggcctggtt tccgtctttg gaaatgacat tgatacattt | 300 |
| tatagtaaac tactggaagg agagagcggg attggcccaa tcgacagatt tgatgcttct | 360 |
| tccttctcag tgagatttgc tggtcagatt cacaatttct catccaaagg atacattgat | 420 |
| gggaagaatg atcgtcggct agatgactgc tggaggtatt gccttgtggc tggaagaaga | 480 |
| gcccttgaag atgccaatct ggaccagag gtattggaaa aaatgaccg atctcgaata | 540 |
| ggggtgctga tagggacagg aatgggtggg ttgtcagcct ttagcaatgg agttgagtct | 600 |
| ctgatccaga agggctacaa gaaaatcact ccattttta ttccttactc catcaccaat | 660 |
| atgggctctg ctctttagc aatcgacacg ggcgtaatgg gaccaaacta ctccatttca | 720 |
| acagcatgtg caaccgcaaa ctattgcttc catgctgctg caaatcatat aagaagggt | 780 |
| gaagctgaaa tcatggtgac tggagggaca gaggcagcag tctcagctac tggagttggc | 840 |
| ggattcatag catgtagagc cttatcgcac aggaatgatg agccccagac ggcctcgaga | 900 |
| ccatgggata aagatcggga tggtttcgtc atgggcgaag gcgctggtgt gctggtgatg | 960 |
| gagagcttgc atcatgcaag aaagagagga gcaaacataa ttgcagagta tttaggagga | 1020 |
| gcagtaacat gtgatgcaca tcacatgaca gatcctcgag ctgatggtct cggggtttct | 1080 |
| tcttgcataa ccaagagctt agaagatgca ggagtctccc cagaagaggt gaactatgtg | 1140 |
| aatgctcatg caacatcaac acttgcagga gatttagcag aggttaatgc cataaagaag | 1200 |
| gtcttcaagg acacatctga aatgaaaatg aatggaacta agtcaatgat tggacactgt | 1260 |

```
cttggagcag ctggtggatt agaagccatt gcgaccatca aagctatcaa tactggctgg      1320
ctacatccaa ccatcaatca atttaacata gaaccagcgg taactatcga cacggtccca      1380
aatgtgaaga aaaagcatga tatccatgtt ggcatctcta actcatttgg ctttggtggg      1440
cacaactcgg tggtcgtttt tgctcccttc atgccatga                              1479
```

<210> SEQ ID NO 23
<211> LENGTH: 1449
<212> TYPE: DNA
<213> ORGANISM: Cinnamonum camphora
<220> FEATURE:
<221> NAME/KEY: misc_feature
<223> OTHER INFORMATION: KASI

<400> SEQUENCE: 23

```
atgcaaatcc tccaaacccc atcatcatca tcgtcttctc tccgcatgtc gtccatggaa        60
tctctctctc tcacccctaa atctctccct ctcaaaaccc ttcttcccct tcgtcctcgc       120
cctaaaaacc tctccagacg caaatcccaa aaccctagac ccatctcctc ctcttcctcc       180
cccgagagag agacggatcc caagaagcga gtcgtcatca ccgggatggg cctcgtctcc       240
gtcttcggca acgatgtcga tgcctactac gaccgcctcc tctcgggaga gagcggcatc       300
gcccccatcg atcgcttcga cgcctccaag ttccccacca gattcgccgg tcagatccga       360
gggttcacct ccgacggcta cattgacggg aagaacgacc gccggttaga cgattgtctc       420
agatactgta ttgttagtgg gaagaaggcg ctcgagaatg ccggcctcgg accccatctc       480
atggacggaa agattgacaa ggagagagct ggtgtgcttg tcgggacagg catgggtggt       540
cttacagttt tctctaatgg ggtccagact ctacatgaga aaggttacag gaaaatgact       600
ccgtttttca tcccttatgc cataacaaac atgggttctg ccttgcttgc aattgaactt       660
ggttttatgg gcccaaacta ttctatctca actgcatgtg ctacctccaa ttattgcttt       720
tatgctgctg ctaaccatat acggagaggt gaggctgatc tgatgcttgc tggtggaact       780
gaagctgcaa ttattcctat tggattagga ggctttgttg catgtagagc tttatcacag       840
agaaatgatg accccagac  agcttcaaga ccatgggaca agatcgaga  cggttttgtt       900 atgggtgaag gtgctggagt attggtaatg gagagcttgg agcatgctat gaaacgtgat       960
gcaccaatta ttgctgagta tttaggaggt gcagtgaact gtgatgcgta tcatatgacg      1020
gatcctagag ctgatgggct cggggtttca acatgcatag aaagaagtct tgaagatgct      1080
ggtgtggcac ctgaagaggt taactacata aatgcacatg caacttccac tcttgcagga      1140
gacctggctg aggtgaatgc gatcaaaaag gtttttacaa acacttcaga gatcaaaatc      1200
aatgcaacca gtctatgat  agggcactgc cttggagcgg ccgggggggtt agaagccatt      1260 gccacaatca aagcaataaa tactggttgg ctgcacccct ctataaacca atttaatcca      1320
gagccctctg ttgagtttga cactgtagca aataaaaagc agcagcatga agtgaatgtt      1380
gccatttcca actctttcgg gtttggcgga cacaactcag tcgtggtgtt ttcggcattc      1440
aagccttga                                                              1449
```

<210> SEQ ID NO 24
<211> LENGTH: 1395
<212> TYPE: DNA
<213> ORGANISM: Umbellularia californica
<220> FEATURE:
<221> NAME/KEY: misc_feature
<223> OTHER INFORMATION: KASI

<400> SEQUENCE: 24

```
atggaatctc tctctctcac ccctaaatct ctccctctca aaaccttct tcccttcgt      60 cctcgcccta aaaacctctc cagacgcaaa tcccaaaacc ctaaacccat ctcctcctct    120
tcctccccgg agagagagac ggatcccaag aagcgagtcg tcatcaccgg gatgggcctc    180
gtctccgtct tcggcaacga cgtcgatgcc tactacgacc gcctcctctc cggagagagc    240
ggcatcgccc ccatcgatcg cttcgacgcc tccaagttcc ccaccagatt cgccggtcag    300
atccgagggt tcacctccga cggctacatt gacgggaaga cgaccgccg gttagacgat     360 tgtctcagat actgtatcgt tagtgggaag aaggcgctcg agaatgccgg cctcggaccc    420
gatctcatgg acgaaagat tgacaaggag cgagctggtg tgcttgtcgg acaggcatg     480 ggtggtctta cagttttctc taatggggtt cagactctcc atgagaaagg ttacaggaaa    540
atgactccgt ttttcatccc ttatgccata acaaacatgg ttctgccctt gcttgcaatt    600
gaccttggtt ttatgggccc aaactattct atctcaactg catgtgctac ctccaattat    660
tgcttttatg ctgctgctaa ccatatacga gaggtgagg ctgatgtgat gcttgctggt     720
ggaactgaag ctgcaattat tcctattggc ttaggaggct ttgttgcatg tagagcttta    780
tcacagcgaa atgatgaccc ccagacagct tcaagaccat gggacaaaga tcgagacggt    840
tttgttatgg gtgaaggtgc tggagtattg gtaatggaga gcttggagca tgctatgaaa    900
cgtgatgcac caattattgc tgagtattta ggaggtgcag tgaactgtga tgcgtatcat    960
atgacggatc ctagagctga tgggctcggg gtttcaacat gcatagaaag aagtcttgaa    1020
gatgctggtg tggcacctga agaggttaac tacataaatg cacatgcaac ttccacactt    1080
gcaggtgacc tggccgaggt gaatgccatc aaaaaggttt ttacaaacac ttcagagatc    1140
aaaatcaatg caaccaagtc tatgataggg cactgccttg gagcggccgg gggttttagaa   1200 gccattgcca caatcaaagc aataaatact ggttggctgc acccttctat aaaccaattt    1260
aatccagagc cctctgttga gtttgacact gtagcaaata aaaagcagca gcatgaagtg    1320
aatgttgcca tttccaactc tttcgggttt ggtggacaca actcggtcgt ggtgttttcg    1380
gcattcaagc cttga                                                      1395

<210> SEQ ID NO 25
<211> LENGTH: 1419
<212> TYPE: DNA
<213> ORGANISM: Umbellularia californica
<220> FEATURE:
<221> NAME/KEY: misc_feature
<223> OTHER INFORMATION: KASIV

<400> SEQUENCE: 25
atgacgcaaa ccctcatctg ccatcctcc atggaaaccc tctctcttac caaacaatcc      60
catttcagac tcaggctacc cactcctcct cacatcagac gcggcggcgg ccatcgccat    120 cctcctcct tcatctccgc ctccgccgcc cctaggagag agaccgatcc gaagaagaga    180
gtcgtcatca cgggaatggg cctcgtctcc gtcttcggca ccaacgtcga tgtctactac    240
gatcgcctcc tcgccggcga gagcggcgtt ggcactatcg atcgcttcga cgcgtcgatg    300
ttcccgacga gattcggcgg ccagatccgg aggttcacgt cggagggta catcgacggg    360 aagaacgacc ggcggctgga tgactacctc cggtactgcc tcgtcagcgg gaagaaggcg    420
atcgagagtg ctggcttcga tctccataac atcaccaaca agattgacaa ggagcgagct    480
gggatacttg ttgggtcagg catgggcggt cttaaagttt tctctgatgg tgttgagtct    540
cttatcgaga aaggttacag gaaaataagt ccattttca tccccttatat gataccaaac    600
```

```
atgggttctg ctttgcttgg aattgacctt ggtttcatgg gaccaaacta ctcaatttca      660
actgcttgtg ctacgtcaaa ttattgcatt tatgctgctg caaatcatat ccgacaaggt      720
gatgccgacc taatggttgc tggtggaact gaggctccaa ttattccaat tggcttaggg      780
ggctttgtag catgtagagc tttgtcaaca agaaatgatg atccccagac agcttcaagg      840
ccatgggaca tagaccgaga tggttttgtt atgggcgaag agctggaat attggtattg      900 gagagcttgg aacatgcaat gaaacgtgat gcaccaattc ttgctgagta tttaggaggt      960
gcagttaact gtgatgctca tcatatgaca gatcctcgag ctgatgggct tggggtttca     1020
acatgcattg aaagcagtct tgaagatgcc ggcgtggcag cagaagaggt taactatata     1080
aatgcacacg cgacttcaac acctacaggt gacctggctg agatgaaggc tataaaaaat     1140
gtatttagga acacttctga gatcaaaatc aatgcaacca gtctatgat tgggcattgc     1200 cttggagcgt ctgggggct agaagccatt gccacattga aagcgattac aactggttgg     1260
cttcatccaa ctataaacca atttaatcca gagccttctg ttgactttga tacggtggca     1320
aagaaaaaga agcagcatga agttaatgtt gccatttcaa actcttttgg attcggagga     1380
cacaactcag tgttggtgtt ttcggcattc aagccttga                             1419

<210> SEQ ID NO 26
<211> LENGTH: 1578
<212> TYPE: DNA
<213> ORGANISM: Cuphea wrightii
<220> FEATURE:
<221> NAME/KEY: misc_feature
<223> OTHER INFORMATION: KASAI

<400> SEQUENCE: 26
atggcttccg cggcattcac catgtcggcg tgccccgcga tgactggcag ggcccctggg       60
gcacgtcgct ccggacggcc agtcgccacc cgcctgaggt acgtattcca gtgcctggtg      120
gccagctgca tcgaccccctg cgaccagtac cgcagcagcg ccagcctgag cttcctgggc      180
gacaacggct cgccagcct gttcggcagc aagcccttca tgagcaaccg cggccaccgc      240
cgcctgcgcc gcgccagcca cagcggcgag gccatggccg tggccctgca gcccgcccag      300
gaggccggca ccaagaagaa gcccgtgatc aagcagcgcc gcgtggtggt gaccggcatg      360
ggcgtggtga ccccctggg ccacgagccc gacgtgttct acaacaacct gctggacggc      420
gtgagcggca tcagcgagat cgagaccttc gactgcaccc agttccccac ccgcatcgcc      480
ggcgagatca agagcttcag caccgacggc tgggtggccc caagctgag caagcgcatg      540 gacaagttca tgctgtacct gctgaccgcc ggcaagaagg ccctggccga cggcggcatc      600
accgacgagg tgatgaagga gctggacaag cgcaagtgcg cgtgctgat cggcagcggc      660 atgggcggca tgaaggtgtt caacgacgcc atcgaggccc tgcgcgtgag ctacaagaag      720
atgaacccct tctgcgtgcc cttcgccacc accaacatgg cagcgccat gctggccatg      780 gacctgggct ggatgggccc caactacagc atcagcaccg cctgcgccac cagcaacttc      840
tgcatcctga acgccgccaa ccacatcatc cgcggcgagg ccgacatgat gctgtgcggc      900
ggcagcgacg ccgtgatcat ccccatcggc ctgggcggct tcgtggcctg ccgcgccctg      960
agccagcgca acagcgaccc caccaaggcc agccgcccct gggacagcaa ccgcgacggc     1020
ttcgtgatgg gcgagggcgc cggcgtgctg ctgctggagg agctggagca cgccaagaag     1080
cgcggcgcca ccatctacgc cgagttcctg ggcggcagct tcacctgcga cgcctaccac     1140
atgaccgagc cccaccccga gggcgccggc gtgatcctgt gcatcgagaa ggccctggcc     1200
```

| | |
|---|---|
| caggccggcg tgagcaagga ggacgtgaac tacatcaacg cccacgccac cagcaccagc | 1260 |
| gccggcgaca tcaaggagta ccaggccctg gcccgctgct tcggccagaa cagcgagctg | 1320 |
| cgcgtgaaca gcaccaagag catgatcggc cacctgctgg gcgccgccgg cggcgtggag | 1380 |
| gccgtgaccg tggtgcaggc catccgcacc ggctggattc accccaacct gaacctggag | 1440 |
| gaccccgaca aggccgtgga cgccaagctg ctggtgggcc caagaagga gcgcctgaac | 1500 |
| gtgaaggtgg gcctgagcaa cagcttcggc ttcggcggcc acaacagcag catcctgttc | 1560 |
| gcccctgca acgtgtga | 1578 |

<210> SEQ ID NO 27
<211> LENGTH: 1515
<212> TYPE: DNA
<213> ORGANISM: Cuphea avigera
<220> FEATURE:
<221> NAME/KEY: misc_feature
<223> OTHER INFORMATION: KASIVb

<400> SEQUENCE: 27

| | |
|---|---|
| atggcggccg cttcttgcat ggctgcgtcc cctttctgta cgtcgctcgt ggctgcatgc | 60 |
| atgtcgactt catccgacaa cgacccatgt ccccttccc gccgcggatc caccttccaa | 120 |
| tgctacatcg gggataacgg attcggatcg aagcctcccc gttcaaatcg tggccacctg | 180 |
| aggctcggcc gcacttcaca ttccggagag gtgatggctg tggctatgca atctgcacaa | 240 |
| gaagtctcca caaaggagaa acctgctacc aagcaaaggc gagttgttgt cacgggtatg | 300 |
| ggtgtggtga ctgctctagg ccatgacccc gatgtttact acaacaatct cctagacgga | 360 |
| gtaagcggca taagcgagat agaaaacttt gactgttctc agcttcccac gagaattgcc | 420 |
| ggagagatca agtcttttc tgcagatggg tgggtggccc cgaagttctc caggaggatg | 480 |
| gacaagttta tgctttacat tctgactgca ggcaagaaag cattagtaga tggtggaatc | 540 |
| actgaagatg tgatgaaaga gctcgataaa agaaagtgtg gagttctcat ggctccgga | 600 |
| ttgggcggta tgaaggtatt tagcgagtcc attgaagctc tgaggacttc atataagaag | 660 |
| atcagtccct tttgtgtacc tttttctacc acgaatatgg gatccgctat tcttgcaatg | 720 |
| gacttgggat ggatgggccc taactattcg atatcgactg cctgtgcaac aagtaacttc | 780 |
| tgtatactga tgctgcgaa ccacataacc aaaggcgaag cagacatgat gctttgtggt | 840 |
| ggctcggatt cggtcatttt acctattggt atgggaggtt tcgtagcatg ccgagctttg | 900 |
| tcacagagga ataatgaccc taccaaagct cgagaccat gggacagtaa tcgtgatgga | 960 |
| tttgtgatgg gagaaggtgc tggagttta cttctcgagg agttagagca tgcaaagaaa | 1020 |
| agaggcgcaa ccatttatgc ggaatttctt ggtgggagtt tcacttgcga tgcctaccac | 1080 |
| atgaccgagc ctcaccctga aggagctgga gtgatcctct gcatagagaa ggccttggct | 1140 |
| cagtccggag tctcgaggga agacgtaaat tacataaatg cgcatgcaac ttccactccc | 1200 |
| gctggagata tcaaggaata ccaagctctc gcccactgtt tcggcaaaaa cagtgagtta | 1260 |
| agagtgaatt ccaccaagtc gatgatcggt caccttcttg gaggagccgg tggcgtagaa | 1320 |
| gcagttacag tcgttcaggc aataaggact ggatggatcc atccaaatat taatttggac | 1380 |
| gacccggacg aaggcgtgga tgcaaaactg ctcgtcggcc ctaagaagga gaaactgaag | 1440 |
| gtcaaggtcg gtttgtccaa ttcattcggg ttcggcggcc ataactcatc catactcttt | 1500 |
| gccccatgca attag | 1515 |

<210> SEQ ID NO 28
<211> LENGTH: 1539
<212> TYPE: DNA
<213> ORGANISM: Cuphea paucipetala
<220> FEATURE:
<221> NAME/KEY: misc_feature
<223> OTHER INFORMATION: KASIVb

<400> SEQUENCE: 28

```
atggcggccg cttcatcaat ggttgcctcc ccattctcta cgtccctcgt agccgcctgc      60
atgtccactt cattcgacaa cgacccacgt tccctttccc acaaccgcat ccgcctccgc     120
ggatccacct tccaatgcct cggggatatc ggattcgctt ccctcatcgg atccaagcct     180
ccgcgttcaa atcgcaacca ccggaggctc ggccgcactt cccattccgg ggaggtcatg     240
gctgtggcta tgcaacctgc acatgaagct tccacaaaga ataaacctgt taccaagcaa     300
aggcgagtag ttgtgacagg tatgggcgtg gcgactcctc taggccatga ccccgatgtt     360
tactacaaca atctcctaga cggagtaagt ggcataagtc agatagagaa cttcgactgc     420
actcagtttc ccacgagaat tgccggagag atcaagtctt tctccacaga agggtatgtg     480
atcccgaagt tcgccaagag gatggacaag ttcatgcttt acttgctgac tgcaggcaag     540
aaaagcattag aagatggtgg aatcactgaa gatgtgatga agagctcga taaaagaaag     600
tgtggagttc tcattggctc cggaatgggc ggtatgaaga taatcaacga ttccattgca     660
gctctgaatg tttcatataa gaagatgact ccctttgtg taccctttc caccacaaat      720
atgggatccg ctatgcttgc gatagacttg ggatggatgg cccgaacta ttcgatatca      780
actgcctgtg caacaagtaa ctactgtata ctgaatgctg cgaaccacat agtcagaggc     840
gaagcagata tgatgctttg tggtggctcg gatgcggtca ttatacctgt tggtttggga     900
ggtttcgtag catgccgagc tttgtcacag aggaacaatg accctaccaa agcttcgaga     960
ccttgggaca gtaaccgtga tggatttgtg atgggagaag gagccggagt gttacttctc    1020
gaggagttag agcatgcaaa gaaaagaggt gcaaccattt atgcggaatt tctaggtggg    1080
agtttcactt gcgatgccta ccacatgacc gagcctcacc ctgatggagc tggagtgatc    1140
ctctgcatag agaaggcttt ggcacagtcc ggagtctcga gggaagacgt caattacata    1200
aatgcgcatg caacttctac tcctgctgga gatatcaagg aataccaagc tctcgcccac    1260
tgtttcggcc aaaacagtga gttaagagtg aattccacca aatcgatgat cggtcacctt    1320
cttggagctg ctggtggcgt agaagcagtt acagtagttc aggcaataag gactgggtgg    1380
atccatccaa atattaattt ggaaaacccg gacgaagctg tggatgcaaa attgctcgtc    1440
ggccctaaga aggagaaact gaaggtcaag gtcggtttgt ccaattcatt tgggttcggt    1500
gggcataact catccatact cttcgcccct tacaattag                          1539
```

<210> SEQ ID NO 29
<211> LENGTH: 1629
<212> TYPE: DNA
<213> ORGANISM: Cuphea ignea
<220> FEATURE:
<221> NAME/KEY: misc_feature
<223> OTHER INFORMATION: KASIVb

<400> SEQUENCE: 29

```
atggcggcgg ccgcttccat gtttacgtcc ccactctgta cgtggctcgt agcctcttgc      60
atgtcgactt ccttcgacaa cgacccacgt tcgccgtccg tcaagcgtct ccccgccgg     120
aggaggattc tctcccaatg ctccctccgc ggatccacct cccaatgcct cgtcacctca     180
```

```
tacatcgacc cttgcaataa gtactgctcc tccgcctccc ttagcttcct cggggataac      240
ggattcgcat ccctttcgg atctaagcca ttccggtcca atcgcggcca ccggaggctc       300
ggccgtgctt cccattccgg ggaggccatg gctgtggctc tgcaacctgc acaggaagtc      360
accacgaaga agaaacctgt gatcaagcaa aggcgagtag ttgttacagg aatgggcgtg      420
gtgactcctc taggccatga acctgatgtt tactacaaca atctcctaga tggagtaagc      480
ggcataagtg agatagagac cttcgactgc actcagtttc ccacgagaat cgccggagag      540
atcaagtctt tttccacaga tgggtgggtg gccccaaagc tctccaagag gatggacaag      600
ttcatgcttt acttgttgac tgctggcaag aaagcattag cagatggtgg aatcaccgat      660
gatgtgatga aagagcttga taaaagaaag tgtggggttc tcattggctc tggaatgggc      720
ggcatgaagt tgttcaacga ttccattgaa gctctgagga tttcatataa aaagatgaat      780 ccctttgtg taccttttgc taccacaaat atgggatcag ctatgcttgc aatggacttg      840
ggatggatgg gtcctaacta ctcgatatca actgcctgtg caacaagtaa tttctgtata      900
ctgaatgctt caaaccacat agtcagaggc gaagctgaca tgatgcttg tggtggctcg       960 gattctgtca ctgtaccttt aggtgtggga ggtttcgtag catgccgagc tttgtcacag     1020
aggaataatg accctaccaa agcttcgaga ccttgggaca gtaatcggga tggatttgtg     1080
atgggagaag gagctggagt gttacttctt gaggagttag agcatgcaaa gaaaagaggt     1140
gcaaccattt atgcggaatt tctcggtggg agctttactt ctgatgccta ccacatgacc     1200
gagcctcacc ccgaaggagc tggagtgatt ctctgcattg agaaggcctt ggctcagtcc     1260
ggagtctcga gggaagacgt gaattatata aatgcgcatg caacttccac tcctgctggt     1320
gatataaagg aataccaagc tctcgcccgc tgtttcggcc aaaacagtga gttaagagtg     1380
aattccacca atcgatgat cggtcacctt cttggagcag ctggtggcgt agaagcagtt      1440
gcagtaattc aggcaataag gactggatgg atccatccaa atattaattt ggaagacccc     1500
gacgaagccg tggatccaaa attgctcgtc ggccctaaga aggagaaact gaaggtcaag     1560
gtagctttgt ccaattcatt cgggttcggc gggcataact catccatact ctttgcccct     1620
tgcaattag                                                             1629

<210> SEQ ID NO 30
<211> LENGTH: 1608
<212> TYPE: DNA
<213> ORGANISM: Cuphea procumbens
<220> FEATURE:
<221> NAME/KEY: misc_feature
<223> OTHER INFORMATION: KASIV

<400> SEQUENCE: 30
atggcggcgg cgccctcttc cccactctgt acgtggctcg tagccgcttg catgtccact       60
tccttcgaca caacccacg ttcgccctcc atcaagcgtc tccccgccg gaggagggtt        120 ctctcccaat gctccctccg tggatccacc ttccaatgcc tcgtcacctc acacaacgac      180
ccttgcaatc agtactgctc ctccgcctcc cttagcttcc tcggggataa cggattcgga      240
tccaagccat tccggtccaa tcgcggccac cggaggctcg gccgtgcttc gcattccggg      300
gaggccatgg ctgtggcctt gcaacctgca caggaagtcg ccacgaagaa gaaacctgct     360
atgaagcaaa ggcgagtagt tgttacagga atgggcgtgg tgactcctct gggccatgaa     420
cctgatgttt actacaacaa tctcctagat ggagtaagcg gcataagtga gatagagacc     480
ttcgactgca ctcagtttcc cacgagaatc gccggagaga tcaagtcttt ttccacagat     540
```

```
ggatgggtgg ccccaaagct ctccaagagg atggacaagt tcatgcttta cttgttgact    600
gctggcaaga aagcattagc agatggtgga atcactgatg atgtgatgaa agagcttgat    660
aaaagaaagt gtggagttct cattggctct ggaatgggcg gcatgaagtt gttcaacgat    720
tccattgaag ctctgagagt ttcatataag aagatgaatc cttttgtgt acctttgct     780 accacaaata tgggatcagc tatgcttgca atggacttgg gatggatggg tcctaactac    840
tcgatatcaa ctgcctgtgc aacaagtaat ttctgtatac tgaatgctgc aaaccacata    900
gtcagaggcg aagctgacat gatgctttgt ggtggctcgg atgcggtcat tatacctatt    960
ggtttgggag gttttgtggc gtgccgagct ttgtcacaga ggataatga ccctaccaag    1020 gcttcgagac catgggatag taatcgtgat ggatttgtaa tgggcgaagg agctggagtg    1080
ttacttctcg aggagttaga gcatgcaaag aaaagaggtg caaccattta tgcggaattt    1140 ttaggggca gtttcacttg cgatgcctac catatgaccg agcctcaccc tgaaggagct    1200
ggagtgatcc tctgcataga aaggccttg gctcagtccg gagtctctag aagacgta     1260 aattacataa atgcgcatgc aacttccact cctgctggaa tatcaaaga ataccaagct    1320 ctcgcccact gtttcggcca aaacagtgag ctgagagtga attccactaa atcgatgatc    1380
ggtcatcttc ttggagcagc tggtggtgta gaagcagtta ccgtaattca ggcgataagg    1440
actgggtgga tccatccaaa tcttaatttg aagacccgg acaaagccgt ggatgcaaaa    1500
tttctcgtgg gacctaagaa ggagagactg aatgtcaagg tcggtttgtc caattcattt    1560
gggttcgggg ggcataactc atccatactc tttgcccctt gcaattag                1608

<210> SEQ ID NO 31
<211> LENGTH: 1608
<212> TYPE: DNA
<213> ORGANISM: Cuphea paucipetala
<220> FEATURE:
<221> NAME/KEY: misc_feature
<223> OTHER INFORMATION: KASIVa

<400> SEQUENCE: 31
atggcggcgg cggcctcttc cccactctgc acatggctcg tagccgcttg catgtccact    60
tcattcgaca caacccacg ttcgccctcc atcaagcgtc tcccccgccg gaggagggtt     120
ctctcccaat gctccctccg cggatccacc ttccaatgcc tcgtcaactc acacatcgac    180
ccttgcaatc agaacgtctc ctccgcctcc cttagcttcc tcggggataa cggattcgga    240
tccaatccat tccggtccaa tcgcggccac cggaggctcg gccgggcttc ccattccggg    300
gaggccatgg ctgttgctct gcaacctgca caggaagtcg ccacgaagaa gaaacctgct    360
atcaagcaaa ggcgagtagt tgttacagga atgggcgtgg tgactcctct aggccatgag    420
cctgatgttt tctacaacaa tctccctagat ggagtaagcg gcataagtga gatagagacc    480
ttcgactgca ctcagttcc cacgagaatt gccggagaga tcaagtcttt ttccacagat    540
gggtgggtgg ccccaaagct ctccaagagg atggacaagt tcatgcttta cttgttgact    600
gctggcaaga aagcattagc agatgctgga attaccgagg atgtgatgaa agagcttgat    660
aaaagaaagt gtggagttct cattggctcc ggaatgggcg gcatgaagtt gttcaacgat    720
tccattgaag ctctgagggt ttcatataag aagatgaatc cttttgtgt acctttgct     780 accacaaata tgggatcagc tatgcttgca atggacttgg gatggatggg tcctaactac    840
tcgatatcga ctgcctgtgc aacaagtaat ttctgtatac tgaatgctgc aaaccacata    900
atcagaggcg aagctgacat gatgctttgt ggtggttcgg atgcggtcat tatacctatt    960
```

-continued

```
ggtttgggag gttttgtggc gtgccgagct ttgtcacaga ggaatagtga ccctaccaaa    1020
gcttcgagac catgggatag taatcgtgat ggatttgtaa tgggcgaagg agctggagtg    1080
ttacttctcg aggagttaga gcatgcaaag aaaagaggtg caaccattta tgcggaattt    1140 ttaggggca gcttcacttg cgatgcctac acatgaccg agcctcaccc tgatggagct    1200
```
```
ttaggggggca gcttcacttg cgatgcctac acatgaccg agcctcaccc tgatggagct    1200
ggagtgatcc tctgcataga aaggctttg gcacagtccg gagtctcgag gaagacgtc    1260 aattacataa atgcgcatgc aacttctact cctgctggag atatcaagga ataccaagct    1320
ctcgcccact gtttcggcca aaacagtgag ctgagagtga attccactaa atcgatgatc    1380
ggtcatcttc ttggtgcagc tggtggtgta aagctgtta ctgtaattca ggcgataagg    1440
actgggtgga ttcatccaaa tcttaatttg aagacccgg acgaagccgt ggatgcaaaa    1500
tttctcgtgg gacctaagaa ggagagatta aatgtcaagg tcggtttgtc caattcattt    1560
gggttcggtg ggcataactc atccatactc ttcgccctt acaattag                 1608
```

<210> SEQ ID NO 32
<211> LENGTH: 1593
<212> TYPE: DNA
<213> ORGANISM: Cuphea painteri
<220> FEATURE:
<221> NAME/KEY: misc_feature
<223> OTHER INFORMATION: KASIV

<400> SEQUENCE: 32

```
atggcggcct cctcttgcat ggttgcgtcc ccgttctgta cgtggctcgt atccgcatgc      60
atgtctactt cattcgacaa cgacccacgt tcccttttccc acaagcggct ccgcctctcc    120
cgtcgccgga ggcctctctc ctctcattgc tccctccgcg gatccactcc ccaatgcctc    180
gacccttgca atcagcactg cttcctcggg gataacggat tcgcttccct catcggatcc    240
aagcctcccc gttccaatct cggccacctg aggctcggcc gcacttccca ttccggggag    300
gtcatggctg tggcacagga agtctccaca aataagaaac atgctaccaa gcaaaggcga    360
gtagttgtga caggtatggg cgtggtgact cctctaggcc atgaccccga tgtttactac    420
aacaatctcc tagaaggagt aagtggcatc agtgagatag agaacttcga ctgctctcag    480
cttcccacga gaattgccgg agagatcaag tctttttcca cagatgggtt ggtggccccg    540
aagctctcca gaggatgga caagttcatg ctttacatcc tgactgcagg caagaaagca    600
ttagcagatg gtggaatcac tgaagatgtg atgaaagagc tcgataaaag aaagtgtgga    660
gttctcattg gctccggatt gggcggtatg aaggtattca gcgactccgt tgaagctctg    720
aggatttcat ataagaagat cagtccctt tgtgtacctt tttctaccac aaatatggga    780
tccgctatgc ttgcaatgga cttgggatgg atgggcccta actattcgat atcaactgcc    840
tgtgcaacaa gtaacttctg tatactgaat gctgcgaacc acataaccaa aggcgaagct    900
gacatgatgc tttgtggtgg ctcggatgcg gccattttac ctattggtat gggaggtttc    960
gtggcatgcc gagctttgtc acagaggaat aatgacccta ccaaagcttc gagaccatgg   1020
gacagtaatc gtgatggatt tgtgatggga gaaggagctg gagtgttact tctcgaggag   1080
ttagagcatg caaagaaaag aggtgcaacc atttatgcgg aatttctagg tgggagtttc   1140
acttgcgatg cctaccacat gaccgagcct caccctgatg gagctggagt gatcctctgc   1200
atagagaagg ccttggctca gtccggagtc tcgagggaag aagtaaatta cataaatgcg   1260
catgcaactt ccactcctgc tggagatatc aaggaatacc aagctctcgc ccattgtttc   1320
ggccaaaaca gtgagttaag agtgaattcc accaaatcga tgatcggtca ccttcttgga   1380
```

-continued

```
ggagctggtg gcgtagaagc agttacagta gttcaggcaa taaggactgg atggatccat    1440
ccaaatatta atttggaaga cccggacaaa ggcgtggatg caaaactgct cgtcggccct    1500
aagaaggaga aactgaaggt caaggtcggt ttgtccaatt catttgggtt cggcggccat    1560
aactcatcca tactctttgc cccatgcaat tag                                 1593
```

<210> SEQ ID NO 33
<211> LENGTH: 1629
<212> TYPE: DNA
<213> ORGANISM: Cuphea avigera
<220> FEATURE:
<221> NAME/KEY: misc_feature
<223> OTHER INFORMATION: KASIVa

<400> SEQUENCE: 33

```
atggcggccg ccgcttccat ggttgcgtcc ccattctgta cgtggctcgt agccgcttgc      60
atgtccactt ccgtcgacaa agacccacgt tcgccgtcta tcaagcgtct ccccgccgg     120 aagaggattc attcccaatg ctccctccgc ggatccacct tccaatgcct cgtcacctca    180
tacaacgacc cttgcgaaca ataccgctca tccgcctccc ttagcttcct cggggataac    240
ggattcgcat ccctttttcgg atccaagcca ttccggtcca atcgcggcca ccggaggctc    300
ggccgtgctt cccattccgg ggaggccatg gccgtggcac tgcaacctgc acaggaagtt    360
ggcacgaaga gaaacctgt tatcaagcaa aggcgagtag ttgttacagg aatgggcgtg     420
gtgactcctc taggccatga acctgatgtt tactacaaca atctcctaga cggagtaagc    480
ggcataagtg agatagagac cttcgactgc actcagtttc ccacgagaat tgccggagag    540
atcaagtctt tttccacaga tgggtgggtg gctccaaagc tctctaagag gatggacaag    600
ttcatgcttt acttgttgac tgctggcaag aaagcattgg cagatggtgg aatcaccgat    660
gatgtgatga aagagcttga taaaagaaag tgtggagttc tcattggctc cggattgggc    720
ggtatgaagg tatttagcga gtccattgaa gctctgagga cttcatataa gaagatcagt    780 ccccttttgtg tacctttttc taccacgaat atgggatccg ctattcttgc aatggacttg    840
ggatggatgg gccctaacta ttcgatatcg actgcctgtg caacaagtaa cttctgtata    900
ctgaatgctg cgaaccacat aaccaaaggc gaagcagaca tgatgctttg tggtggctcg    960
gattcggtca tttacctat tggtatggga ggtttcgtag catgccgagc tttgtcacag    1020
aggaataatg accctaccaa agcttcgaga ccatgggaca gtaatcgtga tggatttgtg    1080
atgggagaag gtgctggagt tttacttctc gaggagttag agcatgcaaa gaaaagaggc    1140
gcaaccattt atgcggaatt tcttggtggg agtttcactt gcgatgccta ccacatgacc    1200
gagcctcacc ctgaaggagc tggagtgatc ctctgcatag agaaggcctt ggctcagtcc    1260
ggagtctcga gggaagacgt aaattacata aatgcgcatg caacttccac tcccgctgga    1320
gatatcaaag aataccaagc tctcgcccac tgtttcggcc aaaacagtga gttaagagtg    1380
aattccacca gtcgatgat cgtcaccctt cttggaggag ccggtggcgt agaagcagtt    1440
acagtcgttc aggcaataag gactggatgg atccatccaa atattaattt ggacgacccg    1500
gacgaaggcg tggatgcaaa actgctcgtc ggccctaaga aggagaaact gaaggtcaag    1560
gtcggtttgt ccaattcatt cgggttcggc ggccataact catccatact ctttgcccca    1620
tgcaattag                                                            1629
```

<210> SEQ ID NO 34
<211> LENGTH: 1629
<212> TYPE: DNA

<213> ORGANISM: Cuphea ignea
<220> FEATURE:
<221> NAME/KEY: misc_feature
<223> OTHER INFORMATION: KASIVa

<400> SEQUENCE: 34

| | |
|---|---|
| atggcggcgg ccgcttccat gtttacgtcc ccactctgta cgtggctcgt agcctcttgc | 60 |
| atgtcgactt ccttcgacaa cgacccacgt tcgccgtccg tcaagcgtct ccccgccgg | 120 |
| aggaggattc tctcccaatg ctccctccgc ggatccacct cccaatgcct cgtcacctca | 180 |
| tacatcgacc cttgcaataa gtactgctcc tccgcctccc ttagcttcct cggggataac | 240 |
| ggattcgcat cccttttcgg atctaagcca ttccggtcca atcgcggcca ccggaggctc | 300 |
| ggccgtgctt cccattccgg ggaggccatg gctgtggctc tgcaacctgc acaggaagtc | 360 |
| accacgaaga gaaacctgt gatcaagcaa aggcgagtag ttgttacagg aatgggcgtg | 420 |
| gtgactcctc taggccatga acctgatgtt tactacaaca atctcctaga tggagtaagc | 480 |
| ggcataagtg agatagagac cttcgactgc actcagtttc ccacgagaat cgccggagag | 540 |
| atcaagtctt tttccacaga tgggtgggtg gccccaaagc tctccaagag gatggacaag | 600 |
| ttcatgcttt acttgttgac tgctggcaag aaagcattag cagatggtgg aatcaccgat | 660 |
| gatgtgatga agagcttga taaaagaaag tgtggggttc tcattggctc tggaatgggc | 720 |
| ggcatgaagt tgttcaacga ttccattgaa gctctgagga tttcatataa aaagatgaat | 780 |
| ccctttttgtg taccttttgc taccacaaat atgggatcag ctatgcttgc aatggacttg | 840 |
| ggatggatgg gtcctaacta ctcgatatca actgcctgtg caacaagtaa tttctgtata | 900 |
| ctgaatgctt caaaccacat agtcagaggc gaagctgaca tgatgctttg tggtggctcg | 960 |
| gatgcggtta ttatacctat tggttttggga ggttttgtgg cgtgccgagc tttgtcacag | 1020 |
| aggaataatg accctaccaa agcttcgagg ccatgggata gtaatcgtga tggatttgta | 1080 |
| atgggcgaag gagctggagt gttacttctc gaggagttag agcatgcaaa gaaaagaggt | 1140 |
| gcaaccattt atgcggaatt tttagggggc agtttcactt gcgatgccta ccacatgacc | 1200 |
| gagcctcacc ctgaaggagc tggagtgatc ctctgcatag agaaggcctt ggctcaggcc | 1260 |
| ggagtctcta agaagatgt aaattacata atgcgcatg caacttctac tcctgctgga | 1320 |
| gatatcaagg aataccaagc tctcgcccaa tgtttcggcc aaaacagtga gctgagagtg | 1380 |
| aattccacta atcgatgat cggtcatctt cttggagcag ctggtggtgt agaagcagtt | 1440 |
| actgtggttc aggcgataag gactgggtgg atccatccaa atcttaattt ggaagacccg | 1500 |
| gacaaagccg tggatgcaaa gttgctcgtg ggacctaaga aggagagact gaatgtcaag | 1560 |
| gtcggttttgt ccaattcatt tgggttcggt gggcataatt cgtccatact cttcgcccct | 1620 |
| tacaattag | 1629 |

<210> SEQ ID NO 35
<211> LENGTH: 1422
<212> TYPE: DNA
<213> ORGANISM: Cuphea avigera
<220> FEATURE:
<221> NAME/KEY: misc_feature
<223> OTHER INFORMATION: KASIa

<400> SEQUENCE: 35

| | |
|---|---|
| atgcaatccc tccattcccc tgccctccgg gcctcccctc tcgaccctct ccgactcaaa | 60 |
| tcctccgcca atggccctc ttccaccgcc gctttccgtc cctccgccg cgccacccctc | 120 |
| cccaacattc gggccgcctc cccaccgtc tccgccccca agcgcgagac cgaccccaag | 180 |

```
aagcgtgtcg tcatcaccgg catgggcctc gtctccgtct tcggctccga tgtcgacgct    240
tattacgaaa agctcctctc cggcgagagc gggatcagct taatcgaccg cttcgacgct    300
tccaagttcc ccacgaggtt cggcggccag atccggggat tcaacgccac gggatacatc    360
gacggcaaaa acgacaggag gctcgacgat tgcctccgct actgcattgt cgccgggaag    420
aaggctctcg aaaattccga tctcggcggc gatagtctct caaagattga taaggagaga    480
gctggagtgc tagttggaac tggcatgggt ggcctaaccg tcttctctga cggggttcag    540
aatctaatcg agaaaggtca ccggaagatc tccccgtttt tcattccata tgccattaca    600
aacatggggt ctgccctgct tgccatcgat ttgggtctga tgggcccaaa ttattcgatt    660
tcaactgcat gtgctacttc caactactgc ttttatgctg ctgctaatca tatccgccga    720
ggcgaggctg acctcatgat tgctggagga actgaggctg caatcattcc aattgggtta    780
ggaggattcg ttgcttgcag ggctttatct caaaggaatg atgaccctca gactgcctca    840
aggccgtggg ataaggaccg tgatggtttt gtgatgggtg aaggggctgg agtattggtt    900
atggagagct agaacatgc aatgaaacga ggagcgccga ttattgcaga atatttggga    960
ggtgcagtca actgtgatgc ttatcatatg actgatccaa gggctgatgg gcttggtgtc   1020
tcctcgtgca ttgagagcag tctcgaagat gccggggtct cacctgaaga ggtcaattac   1080
ataaatgctc atgcgacttc tactcttgct ggggatcttg ccgagataaa tgccatcaag   1140
aaggttttca gaacaccaa ggatatcaaa atcaatgcaa ctaagtcgat gattggacac   1200
tgtcttggag catcaggggg tcttgaagcc attgcgacaa ttaagggaat aaccactggc   1260
tggcttcatc ccagcataaa ccaattcaat cccgagccat cagtggaatt tgacactgtt   1320
gccaacaaga agcagcaaca tgaagtcaat gttgctatct caaattcatt cggattcgga   1380
ggccacaact cagttgtagc tttctcagct ttcaagccat ga                       1422

<210> SEQ ID NO 36
<211> LENGTH: 1398
<212> TYPE: DNA
<213> ORGANISM: Cuphea pulcherrima
<220> FEATURE:
<221> NAME/KEY: misc_feature
<223> OTHER INFORMATION: KASI

<400> SEQUENCE: 36
atgcattccc tccagtcacc ctcccttcgg gcctccccgc tcgacccctt ccgcccaaa     60 tcatccaccg tccgccccct ccaccgagca tcaattccca acgtccgggc cgcttccccc    120
accgtctccg ctcccaagcg cgagaccgac cccaagaagc gcgtcgtgat caccggaatg    180
ggccttgtct ccgttttcgg ctccgacgtc gatgcgtact acgacaagct cctgtcaggc    240
gagagcggga tcggcccaat cgaccgcttc gacgcctcca gttccccac caggttcggc    300 ggccagattc gtggcttcaa ctccatggga tacattgacg gcaaaaacga caggcggctt    360
gatgattgcc ttcgctactg cattgtcgcc gggaagaagt ctcttgagga cgccgatctc    420
ggtgccgacc gcctctccaa gatcgacaag gagagagccg gagtgctggt tgggacagga    480
atgggtggtc tgactgtctt ctctgacggg gttcaatctc ttatcgagaa gggtcaccgg    540
aaaatcaccc ctttcttcat cccctatgcc attacaaaca tggggtctgc cctgctcgct    600
attgaactcg gtcgatgggg cccaaactat tcaatttcca ctgcatgtgc cacttccaac    660
tactgcttcc atgctgctgc taatcatatc cgccgtggtg aggctgatct tatgattgct    720
ggaggcactg aggccgcaat cattccaatt gggttgggag gctttgtggc ttgcagggct    780
```

```
ctgtctcaaa ggaacgatga ccctcagact gcctctaggc cctgggataa agaccgtgat    840
ggttttgtga tgggtgaagg tgctggagtg ttggtgctgg agagcttgga acatgcaatg    900
aaacgaggag cacctattat tgcagagtat ttgggaggtg caatcaactg tgatgcttat    960
cacatgactg acccaagggc tgatggtctc ggtgtctcct cttgcattga gagtagcctt   1020
gaagatgctg gcgtctcacc tgaagaggtc aattacataa atgctcatgc gacttctact   1080
ctagctggga atctcgccga gataaatgcc atcaagaagg ttttcaagaa cacaaaggat   1140
atcaaaatta atgcaactaa gtcaatgatc ggacactgtc ttggagcctc tggaggtctt   1200
gaagctatag cgactattaa gggaataaac accggctggc ttcatcccag cattaatcaa   1260
ttcaatcctg agccatccgt ggagttcgac actgttgcca acaagaagca gcaacacgaa   1320
gttaatgttg cgatctcgaa ttcatttgga ttcggaggcc acaactcagt cgtggctttc   1380
tcggctttca agccatga                                                 1398

<210> SEQ ID NO 37
<211> LENGTH: 1401
<212> TYPE: DNA
<213> ORGANISM: Cuphea avigera
<220> FEATURE:
<221> NAME/KEY: misc_feature
<223> OTHER INFORMATION: mitochondrial KAS

<400> SEQUENCE: 37
atggtgtttc ttccttggcg aaaaatgctc tgtccatctc aataccgttt tttgcggccc     60
ttatcttcat ctacaacttt tgatcctcgt agggttgttg ttacaggcct gggtatggtg    120
actccattag gatgcggggt gaacaccaca tggaaacaac tcatagaggg gaaatgtggg    180
ataagagcaa tatcccttga agacctaaag atggatgctt ttgatattga tactcaggcc    240
tatgtatttg atcagctgac ctcgaaggtc gctgccaccg tgcccaccgg agtgaatccc    300
ggagaattta tgaagatttt atggttcaat cagaaggagc accgtgctat tgcaaggttc    360
atagcttatg cactctgtgc agctgatgaa gctcttaaag atgcaaattg gaacctact    420 gaacctgaag agagagaaat gacgggtgtc tccattggtg gagggactgg aagcattagc    480
gatgtattag atgctggtcg gatgatttgt gagaagaaat tgcgtcgcct aagtccattc    540
ttcattccac gcatattgat aaatatggcc tctggtcatg tgagcatgaa atatggtttc    600
cagggaccca accatgctgc tgtgacagct tgtgcaacag gggctcattc gataggtgat    660
gctgcaagga tgatacagtt tggagatgca gatgtcatgg tcgctggagg cacagaatct    720
agcatagacg ccttatccat tgcaggattt tgcaggtcaa gggctcttac aacaaagtat    780
aattcttgcc cacaagaagc ttcacgaccc tttgataccg atagagatgg gtttgtaata    840
ggtgaagggt ctggcgtctt ggtattggag gaactagatc atgcaagaaa acgtggtgca    900
aagatgtatg ccgagttctg tggatatgga atgtctggtg atgcgcatca tataacccaa    960
cctcatagcg atggaagagg tgccatttta gcaatgaccc gtgcattgaa gcagtcaaat   1020
ctacatccgg atcaggtgga ttatgtaaat gctcacgcta cgtctacttc tttaggtgat   1080
gcaattgaag ctaaggcgat taaaacagtt ttctcggatc atgcgatgtc aggttcgctc   1140
gccctttcct ccaccaaggg agctattggg catctcctcg gagcagcggg tgctgtggaa   1200
gccattttct ccattctggc tataaaaaac ggacttgcgc ctttgacgct aaatgtcgca   1260
agaccagacc ctgtgtttac cgagcggttt gtgcctttga ctgcttcaaa agagatgcat   1320
gtaagggcgg cgttgtcaaa ctcttttggc tttggaggta caaatactac acttcttttc   1380
```
acttcacctc ctcaaaacta a                                                   1401

<210> SEQ ID NO 38
<211> LENGTH: 6169
<212> TYPE: DNA
<213> ORGANISM: Artificial Sequence
<220> FEATURE:
<223> OTHER INFORMATION: Cuphea palustris KAS IV codon optimized for
      Prototheca with cloning sequence and tags

<400> SEQUENCE: 38

| | | | | |
|---|---|---|---|---|
| aacggaggtc | tgtcaccaaa | tggaccccgt | ctattgcggg | aaaccacggc | gatggcacgt |    60 |
| ttcaaaactt | gatgaaatac | aatattcagt | atgtcgcggg | cggcgacggc | ggggagctga |   120 |
| tgtcgcgctg | ggtattgctt | aatcgccagc | ttcgcccccg | tcttggcgcg | aggcgtgaac |   180 |
| aagccgaccg | atgtgcacga | gcaaatcctg | acactagaag | ggctgactcg | cccggcacgg |   240 |
| ctgaattaca | caggcttgca | aaaataccag | aatttgcacg | caccgtattc | gcggtatttt |   300 |
| gttggacagt | gaatagcgat | gcggcaatgg | cttgtggcgt | tagaaggtgc | gacgaaggtg |   360 |
| gtgccaccac | tgtgccagcc | agtcctggcg | gctcccaggg | ccccgatcaa | gagccaggac |   420 |
| atccaaacta | cccacagcat | caacgccccg | gcctatactc | gaaccccact | tgcactctgc |   480 |
| aatggtatgg | gaaccacggg | gcagtcttgt | gtgggtcgcg | cctatcgcgg | tcggcgaaga |   540 |
| ccgggaaggt | accccgctcc | cgtctggtcc | tcacgttcgt | gtacgcctg | gatcccggaa |   600 |
| agggcggatg | cacgtggtgt | tgccccgcca | ttggcgccca | cgtttcaaag | tccccggcca |   660 |
| gaaatgcaca | ggaccggccc | ggctcgcaca | ggccatgacg | aatgcccaga | tttcgacagc |   720 |
| aaaacaatct | ggaataatcg | caaccattcg | cgttttgaac | gaaacgaaaa | gacgctgttt |   780 |
| agcacgtttc | cgatatcgtg | ggggccgaag | catgattggg | gggaggaaag | cgtggcccca |   840 |
| aggtagccca | ttctgtgcca | cacgccgacg | aggaccaatc | cccggcatca | gccttcatcg |   900 |
| acggctgcgc | cgcacatata | aagccggacg | ccttcccgac | acgttcaaac | agttttattt |   960 |
| cctccacttc | ctgaatcaaa | caaatcttca | aggaagatcc | tgctcttgag | caactagtat |  1020 |
| gttcgcgttc | tacttcctga | cggcctgcat | ctccctgaag | ggcgtgttcg | gcgtctcccc |  1080 |
| ctcctacaac | ggcctgggcc | tgacgcccca | gatgggctgg | acaactgga | acacgttcgc |  1140 |
| ctgcgacgtc | tccagcagc | tgctgctgga | cacggccgac | cgcatctccg | acctgggcct |  1200 |
| gaaggacatg | ggctacaagt | acatcatcct | ggacgactgc | tggtcctccg | ccgcgactc |  1260 |
| cgacggcttc | ctggtcgccg | acgagcagaa | gttccccaac | ggcatgggcc | acgtcgccga |  1320 |
| ccacctgcac | aacaactcct | tcctgttcgg | catgtactcc | tccgcgggcg | agtacacgtg |  1380 |
| cgccggctac | cccggctccc | tgggccgcga | ggaggaggac | gcccagttct | tcgcgaacaa |  1440 |
| ccgcgtggac | tacctgaagt | acgacaactg | ctacaacaag | ggccagttcg | gcacgcccga |  1500 |
| gatctcctac | caccgctaca | aggccatgtc | cgacgccctg | aacaagacgg | gccgccccat |  1560 |
| cttctactcc | ctgtgcaact | ggggccagga | cctgaccttc | tactgggct | ccggcatcgc |  1620 |
| gaactcctgg | cgcatgtccg | gcgacgtcac | ggcggagttc | acgcgccccg | actcccgctg |  1680 |
| ccccctgcgac | ggcgacgagt | acgactgcaa | gtacgccgg | ttccactgct | ccatcatgaa |  1740 |
| catcctgaac | aaggccgccc | ccatgggcca | gaacgcgggc | gtcggcggct | ggaacgacct |  1800 |
| ggacaacctg | gaggtcggcg | tcggcaacct | gacggacgac | gaggagaagg | cgcacttctc |  1860 |
| catgtggggcc | atggtgaagt | cccccctgat | catcggcgcg | aacgtgaaca | acctgaaggc |  1920 |
| ctcctcctac | tccatctact | cccaggcgtc | cgtcatcgcc | atcaaccagg | actccaacgg |  1980 |

-continued

```
catccccgcc acgcgcgtct ggcgctacta cgtgtccgac acggacgagt acggccaggg    2040
cgagatccag atgtggtccg gccccctgga caacggcgca caggtcgtgg cgctgctgaa    2100
cggcggctcc gtgtcccgcc ccatgaacac gaccctggag gagatcttct tcgactccaa    2160
cctgggctcc aagaagctga cctccacctg ggacatctac gacctgtggg cgaaccgcgt    2220
cgacaactcc acggcgtccg ccatcctggg ccgcaacaag accgccaccg gcatcctgta    2280
caacgccacc gagcagtcct acaaggacgg cctgtccaag aacgacaccc gcctgttcgg    2340
ccagaagatc ggctccctgt cccccaacgc gatcctgaac acgaccgtcc ccgcccacgg    2400
catcgcgttc taccgcctgc gcccctcctc ctgatacaac ttattacgta ttctgaccgg    2460
cgctgatgtg gcgcggacgc cgtcgtactc tttcagactt tactcttgag gaattgaacc    2520
tttctcgctt gctggcatgt aaacattggc gcaattaatt gtgtgatgaa gaaagggtgg    2580
cacaagatgg atcgcgaatg tacgagatcg acaacgatgg tgattgttat gagggccaa    2640 acctggctca atcttgtcgc atgtccggcg caatgtgatc cagcggcgtg actctcgcaa    2700
cctggtagtg tgtgcgcacc gggtcgcttt gattaaaact gatcgcattg ccatcccgtc    2760
aactcacaag cctactctag ctcccattgc gcactcgggc gcccggctcg atcaatgttc    2820
tgagcggagg gcgaagcgtc aggaaatcgt ctcggcagct ggaagcgcat ggaatgcgga    2880
gcggagatcg aatcaggatc ccgcgtctcg aacagagcgc gcagaggaac gctgaaggtc    2940
tcgcctctgt cgcacctcag cgcggcatac accacaataa ccacctgacg aatgcgcttg    3000
gttcttcgtc cattagcgaa gcgtccggtt cacacacgtg ccacgttggc gaggtggcag    3060
gtgacaatga tcggtggagc tgatggtcga aacgttcaca gcctagggat atcgcctgct    3120
caagcgggcg ctcaacatgc agagcgtcag cgagacgggc tgtggcgatc gcagacgga    3180 cgaggccgcc tctgccctgt ttgaactgag cgtcagcgct ggctaagggg agggagactc    3240
atccccaggc tcgcgccagg gctctgatcc cgtctcgggc ggtgatcggc gcgcatgact    3300
acgacccaac gacgtacgag actgatgtcg gtcccgacga ggagcgccgc gaggcactcc    3360
cgggccaccg accatgttta caccgaccga aagcactcgc tcgtatccat tccgtgcgcc    3420
cgcacatgca tcatcttttg gtaccgactt cggtcttgtt ttaccccctac gacctgcctt    3480 ccaaggtgtg agcaactcgc ccggacatga ccgagggtga tcatccggat ccccaggccc    3540
cagcagcccc tgccagaatg gctcgcgctt tccagcctgc aggcccgtct cccaggtcga    3600
cgcaacctac atgaccaccc caatctgtcc cagaccccaa acaccctcct tccctgcttc    3660
tctgtgatcg ctgatcagca acacatatgg cttccgcggc attcaccatg tcggcgtgcc    3720
ccgcgatgac tggcagggcc cctggggcac gtcgctccgg acggccagtc gccacccgcc    3780 tgagggctc caccttccag tgcctggtga cctcctacat cgaccctgc aaccagttct    3840 cctcctccgc ctccctgtcc ttcctgggcg acaacggctt cgcctccctg ttcggctcca    3900
agcccttccg ctccaaccgc ggccaccgcc gcctgggccg cgcctcccac tccggcgagg    3960
ccatggccgt ggccctggag cccgcccagg aggtggccac caagaagaag cccctggtga    4020
agcagcgccg cgtggtggtg accggcatgg gcgtggtgac cccccctgggc cacgagcccg    4080 acgtgtacta caacaacctg ctggacgcg tgtccgcat ctccgagatc gaggccttcg    4140
actgcaccca gttccccacc cgcatcgccg gcgagatcaa gtccttctcc accgacggct    4200
gggtggcccc caagctgtcc aagcgcatgg acaagttcat gctgtacctg ctgaccgccg    4260
gcaagaaggc cctggccgac ggcggcatca ccgacgacgt gatgaaggag ctggacaagc    4320
```

```
gcaagtgcgg cgtgctgatc ggctccggcc tgggcggcat gaagctgttc tccgactcca    4380
tcgaggccct gcgcatctcc tacaagaaga tgaaccccct ctgcgtgccc ttcgccacca    4440
ccaacatggg ctccgccatg ctggccatgg acctgggctg gatgggcccc aactactcca    4500
tctccaccgc ctgcgccacc tccaacttct gcatcctgaa ctccgccaac acatcgtgc     4560 gcggcgaggc cgacatgatg ctgtgcggcg gctccgacgc cgtgatcatc cccatcggcc    4620
tgggcggctt cgtggcctgc cgcgcccgt  cccagcgcaa caacgacccc accaaggcct    4680
cccgcccctg ggactccaac cgcgacggct tcgtgatggg cgagggcgcc ggcgtgctgc    4740
tgctggagga gctggagcac gccaagaagc gcggcgccac catctacgcc gagttcctgg    4800
gcggctcctt cacctgcgac gcctaccaca tgaccgagcc ccaccccgag ggcgccggcg    4860
tgatcctgtg catcgagaag gccctggccc aggccggcgt gtcccgcgag gacgtgaact    4920
acatcaacgc ccacgccacc tccacccccg ccggcgacat caaggagtac caggccctgg    4980
cccactgctt cggccagaac tccgagctgc gcgtgaactc caccaagtcc atgatcggcc    5040
acctgatcgg cgccgccggc ggcgtggagg ccgtgaccgt ggtgcaggcc atccgcaccg    5100
gctggatcca ccccaacctg aacctggagg accccgacaa ggccgtggac gccaaggtgc    5160
tggtgggccc caagaaggag cgcctgaacg tgaaggtggg cctgtccaac tccttcggct    5220
tcggcggcca caactcctcc atcctgttcg cccccctacaa caccatgtac ccctacgacg    5280
tgcccgacta cgcctgatat cgaggcagca gcagctcgga tagtatcgac acactctgga    5340
cgctggtcgt gtgatggact gttgccgcca cacttgctgc cttgacctgt gaatatccct    5400
gccgctttta tcaaacagcc tcagtgtgtt tgatcttgtg tgtacgcgct tttgcgagtt    5460
gctagctgct tgtgctattt gcgaatacca cccccagcat ccccttccct cgtttcatat    5520
cgcttgcatc ccaaccgcaa cttatctacg ctgtcctgct atccctcagc gctgctcctg    5580
ctcctgctca ctgcccctcg cacagccttg gtttgggctc cgcctgtatt tcctggtac     5640 tgcaacctgt aaaccagcac tgcaatgctg atgcacggga agtagtggga tgggaacaca    5700
aatggaaagc ttgagctcag cggcgacggt cctgctaccg tacgacgttg ggcacgccca    5760
tgaaagtttg taccgagc ttgttgagcg aactgcaagc gcggctcaag gatacttgaa     5820
ctcctggatt gatatcggtc caataatgga tggaaaatcc gaacctcgtg caagaactga    5880
gcaaacctcg ttacatggat gcacagtcgc cagtccaatg aacattgaag tgagcgaact    5940
gttcgcttcg gtggcagtac tactcaaaga tgagctgct gttaaaaatg cactctcgtt     6000
ctctcaagtg agtggcagat gagtgctcac gccttgcact tcgctgcccg tgtcatgccc    6060
tgcgccccaa aatttgaaaa aagggatgag attattgggc aatggacgac gtcgtcgctc    6120
cgggagtcag gaccggcgga aaataagagg caacacactc cgcttctta               6169
```

<210> SEQ ID NO 39
<211> LENGTH: 1611
<212> TYPE: DNA
<213> ORGANISM: Artificial Sequence
<220> FEATURE:
<223> OTHER INFORMATION: Cuphea palustris KAS IV codon optimized for
      Prototheca

<400> SEQUENCE: 39

```
atggcttccg cggcattcac catgtcggcg tgccccgcga tgactggcag ggcccctggg     60
gcacgtcgct ccggacggcc agtcgccacc cgcctgaggg gctccacctt ccagtgcctg    120
gtgacctcct acatcgaccc ctgcaaccag ttctcctcct ccgcctccct gtccttcctg    180
```

-continued

```
ggcgacaacg gcttcgcctc cctgttcggc tccaagccct tccgctccaa ccgcggccac    240
cgccgcctgg gccgcgcctc ccactccggc gaggccatgg ccgtggccct ggagcccgcc    300
caggaggtgg ccaccaagaa gaagcccctg gtgaagcagc gccgcgtggt ggtgaccggc    360
atgggcgtgg tgaccccccct gggccacgag cccgacgtgt actacaacaa cctgctggac    420
ggcgtgtccg gcatctccga gatcgaggcc ttcgactgca cccagttccc cacccgcatc    480
gccggcgaga tcaagtcctt ctccaccgac ggctgggtgg cccccaagct gtccaagcgc    540
atggacaagt tcatgctgta cctgctgacc gccggcaaga aggccctggc cgacggcggc    600
atcaccgacg acgtgatgaa ggagctggac aagcgcaagt gcggcgtgct gatcggctcc    660
ggcctgggcg gcatgaagct gttctccgac tccatcgagg ccctgcgcat ctcctacaag    720
aagatgaacc ccttctgcgt gcccttcgcc accaccaaca tgggctccgc catgctggcc    780
atggacctgg gctggatggg ccccaactac tccatctcca ccgcctgcgc cacctccaac    840
ttctgcatcc tgaactccgc caaccacatc gtgcgcggcg aggccgacat gatgctgtgc    900
ggcggctccg acgccgtgat catccccatc ggcctgggcg gcttcgtggc ctgccgcgcc    960
ctgtcccagc gcaacaacga ccccaccaag gcctcccgcc cctgggactc caaccgcgac   1020
ggcttcgtga tgggcgaggg cgccggcgtg ctgctgctgg aggagctgga gcacgccaag   1080
aagcgcggcg ccaccatcta cgccgagttc ctgggcggct ccttcacctg cgacgcctac   1140
cacatgaccg agccccaccc cgagggcgcc ggcgtgatcc tgtgcatcga gaaggccctg   1200
gcccaggccg gcgtgtcccg cgaggacgtg aactacatca acgcccacgc cacctccacc   1260
cccgccggcg acatcaagga gtaccaggcc ctggcccact gcttcggcca gaactccgag   1320
ctgcgcgtga actccaccaa gtccatgatc ggccacctga tcggcgccgc cggcggcgtg   1380
gaggccgtga ccgtggtgca ggccatccgc accggctgga tccaccccaa cctgaacctg   1440
gaggaccccg acaaggccgt ggacgccaag gtgctggtgg gccccaagaa ggagcgcctg   1500
aacgtgaagg tgggcctgtc caactccttc ggcttcggcg gccacaactc ctccatcctg   1560
ttcgcccccct acaacaccat gtacccctac gacgtgcccg actacgcctg a            1611
```

<210> SEQ ID NO 40
<211> LENGTH: 1512
<212> TYPE: DNA
<213> ORGANISM: Artificial Sequence
<220> FEATURE:
<223> OTHER INFORMATION: C. camphora KASIV codon optimized for Prototheca

<400> SEQUENCE: 40

```
atggccatga tggccggctc ctgctccaac ctggtgatcg gcaaccgcga gctgggcggc     60
aacggcccct ccctgctgca ctacaacggc ctgcgccccc tggagaacat ccagaccgcc    120
tccgccgtga agaagcccaa cggcctgttc gcctcctcca ccgcccgcaa gtccaaggcc    180
gtgcgcgcca tggtgctgcc caccgtgacc gcccccaagc gcgagaagga ccccaagaag    240
cgcatcgtga tcaccggcat gggcctggtg tccgtgttcg gcaacgacat cgacaccttc    300
tactccaagc tgctggaggg cgagtccggc atcggcccca tcgaccgctt cgacgcctcc    360
tccttctccg tgcgcttcgc cggccagatc cacaacttct cctccaaggg ctacatcgac    420
ggcaagaacg accgccgcct ggacgactgc tggcgctact gcctggtggc cggccgccgc    480
gccctggagg acgccaacct gggccccgag gtgctggaga agatggaccg ctcccgcatc    540
ggcgtgctga tcggcaccgg catgggcggc ctgtccgcct tctccaacgg cgtggagtcc    600
```

| | |
|---|---|
| ctgatccaga agggctacaa gaagatcacc cccttcttca tccccctactc catcaccaac | 660 |
| atgggctccg ccctgctggc catcgacacc ggcgtgatgg gccccaacta ctccatctcc | 720 |
| accgcctgcg ccaccgccaa ctactgcttc cacgccgccg ccaaccacat ccgccgcggc | 780 |
| gaggccgaga tcatggtgac cggcggcacc gaggccgccg tgtccgccac cggcgtgggc | 840 |
| ggcttcatcg cctgccgcgc cctgtccac cgcaacgacg agccccagac cgcctcccgc | 900 |
| ccctgggaca aggaccgcga cggcttcgtg atgggcgagg gcgccggcgt gctggtgatg | 960 |
| gagtccctgc accacgcccg caagcgcggc gccaacatca tcgccgagta cctgggcggc | 1020 |
| gccgtgacct gcgacgccca ccacatgacc gaccccgcg ccgacggcct gggcgtgtcc | 1080 |
| tcctgcatca ccaagtccct ggaggacgcc ggcgtgtccc ccgaggaggt gaactacgtg | 1140 |
| aacgcccacg ccacctccac cctgccggc gacctggccg aggtgaacgc catcaagaag | 1200 |
| gtgttcaagg acacctccga gatgaagatg aacggcacca agtccatgat cggccactgc | 1260 |
| ctgggcgccg ccggcggcct ggaggccatc gccaccatca aggccatcaa caccggctgg | 1320 |
| ctgcacccca ccatcaacca gttcaacatc gagcccgccg tgaccatcga caccgtgccc | 1380 |
| aacgtgaaga gaagcacga catccacgtg ggcatctcca actccttcgg cttcggcggc | 1440 |
| cacaactccg tggtggtgtt cgcccccttc atgcccacca tgtaccccta cgacgtgccc | 1500 |
| gactacgcct ga | 1512 |

<210> SEQ ID NO 41
<211> LENGTH: 1482
<212> TYPE: DNA
<213> ORGANISM: Artificial Sequence
<220> FEATURE:
<223> OTHER INFORMATION: C. camphora KASI (D3148, pSZ4339) codon optimized for Prototheca

<400> SEQUENCE: 41

| | |
|---|---|
| atgcagatcc tgcagacccc ctcctcctcc tcctcctccc tgcgcatgtc ctccatggag | 60 |
| tccctgtccc tgacccccaa gtccctgccc ctgaagaccc tgctgcccct cgcccccgc | 120 |
| cccaagaacc tgtcccgccg caagtcccag aaccccgcc ccatctcctc ctcctcctcc | 180 |
| cccgagcgcg agaccgaccc caagaagcgc gtggtgatca ccggcatggg cctggtgtcc | 240 |
| gtgttcggca cgacgtgga cgcctactac gaccgcctgc tgtccggcga gtccggcatc | 300 |
| gcccccatcg accgcttcga cgcctccaag ttccccaccc gcttcgcgg ccagatccgc | 360 |
| ggcttcacct ccgacggcta catcgacggc aagaacgacc gccgcctgga cgactgcctg | 420 |
| cgctactgca tcgtgtccgg caagaaggcc ctggagaacg ccggcctggg ccccacctg | 480 |
| atggacggca agatcgacaa ggagcgcgcc ggcgtgctgg tgggcaccgg catgggcggc | 540 |
| ctgaccgtgt tctccaacgg cgtgcagacc ctgcacgaga agggctaccg caagatgacc | 600 |
| cccttcttca tccccctacgc catcaccaac atgggctccg ccctgctggc catcgagctg | 660 |
| ggcttcatgg gccccaacta ctccatctcc accgcctgcg ccacctccaa ctactgcttc | 720 |
| tacgccgccg ccaaccacat ccgccgcggc gaggccgacc tgatgctggc cggcggcacc | 780 |
| gaggccgcca tcatcccat cggcctgggc ggcttcgtgg cctgccgcgc cctgtcccag | 840 |
| cgcaacgacg accccagac cgcctcccgc ccctgggaca aggaccgcga cggcttcgtg | 900 |
| atgggcgagg gcgccggcgt gctggtgatg gagtccctgg agcacgccat gaagcgcgac | 960 |
| gcccccatca tcgccgagta cctgggcggc gccgtgaact gcgacgccta ccacatgacc | 1020 |
| gaccccgcg ccgacggcct gggcgtgtcc acctgcatcg agcgctccct ggaggacgcc | 1080 |

```
ggcgtggccc ccgaggaggt gaactacatc aacgcccacg ccacctccac cctggccggc      1140
gacctggccg aggtgaacgc catcaagaag gtgttcacca acacctccga gatcaagatc      1200
aacgccacca agtccatgat cggccactgc ctgggcgccg ccggcggcct ggaggccatc      1260
gccaccatca aggccatcaa caccggctgg ctgcacccct ccatcaacca gttcaacccc      1320
gagccctccg tggagttcga caccgtggcc aacaagaagc agcagcacga ggtgaacgtg      1380
gccatctcca actccttcgg cttcggcggc acaactccg tggtggtgtt ctccgccttc       1440
aagcccacca tgtaccccta cgacgtgccc gactacgcct ga                        1482

<210> SEQ ID NO 42
<211> LENGTH: 1428
<212> TYPE: DNA
<213> ORGANISM: Artificial Sequence
<220> FEATURE:
<223> OTHER INFORMATION: U. californica KASI (D3150, pSZ4341) codon
      optimized for Prototheca

<400> SEQUENCE: 42
atggagtccc tgtccctgac ccccaagtcc ctgcccctga gaccctgct gcccttccgc        60 ccccgcccca gaacctgtc ccgccgcaag tcccagaacc ccaagcccat ctcctcctcc       120 tcctccccg agcgcgagac cgaccccaag aagcgcgtgg tgatcaccgg catgggcctg       180
gtgtccgtgt cggcaacga cgtggacgcc tactacgacc gctgctgtc cggcgagtcc       240 ggcatcgccc ccatcgaccg cttcgacgcc tccaagttcc ccacccgctt cgccggccag      300
atccgcggct tcacctccga cggctacatc gacggcaaga acgaccgccg cctggacgac      360
tgcctgcgct actgcatcgt gtccggcaag aaggccctgg agaacgccgg cctgggcccc      420
gacctgatgg acggcaagat cgacaaggag cgcgccggcg tgctggtggg caccggcatg      480
ggcggcctga ccgtgttctc caacggcgtg cagaccctgc acgagaaggg ctaccgcaag      540
atgacccccc tcttcatccc ctacgccatc accaacatgg ctccgccct gctggccatc      600 gacctgggct tcatgggccc caactactcc atctccaccg cctgcgccac ctccaactac      660
tgcttctacg ccgccgccaa ccacatccgc gcggcgagg ccgacgtgat gctggccggc      720
ggcaccgagg ccgccatcat ccccatcggc ctgggcggct tcgtggcctg ccgcgccctg      780
tcccagcgca acgacgaccc ccagaccgcc tcccgcccct gggacaagga ccgcgacggc      840
ttcgtgatgg gcgagggcgc cggcgtgctg gtgatggagt ccctggagca cgccatgaag      900
cgcgacgccc ccatcatcgc cgagtacctg ggcggcgccg tgaactgcga cgcctaccac      960
atgaccgacc ccgcgccga cggcctgggc gtgtccacct gcatcgagcg ctccctggag     1020
gacgccggcg tggcccccga ggaggtgaac tacatcaacg cccacgccac ctccaccctg     1080 gccgcgacc tggccgaggt gaacgccatc aagaaggtgt tcaccaacac ctccgagatc     1140
aagatcaacg ccaccaagtc catgatcggc cactgcctgg gcgccgccgg cggcctggag     1200
gccatcgcca ccatcaaggc catcaacacc ggctggctgc accctccat caaccagttc     1260 aaccccgagc cctccgtgga gttcgacacc gtggccaaca gaagcagca gcacgaggtg     1320 aacgtggcca tctccaactc cttcggcttc ggcggccaca ctccgtggt ggtgttctcc     1380 gccttcaagc ccaccatgta ccccactacgac gtgcccgact acgcctga               1428

<210> SEQ ID NO 43
<211> LENGTH: 1452
<212> TYPE: DNA
<213> ORGANISM: Artificial Sequence
<220> FEATURE:
```

<223> OTHER INFORMATION: U. californica KASIV (D3152, pSZ4343) codon
optimized for Prototheca

<400> SEQUENCE: 43

| | | |
|---|---|---|
| atgacccaga ccctgatctg cccctcctcc atggagaccc tgtccctgac caagcagtcc | 60 |
| cacttccgcc tgcgcctgcc caccccccc cacatccgcc gcggcggcgg ccaccgccac | 120 |
| ccccccccct tcatctccgc ctccgccgcc cccgccgcg agaccgaccc caagaagcgc | 180 |
| gtggtgatca ccggcatggg cctggtgtcc gtgttcggca ccaacgtgga cgtgtactac | 240 |
| gaccgcctgc tggccggcga gtccggcgtg ggcaccatcg accgcttcga cgcctccatg | 300 |
| ttccccaccc gcttcggcgg ccagatccgc gcttcacct ccagggcta catcgacggc | 360 |
| aagaacgacc gccgcctgga cgactacctg cgctactgcc tggtgtccgg caagaaggcc | 420 |
| atcgagtccg ccggcttcga cctgcacaac atcaccaaca agatcgacaa ggagcgcgcc | 480 |
| ggcatcctgg tgggctccgg catgggcggc ctgaaggtgt tctccgacgg cgtggagtcc | 540 |
| ctgatcgaga agggctaccg caagatctcc cccttcttca tcccctacat gatccccaac | 600 |
| atgggctccg ccctgctggg catcgacctg ggcttcatgg gccccaacta ctccatctcc | 660 |
| accgcctgcg ccacctccaa ctactgcatc tacgccgccg ccaaccacat ccgccagggc | 720 |
| gacgccgacc tgatggtggc cggcggcacc gaggccccca tcatccccat cggcctgggc | 780 |
| ggcttcgtgg cctgccgcgc cctgtccacc cgcaacgacg accccagac cgcctcccgc | 840 |
| ccctgggaca tcgaccgcga cggcttcgtg atgggcgagg gcgccggcat cctggtgctg | 900 |
| gagtccctgg agcacgccat gaagcgcgac gcccccatcc tggccgagta cctgggcggc | 960 |
| gccgtgaact gcgacgccca ccacatgacc gaccccgcg ccgacggcct gggcgtgtcc | 1020 |
| acctgcatcg agtcctccct ggaggacgcc ggcgtggccg ccgaggaggt gaactacatc | 1080 |
| aacgcccacg ccacctccac ccccaccggc gacctggccg agatgaaggc catcaagaac | 1140 |
| gtgttccgca acacctccga gatcaagatc aacgccacca agtccatgat cggccactgc | 1200 |
| ctgggcgcct ccggcggcct ggaggccatc gccaccctga aggccatcac caccggctgg | 1260 |
| ctgcaccccca ccatcaacca gttcaacccc gagccctccg tggacttcga caccgtggcc | 1320 |
| aagaagaaga agcagcacga ggtgaacgtg gccatctcca actccttcgg cttcggcggc | 1380 |
| cacaactccg tgctggtgtt ctccgccttc aagcccacca tgtaccccta cgacgtgccc | 1440 |
| gactacgcct ga | 1452 |

<210> SEQ ID NO 44
<211> LENGTH: 1578
<212> TYPE: DNA
<213> ORGANISM: Artificial Sequence
<220> FEATURE:
<223> OTHER INFORMATION: C. wrightii KASAI (D3153, pSZ4379) codon
optimized for Prototheca

<400> SEQUENCE: 44

| | | |
|---|---|---|
| atggcttccg cggcattcac catgtcggcg tgcccgcga tgactggcag ggcccctggg | 60 |
| gcacgtcgct ccggacggcc agtcgccacc cgcctgaggt acgtattcca gtgcctggtg | 120 |
| gccagctgca tcgaccccctg cgaccagtac cgcagcagcg ccagcctgag cttcctgggc | 180 |
| gacaacggct tcgccagcct gttcggcagc aagcccttca tgagcaaccg cggccaccgc | 240 |
| cgcctgcgcc gcgccagcca cagcggcgag ccatggcccg tggccctgca gccgcccag | 300 |
| gaggccggca ccaagaagaa gcccgtgatc aagcagcgcc gcgtggtggt gaccggcatg | 360 |
| ggcgtggtga cccccctggg ccacgagccc gacgtgttct acaacaacct gctggacggc | 420 |

```
gtgagcggca tcagcgagat cgagaccttc gactgcaccc agttccccac ccgcatcgcc    480
ggcgagatca agagcttcag caccgacggc tgggtggccc ccaagctgag caagcgcatg    540
gacaagttca tgctgtacct gctgaccgcc ggcaagaagg ccctggccga cggcggcatc    600
accgacgagg tgatgaagga gctggacaag cgcaagtgcg gcgtgctgat cggcagcggc    660
atgggcggca tgaaggtgtt caacgacgcc atcgaggccc tgcgcgtgag ctacaagaag    720
atgaacccct tctgcgtgcc cttcgccacc accaacatgg gcagcgccat gctggccatg    780
gacctgggct ggatgggccc caactacagc atcagcaccg cctgcgccac cagcaacttc    840
tgcatcctga acgccgccaa ccacatcatc cgcggcgagg ccgacatgat gctgtgcggc    900
ggcagcgacg ccgtgatcat ccccatcggc ctgggcggct tcgtggcctg ccgcgccctg    960
agccagcgca acagcgaccc caccaaggcc agccgcccct gggacagcaa ccgcgacggc   1020
ttcgtgatgg gcgagggcgc cggcgtgctg ctgctggagg agctggagca cgccaagaag   1080
cgcggcgcca ccatctacgc cgagttcctg ggcggcagct tcacctgcga cgcctaccac   1140
atgaccgagc cccaccccga gggcgccggc gtgatcctgt gcatcgagaa ggccctggcc   1200
caggccggcg tgagcaagga ggacgtgaac tacatcaacg cccacgccac cagcaccagc   1260
gccggcgaca tcaaggagta ccaggccctg gcccgctgct tcggccagaa cagcgagctg   1320
cgcgtgaaca gcaccaagag catgatcggc cacctgctgg gcgccgccgg cggcgtggag   1380
gccgtgaccg tggtgcaggc catccgcacc ggctggattc accccaacct gaacctggag   1440
gaccccgaca aggccgtgga cgccaagctg ctggtgggcc ccaagaagga gcgcctgaac   1500
gtgaaggtgg gcctgagcaa cagcttcggc ttcggcggcc acaacagcag catcctgttc   1560 gcccccctgca acgtgtga                                                 1578
```

<210> SEQ ID NO 45
<211> LENGTH: 1542
<212> TYPE: DNA
<213> ORGANISM: Artificial Sequence
<220> FEATURE:
<223> OTHER INFORMATION: C. avigera KASIVb (D3287, pSZ4453) codon optimized for Prototheca

<400> SEQUENCE: 45

```
atggcttccg cggcattcac catgtcggcg tgccccgcga tgactggcag ggcccctggg     60
gcacgtcgct ccggacggcc agtcgccacc cgcctgaggg gctccacctt ccagtgctac    120
atcggcgaca acggcttcgg ctccaagccc ccccgctcca accgcggcca cctgcgcctg    180
ggccgcacct cccactccgg cgaggtgatg gccgtggcca tgcagtccgc ccaggaggtg    240
tccaccaagg agaagcccgc caccaagcag cgccgcgtgg tggtgaccgg catgggcgtg    300
gtgaccgccc tgggccacga ccccgacgtg tactacaaca acctgctgga cggcgtgtcc    360
ggcatctccg agatcgagaa cttcgactgc tcccagctgc ccacccgcat cgccggcgag    420
atcaagtcct tctccgccga cggctgggtg gcccccaagt tctcccgccg catggacaag    480
ttcatgctgt acatcctgac cgccggcaag aaggccctgg tggacggcgg catcaccgag    540
gacgtgatga aggagctgga caagcgcaag tgcggcgtgc tgatcggctc cggcctgggc    600
ggcatgaagg tgttctccga gtccatcgag gccctgcgca cctcctacaa gaagatctcc    660
cccttctgcg tgcccttctc caccaccaac atgggctccg ccatcctggc catggacctg    720
ggctggatgg gccccaacta ctccatctcc accgcctgcg ccacctccaa cttctgcatc    780
ctgaacgccg ccaaccacat caccaagggc gaggccgaca tgatgctgtg cggcggctcc    840
```

```
gactccgtga tcctgcccat cggcatgggc ggcttcgtgg cctgccgcgc cctgtcccag    900
cgcaacaacg accccaccaa ggcctcccgc ccctgggact ccaaccgcga cggcttcgtg    960
atgggcgagg gcgccggcgt gctgctgctg gaggagctgg agcacgccaa gaagcgcggc   1020
gccaccatct acgccgagtt cctgggcggc tccttcacct gcgacgccta ccacatgacc   1080
gagccccacc ccgagggcgc cggcgtgatc ctgtgcatcg agaaggccct ggcccagtcc   1140
ggcgtgtccc gcgaggacgt gaactacatc aacgcccacg ccacctccac ccccgccggc   1200
gacatcaagg agtaccaggc cctggcccac tgcttcggcc agaactccga gctgcgcgtg   1260
aactccacca agtccatgat cggccacctg ctgggcggcg ccggcggcgt ggaggccgtg   1320
accgtggtgc aggccatccg caccggctgg atccacccca acatcaacct ggacgacccc   1380
gacgagggcg tggacgccaa gctgctggtg ggccccaaga aggagaagct gaaggtgaag   1440
gtgggcctgt ccaactcctt cggcttcggc ggccacaact cctccatcct gttcgccccc   1500
tgcaacacca tgtaccccta cgacgtgccc gactacgcct ga                      1542
```

```
<210> SEQ ID NO 46
<211> LENGTH: 1551
<212> TYPE: DNA
<213> ORGANISM: Artificial Sequence
<220> FEATURE:
<223> OTHER INFORMATION: C. paucipetala KASIVb codon optimized for
      Prototheca

<400> SEQUENCE: 46
```

```
atggcttccg cggcattcac catgtcggcg tgccccgcga tgactggcag ggcccctggg     60
gcacgtcgct ccggacggcc agtcgccacc cgcctgaggg gctccacctt ccagtgcctg    120
ggcgacatcg gcttcgcctc cctgatcggc tccaagcccc cccgctccaa ccgcaaccac    180
cgccgcctgg gccgcacctc ccactccggc gaggtgatgg ccgtggccat gcagcccgcc    240
cacgaggcct ccaccaagaa caagcccgtg accaagcagc gccgcgtggt ggtgaccggc    300
atgggcgtgg ccacccccct gggccacgac cccgacgtgt actacaacaa cctgctggac    360
ggcgtgtccg gcatctccca gatcgagaac ttcgactgca cccagttccc cacccgcatc    420
gccggcgaga tcaagtcctt ctccaccgag ggctacgtga tccccaagtt cgccaagcgc    480
atggacaagt tcatgctgta cctgctgacc gccggcaaga aggccctgga ggacggcggc    540
atcaccgagg acgtgatgaa ggagctggac aagcgcaagt gcggcgtgct gatcggctcc    600
ggcatgggcg gcatgaagat catcaacgac tccatcgccg ccctgaacgt gtcctacaag    660
aagatgaccc ccttctgcgt gcccttctcc accaccaaca tgggctccgc catgctggcc    720
atcgacctgg gctggatggg ccccaactac tccatctcca ccgcctgcgc cacctccaac    780
tactgcatcc tgaacgccgc caaccacatc gtgcgcggcg aggccgacat gatgctgtgc    840
ggcggctccg acgccgtgat catccccgtg ggcctgggcg gcttcgtggc ctgccgcgcc    900
ctgtcccagc gcaacaacga ccccaccaag gcctcccgcc cctgggactc caaccgcgac    960
ggcttcgtga tgggcgaggg cgccggcgtg ctgctgctgg aggagctgga gcacgccaag   1020
aagcgcggcg ccaccatcta cgccgagttc ctgggcggct ccttcacctg cgacgcctac   1080
cacatgaccg agccccaccc cgacggcgcc ggcgtgatcc tgtgcatcga gaaggccctg   1140
gcccagtccg gcgtgtcccg cgaggacgtg aactacatca acgcccacgc cacctccacc   1200
cccgccggcg acatcaagga gtaccaggcc ctggcccact gcttcggcca gaactccgag   1260
ctgcgcgtga actccaccaa gtccatgatc ggccacctgc tgggcgccgc cggcggcgtg   1320
```

```
gaggccgtga ccgtggtgca ggccatccgc accggctgga tccaccccaa catcaacctg     1380
gagaaccccg acgaggccgt ggacgccaag ctgctggtgg gccccaagaa ggagaagctg     1440
aaggtgaagg tgggcctgtc caactccttc ggcttcggcg ccacaactc ctccatcctg      1500 ttcgccccct acaacaccat gtaccctac gacgtgcccg actacgcctg a               1551
```

<210> SEQ ID NO 47
<211> LENGTH: 1611
<212> TYPE: DNA
<213> ORGANISM: Artificial Sequence
<220> FEATURE:
<223> OTHER INFORMATION: C. ignea KASIVb (D3289, pSZ4455) codon
      optimized for Prototheca

<400> SEQUENCE: 47

```
atggcttccg cggcattcac catgtcggcg tgccccgcga tgactggcag ggcccctggg      60
gcacgtcgct ccggacggcc agtcgccacc cgcctgaggg gctccacctc ccagtgcctg     120
gtgacctcct acatcgaccc ctgcaacaag tactgctcct ccgcctccct gtccttcctg     180
ggcgacaacg gcttcgcctc cctgttcggc tccaagcct tccgctccaa ccgcggccac      240
cgccgcctgg gccgcgcctc ccactccggc gaggccatgg ccgtggccct gcagcccgcc     300
caggaggtga ccaccaagaa gaagcccgtg atcaagcagc ccgcgtggt ggtgaccggc      360 atgggcgtgg tgacccccct gggccacgag cccgacgtgt actacaacaa cctgctggac     420
ggcgtgtccg gcatctccga gatcgagacc ttcgactgca cccagttccc cacccgcatc     480
gccggcgaga tcaagtcctt ctccaccgac ggctgggtgg ccccccaagct gtccaagcgc    540 atggacaagt tcatgctgta cctgctgacc gccggcaaga aggccctggc cgacggcggc     600
atcaccgacg acgtgatgaa ggagctggac aagcgcaagt gcggcgtgct gatcggctcc     660
ggcatgggcg gcatgaagct gttcaacgac tccatcgagg ccctgcgcat ctcctacaag     720
aagatgaacc ccttctgcgt gccccttcgcc accaccaaca tgggctccgc catgctggcc    780
atggacctgg gctggatggg ccccaactac tccatctcca ccgcctgcgc cacctccaac     840
ttctgcatcc tgaacgcctc caaccacatc gtgcgcggcg aggccgacat gatgctgtgc     900
ggcggctccg actccgtgac cgtgcccctg ggcgtgggcg gcttcgtggc ctgccgcgcc     960
ctgtcccagc gcaacaacga ccccaccaag gcctcccgcc cctgggactc caaccgcgac    1020
ggcttcgtga tgggcgaggg cgccggcgtg ctgctgctgg aggagctgga gcacgccaag    1080
aagcgcggcg ccaccatcta cgccgagttc ctgggcggct ccttcacctc cgacgcctac    1140
cacatgaccg agccccaccc cgagggcgcc ggcgtgatcc tgtgcatcga aaggccctg     1200 gcccagtccg gcgtgtcccg cgaggacgtg aactacatca acgccacgc cacctccacc    1260 cccgccggcg acatcaagga gtaccaggcc ctggcccgct gcttcggcca gaactccgag    1320
ctgcgcgtga actccaccaa gtccatgatc ggccacctgc tgggcgccgc cggcggcgtg    1380
gaggccgtgg ccgtgatcca ggccatccgc accggctgga tccaccccaa catcaacctg    1440
gaggaccccg acgaggccgt ggaccccaag ctgctggtgg gccccaagaa ggagaagctg    1500
aaggtgaagg tgggccctgtc caactccttc ggcttcggcg ccacaactc ctccatcctg    1560 ttcgccccct gcaacaccat gtaccctac gacgtgcccg actacgcctg a              1611
```

<210> SEQ ID NO 48
<211> LENGTH: 1599
<212> TYPE: DNA
<213> ORGANISM: Artificial Sequence
<220> FEATURE:
<223> OTHER INFORMATION: Cuphea procumbens KASIV (D3290, pSZ4456) codon
      optimized for Prototheca

<400> SEQUENCE: 48

```
atggcttccg cggcattcac catgtcggcg tgccccgcga tgactggcag ggcccctggg    60
gcacgtcgct ccggacggcc agtcgccacc cgcctgaggg gctccacctt ccagtgcctg   120
gtgacctccc acaacgaccc ctgcaaccag tactgctcct ccgcctccct gtccttcctg   180
ggcgacaacg gcttcggctc caagcccttc cgctccaacc gcggccaccg ccgcctgggc   240
cgcgcctccc actccggcga ggccatggcc gtggccctgc agcccgccca ggaggtggcc   300
accaagaaga agcccgccat gaagcagcgc cgcgtggtgg tgaccggcat gggcgtggtg   360
accccccctgg ccacgagcc cgacgtgtac tacaacaacc tgctggacgg cgtgtccggc   420
atctccgaga tcgagacctt cgactgcacc cagttcccca cccgcatcgc cggcgagatc   480
aagtccttct ccaccgacgg ctgggtggcc cccaagctgt ccaagcgcat ggacaagttc   540
atgctgtacc tgctgaccgc cggcaagaag gccctggccg acgcggcat caccgacgac   600
gtgatgaagg agctggacaa gcgcaagtgc ggcgtgctga tcggctccgg catgggcggc   660
atgaagctgt tcaacgactc catcgaggcc ctgcgcgtgt cctacaagaa gatgaacccc   720
ttctgcgtgc ccttcgccac caccaacatg ggctccgcca tgctggccat ggacctgggc   780
tggatgggcc ccaactactc catctccacc gcctgcgcca cctccaactt ctgcatcctg   840
aacgccgcca ccacatcgt gcgcggcgag ccgacatga tgctgtgcgg cggctccgac   900
gccgtgatca tccccatcgg cctgggcggc ttcgtggcct gccgcgccct gtcccagcgc   960
aacaacgacc ccaccaaggc ctcccgcccc tgggactcca accgcgacgg cttcgtgatg  1020
ggcgagggcg ccggcgtgct gctgctggag gagctggagc acgccaagaa gcgcggcgcc  1080
accatctacg ccgagttcct gggcggctcc ttcacctgcg acgcctacca catgaccgag  1140
cccccacccg agggcgccgg cgtgatcctg tgcatcgaga aggccctggc ccagtccggc  1200
gtgtcccgcg aggacgtgaa ctacatcaac gcccacgcca cctccacccc gccggcgac  1260
atcaaggagt accaggccct ggcccactgc ttcggccaga ctccgagct gcgcgtgaac  1320
tccaccaagt ccatgatcgg ccacctgctg ggcgccgccg gcggcgtgga ggccgtgacc  1380
gtgatccagg ccatccgcac cggctggatc caccccaacc tgaacctgga ggaccccgac  1440
aaggccgtgg acgccaagtt cctggtgggc cccaagaagg agcgcctgaa cgtgaaggtg  1500
ggcctgtcca actccttcgg cttcggcggc acaactcct ccatcctgtt cgcccctgc  1560
aacaccatgt acccctacga cgtgcccgac tacgcctga                        1599
```

<210> SEQ ID NO 49
<211> LENGTH: 1599
<212> TYPE: DNA
<213> ORGANISM: Artificial Sequence
<220> FEATURE:
<223> OTHER INFORMATION: C paucipetala KASIVa (D3291, pSZ4457) codon
      optimized for Prototheca

<400> SEQUENCE: 49

```
atggcttccg cggcattcac catgtcggcg tgccccgcga tgactggcag ggcccctggg    60
gcacgtcgct ccggacggcc agtcgccacc cgcctgaggg gctccacctt ccagtgcctg   120
gtgaactccc acatcgaccc ctgcaaccag aacgtgtcct ccgcctccct gtccttcctg   180
ggcgacaacg gcttcggctc caaccccttc cgctccaacc gcggccaccg ccgcctgggc   240
```

-continued

```
cgcgcctccc actccggcga ggccatggcc gtggccctgc agcccgccca ggaggtggcc    300
accaagaaga agcccgccat caagcagcgc cgcgtggtgg tgaccggcat gggcgtggtg    360 accccccctgg gccacgagcc cgacgtgttc tacaacaacc tgctggacgg cgtgtccggc    420
atctccgaga tcgagacctt cgactgcacc cagttcccca cccgcatcgc cggcgagatc    480
aagtccttct ccaccgacgg ctgggtggcc cccaagctgt ccaagcgcat ggacaagttc    540
atgctgtacc tgctgaccgc cggcaagaag gccctggccg acgccggcat caccgaggac    600
gtgatgaagg agctggacaa gcgcaagtgc ggcgtgctga tcggctccgg catgggcggc    660
atgaagctgt tcaacgactc catcgaggcc ctgcgcgtgt cctacaagaa gatgaacccc    720
ttctgcgtgc ccttcgccac caccaacatg ggctccgcca tgctggccat ggacctgggc    780
tggatgggcc ccaactactc catctccacc gcctgcgcca cctccaactt ctgcatcctg    840
aacgccgcca accacatcat ccgcggcgag gccgacatga tgctgtgcgg cggctccgac    900
gccgtgatca tccccatcgg cctgggcggc ttcgtggcct gccgcgccct gtcccagcgc    960
aactccgacc ccaccaaggc ctcccgcccc tgggactcca accgcgacgg cttcgtgatg   1020
ggcgagggcg ccggcgtgct gctgctggag gagctggagc acgccaagaa gcgcggcgcc   1080
accatctacg ccgagttcct gggcggctcc ttcacctgcg acgcctacca catgaccgag   1140
ccccaccccg acggcgccgg cgtgatcctg tgcatcgaga aggccctggc ccagtccggc   1200
gtgtcccgcg aggacgtgaa ctacatcaac gcccacgcca cctccacccc cgccggcgac   1260
atcaaggagt accaggccct ggcccactgc ttcggccaga actccgagct gcgcgtgaac   1320
tccaccaagt ccatgatcgg ccacctgctg ggcgccgccg gcggcgtgga ggccgtgacc   1380
gtgatccagg ccatccgcac cggctggatc caccccaacc tgaacctgga ggaccccgac   1440
gaggccgtgg acgccaagtt cctggtgggc cccaagaagg agcgcctgaa cgtgaaggtg   1500
ggcctgtcca actccttcgg cttcggcggc cacaactcct ccatcctgtt cgccccctac   1560
aacaccatgt accccctacga cgtgcccgac tacgcctga                        1599
```

```
<210> SEQ ID NO 50
<211> LENGTH: 1566
<212> TYPE: DNA
<213> ORGANISM: Artificial Sequence
<220> FEATURE:
<223> OTHER INFORMATION: Cuphea painteri KASIV (D3292, pSZ4458) codon
      optimized for Prototheca

<400> SEQUENCE: 50
atggcttccg cggcattcac catgtcggcg tgccccgcga tgactggcag ggcccctggg     60
gcacgtcgct ccggacggcc agtcgccacc cgcctgaggg gctccacccc ccagtgcctg    120
gacccctgca accagcactg cttcctgggc gacaacggct tcgcctccct gatcggctcc    180 aagcccccccc gctccaacct gggccacctg cgcctgggcc gcacctccca ctccggcgag    240
gtgatggccg tggcccagga ggtgtccacc aacaagaagc acgccaccaa gcagcgccgc    300
gtggtggtga ccggcatggg cgtggtgacc cccctgggcc acgaccccga cgtgtactac    360
aacaacctgc tggagggcgt gtccggcatc tccgagatcg agaacttcga ctgctcccag    420
ctgcccaccc gcatcgccgg cgagatcaag tccttctcca ccgacggcct ggtggccccc    480
aagctgtcca agcgcatgga caagttcatg ctgtacatcc tgaccgccgg caagaaggcc    540
ctggccgacg gcggcatcac cgaggacgtg atgaaggagc tggacaagcg caagtgcggc    600
gtgctgatcg gctccggcct gggcggcatg aaggtgttct ccgactccgt ggaggccctg    660
```

-continued

```
cgcatctcct acaagaagat ctccccctc tgcgtgccct tctccaccac caacatgggc     720
tccgccatgc tggccatgga cctgggctgg atgggcccca actactccat ctccaccgcc     780
tgcgccacct ccaacttctg catcctgaac gccgccaacc acatcaccaa gggcgaggcc     840
gacatgatgc tgtgcggcgg ctccgacgcc gccatcctgc ccatcggcat gggcggcttc     900
gtggcctgcc gcgccctgtc ccagcgcaac aacgacccca ccaaggcctc ccgcccctgg     960
gactccaacc gcgacggctt cgtgatgggc gagggcgccg gcgtgctgct gctggaggag    1020
ctggagcacg ccaagaagcg cggcgccacc atctacgccg agttcctggg cggctccttc    1080
acctgcgacg cctaccacat gaccgagccc caccccgacg gcgccggcgt gatcctgtgc    1140
atcgagaagg ccctggccca gtccggcgtg tcccgcgagg aggtgaacta catcaacgcc    1200
cacgccacct ccaccccgc cggcgacatc aaggagtacc aggccctggc ccactgcttc    1260
ggccagaact ccgagctgcg cgtgaactcc accaagtcca tgatcggcca cctgctgggc    1320
ggcgccggcg gcgtggaggc cgtgaccgtg gtgcaggcca tccgcaccgg ctggatccac    1380
cccaacatca acctggagga ccccgacaag ggcgtggacg ccaagctgct ggtgggcccc    1440
aagaaggaga agctgaaggt gaaggtgggc ctgtccaact ccttcggctt cggcggccac    1500
aactcctcca tcctgttcgc cccctgcaac accatgtacc cctacgacgt gcccgactac    1560
gcctga                                                               1566
```

<210> SEQ ID NO 51
<211> LENGTH: 1611
<212> TYPE: DNA
<213> ORGANISM: Artificial Sequence
<220> FEATURE:
<223> OTHER INFORMATION: C. avigera KASIVa (D3293, pSZ4459) codon optimized for Prototheca

<400> SEQUENCE: 51

```
atggcttccg cggcattcac catgtcggcg tgccccgcga tgactggcag ggcccctggg      60
gcacgtcgct ccggacggcc agtcgccacc cgcctgaggg gctccacctt ccagtgcctg     120
gtgacctcct acaacgaccc ctgcgagcag taccgctcct ccgcctccct gtccttcctg     180
ggcgacaacg gcttcgcctc cctgttcggc tccaagccct tccgctccaa ccgcggccac     240
cgccgcctgg gccgcgcctc ccactccggc gaggccatgg ccgtggccct gcagcccgcc     300
caggaggtgg gcaccaagaa gaagcccgtg atcaagcagc gccgcgtggt ggtgaccggc     360
atgggcgtgg tgaccccct gggccacgag cccgacgtgt actacaacaa cctgctggac     420
ggcgtgtccg gcatctccga gatcgagacc ttcgactgca cccagttccc cacccgcatc     480
gccggcgaga tcaagtcctt ctccaccgac ggctgggtgg cccccaagct gtccaagcgc     540
atggacaagt tcatgctgta cctgctgacc gccggcaaga aggccctggc cgacggcggc     600
atcaccgacg acgtgatgaa ggagctggac aagcgcaagt gcggcgtgct gatcggctcc     660
ggcctgggcg gcatgaaggt gttctccgag tccatcgagg ccctgcgcac ctcctacaag     720
aagatctccc ccttctgcgt gcccttctcc accaccaaca tgggctccgc catcctggcc     780
atggacctgg gctggatggg ccccaactac tccatctcca ccgcctgcgc cacctccaac     840
ttctgcatcc tgaacgccgc caaccacatc accaagggcg aggccgacat gatgctgtgc     900
ggcggctccg actccgtgat cctgcccatc ggcatgggcg gcttcgtggc ctgccgcgcc     960
ctgtcccagc gcaacaacga ccccaccaag gcctcccgcc cctgggactc caaccgcgac    1020
ggcttcgtga tgggcgaggg cgccggcgtg ctgctgctgg aggagctgga gcacgccaag    1080
```

```
aagcgcggcg ccaccatcta cgccgagttc ctgggcggct ccttcacctg cgacgcctac    1140
cacatgaccg agccccaccc cgagggcgcc ggcgtgatcc tgtgcatcga aaggccctg     1200 gcccagtccg gcgtgtcccg cgaggacgtg aactacatca acgcccacgc cacctccacc    1260
cccgccggcg acatcaagga gtaccaggcc ctggcccact gcttcggcca gaactccgag    1320
ctgcgcgtga actccaccaa gtccatgatc ggccacctgc tgggcggcgc cggcggcgtg    1380
gaggccgtga ccgtggtgca ggccatccgc accggctgga tccacccaa catcaacctg     1440 gacgaccccg acgagggcgt ggacgccaag ctgctggtgg gccccaagaa ggagaagctg    1500
aaggtgaagg tgggcctgtc caactccttc ggcttcggcg ccacaactc ctccatcctg     1560 ttcgcccct gcaacaccat gtaccctac gacgtgcccg actacgcctg a               1611
```

<210> SEQ ID NO 52
<211> LENGTH: 1611
<212> TYPE: DNA
<213> ORGANISM: Artificial Sequence
<220> FEATURE:
<223> OTHER INFORMATION: C ignea KASIVa (D3294, pSZ4460) codon optimized for Prototheca

<400> SEQUENCE: 52

```
atggcttccg cggcattcac catgtcggcg tgccccgcga tgactggcag ggcccctggg     60
gcacgtcgct ccggacggcc agtcgccacc cgcctgaggg gctccacctc ccagtgcctg    120
gtgacctcct acatcgaccc ctgcaacaag tactgctcct ccgcctccct gtccttcctg    180
ggcgacaacg gcttcgcctc cctgttcggc tccaagccct ccgctccaa ccgcggccac     240 cgccgcctgg gccgcgcctc ccactccggc gaggccatgg ccgtggccct gcagcccgcc    300
caggaggtga ccaccaagaa gaagcccgtg atcaagcagc gccgcgtggt ggtgaccggc    360
atgggcgtgg tgaccccct gggccacgag cccgacgtgt actacaacaa cctgctggac    420
ggcgtgtccg catctccga gatcgagacc ttcgactgca cccagttccc cacccgcatc    480
gccggcgaga tcaagtcctt ctccaccgac ggctgggtgg cccccaagct gtccaagcgc    540
atggacaagt tcatgctgta cctgctgacc gccggcaaga aggccctggc cgacggcggc    600
atcaccgacg acgtgatgaa ggagctggac aagcgcaagt gcgccgtgct gatcggctcc    660
ggcatgggcg gcatgaagct gttcaacgac tccatcgagg ccctgcgcat ctcctacaag    720
aagatgaacc ccttctgcgt gcccttcgcc accaccaaca tgggctccgc catgctggcc    780
atggacctgg ctggatggg ccccaactac tccatctcca ccgcctgcgc cacctccaac    840
ttctgcatcc tgaacgcctc caaccacatc gtgcgcggcg aggccgacat gatgctgtgc    900
ggcggctccg acgccgtgat catccccatc ggcctgggcg gcttcgtggc ctgccgcgcc    960
ctgtcccagc gcaacaacga ccccaccaag gcctcccgcc cctgggactc caaccgcgac    1020
ggcttcgtga tgggcgaggg cgccggcgtg ctgctgctgg aggagctgga gcacgccaag    1080
aagcgcggcg ccaccatcta cgccgagttc ctgggcggct ccttcacctg cgacgcctac    1140
cacatgaccg agccccaccc cgagggcgcc ggcgtgatcc tgtgcatcga aaggccctg     1200 gcccaggccg gcgtgtccaa ggaggacgtg aactacatca acgcccacgc cacctccacc    1260
cccgccggcg acatcaagga gtaccaggcc ctggcccagt gcttcggcca gaactccgag    1320
ctgcgcgtga actccaccaa gtccatgatc ggccacctgc tgggcgccgc cggcggcgtg    1380
gaggccgtga ccgtggtgca ggccatccgc accggctgga tccacccaa cctgaacctg    1440 gaggaccccg acaaggccgt ggacgccaag ctgctggtgg gccccaagaa ggagcgcctg    1500
```

```
aacgtgaagg tgggcctgtc caactccttc ggcttcggcg gccacaactc ctccatcctg    1560
ttcgccccct acaacaccat gtaccnctac gacgtgcccg actacgcctg a             1611
```

<210> SEQ ID NO 53
<211> LENGTH: 1455
<212> TYPE: DNA
<213> ORGANISM: Artificial Sequence
<220> FEATURE:
<223> OTHER INFORMATION: C. avigera KASIa (D3342, pSZ4511) codon
      optimized for Prototheca

<400> SEQUENCE: 53

```
atgcagtccc tgcactcccc cgccctgcgc gcctcccccc tggacccccct gcgcctgaag    60 tcctccgcca acggcccctc ctccaccgcc gccttccgcc ccctgcgccg cgccacctg    120 cccaacatcc gcgccgcctc ccccaccgtg tccgccccca gcgcgagac cgaccccaag    180 aagcgcgtgg tgatcaccgg catgggcctg gtgtccgtgt cggctccga cgtggacgcc    240 tactacgaga gctgctgtc cggcgagtcc ggcatctccc tgatcgaccg cttcgacgcc    300
tccaagttcc ccacccgctt cggcggccag atccgcggct caacgccac cggctacatc    360 gacggcaaga cgaccgccg cctggacgac tgcctgcgct actgcatcgt ggccggcaag    420
aaggccctgg agaactccga cctgggcggc gactccctgt ccaagatcga caaggagcgc    480
gccggcgtgc tggtgggcac cggcatgggc ggcctgaccg tgttctccga cggcgtgcag    540
aacctgatcg agaagggcca ccgcaagatc tccccttct catccccta cgccatcacc    600 aacatgggct ccgccctgct ggccatcgac ctgggcctga tgggcccaa ctactccatc    660 tccaccgcct gcgccacctc caactactgc ttctacgccg ccgccaacca catccgccgc    720
ggcgaggccg acctgatgat cgccggcggc accgaggccg ccatcatccc catcggcctg    780
ggcggcttcg tggcctgccg cgccctgtcc cagcgcaacg acgaccccca gaccgcctcc    840
cgcccctggg acaaggaccg cgacggcttc gtgatgggcg agggcgccgg cgtgctggtg    900
atggagtccc tggagcacgc catgaagcgc ggcgccccca tcatcgccga gtacctgggc    960
ggcgccgtga actgcgacgc ctaccacatg accgaccccc gcgccgacgg cctgggcgtg    1020
tcctcctgca tcgagtcctc cctggaggac gccggcgtgt cccccgagga ggtgaactac    1080
atcaacgccc acgccaccct caccctggcc ggcgacctgg ccgagatcaa cgccatcaag    1140
aaggtgttca gaacaccaa ggacatcaag atcaacgcca ccagtccat gatcggccac    1200 tgcctgggcg cctccggcgg cctggaggcc atcgccacca tcaagggcat caccaccggc    1260
tggctgcacc cctccatcaa ccagttcaac cccgagccct ccgtggagtt cgacaccgtg    1320
gccaacaaga gcagcagca cgaggtgaac gtggccatct ccaactcctt cggcttcggc    1380
ggccacaact ccgtggtggc cttctccgcc ttcaagccca ccatgtaccc ctacgacgtg    1440
cccgactacg cctga                                                    1455
```

<210> SEQ ID NO 54
<211> LENGTH: 1431
<212> TYPE: DNA
<213> ORGANISM: Artificial Sequence
<220> FEATURE:
<223> OTHER INFORMATION: C. pulcherrima KASI (D3343, pSZ4512) codon
      optimized for Prototheca

<400> SEQUENCE: 54

```
atgcactccc tgcagtcccc ctccctgcgc gcctcccccc tggacccctt ccgccccaag    60
tcctccaccg tgcgccccct gcaccgcgcc tccatcccca acgtgcgcgc cgcctccccc    120
```

```
accgtgtccg cccccaagcg cgagaccgac cccaagaagc gcgtggtgat caccggcatg    180
ggcctggtgt ccgtgttcgg ctccgacgtg gacgcctact acgacaagct gctgtccggc    240
gagtccggca tcggcccat  cgaccgcttc gacgcctcca gttccccac  ccgcttcggc    300
ggccagatcc gcggcttcaa ctccatgggc tacatcgacg gcaagaacga ccgccgcctg    360
gacgactgcc tgcgctactg catcgtggcc ggcaagaagt ccctggagga cgccgacctg    420
ggcgccgacc gctgtccaa  gatcgacaag gagcgcgccg gcgtgctggt gggcaccggc    480
atgggcggcc tgaccgtgtt ctccgacggc gtgcagtccc tgatcgagaa gggccaccgc    540
aagatcaccc ccttcttcat cccctacgcc atcaccaaca tgggctccgc cctgctggcc    600
atcgagctgg gcctgatggg ccccaactac tccatctcca ccgcctgcgc cacctccaac    660
tactgcttcc acgccgccgc caaccacatc cgcgcggcg  aggccgacct gatgatcgcc    720
ggcggcaccg aggccgccat catccccatc ggcctgggcg gcttcgtggc ctgccgcgcc    780
ctgtcccagc gcaacgacga ccccagacc  gcctcccgcc cctgggacaa ggaccgcgac    840
ggcttcgtga tgggcgaggg cgccggcgtg ctggtgctgg agtccctgga gcacgccatg    900
aagcgcggcg cccccatcat cgccgagtac ctgggcggcg ccatcaactg cgacgcctac    960
cacatgaccg accccgcgc  cgacggcctg ggcgtgtcct cctgcatcga gtcctccctg   1020
gaggacgccg gcgtgtcccc cgaggaggtg aactacatca cgccacgc  cacctccacc   1080
ctggccggcg acctggccga gatcaacgcc atcaagaagg tgttcaagaa caccaaggac   1140
atcaagatca cgccaccaa  gtccatgatc ggccactgcc tgggcgcctc cggcggcctg   1200
gaggccatcg ccaccatcaa gggcatcaac accggctggc tgcaccccte catcaaccag   1260
ttcaacccog agcctccgt  ggagttcgac accgtggcca acaagaagca gcagcacgag   1320
gtgaacgtgg ccatctccaa ctccttcggc ttcggcggcc acaactccgt ggtggccttc   1380
tccgccttca gcccaccat  gtacccctac gacgtgcccg actacgcctg a            1431
```

<210> SEQ ID NO 55
<211> LENGTH: 1434
<212> TYPE: DNA
<213> ORGANISM: Artificial Sequence
<220> FEATURE:
<223> OTHER INFORMATION: C. avigera mitochondrial KAS (D3344, pSZ4513)
      codon optimized for Prototheca

<400> SEQUENCE: 55

```
atggtgttcc tgccctggcg caagatgctg tgccctccc  agtaccgctt cctgcgcccc     60
ctgtcctcct ccaccacctt cgaccccgc  cgcgtggtgg tgaccggcct gggcatggtg    120
accccctgg  gctgcggcgt gaacaccacc tggaagcagc tgatcgaggg caagtgcggc    180
atccgcgcca tctccctgga ggacctgaag atggacgcct cgacatcga  cacccaggcc    240
tacgtgttcg accagctgac ctccaaggtg gccgccaccg tgcccaccgg cgtgaacccc    300
ggcgagttca cgaggacct  gtggttcaac cagaaggagc ccgccgccat cgcccgcttc    360
atcgcctacg ccctgtgcgc cgccgacgag gccctgaagg acgccaactg ggagcccacc    420
gagcccgagg agcgcgagat gaccggcgtg tccatcggcg gcggcaccgg ctccatctcc    480
gacgtgctgg acgccggccg catgatctgc gagaagaagc tgcgccgcct gtccccttc    540
ttcatccccc gcatcctgat caacatggcc tccggccacg tgtccatgaa gtacggcttc    600
cagggcccca accacgccgc cgtgaccgcc tgcgccaccg cgcccactc  catcggcgac    660
gccgcccgca tgatccagtt cggcgacgcc gacgtgatgg tggccggcgg caccgagtcc    720
```

-continued

```
tccatcgacg ccctgtccat cgccggcttc tgccgctccc gcgccctgac caccaagtac      780
aactcctgcc cccaggaggc ctcccgcccc ttcgacaccg accgcgacgg cttcgtgatc      840
ggcgagggct ccggcgtgct ggtgctggag gagctggacc acgcccgcaa gcgcggcgcc      900
aagatgtacg ccgagttctg cggctacggc atgtccggcg acgcccacca catcacccag      960
ccccactccg acggccgcgg cgccatcctg gccatgaccc gcgccctgaa gcagtccaac     1020
ctgcaccccg accaggtgga ctacgtgaac gcccacgcca cctccacctc cctgggcgac     1080
gccatcgagg ccaaggccat caagaccgtg ttctccgacc acgccatgtc cggctccctg     1140
gccctgtcct ccaccaaggg cgccatcggc cacctgctgg gcgccgccgg cgccgtggag     1200
gccatcttct ccatcctggc catcaagaac ggcctggccc ccctgaccct gaacgtggcc     1260
cgccccgacc ccgtgttcac cgagcgcttc gtgcccctga ccgcctccaa ggagatgcac     1320
gtgcgcgccg ccctgtccaa ctccttcggc ttcggcggca ccaacaccac cctgctgttc     1380
acctcccccc cccagaacac catgtacccc tacgacgtgc ccgactacgc ctga           1434
```

<210> SEQ ID NO 56
<211> LENGTH: 1242
<212> TYPE: DNA
<213> ORGANISM: Artificial Sequence
<220> FEATURE:
<223> OTHER INFORMATION: C. avigera KASIII (D3345, pSZ4514) Codon optimized for Prototheca

<400> SEQUENCE: 56

```
atggccaacg cctacggctt cgtgggctcc tccgtgccca ccgtgggccg cgccgcccag       60
ttccagcaga tgggctccgg cttctgctcc gtggacttca tctccaagcg cgtgttctgc      120
tgctccgccg tgcagggcgc cgacaagccc gcctccggcg actcccgcgc cgagtaccgc      180
accccccgcc tggtgtcccg cggctgcaag ctgatcggct ccggctccgc catccccacc      240
ctgcaggtgt ccaacgacga cctggccaag atcgtggaca ccaacgacga gtggatctcc      300
gtgcgcaccg gcatccgcaa ccgccgcgtg ctgaccggca aggactccct gaccaacctg      360
gccaccgagg ccgcccgcaa ggccctggag atggcccagg tggacgccga ggacgtggac      420
atggtgctga tgtgcacctc caccccgag gacctgttcg gctccgcccc ccagatccag      480
aaggccctgg ctgcaagaa gaacccctg tcctacgaca tcaccgccgc ctgctccggc      540
ttcgtgctgg gcctggtgtc cgccgcctgc cacatccgcg gcggcggctt caacaacgtg      600
ctggtgatcg gcgccgactc cctgtcccgc tacgtggact ggaccgaccg cggcacctgc      660
atcctgttcg gcgacgccgc cggcgccgtg ctggtgcagt cctgcgacgc cgaggaggac      720
ggcctgttcg ccttcgacct gcactccgac ggcgacggcc agcgccacct gcgcgccgtg      780
atcaccgaga acgagaccga ccacgccgtg ggcaccaacg gctccgtgtc cgacttcccc      840
ccccgccgct cctcctactc ctgcatccag atgaacggca aggaggtgtt ccgcttcgcc      900
tgccgctccg tgcccagtc catcgagctg gccctgggca aggccggcct gaacggctcc      960
aacatcgact ggctgctgct gcaccaggcc aaccagcgca tcatcgacgc cgtggccacc     1020
cgcctggagg tgcccagga gcgcgtgatc tccaacctgg ccaactacgg caacacctcc     1080
gccgcctcca tccccctggc cctggacgag gccgtgcgcg cggcaaggt gaagcccggc     1140
cacctgatcg ccaccgccgg cttcggcgcc ggcctgacct ggggctccgc catcgtgcgc     1200
tggggcacca tgtaccccta cgacgtgccc gactacgcct ga                         1242
```

```
<210> SEQ ID NO 57
<211> LENGTH: 415
<212> TYPE: PRT
<213> ORGANISM: Cuphea hookeriana
<220> FEATURE:
<221> NAME/KEY: MISC_FEATURE
<223> OTHER INFORMATION: FATB2

<400> SEQUENCE: 57

Met Val Ala Ala Ala Ser Ser Ala Phe Phe Pro Val Pro Ala Pro
1               5                   10                  15

Gly Ala Ser Pro Lys Pro Gly Lys Phe Gly Asn Trp Pro Ser Ser Leu
                20                  25                  30

Ser Pro Ser Phe Lys Pro Lys Ser Ile Pro Asn Gly Gly Phe Gln Val
            35                  40                  45

Lys Ala Asn Asp Ser Ala His Pro Lys Ala Asn Gly Ser Ala Val Ser
50                  55                  60

Leu Lys Ser Gly Ser Leu Asn Thr Gln Glu Asp Thr Ser Ser Ser Pro
65                  70                  75                  80

Pro Pro Arg Thr Phe Leu His Gln Leu Pro Asp Trp Ser Arg Leu Leu
                85                  90                  95

Thr Ala Ile Thr Thr Val Phe Val Lys Ser Lys Arg Pro Asp Met His
                100                 105                 110

Asp Arg Lys Ser Lys Arg Pro Asp Met Leu Val Asp Ser Phe Gly Leu
            115                 120                 125

Glu Ser Thr Val Gln Asp Gly Leu Val Phe Arg Gln Ser Phe Ser Ile
130                 135                 140

Arg Ser Tyr Glu Ile Gly Thr Asp Arg Thr Ala Ser Ile Glu Thr Leu
145                 150                 155                 160

Met Asn His Leu Gln Glu Thr Ser Leu Asn His Cys Lys Ser Thr Gly
                165                 170                 175

Ile Leu Leu Asp Gly Phe Gly Arg Thr Leu Glu Met Cys Lys Arg Asp
            180                 185                 190

Leu Ile Trp Val Val Ile Lys Met Gln Ile Lys Val Asn Arg Tyr Pro
            195                 200                 205

Ala Trp Gly Asp Thr Val Glu Ile Asn Thr Arg Phe Ser Arg Leu Gly
        210                 215                 220

Lys Ile Gly Met Gly Arg Asp Trp Leu Ile Ser Asp Cys Asn Thr Gly
225                 230                 235                 240

Glu Ile Leu Val Arg Ala Thr Ser Ala Tyr Ala Met Met Asn Gln Lys
                245                 250                 255

Thr Arg Arg Leu Ser Lys Leu Pro Tyr Glu Val His Gln Glu Ile Val
            260                 265                 270

Pro Leu Phe Val Asp Ser Pro Val Ile Glu Asp Ser Asp Leu Lys Val
        275                 280                 285

His Lys Phe Lys Val Lys Thr Gly Asp Ser Ile Gln Lys Gly Leu Thr
        290                 295                 300

Pro Gly Trp Asn Asp Leu Asp Val Asn Gln His Val Ser Asn Val Lys
305                 310                 315                 320

Tyr Ile Gly Trp Ile Leu Glu Ser Met Pro Thr Glu Val Leu Glu Thr
                325                 330                 335

Gln Glu Leu Cys Ser Leu Ala Leu Glu Tyr Arg Arg Glu Cys Gly Arg
            340                 345                 350

Asp Ser Val Leu Glu Ser Val Thr Ala Met Asp Pro Ser Lys Val Gly
        355                 360                 365
```

```
Val Arg Ser Gln Tyr Gln His Leu Leu Arg Leu Glu Asp Gly Thr Ala
        370                 375                 380

Ile Val Asn Gly Ala Thr Glu Trp Arg Pro Lys Asn Ala Gly Ala Asn
385                 390                 395                 400

Gly Ala Ile Ser Thr Gly Lys Thr Ser Asn Gly Asn Ser Val Ser
                405                 410                 415

<210> SEQ ID NO 58
<211> LENGTH: 573
<212> TYPE: DNA
<213> ORGANISM: Prototheca moriformis
<220> FEATURE:
<221> NAME/KEY: misc_feature
<223> OTHER INFORMATION: 23S rRNA for UTEX 1439, UTEX 1441, UTEX 1435,
      UTEX 1437 Prototheca moriformis

<400> SEQUENCE: 58
tgttgaagaa tgagccggcg acttaaaata aatggcaggc taagagaatt aataactcga      60
aacctaagcg aaagcaagtc ttaatagggc gctaatttaa caaaacatta aataaaatct    120
aaagtcattt attttagacc cgaacctgag tgatctaacc atggtcagga tgaaacttgg    180
gtgacaccaa gtggaagtcc gaaccgaccg atgttgaaaa atcggcggat gaactgtggt    240
tagtggtgaa ataccagtcg aactcagagc tagctggttc tccccgaaat gcgttgaggc    300
gcagcaatat atctcgtcta tctaggggta aagcactgtt tcggtgcggg ctatgaaaat    360
ggtaccaaat cgtggcaaac tctgaatact agaaatgacg atatattagt gagactatgg    420
gggataagct ccatagtcga gagggaaaca gcccagacca ccagttaagg ccccaaaatg    480
ataatgaagt ggtaaaggag gtgaaaatgc aaatacaacc aggaggttgg cttagaagca    540
gccatccttt aaagagtgcg taatagctca ctg                                 573

<210> SEQ ID NO 59
<211> LENGTH: 514
<212> TYPE: PRT
<213> ORGANISM: Cuphea hookeriana
<220> FEATURE:
<221> NAME/KEY: MISC_FEATURE
<223> OTHER INFORMATION: KASIV

<400> SEQUENCE: 59

Met Ala Ser Ala Ala Phe Thr Met Ser Ala Cys Pro Ala Met Thr Gly
1               5                   10                  15

Arg Ala Pro Gly Ala Arg Arg Ser Gly Arg Pro Val Ala Thr Arg Leu
            20                  25                  30

Arg Gly Ser Thr Phe Gln Cys Leu Asp Pro Cys Asn Gln Gln Arg Phe
        35                  40                  45

Leu Gly Asp Asn Gly Phe Ala Ser Leu Phe Gly Ser Lys Pro Leu Arg
    50                  55                  60

Ser Asn Arg Gly His Leu Arg Leu Gly Arg Thr Ser His Ser Gly Glu
65                  70                  75                  80

Val Met Ala Val Ala Met Gln Pro Ala Gln Glu Val Ser Thr Asn Lys
                85                  90                  95

Lys Pro Ala Thr Lys Gln Arg Arg Val Val Val Thr Gly Met Gly Val
            100                 105                 110

Val Thr Pro Leu Gly His Asp Pro Asp Val Tyr Tyr Asn Asn Leu Leu
        115                 120                 125

Asp Gly Ile Ser Gly Ile Ser Glu Ile Glu Asn Phe Asp Cys Ser Gln
    130                 135                 140
```

Phe Pro Thr Arg Ile Ala Gly Glu Ile Lys Ser Phe Ser Thr Asp Gly
145                 150                 155                 160

Trp Val Ala Pro Lys Phe Ser Glu Arg Met Asp Lys Phe Met Leu Tyr
                165                 170                 175

Met Leu Thr Ala Gly Lys Lys Ala Leu Ala Asp Gly Gly Ile Thr Glu
            180                 185                 190

Asp Ala Met Lys Glu Leu Asn Lys Arg Lys Cys Gly Val Leu Ile Gly
        195                 200                 205

Ser Gly Leu Gly Gly Met Lys Val Phe Ser Asp Ser Ile Glu Ala Leu
    210                 215                 220

Arg Thr Ser Tyr Lys Lys Ile Ser Pro Phe Cys Val Pro Phe Ser Thr
225                 230                 235                 240

Thr Asn Met Gly Ser Ala Ile Leu Ala Met Asp Leu Gly Trp Met Gly
                245                 250                 255

Pro Asn Tyr Ser Ile Ser Thr Ala Cys Ala Thr Ser Asn Phe Cys Ile
            260                 265                 270

Leu Asn Ala Ala Asn His Ile Ile Lys Gly Glu Ala Asp Met Met Leu
        275                 280                 285

Cys Gly Gly Ser Asp Ala Ala Val Leu Pro Val Gly Leu Gly Gly Phe
    290                 295                 300

Val Ala Cys Arg Ala Leu Ser Gln Arg Asn Asn Asp Pro Thr Lys Ala
305                 310                 315                 320

Ser Arg Pro Trp Asp Ser Asn Arg Asp Gly Phe Val Met Gly Glu Gly
                325                 330                 335

Ala Gly Val Leu Leu Leu Glu Glu Leu Glu His Ala Lys Lys Arg Gly
            340                 345                 350

Ala Thr Ile Tyr Ala Glu Phe Leu Gly Gly Ser Phe Thr Cys Asp Ala
        355                 360                 365

Tyr His Met Thr Glu Pro His Pro Glu Gly Ala Gly Val Ile Leu Cys
    370                 375                 380

Ile Glu Lys Ala Leu Ala Gln Ser Gly Val Ser Arg Glu Asp Val Asn
385                 390                 395                 400

Tyr Ile Asn Ala His Ala Thr Ser Thr Pro Ala Gly Asp Ile Lys Glu
                405                 410                 415

Tyr Gln Ala Leu Ala His Cys Phe Gly Gln Asn Ser Glu Leu Arg Val
            420                 425                 430

Asn Ser Thr Lys Ser Met Ile Gly His Leu Leu Gly Gly Ala Gly Gly
        435                 440                 445

Val Glu Ala Val Ala Val Val Gln Ala Ile Arg Thr Gly Trp Ile His
    450                 455                 460

Pro Asn Ile Asn Leu Glu Asp Pro Asp Glu Gly Val Asp Ala Lys Leu
465                 470                 475                 480

Leu Val Gly Pro Lys Lys Glu Lys Leu Lys Val Lys Val Gly Leu Ser
                485                 490                 495

Asn Ser Phe Gly Phe Gly Gly His Asn Ser Ser Ile Leu Phe Ala Pro
            500                 505                 510

Cys Asn

<210> SEQ ID NO 60
<211> LENGTH: 6227
<212> TYPE: DNA
<213> ORGANISM: Artificial Sequence
<220> FEATURE:
<223> OTHER INFORMATION: C. hookeriana KASIV (D3668, pSZ4756) expression
      vector

<400> SEQUENCE: 60

```
gccggtcacc acccgcatgc tcgtactaca gcgcacgcac cgcttcgtga tccaccgggt    60
gaacgtagtc ctcgacggaa acatctggtt cgggcctcct gcttgcactc ccgcccatgc   120
cgacaacctt tctgctgtta ccacgaccca caatgcaacg cgacacgacc gtgtgggact   180
gatcggttca ctgcacctgc atgcaattgt cacaagcgct tactccaatt gtattcgttt   240
gttttctggg agcagttgct cgaccgcccg cgtcccgcag gcagcgatga cgtgtgcgtg   300
gcctgggtgt ttcgtcgaaa ggccagcaac cctaaatcgc aggcgatccg gagattggga   360
tctgatccga gtttggacca gatccgcccc gatgcgcac gggaactgca tcgactcggc   420
gcggaaccca gctttcgtaa atgccagatt ggtgtccgat acctggattt gccatcagcg   480
aaacaagact tcagcagcga gcgtatttgg cgggcgtgct accaggggttg catacattgc   540
ccatttctgt ctggaccgct ttactggcgc agagggtgag ttgatggggt tggcaggcat   600
cgaaacgcgc gtgcatggtg tgcgtgtctg ttttcggctg cacgaattca atagtcggat   660
gggcgacggt agaattgggt gtggcgctcg cgtgcatgcc tcgccccgtc gggtgtcatg   720
accgggactg gaatccccc tcgcgaccat cttgctaacg ctcccgactc tcccgaccgc   780
gcgcaggata gactcttgtt caaccaatcg acaggtacca tggcttccgc ggcattcacc   840
atgtcggcgt gccccgcgat gactggcagg gcccctgggg cacgtcgctc cggacggcca   900
gtcgccaccc gcctgagggg cagcaccttc cagtgcctgg acccctgcaa ccagcagcgc   960
ttcctgggcg acaacggctt cgcgtcgctg ttcggctcca gcccctgcg cagcaaccgc  1020
ggccacctgc gcctgggccg cacctcgcac tccggcgagg tgatggccgt cgcgatgcag  1080
cccgcccagg aggtgagcac caacaagaag cccgcgacca gcagcgccg cgtggtcgtg  1140
accggcatgg gcgtcgtgac cccctgggc cacgaccccg acgtgtatta taacaacctg  1200
ctggacggca tctcgggcat ctccgagatc gagaacttcg actgcagcca gttccccacc  1260
cgcatcgccg gcgagatcaa gtcgttctcc accgacggct gggtcgcgcc caagttcagc  1320
gagcgcatgg acaagttcat gctgtatatg ctgaccgccg gcaagaaggc gctggccgac  1380
ggcggcatca ccgaggacgc gatgaaggag ctgaacaagc gcaagtgcgg cgtgctgatc  1440
ggctcgggcc tggcggcat gaaggtcttc tccgacagca tcgaggccct gcgcacctcg  1500
tataagaaga tctccccctt ctgcgtgccc ttcagcacca ccaacatggg ctcggcgatc  1560
ctggcgatgg acctgggctg gatgggcccc aactattcca tcagcaccgc gtgcgccacc  1620
tcgaacttct gcatcctgaa cgcggccaac cacatcatca agggcgaggc ggacatgatg  1680
ctgtgcggcg gctccgacgc cgcggtgctg cccgtcggcc tgggcggctt cgtggcctgc  1740
cgcgcgctga ccagcgcaa caacgacccc accaaggcct cgcgcccctg ggactccaac  1800
cgcgacggct tcgtcatggg cgagggcgcg ggcgtgctgc tgctggagga gctggagcac  1860
gccaagaagc gcgcgcgac catctatgcc gagttcctgg gcggcagctt cacctgcgac  1920
gcgtatcaca tgaccgagcc ccaccccgag ggcgccggcg tcatcctgtg catcgagaag  1980
gcgctggccc agtcgggcgt gtcccgcgag gacgtgaact atatcaacgc gcacgccacc  2040
agcacccccg cgggcgacat caaggagtat caggccctgg cgcactgctt cggccagaac  2100
tcggagctgc gcgtcaactc caccaagagc atgatcggcc acctgctggg cggcgccggc  2160
ggcgtggagg cggtcgccgt ggtccaggcg atccgcaccg gctggatcca ccccaacatc  2220
aacctggagg accccgacga gggcgtggac gccaagctgc tggtcggccc caagaaggag  2280
```

```
aagctgaagg tgaaggtcgg cctgtcgaac tccttcggct tcggcggcca caacagctcg    2340
atcctgttcg cgccctgcaa ctgactcgag acagacgacc ttggcaggcg tcgggtaggg    2400
aggtggtggt gatggcgtct cgatgccatc gcacgcatcc aacgaccgta tacgcatcgt    2460
ccaatgaccg tcggtgtcct ctctgcctcc gttttgtgag atgtctcagg cttggtgcat    2520
cctcgggtgg ccagccacgt tgcgcgtcgt gctgcttgcc tctcttgcgc tctgtggta    2580 ctggaaaata tcatcgaggc ccgttttttt gctcccattt cctttccgct acatcttgaa    2640
agcaaacgac aaacgaagca gcaagcaaag agcacgagga cggtgaacaa gtctgtcacc    2700
tgtatacatc tatttcccg cggtgcacc tactctctct cctgcccgg cagagtcagc    2760 tgccttacgt gaccctaggt gcggtgagaa tcgaaaatgc atcgtttcta ggttcggaga    2820
cggtcaattc cctgctccgg cgaatctgtc ggtcaagctg ccagtggac aatgttgcta    2880 tggcagcccg cgcacatggg cctcccgacg cggccatcag gagcccaaac agcgtgtcag    2940
ggtatgtgaa actcaagagg tccctgctgg gcactccggc cccactccgg gggcgggacg    3000
ccaggcattc gcggtcggtc ccgcgcgacg agcgaaatga tgattcggtt acgagaccag    3060
gacgtcgtcg aggtcgagag gcagcctcgg acacgtctcg ctagggcaac gccccgagtc    3120
cccgcgaggg ccgtaaacat tgtttctggg tgtcggagtg ggcattttgg gcccgatcca    3180
atcgcctcat gccgctctcg tctggtcctc acgttcgcgt acggcctgga tcccggaaag    3240
ggcggatgca cgtggtgttg ccccgccatt ggcgcccacg tttcaaagtc cccggccaga    3300
aatgcacagg accggcccgg ctcgcacagg ccatgctgaa cgcccagatt cgacagcaa    3360 caccatctag aataatcgca accatccgcg ttttgaacga aacgaaacgg cgctgtttag    3420
catgtttccg acatcgtggg ggccgaagca tgctccgggg ggaggaaagc gtggcacagc    3480
ggtagcccat tctgtgccac acgccgacga ggaccaatcc ccggcatcag ccttcatcga    3540
cggctgcgcc gcacatataa agccggacgc ctaaccggtt tcgtggttat gactagtatg    3600
ttcgcgttct acttcctgac ggcctgcatc tccctgaagg gcgtgttcgg cgtctccccc    3660
tcctacaacg gcctgggcct gacgccccag atgggctggg acaactggaa cacgttcgcc    3720
tgcgacgtct ccgagcagct gctgctgac acggccgacc gcatctccga cctgggcctg    3780
aaggacatgg gctacaagta catcatcctg gacgactgct ggtcctccgg ccgcgactcc    3840
gacggcttcc tggtcgccga cgagcagaag ttccccaacg gcatgggcca cgtcgccgac    3900
cacctgcaca caactccttt cctgttcggc atgtactcct ccgcgggcga gtacacgtgc    3960
gccggctacc ccggctccct gggccgcgag gaggaggacg cccagttctt cgcgaacaac    4020
cgcgtggact acctgaagta cgacaactgc tacaacaagg gccagttcgg cacgcccgag    4080
atctcctacc accgctacaa ggccatgtcc gacgccctga acaagacggg ccgcccatc    4140 ttctactccc tgtgcaactg gggccaggac ctgaccttct actgggctc cggcatcgcg    4200 aactcctggc gcatgtccgg cgacgtcacg gcggagttca cgcgcccga ctcccgctgc    4260 ccctgcgacg gcgacgagta cgactgcaag tacgccggct ccactgctc catcatgaac    4320 atcctgaaca aggccgcccc catgggccag aacgcgggcg tcggcggctg aacgacctg    4380 gacaacctgg aggtcggcgt cggcaacctg acggacgacg aggagaaggc gcacttctcc    4440
atgtgggcca tggtgaagtc ccccctgatc atcgcgcga acgtgaacaa cctgaaggcc    4500
tcctcctact ccatctactc ccaggcgtcc gtcatcgcca tcaaccagga ctccaacgga    4560
atccccgcca cgcgcgtctg gcgctactac gtgtccgaca cggacgagta cggccagggc    4620
gagatccaga tgtggtccgg cccccctggac aacggcgacc aggtcgtggc gctgctgaac    4680
```

-continued

```
ggcggctccg tgtcccgccc catgaacacg accctggagg agatcttctt cgactccaac    4740
ctgggctcca agaagctgac ctccacctgg gacatctacg acctgtgggc gaaccgcgtc    4800
gacaactcca cggcgtccgc catcctgggc cgcaacaaga ccgccaccgg catcctgtac    4860
aacgccaccg agcagtccta caaggacggc ctgtccaaga cgacacccg cctgttcggc     4920 cagaagatcg gctccctgtc ccccaacgcg atcctgaaca cgaccgtccc cgcccacggc    4980
atcgcgttct accgcctgcg cccctcctcc tgatacaact tattacgtat tctgaccggc    5040
gctgatgtgg cgcggacgcc gtcgtactct ttcagacttt actcttgagg aattgaacct    5100
ttctcgcttg ctggcatgta acattggcg caattaattg tgtgatgaag aaagggtggc     5160
acaagatgga tcgcgaatgt acgagatcga aacgatggt gattgttatg aggggccaaa     5220
cctggctcaa tcttgtcgca tgtccggcgc aatgtgatcc agcggcgtga ctctcgcaac    5280
ctggtagtgt gtgcgcaccg ggtcgctttg attaaaactg atcgcattgc catcccgtca    5340
actcacaagc ctactctagc tcccattgcg cactcgggcg cccggctcga tcaatgttct    5400
gagcggaggg cgaagcgtca ggaaatcgtc tcggcagctg aagcgcatg gaatgcggag     5460 cggagatcga atcagatatc aagctccatc gagctccagc cacggcaaca ccgcgcgcct    5520
tgcggccgag cacggcgaca agaacctgag caagatctgc gggctgatcg ccagcgacga    5580 gggcggcac gagatcgcct acacgcgcat cgtggacgag ttcttccgcc tgaccccga     5640 gggcgccgtc gccgcctacg ccaacatgat gcgcaagcag atcaccatgc ccgcgcacct    5700 catgacgac atgggccacg cgcaggccaa cccgggccgc aacctcttcg ccgacttctc    5760
cgcggtcgcc gagaagatcg acgtctacga cgccgaggac tactgccgca tcctggagca    5820
cctcaacgcg cgctggaagg tggacgagcg ccaggtcagc ggccaggccg ccgcggacca    5880
ggagtacgtc ctgggcctgc cccagcgctt ccggaaactc gccgagaaga ccgccgccaa    5940
gcgcaagcgc gtcgcgcgca ggcccgtcgc cttctcctgg atctccgggc gcagagatcat    6000 ggtctaggga gcgacgagtg tgcgtgcggg gctggcggga gtgggacgcc ctcctcgctc    6060
ctctctgttc tgaacggaac aatcggccac cccgcgctac gcgccacgca tcgagcaacg    6120
aagaaaaccc cccgatgata ggttgcggtg gctgccggga tatagatccg gccgcacatc    6180
aaagggcccc tccgccagag aagaagctcc tttcccagca gactcct              6227
```

<210> SEQ ID NO 61
<211> LENGTH: 1545
<212> TYPE: DNA
<213> ORGANISM: Artificial Sequence
<220> FEATURE:
<223> OTHER INFORMATION: C. hookeriana KASIV CDS codon optimized for P. moriformis

<400> SEQUENCE: 61

```
atggcttccg cggcattcac catgtcggcg tgccccgcga tgactggcag ggcccctggg     60
gcacgtcgct ccggacggcc agtcgccacc cgcctgaggg gcagcacctt ccagtgcctg    120 gaccccctgca accagcagcg cttcctgggc gacaacggct tcgcgtcgct gttcggctcc    180 aagccctgc gcagcaaccg cggccacctg cgcctgggcc gcacctcgca ctccggcgag    240
gtgatggccg tcgcgatgca gcccgcccag gaggtgagca ccaacaagaa gcccgcgacc    300
aagcagcgcc gcgtggtcgt gaccggcatg ggcgtcgtga ccccctggg ccacgacccc    360 gacgtgtatt ataacaacct gctggacggc atctcgggca tctccgagat cgagaacttc    420
gactgcagcc agttccccac ccgcatcgcc ggcgagatca gtcgttctc caccgacggc    480
```

```
tgggtcgcgc ccaagttcag cgagcgcatg gacaagttca tgctgtatat gctgaccgcc    540
ggcaagaagg cgctggccga cggcggcatc accgaggacg cgatgaagga gctgaacaag    600
cgcaagtgcg gcgtgctgat cggctcgggc ctgggcggca tgaaggtctt ctccgacagc    660
atcgaggccc tgcgcacctc gtataagaag atctccccct tctgcgtgcc cttcagcacc    720
accaacatgg gctcggcgat cctggcgatg gacctgggct ggatgggccc caactattcc    780
atcagcaccg cgtgcgccac ctcgaacttc tgcatcctga acgcggccaa ccacatcatc    840
aagggcgagg cggacatgat gctgtgcggc ggctccgacg ccgcggtgct gcccgtcggc    900
ctgggcggct tcgtggcctg ccgcgcgctg agccagcgca caacgaccc caccaaggcc    960
tcgcgcccct gggactccaa ccgcgacggc ttcgtcatgg gcgagggcgc gggcgtgctg   1020
ctgctggaga gctggagca cgccaagaag cgcggcgcga ccatctatgc cgagttcctg   1080
ggcggcagct tcacctgcga cgcgtatcac atgaccgagc cccaccccga gggcgccggc   1140
gtcatcctgt gcatcgagaa ggcgctggcc cagtcgggcg tgtcccgcga ggacgtgaac   1200
tatatcaacg cgcacgccac cagcaccccc gcgggcgaca tcaaggagta tcaggccctg   1260
gcgcactgct tcggccagaa ctcggagctg cgcgtcaact ccaccaagag catgatcggc   1320
cacctgctgg gcggcgccgg cggcgtggag gcggtcgccg tggtccaggc gatccgcacc   1380
ggctggatcc accccaacat caacctggag gaccccgacg agggcgtgga cgccaagctg   1440
ctggtcggcc ccaagaagga gaagctgaag gtgaaggtcg gcctgtcgaa ctccttcggc   1500
ttcggcggcc acaacagctc gatcctgttc gcgccctgca actga                   1545
```

<210> SEQ ID NO 62
<211> LENGTH: 542
<212> TYPE: PRT
<213> ORGANISM: Cuphea aequipetala
<220> FEATURE:
<221> NAME/KEY: MISC_FEATURE
<223> OTHER INFORMATION: KASIV

<400> SEQUENCE: 62

Met Ala Ala Ala Ser Met Val Ala Ser Pro Leu Cys Thr Trp Leu
1               5                   10                  15

Val Ala Ala Cys Met Ser Thr Ser Phe Asp Asn Asp Pro Arg Ser Pro
            20                  25                  30

Ser Ile Lys Arg Ile Pro Arg Arg Arg Ile Leu Ser Gln Ser Ser
        35                  40                  45

Leu Arg Gly Ser Thr Phe Gln Cys Leu Val Thr Ser Tyr Ile Asp Pro
    50                  55                  60

Cys Asn Gln Phe Ser Ser Ser Ala Ser Leu Ser Phe Leu Gly Asp Asn
65                  70                  75                  80

Gly Phe Ala Ser Leu Phe Gly Ser Lys Pro Phe Arg Ser Ile Arg Gly
                85                  90                  95

His Arg Arg Leu Gly Arg Ala Ser His Ser Gly Glu Ala Met Ala Val
            100                 105                 110

Ala Leu Glu Pro Ala Gln Glu Val Ala Thr Lys Lys Pro Val Val
        115                 120                 125

Lys Gln Arg Arg Val Val Val Thr Gly Met Gly Val Val Thr Pro Leu
    130                 135                 140

Gly His Glu Pro Asp Val Tyr Tyr Asn Asn Leu Leu Asp Gly Val Ser
145                 150                 155                 160

Gly Ile Ser Glu Ile Glu Thr Phe Asp Cys Asn Gln Phe Pro Thr Arg

```
            165                 170                 175
Ile Ala Gly Glu Ile Lys Ser Phe Ser Thr Asp Gly Trp Val Ala Pro
            180                 185                 190

Lys Leu Ser Lys Arg Met Asp Lys Phe Met Leu Tyr Leu Leu Thr Ala
            195                 200                 205

Gly Lys Lys Ala Leu Ala Asp Gly Gly Ile Thr Asp Asp Val Met Lys
            210                 215                 220

Glu Leu Asp Lys Arg Lys Cys Gly Val Leu Ile Gly Ser Gly Leu Gly
225                 230                 235                 240

Gly Met Lys Leu Phe Ser Asp Ser Ile Glu Ala Leu Arg Ile Ser Tyr
            245                 250                 255

Lys Lys Met Asn Pro Phe Cys Val Pro Phe Ala Thr Thr Asn Met Gly
            260                 265                 270

Ser Ala Met Leu Ala Met Asp Leu Gly Trp Met Gly Pro Asn Tyr Ser
            275                 280                 285

Ile Ser Thr Ala Cys Ala Thr Ser Asn Phe Cys Ile Leu Asn Ser Ala
            290                 295                 300

Asn His Ile Val Arg Gly Glu Ala Asp Met Met Leu Cys Gly Gly Ser
305                 310                 315                 320

Asp Ala Val Ile Ile Pro Ile Gly Leu Gly Gly Phe Val Ala Cys Arg
            325                 330                 335

Ala Leu Ser Gln Arg Asn Asn Asp Pro Thr Lys Ala Ser Arg Pro Trp
            340                 345                 350

Asp Ser Asn Arg Asp Gly Phe Val Met Gly Glu Gly Ala Gly Val Leu
            355                 360                 365

Leu Leu Glu Glu Leu Glu His Ala Lys Lys Arg Gly Ala Thr Ile Tyr
370                 375                 380

Ala Glu Phe Leu Gly Gly Ser Phe Thr Cys Asp Ala Tyr His Met Thr
385                 390                 395                 400

Glu Pro His Pro Glu Gly Ala Gly Val Ile Leu Cys Ile Glu Lys Ala
            405                 410                 415

Leu Ala Gln Ala Gly Val Ser Arg Glu Asp Val Asn Tyr Ile Asn Ala
            420                 425                 430

His Ala Thr Ser Thr Pro Ala Gly Asp Ile Lys Glu Tyr Gln Ala Leu
            435                 440                 445

Ala His Cys Phe Gly His Asn Ser Glu Leu Arg Val Asn Ser Thr Lys
450                 455                 460

Ser Met Ile Gly His Leu Ile Gly Ala Ala Gly Gly Val Glu Ala Val
465                 470                 475                 480

Thr Val Val Gln Ala Ile Arg Thr Gly Trp Ile His Pro Asn Leu Asn
            485                 490                 495

Leu Glu Asp Pro Asp Lys Ala Val Asp Ala Lys Leu Leu Val Gly Pro
            500                 505                 510

Lys Lys Glu Arg Leu Asn Val Lys Val Gly Leu Ser Asn Ser Phe Gly
            515                 520                 525

Phe Gly Gly His Asn Ser Ser Ile Leu Phe Ala Pro Tyr Asn
            530                 535                 540

<210> SEQ ID NO 63
<211> LENGTH: 539
<212> TYPE: PRT
<213> ORGANISM: Cuphea glassostoma
<220> FEATURE:
<221> NAME/KEY: MISC_FEATURE
<223> OTHER INFORMATION: C. glassostoma KASIV S07 Cg  Locus 4548
```

Transcript 4/9 translation

<400> SEQUENCE: 63

```
Met Ala Ala Ala Ser Ser Gln Leu Cys Thr Trp Leu Val Ala Ala
1               5                   10                  15

Cys Met Ser Thr Ser Phe Asp Asn Asn Pro Arg Ser Pro Ser Ile Lys
            20                  25                  30

Arg Leu Pro Arg Arg Arg Val Leu Ser His Cys Ser Leu Arg Gly
        35                  40                  45

Ser Thr Phe Gln Cys Leu Val Thr Ser Tyr Ile Asp Pro Cys Asn Gln
        50                  55                  60

Tyr Cys Ser Ser Ala Ser Leu Ser Phe Leu Gly Asp Asn Gly Phe Thr
65                  70                  75                  80

Pro Leu Ile Gly Ser Lys Pro Phe Arg Ser Asn Arg Gly His Pro Arg
                85                  90                  95

Leu Gly Arg Ala Ser His Ser Gly Glu Ala Met Ala Val Ala Leu Gln
            100                 105                 110

Pro Ala Gln Glu Val Ala Thr Lys Lys Pro Ala Met Lys Gln Arg
        115                 120                 125

Arg Val Val Val Thr Gly Met Gly Val Val Thr Pro Leu Gly His Glu
        130                 135                 140

Pro Asp Val Tyr Tyr Asn Asn Leu Leu Asp Gly Val Ser Gly Ile Ser
145                 150                 155                 160

Glu Ile Glu Thr Phe Asp Cys Thr Gln Phe Pro Thr Arg Ile Ala Gly
                165                 170                 175

Glu Ile Lys Ser Phe Ser Thr Asp Gly Trp Val Ala Pro Lys Leu Ser
            180                 185                 190

Lys Arg Met Asp Lys Phe Met Leu Tyr Leu Leu Thr Ala Gly Lys Lys
        195                 200                 205

Ala Leu Ala Asp Gly Gly Ile Thr Asp Asp Val Met Lys Glu Leu Asp
        210                 215                 220

Lys Arg Lys Cys Gly Val Leu Ile Gly Ser Gly Met Gly Gly Met Lys
225                 230                 235                 240

Leu Phe Asn Asp Ser Ile Glu Ala Leu Arg Val Ser Tyr Lys Lys Met
                245                 250                 255

Asn Pro Phe Cys Val Pro Phe Ala Thr Thr Asn Met Gly Ser Ala Met
            260                 265                 270

Leu Ala Met Asp Leu Gly Trp Met Gly Pro Asn Tyr Ser Ile Ser Thr
        275                 280                 285

Ala Cys Ala Thr Ser Asn Phe Cys Ile Leu Asn Ala Ala Asn His Ile
        290                 295                 300

Val Arg Gly Glu Ala Asp Met Met Leu Cys Gly Gly Ser Asp Ala Val
305                 310                 315                 320

Ile Ile Pro Ile Gly Leu Gly Gly Phe Val Ala Cys Arg Ala Leu Ser
                325                 330                 335

Gln Arg Asn Asn Asp Pro Thr Lys Ala Ser Arg Pro Trp Asp Ser Asn
            340                 345                 350

Arg Asp Gly Phe Val Met Gly Glu Gly Ala Gly Val Leu Leu Leu Glu
        355                 360                 365

Glu Leu Glu His Ala Lys Lys Arg Gly Ala Thr Ile Tyr Ala Glu Phe
        370                 375                 380

Leu Gly Gly Ser Phe Thr Cys Asp Ala Tyr His Met Thr Glu Pro His
385                 390                 395                 400
```

Pro Glu Gly Ala Gly Val Ile Leu Cys Ile Glu Lys Ala Leu Ala Gln
                405                 410                 415

Ala Gly Val Ser Arg Glu Asp Val Asn Tyr Ile Asn Ala His Ala Thr
            420                 425                 430

Ser Thr Pro Ala Gly Asp Ile Lys Glu Tyr Gln Ala Leu Ala His Cys
        435                 440                 445

Phe Gly Gln Asn Ser Glu Leu Arg Val Asn Ser Thr Lys Ser Met Ile
450                 455                 460

Gly His Leu Leu Gly Ala Ala Gly Val Glu Ala Val Thr Val Ile
465                 470                 475                 480

Gln Ala Ile Arg Thr Gly Trp Ile His Pro Asn Leu Asn Leu Asp Asp
                485                 490                 495

Pro Asp Lys Ala Val Asp Ala Lys Phe Leu Val Gly Pro Lys Lys Glu
            500                 505                 510

Arg Leu Asn Val Lys Val Gly Leu Ser Asn Ser Phe Gly Phe Gly Gly
        515                 520                 525

His Asn Ser Ser Ile Leu Phe Ala Pro Tyr Asn
    530                 535

<210> SEQ ID NO 64
<211> LENGTH: 530
<212> TYPE: PRT
<213> ORGANISM: Cuphea hookeriana
<220> FEATURE:
<221> NAME/KEY: MISC_FEATURE
<223> OTHER INFORMATION: KASIV

<400> SEQUENCE: 64

Met Ala Ala Ser Ser Cys Met Val Gly Ser Pro Phe Cys Thr Trp Leu
1               5                   10                  15

Val Ser Ala Cys Met Ser Thr Ser Phe Asp Asn Asp Pro Arg Ser Leu
            20                  25                  30

Ser His Lys Arg Leu Arg Leu Ser Arg Arg Arg Thr Leu Ser Ser
        35                  40                  45

His Cys Ser Leu Arg Gly Ser Thr Pro Gln Cys Leu Asp Pro Cys Asn
    50                  55                  60

Gln His Cys Phe Leu Gly Asp Asn Gly Phe Ala Ser Leu Phe Gly Ser
65                  70                  75                  80

Lys Pro Pro Arg Ser Asp Leu Gly His Leu Arg Leu Gly Arg Thr Ser
                85                  90                  95

His Ser Gly Glu Val Met Ala Val Ala Gln Glu Val Ser Thr Asn Lys
            100                 105                 110

Lys Pro Ala Thr Lys Gln Arg Val Val Val Thr Gly Met Gly Val
        115                 120                 125

Val Thr Pro Leu Gly His Asp Pro Asp Val Tyr Tyr Asn Asn Leu Leu
    130                 135                 140

Asp Gly Val Ser Gly Ile Ser Glu Ile Glu Thr Phe Asp Cys Thr Gln
145                 150                 155                 160

Phe Pro Thr Arg Ile Ala Gly Glu Ile Lys Ser Phe Ser Thr Asp Gly
                165                 170                 175

Leu Val Ala Pro Lys Leu Ser Lys Arg Met Asp Lys Phe Met Leu Tyr
            180                 185                 190

Ile Leu Thr Ala Gly Lys Lys Ala Leu Ala Asp Gly Gly Ile Thr Glu
        195                 200                 205

Asp Val Met Lys Glu Leu Asp Lys Arg Lys Cys Gly Val Leu Ile Gly
    210                 215                 220

Ser Gly Leu Gly Gly Met Lys Val Phe Ser Asp Ser Val Glu Ala Leu
225                 230                 235                 240

Arg Ile Ser Tyr Lys Ile Ser Pro Phe Cys Val Pro Phe Ser Thr
            245                 250                 255

Thr Asn Met Gly Ser Ala Ile Leu Ala Met Asp Leu Gly Trp Met Gly
            260                 265                 270

Pro Asn Tyr Ser Ile Ser Thr Ala Cys Ala Thr Ser Asn Phe Cys Ile
            275                 280                 285

Leu Asn Ala Ala Asn His Ile Thr Lys Gly Glu Ala Asp Met Met Leu
            290                 295                 300

Cys Gly Gly Ser Asp Ala Ala Ile Leu Pro Ile Gly Met Gly Gly Phe
305                 310                 315                 320

Val Ala Cys Arg Ala Leu Ser Gln Arg Asn Asn Asp Pro Thr Lys Ala
                325                 330                 335

Ser Arg Pro Trp Asp Ser Asn Arg Asp Gly Phe Val Met Gly Glu Gly
            340                 345                 350

Ala Gly Val Leu Leu Leu Glu Glu Leu Glu His Ala Lys Lys Arg Gly
            355                 360                 365

Ala Thr Ile Tyr Ala Glu Phe Leu Gly Gly Ser Phe Thr Cys Asp Ala
370                 375                 380

Tyr His Met Thr Glu Pro His Pro Glu Gly Ala Gly Val Ile Leu Cys
385                 390                 395                 400

Ile Glu Lys Ala Leu Ala Gln Ala Gly Val Ser Arg Glu Asp Val Asn
                405                 410                 415

Tyr Ile Asn Ala His Ala Thr Ser Thr Pro Ala Gly Asp Ile Lys Glu
            420                 425                 430

Tyr Gln Ala Leu Ala His Cys Phe Gly Gln Asn Ser Glu Leu Arg Val
            435                 440                 445

Asn Ser Thr Lys Ser Met Ile Gly His Leu Ile Gly Ala Ala Gly Gly
            450                 455                 460

Val Glu Ala Val Thr Val Ile Gln Ala Ile Arg Thr Gly Trp Ile His
465                 470                 475                 480

Pro Asn Leu Asn Leu Glu Asn Pro Asp Lys Ala Val Asp Ala Lys Leu
                485                 490                 495

Leu Val Gly Pro Lys Lys Glu Arg Leu Asp Val Lys Val Gly Leu Ser
            500                 505                 510

Asn Ser Phe Gly Phe Gly Gly His Asn Ser Ser Ile Leu Phe Ala Pro
            515                 520                 525

Tyr Asn
    530

<210> SEQ ID NO 65
<211> LENGTH: 515
<212> TYPE: PRT
<213> ORGANISM: Cuphea glassostoma
<220> FEATURE:
<221> NAME/KEY: MISC_FEATURE
<223> OTHER INFORMATION: C. glassostoma KASIV S07 Cg Locus 3059
      Transcript 2/2 translation

<400> SEQUENCE: 65

Met Ala Ala Ala Ser Ser Met Val Ala Ser Ser Phe Ser Thr Ser Leu
1               5                   10                  15

Val Ala Ala Cys Met Ser Thr Ser Phe Asp Asn Asp Pro Arg Phe Leu
            20                  25                  30

```
Ser His Lys Arg Ile Arg Leu Ser Leu Arg Arg Gly Ser Thr Phe Gln
         35                  40                  45

Cys Leu Gly Asp Asn Gly Phe Ala Ser Leu Ile Gly Ser Lys Pro Pro
 50                  55                  60

Arg Ser Asn His Gly His Arg Arg Leu Gly Arg Thr Ser His Ser Gly
 65                  70                  75                  80

Glu Ala Met Ala Val Ala Met Gln Pro Ala Gln Glu Ala Ser Thr Lys
                 85                  90                  95

Asn Lys His Val Thr Lys Gln Arg Arg Val Val Val Thr Gly Met Gly
                100                 105                 110

Val Val Thr Pro Leu Gly His Asp Pro Asp Val Tyr Tyr Asn Asn Leu
            115                 120                 125

Leu Asp Gly Val Ser Gly Ile Ser Glu Ile Glu Asn Phe Asp Cys Ser
    130                 135                 140

Gln Phe Pro Thr Arg Ile Ala Gly Glu Ile Lys Ser Phe Ser Thr Glu
145                 150                 155                 160

Gly Tyr Val Ile Pro Lys Phe Ala Lys Arg Met Asp Lys Phe Met Leu
                165                 170                 175

Tyr Leu Leu Thr Ala Gly Lys Lys Ala Leu Glu Asp Gly Gly Ile Thr
            180                 185                 190

Glu Asp Val Met Lys Glu Leu Asp Lys Arg Lys Cys Gly Val Leu Ile
        195                 200                 205

Gly Ser Gly Met Gly Gly Met Lys Ile Ile Asn Asp Ser Ile Ala Ala
    210                 215                 220

Leu Asn Val Ser Tyr Lys Lys Met Thr Pro Phe Cys Val Pro Phe Ser
225                 230                 235                 240

Thr Thr Asn Met Gly Ser Ala Met Leu Ala Ile Asp Leu Gly Trp Met
                245                 250                 255

Gly Pro Asn Tyr Ser Ile Ser Thr Ala Cys Ala Thr Ser Asn Tyr Cys
            260                 265                 270

Ile Leu Asn Ala Ala Asn His Ile Ile Arg Gly Glu Ala Asn Met Met
        275                 280                 285

Leu Cys Gly Gly Ser Asp Ala Val Val Ile Pro Val Gly Leu Gly Gly
    290                 295                 300

Phe Val Ala Cys Arg Ala Leu Ser Gln Arg Asn Asn Asp Pro Thr Lys
305                 310                 315                 320

Ala Ser Arg Pro Trp Asp Ser Asn Arg Asp Gly Phe Val Met Gly Glu
                325                 330                 335

Gly Ala Gly Val Leu Leu Leu Glu Glu Leu Glu His Ala Lys Lys Arg
            340                 345                 350

Gly Ala Thr Ile Tyr Ala Glu Phe Leu Gly Gly Ser Phe Thr Cys Asp
        355                 360                 365

Ala Tyr His Met Thr Glu Pro His Pro Asp Gly Ala Gly Val Ile Leu
    370                 375                 380

Cys Ile Glu Lys Ala Leu Ala Gln Ser Gly Val Ser Arg Glu Asp Val
385                 390                 395                 400

Asn Tyr Ile Asn Ala His Ala Thr Ser Thr Pro Ala Gly Asp Ile Lys
                405                 410                 415

Glu Tyr Gln Ala Leu Ala His Cys Phe Gly Gln Asn Ser Glu Leu Arg
            420                 425                 430

Val Asn Ser Thr Lys Ser Met Ile Gly His Leu Leu Gly Ala Ala Gly
        435                 440                 445

Gly Val Glu Ala Val Ser Val Val Gln Ala Ile Arg Thr Gly Trp Ile
```

```
                    450                 455                 460
His Pro Asn Ile Asn Leu Glu Asp Pro Asp Glu Ala Val Asp Ala Lys
465                 470                 475                 480

Leu Leu Val Gly Pro Lys Lys Glu Lys Leu Lys Val Lys Val Gly Leu
                    485                 490                 495

Ser Asn Ser Phe Gly Phe Gly His Asn Ser Ser Ile Leu Phe Ala
                    500                 505                 510

Pro Cys Asn
        515

<210> SEQ ID NO 66
<211> LENGTH: 545
<212> TYPE: PRT
<213> ORGANISM: Cuphea carthagenesis
<220> FEATURE:
<221> NAME/KEY: MISC_FEATURE
<223> OTHER INFORMATION: C. carthagenesis KASIV S05 CcrKASIV 17190 Seq
      7/7 translation

<400> SEQUENCE: 66

Met Ala Ala Ala Ala Phe Ala Ser Pro Phe Cys Thr Trp Leu Val
1               5                   10                  15

Ala Ala Cys Met Ser Ser Ala Ser Arg His Asp Pro Leu Pro Ser Pro
                20                  25                  30

Ser Ser Lys Pro Arg Leu Arg Arg Lys Ile Leu Phe Gln Cys Ala Gly
            35                  40                  45

Arg Gly Ser Ser Ala Gly Ser Gly Ser Ser Phe His Ser Leu Val Thr
        50                  55                  60

Ser Tyr Leu Gly Cys Leu Glu Pro Cys His Glu Tyr Tyr Thr Ser Ser
65                  70                  75                  80

Ser Ser Leu Gly Phe Ser Ser Leu Phe Gly Ser Thr Pro Gly Arg Thr
                85                  90                  95

Ser Arg Arg Gln Arg Arg Leu His Arg Ala Ser His Ser Gly Glu Ala
            100                 105                 110

Met Ala Val Ala Leu Gln Pro Ala Gln Glu Val Thr Thr Lys Lys Lys
        115                 120                 125

Pro Ser Ile Lys Gln Arg Arg Val Val Val Thr Gly Met Gly Val Val
130                 135                 140

Thr Pro Leu Gly His Asp Pro Asp Val Phe Tyr Asn Asn Leu Leu Asp
145                 150                 155                 160

Gly Ala Ser Gly Ile Ser Glu Ile Glu Thr Phe Asp Cys Ala Gln Phe
                165                 170                 175

Pro Thr Arg Ile Ala Gly Glu Ile Lys Ser Phe Ser Thr Asp Gly Trp
            180                 185                 190

Val Ala Pro Lys Leu Ser Lys Arg Met Asp Lys Phe Met Leu Tyr Met
        195                 200                 205

Leu Thr Ala Gly Lys Lys Ala Leu Ala Asp Gly Gly Ile Ser Glu Asp
        210                 215                 220

Val Met Lys Glu Leu Asp Lys Arg Lys Cys Gly Val Leu Ile Gly Ser
225                 230                 235                 240

Ala Met Gly Gly Met Lys Val Phe Asn Asp Ala Ile Glu Ala Leu Arg
                245                 250                 255

Ile Ser Tyr Lys Lys Met Asn Pro Phe Cys Val Pro Phe Ala Thr Thr
            260                 265                 270

Asn Met Gly Ser Ala Met Leu Ala Met Asp Leu Gly Trp Met Gly Pro
        275                 280                 285
```

Asn Tyr Ser Ile Ser Thr Ala Cys Ala Thr Ser Asn Phe Cys Ile Leu
            290                 295                 300

Asn Ala Ala Asn His Ile Thr Arg Gly Glu Ala Asp Met Met Leu Cys
305                 310                 315                 320

Gly Gly Ser Asp Ala Val Ile Ile Pro Ile Gly Leu Gly Gly Phe Val
            325                 330                 335

Ala Cys Arg Ala Leu Ser Gln Arg Asn Asn Asp Pro Thr Lys Ala Ser
            340                 345                 350

Arg Pro Trp Asp Ser Asn Arg Asp Gly Phe Val Met Gly Glu Gly Ala
            355                 360                 365

Gly Val Leu Leu Leu Glu Glu Leu Glu His Ala Lys Lys Arg Gly Ala
370                 375                 380

Thr Ile Tyr Ala Glu Phe Leu Gly Gly Ser Phe Thr Cys Asp Ala Tyr
385                 390                 395                 400

His Met Thr Glu Pro His Pro Lys Gly Ala Gly Val Ile Leu Cys Ile
            405                 410                 415

Glu Arg Ala Leu Ala Gln Ser Gly Val Ser Arg Glu Asp Val Asn Tyr
            420                 425                 430

Ile Asn Ala His Ala Thr Ser Thr Pro Ala Gly Asp Ile Lys Glu Tyr
            435                 440                 445

Gln Ala Leu Ala His Cys Phe Gly Gln Asn Ser Glu Leu Arg Val Asn
450                 455                 460

Ser Thr Lys Ser Met Ile Gly His Leu Leu Gly Ala Ala Gly Gly Val
465                 470                 475                 480

Glu Ala Val Thr Val Val Gln Ala Ile Arg Thr Gly Trp Val His Pro
            485                 490                 495

Asn Ile Asn Leu Glu Asn Pro Asp Glu Gly Val Asp Ala Lys Leu Leu
            500                 505                 510

Val Gly Pro Lys Lys Glu Lys Leu Lys Val Lys Val Gly Leu Ser Asn
            515                 520                 525

Ser Phe Gly Phe Gly Gly His Asn Ser Ser Ile Leu Phe Ala Pro Tyr
            530                 535                 540

Asn
545

<210> SEQ ID NO 67
<211> LENGTH: 516
<212> TYPE: PRT
<213> ORGANISM: Cuphea carthagenesis
<220> FEATURE:
<221> NAME/KEY: MISC_FEATURE
<223> OTHER INFORMATION: C. carthagenesis KASIV S05 CcrKASIV 17190 Seq
      6/7 translation

<400> SEQUENCE: 67

Met Ala Ala Ala Ala Ser Val Val Ala Ser Pro Phe Cys Thr Trp Leu
1               5                   10                  15

Val Ala Ala Cys Met Ser Ala Ser Phe Asp Asn Glu Pro Arg Ser Leu
            20                  25                  30

Ser Pro Lys Arg Arg Arg Ser Leu Ser Arg Ser Ser Ala Ser Leu
            35                  40                  45

Arg Phe Leu Gly Gly Asn Gly Phe Ala Ser Leu Phe Gly Ser Asp Pro
50                  55                  60

Leu Arg Pro Asn Arg Gly His Arg Arg Leu Arg His Ala Ser His Ser
65                  70                  75                  80

```
Gly Glu Ala Met Ala Val Ala Leu Gln Pro Ala Gln Glu Val Ser Thr
                85                  90                  95
Lys Lys Lys Pro Val Thr Lys Gln Arg Arg Val Val Thr Gly Met
            100                 105                 110
Gly Val Val Thr Pro Leu Gly His Asp Pro Asp Val Tyr Tyr Asn Asn
            115                 120                 125
Leu Leu Asp Gly Val Ser Gly Ile Ser Glu Ile Glu Thr Phe Asp Cys
130                 135                 140
Thr Gln Phe Pro Thr Arg Ile Ala Gly Glu Ile Lys Ser Phe Ser Thr
145                 150                 155                 160
Asp Gly Trp Val Ala Pro Lys Leu Ser Lys Arg Met Asp Lys Phe Met
                165                 170                 175
Leu Tyr Met Leu Thr Ala Gly Lys Lys Ala Leu Ala Asp Gly Gly Ile
                180                 185                 190
Thr Glu Glu Val Met Lys Glu Leu Asp Lys Arg Lys Cys Gly Val Leu
                195                 200                 205
Ile Gly Ser Gly Met Gly Gly Met Lys Leu Phe Asn Asp Ser Ile Glu
            210                 215                 220
Ala Leu Arg Ile Ser Tyr Lys Lys Met Asn Pro Phe Cys Val Pro Phe
225                 230                 235                 240
Ala Thr Thr Asn Met Gly Ser Ala Met Leu Ala Met Asp Leu Gly Trp
                245                 250                 255
Met Gly Pro Asn Tyr Ser Ile Ser Thr Ala Cys Ala Thr Ser Asn Phe
                260                 265                 270
Cys Ile Leu Asn Ala Ala Asn His Ile Thr Arg Gly Glu Ala Asp Met
            275                 280                 285
Met Leu Cys Gly Gly Ser Asp Ala Val Ile Ile Pro Ile Gly Leu Gly
            290                 295                 300
Gly Phe Val Ala Cys Arg Ala Leu Ser Gln Arg Asn Asn Asp Pro Thr
305                 310                 315                 320
Lys Ala Ser Arg Pro Trp Asp Ser Asn Arg Asp Gly Phe Val Met Gly
                325                 330                 335
Glu Gly Ala Gly Val Leu Leu Leu Glu Glu Leu Glu His Ala Lys Lys
            340                 345                 350
Arg Gly Ala Thr Ile Tyr Ala Glu Phe Leu Gly Gly Ser Phe Thr Cys
            355                 360                 365
Asp Ala Tyr His Met Thr Glu Pro His Pro Lys Gly Ala Gly Val Ile
            370                 375                 380
Leu Cys Ile Glu Arg Ala Leu Ala Gln Ser Gly Val Ser Arg Glu Asp
385                 390                 395                 400
Val Asn Tyr Ile Asn Ala His Ala Thr Ser Thr Pro Ala Gly Asp Ile
                405                 410                 415
Lys Glu Tyr Gln Ala Leu Ala His Cys Phe Gly Gln Asn Ser Glu Leu
                420                 425                 430
Arg Val Asn Ser Thr Lys Ser Met Ile Gly His Leu Leu Gly Ala Ala
            435                 440                 445
Gly Gly Val Glu Ala Val Thr Val Val Gln Ala Ile Arg Thr Gly Trp
450                 455                 460
Val His Pro Asn Ile Asn Leu Glu Asn Pro Asp Glu Gly Val Asp Ala
465                 470                 475                 480
Lys Leu Leu Val Gly Pro Lys Lys Glu Lys Leu Lys Val Lys Val Gly
                485                 490                 495
Leu Ser Asn Ser Phe Gly Phe Gly Gly His Asn Ser Ser Ile Leu Phe
```

```
                    500                 505                 510

Ala Pro Tyr Asn
            515

<210> SEQ ID NO 68
<211> LENGTH: 546
<212> TYPE: PRT
<213> ORGANISM: Cuphea pulcherrima
<220> FEATURE:
<221> NAME/KEY: MISC_FEATURE
<223> OTHER INFORMATION: KASIV

<400> SEQUENCE: 68

Met Pro Ala Ala Ser Ser Leu Leu Ala Ser Pro Leu Cys Thr Trp Leu
1               5                   10                  15

Leu Ala Ala Cys Met Ser Thr Ser Phe His Pro Ser Asp Pro Leu Pro
            20                  25                  30

Pro Ser Ile Ser Ser Pro Arg Arg Leu Ser Arg Arg Ile Leu
        35                  40                  45

Ser Gln Cys Ala Pro Leu Pro Ser Ala Ser Ser Ala Leu Arg Gly Ser
    50                  55                  60

Ser Phe His Thr Leu Val Thr Ser Tyr Leu Ala Cys Phe Glu Pro Cys
65                  70                  75                  80

His Asp Tyr Tyr Thr Ser Ala Ser Leu Phe Gly Ser Arg Pro Ile Arg
                85                  90                  95

Thr Thr Arg Arg His Arg Arg Leu Asn Arg Ala Ser Pro Ser Arg Glu
            100                 105                 110

Ala Met Ala Val Ala Leu Gln Pro Glu Gln Val Thr Thr Lys Lys
        115                 120                 125

Lys Pro Ser Ile Lys Gln Arg Arg Val Val Thr Gly Met Gly Val
130                 135                 140

Val Thr Pro Leu Gly His Asp Pro Asp Val Phe Tyr Asn Asn Leu Leu
145                 150                 155                 160

Asp Gly Thr Ser Gly Ile Ser Glu Ile Glu Thr Phe Asp Cys Ala Gln
                165                 170                 175

Phe Pro Thr Arg Ile Ala Gly Glu Ile Lys Ser Phe Ser Thr Asp Gly
            180                 185                 190

Trp Val Ala Pro Lys Leu Ser Lys Arg Met Asp Lys Phe Met Leu Tyr
        195                 200                 205

Met Leu Thr Ala Gly Lys Lys Ala Leu Thr Asp Gly Ile Thr Glu
    210                 215                 220

Asp Val Met Lys Glu Leu Asp Lys Arg Lys Cys Gly Val Leu Ile Gly
225                 230                 235                 240

Ser Ala Met Gly Gly Met Lys Val Phe Asn Asp Ala Ile Glu Ala Leu
                245                 250                 255

Arg Ile Ser Tyr Lys Lys Met Asn Pro Phe Cys Val Pro Phe Ala Thr
            260                 265                 270

Thr Asn Met Gly Ser Ala Met Leu Ala Met Asp Leu Gly Trp Met Gly
        275                 280                 285

Pro Asn Tyr Ser Ile Ser Thr Ala Cys Ala Thr Ser Asn Phe Cys Ile
    290                 295                 300

Met Asn Ala Ala Asn His Ile Ile Arg Gly Glu Ala Asp Val Met Leu
305                 310                 315                 320

Cys Gly Gly Ser Asp Ala Val Ile Ile Pro Ile Gly Met Gly Gly Phe
                325                 330                 335
```

```
Val Ala Cys Arg Ala Leu Ser Gln Arg Asn Ser Asp Pro Thr Lys Ala
            340                 345                 350

Ser Arg Pro Trp Asp Ser Asn Arg Asp Gly Phe Val Met Gly Glu Gly
        355                 360                 365

Ala Gly Val Leu Leu Glu Glu Leu Glu His Ala Lys Lys Arg Gly
    370                 375                 380

Ala Thr Ile Tyr Ala Glu Phe Leu Gly Gly Ser Phe Thr Cys Asp Ala
385                 390                 395                 400

Tyr His Met Thr Glu Pro His Pro Asp Gly Ala Gly Val Ile Leu Cys
                405                 410                 415

Ile Glu Lys Ala Leu Ala Gln Ser Gly Val Ser Arg Glu Asp Val Asn
                420                 425                 430

Tyr Ile Asn Ala His Ala Thr Ser Thr Pro Ala Gly Asp Ile Lys Glu
                435                 440                 445

Tyr Gln Ala Leu Ile His Cys Phe Gly Gln Asn Arg Glu Leu Lys Val
            450                 455                 460

Asn Ser Thr Lys Ser Met Ile Gly His Leu Leu Gly Ala Ala Gly Gly
465                 470                 475                 480

Val Glu Ala Val Ser Val Val Gln Ala Ile Arg Thr Gly Trp Ile His
                485                 490                 495

Pro Asn Ile Asn Leu Glu Asn Pro Asp Glu Gly Val Asp Thr Lys Leu
                500                 505                 510

Leu Val Gly Pro Lys Lys Glu Arg Leu Asn Val Lys Val Gly Leu Ser
            515                 520                 525

Asn Ser Phe Gly Phe Gly Gly His Asn Ser Ser Ile Leu Phe Ala Pro
530                 535                 540

Tyr Ile
545

<210> SEQ ID NO 69
<211> LENGTH: 534
<212> TYPE: PRT
<213> ORGANISM: Artificial Sequence
<220> FEATURE:
<223> OTHER INFORMATION: Clade 1 KASIV consensus C8 and C10
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid

<400> SEQUENCE: 69

Met Ala Ala Ala Ser Cys Met Val Ala Ser Pro Phe Cys Thr Trp Leu
1               5                   10                  15

Val Ala Ala Cys Met Ser Thr Ser Xaa Asp Asn Asp Pro Arg Ser Leu
                20                  25                  30

Ser His Lys Arg Leu Arg Leu Ser Arg Arg Arg Thr Leu Ser Ser
            35                  40                  45

His Cys Ser Leu Arg Gly Ser Thr Phe Gln Cys Leu Asp Pro Cys Asn
        50                  55                  60

Gln His Cys Phe Leu Gly Asp Asn Gly Phe Ala Ser Leu Phe Gly Ser
65                  70                  75                  80
```

```
Lys Pro Pro Arg Ser Asn Arg Gly His Leu Arg Leu Gly Arg Thr Ser
                85                  90                  95
His Ser Gly Glu Val Met Ala Val Ala Xaa Gln Xaa Ala Gln Glu Val
            100                 105                 110
Ser Thr Asn Lys Lys Pro Ala Thr Lys Gln Arg Arg Val Val Val Thr
        115                 120                 125
Gly Met Gly Val Val Thr Pro Leu Gly His Asp Pro Asp Val Tyr Tyr
    130                 135                 140
Asn Asn Leu Leu Asp Gly Val Ser Gly Ile Ser Glu Ile Glu Asn Phe
145                 150                 155                 160
Asp Cys Ser Gln Phe Pro Thr Arg Ile Ala Gly Glu Ile Lys Ser Phe
                165                 170                 175
Ser Thr Asp Gly Trp Val Ala Pro Lys Leu Ser Lys Arg Met Asp Lys
            180                 185                 190
Phe Met Leu Tyr Ile Leu Thr Ala Gly Lys Lys Ala Leu Ala Asp Gly
        195                 200                 205
Gly Ile Thr Glu Asp Val Met Lys Glu Leu Asp Lys Arg Lys Cys Gly
    210                 215                 220
Val Leu Ile Gly Ser Gly Leu Gly Gly Met Lys Val Phe Ser Asp Ser
225                 230                 235                 240
Ile Glu Ala Leu Arg Thr Ser Tyr Lys Lys Ile Ser Pro Phe Cys Val
                245                 250                 255
Pro Phe Ser Thr Thr Asn Met Gly Ser Ala Ile Leu Ala Met Asp Leu
            260                 265                 270
Gly Trp Met Gly Pro Asn Tyr Ser Ile Ser Thr Ala Cys Ala Thr Ser
        275                 280                 285
Asn Phe Cys Ile Leu Asn Ala Ala Asn His Ile Thr Lys Gly Glu Ala
    290                 295                 300
Asp Met Met Leu Cys Gly Gly Ser Asp Ala Ala Ile Leu Pro Ile Gly
305                 310                 315                 320
Met Gly Gly Phe Val Ala Cys Arg Ala Leu Ser Gln Arg Asn Asn Asp
                325                 330                 335
Pro Thr Lys Ala Ser Arg Pro Trp Asp Ser Asn Arg Asp Gly Phe Val
            340                 345                 350
Met Gly Glu Gly Ala Gly Val Leu Leu Leu Glu Glu Leu Glu His Ala
        355                 360                 365
Lys Lys Arg Gly Ala Thr Ile Tyr Ala Glu Phe Leu Gly Gly Ser Phe
    370                 375                 380
Thr Cys Asp Ala Tyr His Met Thr Glu Pro His Pro Glu Gly Ala Gly
385                 390                 395                 400
Val Ile Leu Cys Ile Glu Lys Ala Leu Ala Gln Ser Gly Val Ser Arg
                405                 410                 415
Glu Asp Val Asn Tyr Ile Asn Ala His Ala Thr Ser Thr Pro Ala Gly
            420                 425                 430
Asp Ile Lys Glu Tyr Gln Ala Leu Ala His Cys Phe Gly Gln Asn Ser
        435                 440                 445
Glu Leu Arg Val Asn Ser Thr Lys Ser Met Ile Gly His Leu Leu Gly
    450                 455                 460
Gly Ala Gly Gly Val Glu Ala Val Thr Val Val Gln Ala Ile Arg Thr
465                 470                 475                 480
Gly Trp Ile His Pro Asn Ile Asn Leu Glu Asp Pro Asp Glu Gly Val
                485                 490                 495
Asp Ala Lys Leu Leu Val Gly Pro Lys Lys Glu Lys Leu Lys Val Lys
```

-continued

```
                500                 505                 510
Val Gly Leu Ser Asn Ser Phe Gly Phe Gly Gly His Asn Ser Ser Ile
            515                 520                 525

Leu Phe Ala Pro Cys Asn
        530

<210> SEQ ID NO 70
<211> LENGTH: 543
<212> TYPE: PRT
<213> ORGANISM: Artificial Sequence
<220> FEATURE:
<223> OTHER INFORMATION: Clade 2 KASIV consensus C10 only
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (483)..(483)
<223> OTHER INFORMATION: Xaa can be any naturally occurring amino acid

<400> SEQUENCE: 70

Met Ala Ala Ala Ser Met Xaa Xaa Ser Pro Leu Cys Thr Trp Leu
1               5                   10                  15

Val Ala Ala Cys Met Ser Thr Ser Phe Asp Asn Asp Pro Arg Ser Pro
            20                  25                  30

Ser Ile Lys Arg Leu Pro Arg Arg Arg Val Leu Ser Gln Cys Ser
        35                  40                  45

Leu Arg Gly Ser Thr Phe Gln Cys Leu Val Thr Ser Tyr Ile Asp Pro
50                  55                  60

Cys Asn Gln Tyr Cys Ser Ser Ala Ser Leu Ser Phe Leu Gly Asp Asn
65                  70                  75                  80

Gly Phe Ala Ser Leu Phe Gly Ser Lys Pro Phe Arg Ser Asn Arg Gly
                85                  90                  95

His Arg Arg Leu Gly Arg Ala Ser His Ser Gly Glu Ala Met Ala Val
            100                 105                 110

Ala Leu Gln Pro Ala Gln Glu Val Ala Thr Lys Lys Pro Val Ile
        115                 120                 125

Lys Gln Arg Arg Val Val Val Thr Gly Met Gly Val Val Thr Pro Leu
130                 135                 140

Gly His Glu Pro Asp Val Tyr Tyr Asn Asn Leu Leu Asp Gly Val Ser
145                 150                 155                 160

Gly Ile Ser Glu Ile Glu Thr Phe Asp Cys Thr Gln Phe Pro Thr Arg
                165                 170                 175

Ile Ala Gly Glu Ile Lys Ser Phe Ser Thr Asp Gly Trp Val Ala Pro
            180                 185                 190

Lys Leu Ser Lys Arg Met Asp Lys Phe Met Leu Tyr Leu Leu Thr Ala
        195                 200                 205

Gly Lys Lys Ala Leu Ala Asp Gly Gly Ile Thr Asp Val Met Lys
210                 215                 220

Glu Leu Asp Lys Arg Lys Cys Gly Val Leu Ile Gly Ser Gly Met Gly
225                 230                 235                 240

Gly Met Lys Leu Phe Asn Asp Ser Ile Glu Ala Leu Arg Xaa Ser Tyr
                245                 250                 255

Lys Lys Met Asn Pro Phe Cys Val Pro Phe Ala Thr Thr Asn Met Gly
```

```
                    260                 265                 270

Ser Ala Met Leu Ala Met Asp Leu Gly Trp Met Gly Pro Asn Tyr Ser
                275                 280                 285

Ile Ser Thr Ala Cys Ala Thr Ser Asn Phe Cys Ile Leu Asn Ala Ala
            290                 295                 300

Asn His Ile Val Arg Gly Glu Ala Asp Met Met Leu Cys Gly Gly Ser
305                 310                 315                 320

Asp Ala Val Ile Ile Pro Ile Gly Leu Gly Gly Phe Val Ala Cys Arg
                325                 330                 335

Ala Leu Ser Gln Arg Asn Asn Asp Pro Thr Lys Ala Ser Arg Pro Trp
            340                 345                 350

Asp Ser Asn Arg Asp Gly Phe Val Met Gly Glu Gly Ala Gly Val Leu
        355                 360                 365

Leu Leu Glu Glu Leu Glu His Ala Lys Lys Arg Gly Ala Thr Ile Tyr
    370                 375                 380

Ala Glu Phe Leu Gly Gly Ser Phe Thr Cys Asp Ala Tyr His Met Thr
385                 390                 395                 400

Glu Pro His Pro Glu Gly Ala Gly Val Ile Leu Cys Ile Glu Lys Ala
                405                 410                 415

Leu Ala Gln Ala Gly Val Ser Arg Glu Asp Val Asn Tyr Ile Asn Ala
            420                 425                 430

His Ala Thr Ser Thr Pro Ala Gly Asp Ile Lys Glu Tyr Gln Ala Leu
        435                 440                 445

Ala His Cys Phe Gly Gln Asn Ser Glu Leu Arg Val Asn Ser Thr Lys
    450                 455                 460

Ser Met Ile Gly His Leu Leu Gly Ala Ala Gly Gly Val Glu Ala Val
465                 470                 475                 480

Thr Val Xaa Gln Ala Ile Arg Thr Gly Trp Ile His Pro Asn Leu Asn
                485                 490                 495

Leu Glu Asp Pro Asp Lys Ala Val Asp Ala Lys Leu Leu Val Gly Pro
            500                 505                 510

Lys Lys Glu Arg Leu Asn Val Lys Val Gly Leu Ser Asn Ser Phe Gly
        515                 520                 525

Phe Gly Gly His Asn Ser Ser Ile Leu Phe Ala Pro Tyr Asn Val
    530                 535                 540

<210> SEQ ID NO 71
<211> LENGTH: 414
<212> TYPE: PRT
<213> ORGANISM: Artificial Sequence
<220> FEATURE:
<223> OTHER INFORMATION: Clade 1 KASIV consensus mature protein

<400> SEQUENCE: 71

Lys Gln Arg Arg Val Val Thr Gly Met Gly Val Val Thr Pro Leu
1               5                   10                  15

Gly His Asp Pro Asp Val Tyr Tyr Asn Asn Leu Leu Gly Val Ser
            20                  25                  30

Gly Ile Ser Glu Ile Glu Asn Phe Asp Cys Ser Gln Phe Pro Thr Arg
        35                  40                  45

Ile Ala Gly Glu Ile Lys Ser Phe Ser Thr Asp Gly Trp Val Ala Pro
    50                  55                  60

Lys Leu Ser Lys Arg Met Asp Lys Phe Met Leu Tyr Ile Leu Thr Ala
65                  70                  75                  80

Gly Lys Lys Ala Leu Ala Asp Gly Gly Ile Thr Glu Asp Val Met Lys
```

```
                85                  90                  95
Glu Leu Asp Lys Arg Lys Cys Gly Val Leu Ile Gly Ser Gly Leu Gly
            100                 105                 110
Gly Met Lys Val Phe Ser Asp Ser Ile Glu Ala Leu Arg Thr Ser Tyr
        115                 120                 125
Lys Lys Ile Ser Pro Phe Cys Val Pro Phe Ser Thr Thr Asn Met Gly
    130                 135                 140
Ser Ala Ile Leu Ala Met Asp Leu Gly Trp Met Gly Pro Asn Tyr Ser
145                 150                 155                 160
Ile Ser Thr Ala Cys Ala Thr Ser Asn Phe Cys Ile Leu Asn Ala Ala
                165                 170                 175
Asn His Ile Thr Lys Gly Glu Ala Asp Met Met Leu Cys Gly Gly Ser
            180                 185                 190
Asp Ala Ala Ile Leu Pro Ile Gly Met Gly Phe Val Ala Cys Arg
        195                 200                 205
Ala Leu Ser Gln Arg Asn Asn Asp Pro Thr Lys Ala Ser Arg Pro Trp
    210                 215                 220
Asp Ser Asn Arg Asp Gly Phe Val Met Gly Glu Gly Ala Gly Val Leu
225                 230                 235                 240
Leu Leu Glu Glu Leu Glu His Ala Lys Lys Arg Gly Ala Thr Ile Tyr
                245                 250                 255
Ala Glu Phe Leu Gly Gly Ser Phe Thr Cys Asp Ala Tyr His Met Thr
            260                 265                 270
Glu Pro His Pro Glu Gly Ala Gly Val Ile Leu Cys Ile Glu Lys Ala
        275                 280                 285
Leu Ala Gln Ser Gly Val Ser Arg Glu Asp Val Asn Tyr Ile Asn Ala
    290                 295                 300
His Ala Thr Ser Thr Pro Ala Gly Asp Ile Lys Glu Tyr Gln Ala Leu
305                 310                 315                 320
Ala His Cys Phe Gly Gln Asn Ser Glu Leu Arg Val Asn Ser Thr Lys
                325                 330                 335
Ser Met Ile Gly His Leu Leu Gly Gly Ala Gly Gly Val Glu Ala Val
            340                 345                 350
Thr Val Val Gln Ala Ile Arg Thr Gly Trp Ile His Pro Asn Ile Asn
        355                 360                 365
Leu Glu Asp Pro Asp Glu Gly Val Asp Ala Lys Leu Leu Val Gly Pro
    370                 375                 380
Lys Lys Glu Lys Leu Lys Val Lys Val Gly Leu Ser Asn Ser Phe Gly
385                 390                 395                 400
Phe Gly Gly His Asn Ser Ser Ile Leu Phe Ala Pro Cys Asn
                405                 410

<210> SEQ ID NO 72
<211> LENGTH: 415
<212> TYPE: PRT
<213> ORGANISM: Artificial Sequence
<220> FEATURE:
<223> OTHER INFORMATION: Clade 2 KASIV consensus mature protein
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (355)..(355)
<223> OTHER INFORMATION: Xaa can be any naturally occurring amino acid

<400> SEQUENCE: 72
```

```
Lys Gln Arg Arg Val Val Thr Gly Met Gly Val Val Thr Pro Leu
1               5                   10                  15

Gly His Glu Pro Asp Val Tyr Tyr Asn Asn Leu Leu Asp Gly Val Ser
                20                  25                  30

Gly Ile Ser Glu Ile Glu Thr Phe Asp Cys Thr Gln Phe Pro Thr Arg
            35                  40                  45

Ile Ala Gly Glu Ile Lys Ser Phe Ser Thr Asp Gly Trp Val Ala Pro
50                      55                  60

Lys Leu Ser Lys Arg Met Asp Lys Phe Met Leu Tyr Leu Leu Thr Ala
65                  70                  75                  80

Gly Lys Lys Ala Leu Ala Asp Gly Gly Ile Thr Asp Asp Val Met Lys
                85                  90                  95

Glu Leu Asp Lys Arg Lys Cys Gly Val Leu Ile Gly Ser Gly Met Gly
                100                 105                 110

Gly Met Lys Leu Phe Asn Asp Ser Ile Glu Ala Leu Arg Xaa Ser Tyr
            115                 120                 125

Lys Lys Met Asn Pro Phe Cys Val Pro Phe Ala Thr Thr Asn Met Gly
            130                 135                 140

Ser Ala Met Leu Ala Met Asp Leu Gly Trp Met Gly Pro Asn Tyr Ser
145                 150                 155                 160

Ile Ser Thr Ala Cys Ala Thr Ser Asn Phe Cys Ile Leu Asn Ala Ala
                165                 170                 175

Asn His Ile Val Arg Gly Glu Ala Asp Met Met Leu Cys Gly Gly Ser
            180                 185                 190

Asp Ala Val Ile Ile Pro Ile Gly Leu Gly Gly Phe Val Ala Cys Arg
            195                 200                 205

Ala Leu Ser Gln Arg Asn Asn Asp Pro Thr Lys Ala Ser Arg Pro Trp
210                 215                 220

Asp Ser Asn Arg Asp Gly Phe Val Met Gly Glu Gly Ala Gly Val Leu
225                 230                 235                 240

Leu Leu Glu Glu Leu Glu His Ala Lys Lys Arg Gly Ala Thr Ile Tyr
                245                 250                 255

Ala Glu Phe Leu Gly Gly Ser Phe Thr Cys Asp Ala Tyr His Met Thr
            260                 265                 270

Glu Pro His Pro Glu Gly Ala Gly Val Ile Leu Cys Ile Glu Lys Ala
            275                 280                 285

Leu Ala Gln Ala Gly Val Ser Arg Glu Asp Val Asn Tyr Ile Asn Ala
            290                 295                 300

His Ala Thr Ser Thr Pro Ala Gly Asp Ile Lys Glu Tyr Gln Ala Leu
305                 310                 315                 320

Ala His Cys Phe Gly Gln Asn Ser Glu Leu Arg Val Asn Ser Thr Lys
            325                 330                 335

Ser Met Ile Gly His Leu Leu Gly Ala Ala Gly Gly Val Glu Ala Val
            340                 345                 350

Thr Val Xaa Gln Ala Ile Arg Thr Gly Trp Ile His Pro Asn Leu Asn
            355                 360                 365

Leu Glu Asp Pro Asp Lys Ala Val Asp Ala Lys Leu Leu Val Gly Pro
            370                 375                 380

Lys Lys Glu Arg Leu Asn Val Lys Val Gly Leu Ser Asn Ser Phe Gly
385                 390                 395                 400

Phe Gly Gly His Asn Ser Ser Ile Leu Phe Ala Pro Tyr Asn Val
                405                 410                 415
```

KETOACYL ACP SYNTHASE GENES AND USES THEREOF

CROSS REFERENCE TO RELATED APPLICATIONS

This application is a divisional of U.S. patent application Ser. No. 14/796,406, filed Jul. 10, 2015, entitled "Novel Ketoacyl ACP Synthase Genes and Uses Thereof", which claims the benefit under 35 U.S.C. 119(e) of U.S. Provisional Patent Application No. 62/023,112, filed Jul. 10, 2014, and U.S. Provisional Patent Application No. 62/081,143, filed Nov. 18, 2014, each of which is incorporated herein by reference in its entirety. This application includes subject matter related to that disclosed in U.S. provisional patent application No. 62/023,109, entitled "Tailored Oils," filed Jul. 10, 2014, which is hereby incorporated by reference in its entirety for all purposes.

REFERENCE TO A SEQUENCE LISTING

This application includes include an electronic sequence listing in a file names "465964-Sequence.txt", created on Sep. 28, 2015, and contains 235,869 bytes, which is hereby incorporated by reference in its entirety for all purposes.

TECHNICAL FIELD

The present invention relates to novel β-ketoacyl ACP synthase genes and methods for using the genes including expressing the genes in oleaginous host cells to produce triglycerides with altered fatty acid profiles.

BACKGROUND

Certain organisms including plants and some microalgae use a type II fatty acid biosynthetic pathway, characterized by the use of discrete enzymes in a multimeric complex for fatty acid synthesis. In contrast, mammals and fungi use a single, large, multifunctional protein.

In organisms that use a type II fatty acid biosynthetic pathway, β-ketoacyl-ACP synthase I (KAS I, EC 2.3.1.41) is one of the enzymes responsible for elongation of growing medium-chain fatty acyl-ACP from 4 to 16 carbon atoms in length. KAS I uses C2-C14 acyl-ACPs as substrates for condensation with a C2 unit derived from malonyl-ACP. KASIV is a related enzyme that serves a similar elongation function. Thus, KASI and KASIV can both be considered KASI-like enzymes.

Such genes have been introduced to plants using recombinant DNA technology. See for example U.S. Pat. Nos. 7,301,070, 6,348,642, 6,660,849, 6,770,465 and US2006/0094088 (of which ¶¶194-200 and the entirety of the document are hereby incorporated herein by reference). In plastidic cells such as those from plants, macroalgae and microalgae, KAS I-like enzymes are located in the chloroplasts or other plastids together with other enzyme of the fatty acid synthesis (FAS) pathway.

PCT publications WO2010/063032, WO2011/150411, WO2012/106560, and WO2013/158938 disclose genetic engineering of oleaginous microalgae including targeting of exogenous FAS gene products to the microalgal plastid.

SUMMARY

In one aspect, embodiments of the invention include a non-natural, isolated polynucleotide having at least 80, 85, 90, 91, 92, 93, 94, 95, 96, 97, 98, or 99% sequence identity or equivalent sequence by virtue of the degeneracy of the genetic code to any one of SEQ ID NOs: 21-37, or 39-55, or encoding a KASI-like protein having at least 80, 85, 85.5, 86, 86.5, 87, 87.5, 88, 88.5, 89, 89.5, 90, 90.5, 91, 91.5, 92, 92.5, 93, 93.5, 94, 94.5, 95, 95.5, 96, 96.5, 97, 97.5, 98, 98.5, 99 or 99.5% amino acid sequence identity to any one of SEQ ID NOs: 2-18, 62-72, or a mature protein produced therefrom, or the complement of the polynucleotide.

In another aspect, embodiments of the invention include a transformation vector comprising a cDNA molecule comprising a polynucleotide as discussed above. In some cases, the vector comprises promoter and 3'UTR sequences in operable linkage to the cDNA, and optionally a flanking sequence for homologous recombination. The promoter or the 3'UTR sequences are heterologous nucleotide sequences. The heterologous promoter or the heterologous 3'UTR sequences can be from a different organism than the organism from which the nucleotide sequences encoding KAS was first obtained.

In one aspect, the transformation vector comprises a heterologous promoter or a heterologous 3'UTR sequence obtained from the same organism from which the KAS gene was first isolated. When the promoter sequence, the 3'UTR sequence and the KAS nucleotide sequences are from the same organism, the heterologous promoter does not naturally drive the expression of KAS, and the 3'UTR does not naturally occur downstream from the KAS nucleotide sequences in the source organism.

In yet another aspect, the transformation vector is used to express the KAS gene in the organism from which the KAS gene was first isolated. When the KAS gene is recombinantly expressed in the organism from which the KAS gene was first isolated, the gene is expressed in a different chromosomal locus than the natural chromosomal locus of the KAS gene. Alternatively, the KAS gene is expressed in the cytoplasm.

In another aspect, embodiments of the invention include a host cell comprising the polynucleotide and/or the vector discussed above, and expressing a functional KAS protein encoded by the cDNA. In some cases, the host cell further comprises an exogenous gene encoding a functional FATA acyl-ACP thioesterase or FATB acyl-ACP thioesterase. In one aspect, the FATB acyl-ACP thioesterase has at least 80, 85, 90, 91, 92, 93, 94, 95, 96, 97, 98, or 99% amino acid sequence identity to any one of SEQ ID NOs: 1 or SEQ ID NO: 57. In some cases, the host cell produces a cell oil characterized by a fatty acid profile with (i) at least 30, 40, 50, or 55% C14:0, (ii) at least 7, 8, 9, 10, 11, 12, 13, or 14% C8:0, (iii) at least 10, 15, 20, 25, 30, or 35 area % for the sum of C8:0 and C10:0, or (iv) a C8/C10 ratio in the range of 2.2-2.5, 2.5-3.0, or 3.0-3.4. In some cases, the host cell is a plastidic oleaginous cell having a type II fatty acid biosynthesis pathway. In some cases, the host cell is a microalga. In some cases, the host cell is of Trebouxiophyceae, and optionally of the genus *Chlorella* or *Prototheca*. In some cases, the microalga is of the species *Prototheca moriformis*.

In another aspect, embodiments of the invention include a method for making a cell-oil, the method comprising cultivating a host cell as discussed above so as produce the cell-oil, wherein the oil comprises triglcyerides and microalgal sterols. In some cases, the cell oil comprises sterols characterized by a sterol profile and the sterol profile has an excess of ergosterol over β-sitosterol and/or the presence of 22, 23-dihydrobrassicasterol, poriferasterol or clionasterol.

BRIEF DESCRIPTION OF THE DRAWINGS

FIG. 1 shows a phylogenetic tree for KASI-like genes in connection with Example 3.

DETAILED DESCRIPTION OF EMBODIMENTS OF THE INVENTION

As used with respect to nucleic acids, the term "isolated" refers to a nucleic acid that is free of at least one other component that is typically present with the naturally occurring nucleic acid. Thus, a naturally occurring nucleic acid is isolated if it has been purified away from at least one other component that occurs naturally with the nucleic acid.

A "cell oil" or "cell fat" shall mean a predominantly triglyceride oil obtained from an organism, where the oil has not undergone blending with another natural or synthetic oil, or fractionation so as to substantially alter the fatty acid profile of the triglyceride. In connection with an oil comprising triglycerides of a particular regiospecificity, the cell oil or cell fat has not been subjected to interesterification or other synthetic process to obtain that regiospecific triglyceride profile, rather the regiospecificity is produced naturally, by a cell or population of cells. For a cell oil or cell fat produced by a cell, the sterol profile of oil is generally determined by the sterols produced by the cell, not by artificial reconstitution of the oil by adding sterols in order to mimic the cell oil. In connection with a cell oil or cell fat, and as used generally throughout the present disclosure, the terms oil and fat are used interchangeably, except where otherwise noted. Thus, an "oil" or a "fat" can be liquid, solid, or partially solid at room temperature, depending on the makeup of the substance and other conditions. Here, the term "fractionation" means removing material from the oil in a way that changes its fatty acid profile relative to the profile produced by the organism, however accomplished. The terms "cell oil" and "cell fat" encompass such oils obtained from an organism, where the oil has undergone minimal processing, including refining, bleaching and/or degumming, which does not substantially change its triglyceride profile. A cell oil can also be a "noninteresterified cell oil", which means that the cell oil has not undergone a process in which fatty acids have been redistributed in their acyl linkages to glycerol and remain essentially in the same configuration as when recovered from the organism.

"Exogenous gene" shall mean a nucleic acid that codes for the expression of an RNA and/or protein that has been introduced into a cell (e.g. by transformation/transfection), and is also referred to as a "transgene". A cell comprising an exogenous gene may be referred to as a recombinant cell, into which additional exogenous gene(s) may be introduced. The exogenous gene may be from a different species (and so heterologous), or from the same species (and so homologous), relative to the cell being transformed. Thus, an exogenous gene can include a homologous gene that occupies a different location in the genome of the cell or is under different control, relative to the endogenous copy of the gene. An exogenous gene may be present in more than one copy in the cell. An exogenous gene may be maintained in a cell, for example, as an insertion into the genome (nuclear or plastid) or as an episomal molecule.

"Fatty acids" shall mean free fatty acids, fatty acid salts, or fatty acyl moieties in a glycerolipid. It will be understood that fatty acyl groups of glycerolipids can be described in terms of the carboxylic acid or anion of a carboxylic acid that is produced when the triglyceride is hydrolyzed or saponified.

"Microalgae" are microbial organisms that contain a chloroplast or other plastid, and optionally that are capable of performing photosynthesis, or a prokaryotic microbial organism capable of performing photosynthesis. Microalgae include obligate photoautotrophs, which cannot metabolize a fixed carbon source as energy, as well as heterotrophs, which can live solely off of a fixed carbon source. Microalgae include unicellular organisms that separate from sister cells shortly after cell division, such as *Chlamydomonas*, as well as microbes such as, for example, Volvox, which is a simple multicellular photosynthetic microbe of two distinct cell types. Microalgae include cells such as *Chlorella, Dunaliella*, and *Prototheca*. Microalgae also include other microbial photosynthetic organisms that exhibit cell-cell adhesion, such as *Agmenellum, Anabaena*, and *Pyrobotrys*. Microalgae also include obligate heterotrophic microorganisms that have lost the ability to perform photosynthesis, such as certain dinoflagellate algae species and species of the genus *Prototheca*.

An "oleaginous" cell is a cell capable of producing at least 20% lipid by dry cell weight, naturally or through recombinant or classical strain improvement. An "oleaginous microbe" or "oleaginous microorganism" is a microbe, including a microalga that is oleaginous.

The term "percent sequence identity," in the context of two or more amino acid or nucleic acid sequences, refers to two or more sequences or subsequences that are the same or have a specified percentage of amino acid residues or nucleotides that are the same, when compared and aligned for maximum correspondence, as measured using a sequence comparison algorithm or by visual inspection. For sequence comparison to determine percent nucleotide or amino acid identity, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted using the NCBI BLAST software (ncbi.nlm.nih.gov/BLAST/) set to default parameters. For example, to compare two nucleic acid sequences, one may use blastn with the "BLAST 2 Sequences" tool Version 2.0.12 (Apr. 21, 2000) set at the following default parameters: Matrix: BLOSUM62; Reward for match: 1; Penalty for mismatch: −2; Open Gap: 5 and Extension Gap: 2 penalties; Gap x drop-off: 50; Expect: 10; Word Size: 11; Filter: on. For a pairwise comparison of two amino acid sequences, one may use the "BLAST 2 Sequences" tool Version 2.0.12 (Apr. 21, 2000) with blastp set, for example, at the following default parameters: Matrix: BLOSUM62; Open Gap: 11 and Extension Gap: 1 penalties; Gap x drop-off 50; Expect: 10; Word Size: 3; Filter: on.

Where multiple sequence identities are given for a strain having a pair of exogenous genes, this encompasses all combinations of sequence identities. For example, coexpression of a first gene encoding a first protein having at least 85, 90, 91, 92, 93, 94, 95, 96, 97, 98, or 99% with gene A and a second gene encoding a second protein having at least 85, 90, 91, 92, 93, 94, 95, 96, 97, 98, or 99% with gene A shall be understood to encompass (i) at least 85% identity with gene A and least 85% identity with gene B, (ii)) at least 85% identity with gene A and least 99% identity with gene B, (iii)

at least 92% identity with gene A and least 95% identity with gene B, and all other combinations.

In connection with a cell oil, a "profile" is the distribution of particular species of triglycerides or fatty acyl groups within the oil. A "fatty acid profile" is the distribution of fatty acyl groups in the triglycerides of the oil without reference to attachment to a glycerol backbone. Fatty acid profiles are typically determined by conversion to a fatty acid methyl ester (FAME), followed by gas chromatography (GC) analysis with flame ionization detection (FID). The fatty acid profile can be expressed as one or more percent of a fatty acid in the total fatty acid signal determined from the area under the curve for that fatty acid. FAME-GC-FID measurement approximate weight percentages of the fatty acids.

As used herein, an oil is said to be "enriched" in one or more particular fatty acids if there is at least a 10% increase in the mass of that fatty acid in the oil relative to the non-enriched oil. For example, in the case of a cell expressing a heterologous FatB gene described herein, the oil produced by the cell is said to be enriched in, e.g., C8 and C16 fatty acids if the mass of these fatty acids in the oil is at least 10% greater than in oil produced by a cell of the same type that does not express the heterologous FatB gene (e.g., wild type oil).

"Recombinant" is a cell, nucleic acid, protein or vector that has been modified due to the introduction of an exogenous nucleic acid or the alteration of a native nucleic acid. Thus, e.g., recombinant (host) cells can express genes that are not found within the native (non-recombinant) form of the cell or express native genes differently than those genes are expressed by a non-recombinant cell. Recombinant cells can, without limitation, include recombinant nucleic acids that encode a gene product or suppression elements such as mutations, knockouts, antisense, interfering RNA (RNAi) or dsRNA that reduce the levels of active gene product in a cell. A "recombinant nucleic acid" is a nucleic acid originally formed in vitro, in general, by the manipulation of nucleic acid, e.g., using polymerases, ligases, exonucleases, and endonucleases, using chemical synthesis, or otherwise is in a form not normally found in nature. Recombinant nucleic acids may be produced, for example, to place two or more nucleic acids in operable linkage. Thus, an isolated nucleic acid or an expression vector formed in vitro by nucleic by ligating DNA molecules that are not normally joined in nature, are both considered recombinant for the purposes of this invention. Recombinant nucleic acids can also be produced in other ways; e.g., using chemical DNA synthesis. Once a recombinant nucleic acid is made and introduced into a host cell or organism, it may replicate using the in vivo cellular machinery of the host cell; however, such nucleic acids, once produced recombinantly, although subsequently replicated intracellularly, are still considered recombinant for purposes of this invention. Similarly, a "recombinant protein" is a protein made using recombinant techniques, i.e., through the expression of a recombinant nucleic acid.

A "KAS I-like" gene or enzyme shall mean either a KAS I or KAS IV gene or enzyme.

Embodiments of the present invention relate to the use of KASI-like genes isolated from plants or other organisms, which can be expressed in a transgenic host cell in order to alter the fatty acid profile of a cell-oil produced by the host cell. Although the microalga *Prototheca moriformis* was used to screen the genes for ability to the alter fatty acid profile, the genes discovered are useful in a wide variety of host cells for which genetic transformation techniques are known. For example, the genes can be expressed in bacteria, cyanobacteria, other eukaryotic microalgae, or higher plants. The genes can be expressed in higher plants according to the methods disclosed in U.S. Pat. Nos. 7,301,070, 6,348,642, 6,660,849, and 6,770,465. We have found that KASI-like transgenes can be used alone or in combination with a FatB transgene (encoding an active acyl-ACP thioesterase) can boost the levels of mid-chain fatty acids (e.g., capric, caprylic, lauric, myristic or palmitic acids) in the fatty acid profile of the cell oil. Combining an exogenous KASI-like gene with an exogenous FATA or FATB gene in a host cell can give levels of mid-chain fatty acids and/or long-chain fatty acids (e.g., stearic or oleic) greater than either exogenous gene alone. The fatty acids of the cell oil can be further converted to triglycerides, fatty aldehydes, fatty alcohols and other oleochemicals either synthetically or biosynthetically.

In specific embodiments, triglycerides are produced by a host cell expressing a novel KASI-like gene (from a novel cDNA and/or under control of a heterologous promoter). A cell oil can be recovered from the host cell. Typically, the cell oil comprises mainly triglycerides and sterols. The cell oil can be refined, degummed, bleached and/or deodorized. The oil, in its unprocesssed or processed form, can be used for foods, chemicals, fuels, cosmetics, plastics, and other uses. In other embodiments, the KASI-like gene may not be novel, but the expression of the gene in a microalga is novel.

The KAS genes can be used in a variety of genetic constructs including plasmids or other vectors for expression or recombination in a host cell. The genes can be codon optimized for expression in a target host cell. The genes can be included in an expression cassette that includes a promoter (e.g., a heterologous promoter) and downstream regulatory element. The vector can include flanking sequences for homologous recombination. For example, the vector can cause insertion into a chromosome of the host cell, where it can be stably expressed. The proteins produced by the genes can be used in vivo or in purified form. In an embodiment, an expression cassette comprises a homologous promoter, a CDS operable to express a KASI-like enzyme of Table 1 and a 3'UTR. The 3'UTR can comprise a polyadenylation site.

As described in the examples below, novel KAS genes are were discovered from cDNA produced from plant seed mRNA transcripts. Accordingly the gene sequences are non-natural because they lack introns that are present in the plant genes and mRNA transcripts of the genes prior to mRNA splicing. Accordingly, the invention comprises an isolated non-natural KASI-like gene of Table 1. Further departure from the natural gene is in the use of heterologous regulatory elements and expression in host cells for which such genes do not occur in nature.

For example, the gene can be prepared in an expression vector comprising an operably linked promoter and 5'UTR. Where a plastidic cell is used as the host, a suitably active plastid targeting peptide (also referred to below as a "transit peptide") can be fused to the KASI-like gene, as in the examples below. The disclosed genes comprise a hydrophobic N-terminal plastid targeting sequence, which can be replaced with alternative targeting sequence and varied in length. Varying the plastid targeting peptide can improve cellular localization and enzyme activity for a given host-cell type. Thus, the invention contemplates deletions and fusion proteins in order to optimize enzyme activity in a given host cell. For example, a transit peptide from the host or related species may be used instead of that of the newly discovered plant genes described here. Additional terminal or internal deletions may be made so-long as the enzymatic activity is retained. The targeting peptide can be cleaved by the host cell to produce a mature KASI-like protein that lacks the targeting peptide.

A selectable marker gene may be included in the vector to assist in isolating a transformed cell. Examples of selectable markers useful in microalgae include sucrose invertase, alpha galactosidase (for selection on melibiose) and antibiotic resistance genes.

The gene sequences disclosed can also be used to prepare antisense, or inhibitory RNA (e.g., RNAi or hairpin RNA) to inhibit complementary genes in a plant or other organism. For example, armed with the knowledge of a gene sequence of Table 1, one can engineer a plant with the same or similar KASI-like gene to express an RNAi construct, gene knock-out, point mutation, or the like, and thereby reduce the KASI or KASIV activity of the plant's seed. As a result, the plant can produce an oil with an altered fatty acid profile in which the mean chain length is decreased or increased, depending on the presence of other fatty acid synthesis genes.

KASI-like genes/proteins found to be useful in producing desired fatty acid profiles in a cell are summarized below in Table 1, and related proteins discovered from transcript sequencing (as in Examples 1-2) are shown in Table 1a. Nucleic acids or proteins having the sequence of SEQ ID NOS: 2-18, 59, 62-72, 21-37 or 39-55 can be used to alter the fatty acid profile of a recombinant cell. Variant nucleic acids can also be used; e.g., variants having at least 70, 80, 85, 90, 95, 96, 97, 98, or 99% sequence identity to SEQ ID NOS: 21-37 or 39-55. Codon optimization of the genes for a variety of host organisms is contemplated, as is the use of gene fragments. Preferred codons for *Protheca* strains and for *Chlorella protothecoides* are shown below in Tables 2 and 3, respectively. Codon usage for *Cuphea wrightii* is shown in Table 4. Codon usage for *Arabidopsis* is shown in Table 5; for example, the most preferred codon for each amino acid can be selected. Codon tables for other organisms including microalgae and higher plants are known in the art. In some embodiments, the first and/or second most preferred *Prototheca* codons are employed for codon optimization. In specific embodiments, the novel amino acid sequences contained in the sequence listings below are converted into nucleic acid sequences according to the most preferred codon usage in *Prototheca, Chlorella, Cuphea wrightii*, or *Arabidopsis* as set forth in tables 2 through 3b or nucleic acid sequences having at least 70, 80, 85, 90, 95, 96, 97, 98, or 99% sequence identity to these derived nucleic acid sequences. For example, the KASI-like gene can be codon optimized for *Prototheca moriformis* by substituting most preferred codons according to Table 2 for at least 10, 20, 30, 40, 50, 60, 70, 80, or 90% of all codons. Likewise, the KASI-like gene can be codon optimized for *Chlorella protothecoides* by substituting most-preferred codons according to Table 3 for at least 10, 20, 30, 40, 50, 60, 70, 80, or 90% of all codons. Alternately, the KASI-like gene can be codon optimized for *Chlorella protothecoides* or *Prototheca moriformis* by substituting first or second most-preferred codons according to Table 2 or 3 for at least 10, 20, 30, 40, 50, 60, 70, 80, or 90% of all codons. Codon-optimized genes are non-naturally occurring because they are optimized for expression in a host organism.

In certain embodiments, percent sequence identity for variants of the nucleic acids or proteins discussed above can be calculated by using the full-length nucleic acid sequence (e.g., one of SEQ ID NOS: 21-37 or 39-55 or full-length amino acid sequence (e.g., one of SEQ ID NOS: 2-18) as the reference sequence and comparing the full-length test sequence to this reference sequence. For fragments, percent sequence identity for variants of nucleic acid or protein fragments can be calculated over the entire length of the fragment. In certain embodiments, there is a nucleic acid or protein fragment have at least 70, 80, 85, 90, 95, 96, 97, 98, or 99% sequence identity to one of SEQ ID NOS: 21-37, 39-55 or 2-18.

Optionally, the plastidic targeting peptide can be swapped with another peptide that functions to traffic the KASI-like enzyme to a fatty acid synthesizing plastid of a plastidic host cell. Accordingly, in various embodiments of the invention, a transgene or transgenic host cell comprises a nucleotide or corresponding peptidic fusion of a plastic targeting sequence and an enzyme-domain sequence (the sequence remaining after deletion of the transit peptide), where the mature protein has at least 70, 80, 85, 90, 95, 96, 97, 98, or 99% sequence identity to an mature protein sequence listed in Table 1 or Table 1a. Plastid transit/targeting peptides are underlined in the accompanying informal sequence listing. Examples of targeting peptides include those of Table 1 and others known in the art, especially in connection with the targeting of KAS I, KAS II, KAS III, FATA, FATB and SAD (stearoyl-ACP desaturase) gene products to chloroplasts or other plastids of plants and microalgae. See examples of *Chorophyta* given in PCT publications WO2010/063032, WO2011/150411, WO2012/106560, and WO2013/158938.

Optionally, the KASI-like genes encode 450, 475 or 500 amino acids or more (with or without the transit peptide), or about 555 residues (with the transit peptide,) in contrast to known truncated sequences.

TABLE 1

KASI-like genes: The expression cassette used to test the genes in combination with a FATB transgene is given in SEQ ID NO: 38 (i.e., substituting the Cpal KASIV coding sequence of SEQ ID NO: 38 with various other coding sequences of Table 1), except that the *Cuphea hookeriana* KASIV was tested using the expression cassette of SEQ ID NO: 61. See Examples 1-4.

| Species | Gene Name | Amino Acid Sequence | nucleotide coding sequence (from cDNA produced from seed mRNA, not codon-optimized) | *Prototheca moriformis* codon-optimized nucleotide sequence |
|---|---|---|---|---|
| *Cuphea palustris* | KASIV | 2 | 21 | 39 |
| *Cinnamonum camphora* | KASIV | 3 | 22 | 40 |
| *Cinnamonum camphora* | KASI | 4 | 23 | 41 |
| *Umbellularia californica* | KASI | 5 | 24 | 42 |
| *U. californica* | KASIV | 6 | 25 | 43 |
| *Cuphea. wrightii* | KASAI | 7 | 26 | 44 |
| *Cuphea avigera* | KASIVb | 8 | 27 | 45 |
| *Cuphea paucipetala* | KASIVb | 9 | 28 | 46 |
| *C. ignea* | KASIVb | 10 | 29 | 47 |
| *Cuphea procumbens* | KASIV | 11 | 30 | 48 |
| *C. paucipetala* | KASIVa | 12 | 31 | 49 |
| *Cuphea painteri* | KASIV | 13 | 32 | 50 |
| *C. avigera* | KASIVa | 14 | 33 | 51 |
| *C. ignea* | KASIVa | 15 | 34 | 52 |
| *C. avigera* | KASIa | 16 | 35 | 53 |
| *C. pulcherrima* | KASI | 17 | 36 | 54 |
| *C. avigera* | mitochondrial KAS | 18 | 37 | 55 |
| *Cuphea hookeriana* | KASIV | 59 | | 60, 61 |

TABLE 1a

Additional proteins encoded by cDNA discovered from transcript profiling of seeds. Coding sequences can be derived from codon tables for various host cells.

| Species | Gene Name | Amino Acid Sequence |
|---|---|---|
| Various (Clade 1) | KASIV consensus sequence | 69, 71 |
| Various (Clade 2) | KASIV consensus sequence | 70, 72 |
| *Cuphea aequipetala* | KASIV | 62 |
| *Cuphea glassostoma* | KASIV | 63 |
| *Cuphea hookeriana* | KASIV | 64 |
| *Cuphea glassostoma* | KASIV | 65 |
| *Cuphea carthagenesis* | KASIV | 66, 67 |
| *C. pulcherrima* | KASIV | 68 |

TABLE 2

Codon usage in *Prototheca* strains.

| | | | | | |
|---|---|---|---|---|---|
| Ala | GCG | 345 (0.36) | Asn | AAT | 8 (0.04) |
| | GCA | 66 (0.07) | | AAC | 201 (0.96) |
| | GCT | 101 (0.11) | Pro | CCG | 161 (0.29) |
| | GCC | 442 (0.46) | | CCA | 49 (0.09) |
| Cys | TGT | 12 (0.10) | | CCT | 71 (0.13) |
| | TGC | 105 (0.90) | | CCC | 267 (0.49) |
| Asp | GAT | 43 (0.12) | Gln | CAG | 226 (0.82) |
| | GAC | 316 (0.88) | | CAA | 48 (0.18) |
| Glu | GAG | 377 (0.96) | Arg | AGG | 33 (0.06) |
| | GAA | 14 (0.04) | | AGA | 14 (0.02) |
| Phe | TTT | 89 (0.29) | | CGG | 102 (0.18) |
| | TTC | 216 (0.71) | | CGA | 49 (0.08) |
| Gly | GGG | 92 (0.12) | | CGT | 51 (0.09) |
| | GGA | 56 (0.07) | | CGC | 331 (0.57) |
| | GGT | 76 (0.10) | Ser | AGT | 16 (0.03) |
| | GGC | 559 (0.71) | | AGC | 123 (0.22) |
| His | CAT | 42 (0.21) | | TCG | 152 (0.28) |
| | CAC | 154 (0.79) | | TCA | 31 (0.06) |
| Ile | ATA | 4 (0.01) | | TCT | 55 (0.10) |
| | ATT | 30 (0.08) | | TCC | 173 (0.31) |
| | ATC | 338 (0.91) | Thr | ACG | 184 (0.38) |
| Lys | AAG | 284 (0.98) | | ACA | 24 (0.05) |
| | AAA | 7 (0.02) | | ACT | 21 (0.05) |
| Leu | TTG | 26 (0.04) | | ACC | 249 (0.52) |
| | TTA | 3 (0.00) | Val | GTG | 308 (0.50) |
| | CTG | 447 (0.61) | | GTA | 9 (0.01) |
| | CTA | 20 (0.03) | | GTT | 35 (0.06) |
| | CTT | 45 (0.06) | | GTC | 262 (0.43) |
| | CTC | 190 (0.26) | Trp | TGG | 107 (1.00) |
| Met | ATG | 191 (1.00) | Tyr | TAT | 10 (0.05) |
| | | | | TAC | 180 (0.95) |
| | | | Stop | TGA/TAG/TAA | |

TABLE 3

Preferred codon usage in *Chlorella protothecoides*.

| | | | |
|---|---|---|---|
| TTC (Phe) | TAC (Tyr) | TGC (Cys) | TGA (Stop) |
| TGG (Trp) | CCC (Pro) | CAC (His) | CGC (Arg) |
| CTG (Leu) | CAG (Gln) | ATC (Ile) | ACC (Thr) |
| GAC (Asp) | TCC (Ser) | ATG (Met) | AAG (Lys) |
| GCC (Ala) | AAC (Asn) | GGC (Gly) | GTG (Val) |
| GAG (Glu) | | | |

TABLE 4

Codon usage for *Cuphea wrightii* (codon, amino acid, frequency, per thousand, number)

| | | | |
|---|---|---|---|
| UUU F 0.48 19.5 (52) | UCU S 0.21 19.5 (52) | UAU Y 0.45 6.4 (17) | UGU C 0.41 10.5 (28) |
| UUC F 0.52 21.3 (57) | UCC S 0.26 23.6 (63) | UAC Y 0.55 7.9 (21) | UGC C 0.59 15.0 (40) |
| UUA L 0.07 5.2 (14) | UCA S 0.18 16.8 (45) | UAA * 0.33 0.7 (2) | UGA * 0.33 0.7 (2) |
| UUG L 0.19 14.6 (39) | UCG S 0.11 9.7 (26) | UAG * 0.33 0.7 (2) | UGG W 1.00 15.4 (41) |
| CUU L 0.27 21.0 (56) | CCU P 0.48 21.7 (58) | CAU H 0.60 11.2 (30) | CGU R 0.09 5.6 (15) |
| CUC L 0.22 17.2 (46) | CCC P 0.16 7.1 (19) | CAC H 0.40 7.5 (20) | CGC R 0.13 7.9 (21) |
| CUA L 0.13 10.1 (27) | CCA P 0.21 9.7 (26) | CAA Q 0.31 8.6 (23) | CGA R 0.11 6.7 (18) |
| CUG L 0.12 9.7 (26) | CCG P 0.16 7.1 (19) | CAG Q 0.69 19.5 (52) | CGG R 0.16 9.4 (25) |
| AUU I 0.44 22.8 (61) | ACU T 0.33 16.8 (45) | AAU N 0.66 31.4 (84) | AGU S 0.18 16.1 (43) |
| AUC I 0.29 15.4 (41) | ACC T 0.27 13.9 (37) | AAC N 0.34 16.5 (44) | AGC S 0.07 6.0 (16) |
| AUA I 0.27 13.9 (37) | ACA T 0.26 13.5 (36) | AAA K 0.42 21.0 (56) | AGA R 0.24 14.2 (38) |
| AUG M 1.00 28.1 (75) | ACG T 0.14 7.1 (19) | AAG K 0.58 29.2 (78) | AGG R 0.27 16.1 (43) |
| GUU V 0.28 19.8 (53) | GCU A 0.35 31.4 (84) | GAU D 0.63 35.9 (96) | GGU G 0.29 26.6 (71) |
| GUC V 0.21 15.0 (40) | GCC A 0.20 18.0 (48) | GAC D 0.37 21.0 (56) | GGC G 0.20 18.0 (48) |
| GUA V 0.14 10.1 (27) | GCA A 0.33 29.6 (79) | GAA E 0.41 18.3 (49) | GGA G 0.35 31.4 (84) |
| GUG V 0.36 25.1 (67) | GCG A 0.11 9.7 (26) | GAG E 0.59 26.2 (70) | GGG G 0.16 14.2 (38) |

TABLE 5

Codon usage for *Arabidopsis* (codon, amino acid, frequency, per thousand)

| | | | |
|---|---|---|---|
| UUU F 0.51 21.8 | UCU S 0.28 25.2 | UAU Y 0.52 14.6 | UGU C 0.60 10.5 |
| UUC F 0.49 20.7 | UCC S 0.13 11.2 | UAC Y 0.48 13.7 | UGC C 0.40 7.2 |
| UUA L 0.14 12.7 | UCA S 0.20 18.3 | UAA * 0.36 0.9 | UGA * 0.44 1.2 |
| UUG L 0.22 20.9 | UCG S 0.10 9.3 | UAG * 0.20 0.5 | UGG W 1.00 12.5 |
| CUU L 0.26 24.1 | CCU P 0.38 18.7 | CAU H 0.61 13.8 | CGU R 0.17 9.0 |
| CUC L 0.17 16.1 | CCC P 0.11 5.3 | CAC H 0.39 8.7 | CGC R 0.07 3.8 |
| CUA L 0.11 9.9 | CCA P 0.33 16.1 | CAA Q 0.56 19.4 | CGA R 0.12 6.3 |
| CUG L 0.11 9.8 | CCG P 0.18 8.6 | CAG Q 0.44 15.2 | CGG R 0.09 4.9 |
| AUU I 0.41 21.5 | ACU T 0.34 17.5 | AAU N 0.52 22.3 | AGU S 0.16 14.0 |
| AUC I 0.35 18.5 | ACC T 0.20 10.3 | AAC N 0.48 20.9 | AGC S 0.13 11.3 |
| AUA I 0.24 12.6 | ACA T 0.31 15.7 | AAA K 0.49 30.8 | AGA R 0.35 19.0 |
| AUG M 1.00 24.5 | ACG T 0.15 7.7 | AAG K 0.51 32.7 | AGG R 0.20 11.0 |
| GUU V 0.40 27.2 | GCU A 0.43 28.3 | GAU D 0.68 36.6 | GGU G 0.34 22.2 |
| GUC V 0.19 12.8 | GCC A 0.16 10.3 | GAC D 0.32 17.2 | GGC G 0.14 9.2 |
| GUA V 0.15 9.9 | GCA A 0.27 17.5 | GAA E 0.52 34.3 | GGA G 0.37 24.2 |
| GUG V 0.26 17.4 | GCG A 0.14 9.0 | GAG E 0.48 32.2 | GGG G 0.16 10.2 |

Gene Combinations

In an embodiment, a gene/gene-product of Table 1 is co-expressed in a host cell with an exogenous FATA or FATB acyl-ACP thioesterase gene. In a specific embodiment, the FATB gene product has at least 85, 90, 91, 92, 93, 94, 95, 95.5, 96, 96.5 97, 97.5, 98, 98.5 or 99% amino acid sequence identity to the *Cuphea palustris* FATB2 ("Cpal FATB2", accession AAC49180, SEQ ID NO: 1) or *C. hookeriana* FATB2 ("Ch FATB2", accession U39834, SEQ ID NO: 57) or fragment thereof. Optionally the FATB gene product has at least 85, 90, 91, 92, 93, 94, 95, 95.5, 96, 96.5 97, 97.5, 98, 98.5 or 99% amino acid sequence identity to the non-transit-peptide domain of *Cuphea palustris* FATB2 ("Cpal FATB2", accession AAC49180, SEQ ID NO: 1) or *C. hookeriana* FATB2 ("Ch FATB2", accession U39834 SEQ ID NO: 57)).

FATA genes encode enzymes that preferentially, but not exclusively, hydrolyze long-chain fatty acids with highest activity towards C18:1. FATB genes encode a group of enzymes with more heterogeneous substrate specificities but generally show higher activity toward saturated fatty acids. The substrate specificities of FATB enzymes are quite heterogeneous; there are a number of FATB enzymes that show high activity towards C18:0 and C18:1. FATA and FATB enzymes terminate the synthesis of fatty acids by hydrolyzing the thioester bond between the acyl moiety and the acyl carrier protein (ACP).

In an embodiment, a host cell is transformed to express both a FATA or FATB and KASI-like transgene. The host-cell produces a cell oil. Together, the FATA or FATB and KASI-like genes are expressed to produce their respective gene products and thereby alter the fatty acid profile of the cell oil. The two genes function either additively or synergistically with respect to control strains lacking one of the two genes. Optionally, the host cell is oleaginous and can be an oleaginous eukaryotic microalgae such as those described above or below. The fatty acid profile of the cell oil can be enriched (relative to an appropriate control) in C14:0 (myristic), C8:0, C10:0 or a combination of C8/C10.

In an embodiment, the fatty acid profile of the cell is enriched in C14:0 fatty acids. In this embodiment, the FATB gene expresses an acyl-ACP thioesterase enzyme having at least 85, 90, 91, 92, 93, 94, 95, 95.5, 96, 96.5 97, 97.5, 98, 98.5 or 99% amino acid sequence identity percent amino acid identity to the enzyme of SEQ ID NO: 1. The co-expressed KASI-like gene encodes a beta-ketoacyl ACP synthase having at least 85, 90, 91, 92, 93, 94, 95, 95.5, 96, 96.5 97, 97.5, 98, 98.5 or 99% amino acid sequence identity percent amino acid identity to the enzyme of SEQ ID NO: 2. Alternately The co-expressed KASI-like gene encodes a beta-ketoacyl ACP synthase having at least 85, 90, 91, 92, 93, 94, 95, 95.5, 96, 96.5 97, 97.5, 98, 98.5 or 99% amino acid sequence identity percent amino acid identity to the enzyme of SEQ ID NO: 7. Optionally, the cell oil has a fatty acid profile characterized by at least 10%, 20%, 30%, 40%, 50% or at least 55% C14:0 (area % by FAME-GC-FID).

In another embodiment, the fatty acid profile of the cell is enriched in C8:0 and/or C10:0 fatty acids. In this embodiment, the FATB gene expresses an acyl-ACP thioesterase enzyme having at least 85, 90, 91, 92, 93, 94, 95, 95.5, 96, 96.5 97, 97.5, 98, 98.5 or 99% amino acid sequence identity percent amino acid identity to the enzyme of SEQ ID NO: 57. The co-expressed KASI-like gene encodes a beta-ketoacyl ACP synthase having at least 85, 90, 91, 92, 93, 94, 9595.5, 96, 96.5 97, 97.5, 98, 98.5 or 99% amino acid sequence identity percent amino acid identity to an enzyme of one of SEQ ID NOs: 2, 8, 9, 10, 11, 12, 13, 14, 15, 16, 17, 19, 37. In a related embodiment, the co-expressed KASI-like gene encodes a beta-ketoacyl ACP synthase having at least 85, 90, 91, 92, 93, 94, 95, 95.5, 96, 96.5 97, 97.5, 98, 98.5 or 99% amino acid sequence identity percent amino acid identity to enzyme of one of SEQ ID NO: 2, 8, 11, 12, 13, 14, or 15. Optionally, the cell oil has a fatty acid profile characterized by at least 7, 8, 9, 10, 11, 12, 13, or 14 area % C8:0 (by FAME-GC-FID). Optionally, the cell oil has a fatty acid profile characterized by at least 10, 15, 20, 25, 30, or 35 area % for the sum of C8:0 and C10:0 fatty acids (by FAME-GC-FID). Optionally, the C8/C10 ratio of the cell oil is in the range of 2.2-2.5, 2.5-3.0, or 3.0-3.4.

Optionally, the oils produced by these methods can have a sterol profile in accord with those described below.

Host Cells

The host cell can be a single cell (e.g., microalga, bacteria, yeast) or part of a multicellular organism such as a plant or fungus. Methods for expressing KASI-like genes in a plant are given in U.S. Pat. Nos. 7,301,070, 6,348,642, 6,660,849, and 6,770,465, or can be accomplished using other techniques generally known in plant biotechnology. Engineering of eukaryotic oleaginous microbes including eukaryotic microalgae (e.g., of Chlorophyta) is disclosed in WO2010/063032, WO2011/150411, and WO2012/106560 and in the examples below.

Examples of oleaginous host cells include plant cells and microbial cells having a type II fatty acid biosynthetic pathway, including plastidic oleaginous cells such as those of oleaginous algae. Specific examples of microalgal cells include heterotrophic or obligate heterotrophic eukaryotic microalgae of the phylum Chlorophyta, the class Trebouxiophytae, the order Chlorellales, or the family Chlorellacae. Examples of eukaryotic oleaginous microalgae host cells are provided in Published PCT Patent Applications WO2008/151149, WO2010/06032, WO2011/150410, and WO2011/150411, including species of *Chlorella* and *Prototheca*, a genus comprising obligate heterotrophs. The oleaginous cells can be, for example, capable of producing 25, 30, 40, 50, 60, 70, 80, 85, or about 90% oil by cell weight, ±5%. Optionally, the oils produced can be low in DHA or EPA fatty acids. For example, the oils can comprise less than 5%, 2%, or 1% DHA and/or EPA. The above-mentioned publications also disclose methods for cultivating such cells and extracting oil, especially from microalgal cells; such methods are applicable to the cells disclosed herein and incorporated by reference for these teachings. When microalgal cells are used they can be cultivated autotrophically (unless an obligate heterotroph) or in the dark using a sugar (e.g., glucose, fructose and/or sucrose). When cultivated heterotrophically, the cells and cell oil can comprise less than 200 ppm, 20 ppm, or 2 ppm of color-generating impurities or of chlorophyll. In any of the embodiments described herein, the cells can be heterotrophic cells comprising an exogenous invertase gene so as to allow the cells to produce oil from a sucrose feedstock. Alternately, or in addition, the cells can metabolize xylose from cellulosic feedstocks. For example, the cells can be genetically engineered to express one or more xylose metabolism genes such as those encoding an active xylose transporter, a xylulose-5-phosphate transporter, a xylose isomerase, a xylulokinase, a xylitol dehydrogenase and a xylose reductase. See WO2012/154626, "GENETICALLY ENGINEERED MICROORGANISMS THAT METABOLIZE XYLOSE", published Nov. 15, 2012. The cells can be cultivated on a depolymerized cellulosic feedstock such as acid or enzyme hydrolyzed bagasse, sugar beet pulp, corn stover, wood chips, sawdust or switchgrass. Optionally, the cells can be cultivated on a depolymerized cellulosic feedstock comprising glucose and at least 5, 10, 20, 30 or 40% xylose, while producing at least 20% lipid by dry weight. Optionally, the lipid comprises triglycerides having a fatty acid profile characterized by at least 10, 15 or 20% C12:0

Optionally, the host cell comprises 23S rRNA having at least 65, 70, 75, 80, 85, 90 or 95% nucleotide sequence identity to SEQ ID NO: 58.

Oils and Related Products

The oleaginous cells express one or more exogenous genes encoding fatty acid biosynthesis enzymes. As a result, some embodiments feature cell oils that were not obtainable from a non-plant or non-seed oil, or not obtainable at all.

The oleaginous cells produce a storage oil, which is primarily triacylglyceride and may be stored in storage bodies of the cell. A raw oil may be obtained from the cells by disrupting the cells and isolating the oil. WO2008/151149, WO2010/06032, WO2011/150410, and WO2011/1504 disclose heterotrophic cultivation and oil isolation techniques. For example, oil may be obtained by cultivating, drying and pressing the cells. The cell oils produced may be refined, bleached and deodorized (RBD) as known in the seed-oil art or as described in WO2010/120939. The refining step may comprise degumming. The raw, refined, or RBD oils may be used in a variety of food, chemical, and industrial products or processes. After recovery of the oil, a valuable residual biomass remains. Uses for the residual biomass include the production of paper, plastics, absorbents, adsorbents, as animal feed, for human nutrition, or for fertilizer.

Where a fatty acid profile of a triglyceride (also referred to as a "triacylglyceride" or "TAG") cell oil is given here, it will be understood that this refers to a nonfractionated sample of the storage oil extracted from the cell analyzed under conditions in which phospholipids have been removed or with an analysis method that is substantially insensitive to the fatty acids of the phospholipids (e.g. using chromatography and mass spectrometry). The oil may be subjected to an RBD process to remove phospholipids, free fatty acids and odors yet have only minor or negligible changes to the fatty acid profile of the triglycerides in the oil. Because the cells are oleaginous, in some cases the storage oil will constitute the bulk of all the TAGs in the cell.

The stable carbon isotope value δ13C is an expression of the ratio of 13C/12C relative to a standard (e.g. PDB, carbonite of fossil skeleton of *Belemnite americana* from Peedee formation of South Carolina). The stable carbon isotope value δ13C (0/00) of the oils can be related to the δ13C value of the feedstock used. In some embodiments, the oils are derived from oleaginous organisms heterotrophically grown on sugar derived from a C4 plant such as corn or sugarcane. In some embodiments the δ13C (0/00) of the oil is from −10 to −17 0/00 or from −13 to −16 0/00.

The oils produced according to the above methods in some cases are made using a microalgal host cell. As described above, the microalga can be, without limitation, be a eukaryotic microalga falling in the classification of Chlorophyta, Trebouxiophyceae, Chlorellales, Chlorellaceae, or Chlorophyceae. It has been found that microalgae of Trebouxiophyceae can be distinguished from vegetable oils based on their sterol profiles. Oil produced by *Chlorella protothecoides* (a close relative of *Prototheca moriformis*) was found to produce sterols that appeared to be brassicasterol, ergosterol, campesterol, stigmasterol, and beta-sitosterol, when detected by GC-MS. However, it is believed that all sterols produced by *Chlorella* have C24β stereochemistry. Thus, it is believed that the molecules detected as campesterol, stigmasterol, and beta-sitosterol, are actually 22,23-dihydrobrassicasterol, proferasterol and clionasterol, respectively. Thus, the oils produced by the microalgae described above can be distinguished from plant oils by the presence of sterols with C24α stereochemistry and the absence of C24α stereochemistry in the sterols present. For example, the oils produced may contain 22, 23-dihydrobrassicasterol while lacking campesterol; contain clionasterol, while lacking in beta-sitosterol, and/or contain poriferasterol while lacking stigmasterol. Alternately, or in addition, the oils may contain significant amounts of $\Delta^7$-poriferasterol.

In one embodiment, the oils provided herein are not vegetable oils. Vegetable oils are oils extracted from plants and plant seeds. Vegetable oils can be distinguished from the non-plant oils provided herein on the basis of their oil content. A variety of methods for analyzing the oil content can be employed to determine the source of the oil or whether adulteration of an oil provided herein with an oil of a different (e.g. plant) origin has occurred. The determination can be made on the basis of one or a combination of the analytical methods. These tests include but are not limited to analysis of one or more of free fatty acids, fatty acid profile, total triacylglycerol content, diacylglycerol content, peroxide values, spectroscopic properties (e.g. UV absorption), sterol profile, sterol degradation products, antioxidants (e.g. tocopherols), pigments (e.g. chlorophyll), d13C values and sensory analysis (e.g. taste, odor, and mouth feel). Many such tests have been standardized for commercial oils such as the Codex Alimentarius standards for edible fats and oils.

Sterol profile analysis is a particularly well-known method for determining the biological source of organic matter. Campesterol, β-sitosterol, and stigmasterol are common plant sterols, with β-sitosterol being a principle plant sterol. For example, β-sitosterol was found to be in greatest abundance in an analysis of certain seed oils, approximately 64% in corn, 29% in rapeseed, 64% in sunflower, 74% in cottonseed, 26% in soybean, and 79% in olive oil (Gul et al. J. Cell and Molecular Biology 5:71-79, 2006).

Oil isolated from *Prototheca moriformis* strain UTEX1435 were separately clarified (CL), refined and bleached (RB), or refined, bleached and deodorized (RBD) and were tested for sterol content according to the procedure described in JAOCS vol. 60, no. 8, August 1983. Results of the analysis are shown below (units in mg/100 g) in Table 6.

TABLE 6

Sterols in microalgal oil.

| | Sterol | Crude | Clarified | Refined & bleached | Refined, bleached, & deodorized |
|---|---|---|---|---|---|
| 1 | Ergosterol | 384 (56%) | 398 (55%) | 293 (50%) | 302 (50%) |
| 2 | 5,22-cholestadien-24-methyl-3-ol (Brassicasterol) | 14.6 (2.1%) | 18.8 (2.6%) | 14 (2.4%) | 15.2 (2.5%) |
| 3 | 24-methylcholest-5-en-3-ol (Campesterol or 22,23-dihydrobrassicasterol) | 10.7 (1.6%) | 11.9 (1.6%) | 10.9 (1.8%) | 10.8 (1.8%) |
| 4 | 5,22-cholestadien-24-ethyl-3-ol (Stigmasterol or poriferasterol) | 57.7 (8.4%) | 59.2 (8.2%) | 46.8 (7.9%) | 49.9 (8.3%) |
| 5 | 24-ethylcholest-5-en-3-ol (β-Sitosterol or clionasterol) | 9.64 (1.4%) | 9.92 (1.4%) | 9.26 (1.6%) | 10.2 (1.7%) |
| 6 | Other sterols | 209 | 221 | 216 | 213 |
| | Total sterols | 685.64 | 718.82 | 589.96 | 601.1 |

These results show three striking features. First, ergosterol was found to be the most abundant of all the sterols, accounting for about 50% or more of the total sterols. The amount of ergosterol is greater than that of campesterol, beta-sitosterol, and stigmasterol combined. Ergosterol is steroid commonly found in fungus and not commonly found in plants, and its presence particularly in significant amounts serves as a useful marker for non-plant oils. Secondly, the oil was found to contain brassicasterol. With the exception of rapeseed oil, brassicasterol is not commonly found in plant based oils. Thirdly, less than 2% beta-sitosterol was found to be present. Beta-sitosterol is a prominent plant sterol not commonly found in microalgae, and its presence particularly in significant amounts serves as a useful marker for oils of plant origin. In summary, *Prototheca moriformis* strain UTEX1435 has been found to contain both significant amounts of ergosterol and only trace amounts of beta-sitosterol as a percentage of total sterol content. Accordingly, the ratio of ergosterol:beta-sitosterol or in combination with the presence of brassicasterol can be used to distinguish this oil from plant oils.

In some embodiments, the oil content of an oil provided herein contains, as a percentage of total sterols, less than 20%, 15%, 10%, 5%, 4%, 3%, 2%, or 1% beta-sitosterol. In other embodiments the oil is free from beta-sitosterol.

In some embodiments, the oil is free from one or more of beta-sitosterol, campesterol, or stigmasterol. In some embodiments the oil is free from beta-sitosterol, campesterol, and stigmasterol. In some embodiments the oil is free from campesterol. In some embodiments the oil is free from stigmasterol.

In some embodiments, the oil content of an oil provided herein comprises, as a percentage of total sterols, less than 20%, 15%, 10%, 5%, 4%, 3%, 2%, or 1% 24-ethylcholest-5-en-3-ol. In some embodiments, the 24-ethylcholest-5-en-3-ol is clionasterol. In some embodiments, the oil content of an oil provided herein comprises, as a percentage of total sterols, at least 1%, 2%, 3%, 4%, 5%, 6%, 7%, 8%, 9%, or 10% clionasterol.

In some embodiments, the oil content of an oil provided herein contains, as a percentage of total sterols, less than 20%, 15%, 10%, 5%, 4%, 3%, 2%, or 1% 24-methylcholest-5-en-3-ol. In some embodiments, the 24-methylcholest-5-en-3-ol is 22, 23-dihydrobrassicasterol. In some embodiments, the oil content of an oil provided herein comprises, as a percentage of total sterols, at least 1%, 2%, 3%, 4%, 5%, 6%, 7%, 8%, 9%, or 10% 22,23-dihydrobrassicasterol.

In some embodiments, the oil content of an oil provided herein contains, as a percentage of total sterols, less than 20%, 15%, 10%, 5%, 4%, 3%, 2%, or 1% 5,22-cholestadien-24-ethyl-3-ol. In some embodiments, the 5, 22-cholestadien-24-ethyl-3-ol is poriferasterol. In some embodiments, the oil content of an oil provided herein comprises, as a percentage of total sterols, at least 1%, 2%, 3%, 4%, 5%, 6%, 7%, 8%, 9%, or 10% poriferasterol.

In some embodiments, the oil content of an oil provided herein contains ergosterol or brassicasterol or a combination of the two. In some embodiments, the oil content contains, as a percentage of total sterols, at least 5%, 10%, 20%, 25%, 35%, 40%, 45%, 50%, 55%, 60%, or 65% ergosterol. In some embodiments, the oil content contains, as a percentage of total sterols, at least 25% ergosterol. In some embodiments, the oil content contains, as a percentage of total sterols, at least 40% ergosterol. In some embodiments, the oil content contains, as a percentage of total sterols, at least 5%, 10%, 20%, 25%, 35%, 40%, 45%, 50%, 55%, 60%, or 65% of a combination of ergosterol and brassicasterol.

In some embodiments, the oil content contains, as a percentage of total sterols, at least 1%, 2%, 3%, 4% or 5% brassicasterol. In some embodiments, the oil content contains, as a percentage of total sterols less than 10%, 9%, 8%, 7%, 6%, or 5% brassicasterol.

In some embodiments the ratio of ergosterol to brassicasterol is at least 5:1, 10:1, 15:1, or 20:1.

In some embodiments, the oil content contains, as a percentage of total sterols, at least 5%, 10%, 20%, 25%, 35%, 40%, 45%, 50%, 55%, 60%, or 65% ergosterol and less than 20%, 15%, 10%, 5%, 4%, 3%, 2%, or 1% beta-sitosterol. In some embodiments, the oil content contains, as a percentage of total sterols, at least 25% ergosterol and less than 5% beta-sitosterol. In some embodiments, the oil content further comprises brassicasterol. For any of the oils or cell-oils disclosed in this application, the oil can have the sterol profile of any column of Table 6, above, with a sterol-by-sterol variation of 30%, 20%, 10% or less.

Sterols contain from 27 to 29 carbon atoms (C27 to C29) and are found in all eukaryotes. Animals exclusively make C27 sterols as they lack the ability to further modify the C27 sterols to produce C28 and C29 sterols. Plants however are able to synthesize C28 and C29 sterols, and C28/C29 plant sterols are often referred to as phytosterols. The sterol profile of a given plant is high in C29 sterols, and the primary sterols in plants are typically the C29 sterols beta-sitosterol and stigmasterol. In contrast, the sterol profile of non-plant organisms contain greater percentages of C27 and C28 sterols. For example the sterols in fungi and in many microalgae are principally C28 sterols. The sterol profile and particularly the striking predominance of C29 sterols over C28 sterols in plants has been exploited for determining the proportion of plant and marine matter in soil samples (Huang, Wen-Yen, Meinschein W. G., "Sterols as ecological indicators"; Geochimica et Cosmochimia Acta. Vol 43. pp 739-745).

In some embodiments the primary sterols in the microalgal oils provided herein are sterols other than beta-sitosterol and stigmasterol. In some embodiments of the microalgal oils, C29 sterols make up less than 50%, 40%, 30%, 20%, 10%, or 5% by weight of the total sterol content.

In some embodiments the microalgal oils provided herein contain C28 sterols in excess of C29 sterols. In some embodiments of the microalgal oils, C28 sterols make up greater than 50%, 60%, 70%, 80%, 90%, or 95% by weight of the total sterol content. In some embodiments the C28 sterol is ergosterol. In some embodiments the C28 sterol is brassicasterol.

In embodiments of the present invention, oleaginous cells expressing one or more of the genes of Table 1 can produce an oil with at least 20, 40, 60 or 70% of C8, C10, C12, C14 or C16 fatty acids. In a specific embodiment, the level of myristate (C14:0) in the oil is greater than 30%.

Thus, in embodiments of the invention, there is a process for producing an oil, triglyceride, fatty acid, or derivative of any of these, comprising transforming a cell with any of the nucleic acids discussed herein. In another embodiment, the transformed cell is cultivated to produce an oil and, optionally, the oil is extracted. Oil extracted in this way can be used to produce food, oleochemicals or other products.

The oils discussed above alone or in combination are useful in the production of foods, fuels and chemicals (including plastics, foams, films, detergents, soaps, etc). The oils, triglycerides, fatty acids from the oils may be subjected to C—H activation, hydroamino methylation, methoxy-carbonation, ozonolysis, enzymatic transformations, epoxidation, methylation, dimerization, thiolation, metathesis, hydro-alkylation, lactonization, or other chemical processes.

After extracting the oil, a residual biomass may be left, which may have use as a fuel, as an animal feed, or as an ingredient in paper, plastic, or other product. For example, residual biomass from heterotrophic algae can be used in such products.

EXAMPLES

Example 1: Screening KAS Genes in Combination with *Cuphea palustris* FATB2 Acyl-ACP Thioesterase A *Prototheca moriformis* strain expressing codon optimized *Cuphea palustris* (Cpal) FATB2 was constructed as described in WO2013/158938, example 53 (p. 231). The amino acid sequence of the Cpal FATB2 gene is given in SEQ ID NO: 1. This strain (S6336) produced a cell oil characterized by a fatty acid profile having about 38% myristic acid (C14:0).

Six KASI-like genes were cloned from seed oil genomes. Total RNA was extracted from dried mature seeds using a liquid-nitrogen-chilled mortar and pestle to break open the seed walls. RNA was then precipitated with an 8M urea, 3M LiCl solution followed by a phenol-chloroform extraction. A cDNA library was generated with oligo dT primers using the purified RNA and subjected to Next Generation sequencing. The novel KAS genes were identified from the assembled transcriptome using BLAST with known KAS genes as bait. The identified KAS gene sequences were codon optimized for expression in *Prototheca* and synthesized for incorporation into an expression cassette.

To test the impact on myristate accumulation, S6336 was transformed with a linearized plasmid designed for homologous recombination at the pLOOP locus and to express the KASI-like genes with coexpression of a selection marker (see WO2013/1589380). The vector is described in SEQ ID NO 38, the remaining codon optimized KAS genes were substituted into the KAS CDS segment of this vector prior to transformation. As shown in Table 7, increases in C14:0 levels in extracted cell oil were observed with the expression of the *C. camphora* KASIV (D3147), *C. camphora* KASI (D3148), *U. cahfornica* KASI (D3150) or *U. cahfornica* KASVI (D3152) genes in S6336. Even greater increases in C14:0 levels resulted from expression the KASI gene from *C. palustris* KASIV (D3145) or *C. wrightii* KASAI (D3153), with some individual lines producing >50% or >55% C14:0. The C14 production far exceeded the negligible amount found in the wild-type oil (see Table 7a).

TABLE 7

KAS genes that effect an increase in C14 fatty acids in eukaryotic microalgal oil.

| Gene (transformant ID) | SEQ ID NOs: | C14:0 (area %. mean of 4 transformants) | Highest C14:0 observed |
|---|---|---|---|
| *C. camphora* KASIV | 3, 22, 40 | 38.0 | 40.3 |
| *C. camphora* KASI | 4, 23, 41 | 33.8 | 39.3 |
| *U. californica* KASI | 5, 24, 42 | 37.4 | 42.3 |
| *U. californica* KASVI | 6, 25, 43 | 38.4 | 41.6 |
| *C. palustris* KASIV | 2, 21, 39 | 45.4 | 58.4 |
| *C. wrightii* KASAI | 7, 26, 44 | 43.2 | 53.6 |

TABLE 7a

Fatty acid profile of wild-type *Prototheca moriformis* oil (area %).

| C8:0 | C10:0 | C12:0 | C14:0 | C16:0 | C18:0 | C18:1 | C18:2 | C18:3 |
|---|---|---|---|---|---|---|---|---|
| 0 | 0 | 0 | 2 | 38 | 4 | 48 | 5 | 1 |

Example 2: Screening KAS Genes in Combination with *Cuphea hookeriana* FATB Acyl-ACP Thioesterase

*P. moriformis* strains were constructed that express ChFATB2 acyl-ACP thioesterase together with a KAS gene selected from ten KASI, one KASIII and one mitochondrial KAS were cloned from seed oil genomes, codon optimized and introduced into *Prototheca* as described in Example 1. The KAS genes were fused to an HA epitope TAG at the c-terminus of each KAS to allow confirmation of protein expression.

TABLE 8

Mean C8:0-C10:0 fatty acid profiles derived from transformation of FATB2-expressing microalgal strain with KASI-like genes isolated from seed oil genomes.

| KAS Gene | SEQ ID NOS: (amino acid, CDS, codon optimized CDS) | C8:0 (mean area %) | C10:0 (mean area %) | Sum C8:0 + C10:0 | C10/C8 ratio |
|---|---|---|---|---|---|
| *C. avigera* KASIa | 16, 35, 53 | 8.0 | 21.4 | 29.3 | 2.7 |
| *C. pulcherrima* KASI | 17, 36, 54 | 7.7 | 20.3 | 28.0 | 2.6 |
| *C. avigera* Mitochondrial KAS | NL, 37, 55 | 7.8 | 20.4 | 28.2 | 2.6 |
| *C. avigera* KAS III | 19, NL, 56 | 9.5 | 22.8 | 32.3 | 2.4 |
| *C. paucipetala* KASIVb | 9, 28, 46 | 7.9 | 22.5 | 30.3 | 2.9 |
| *C. ignea* KASIVb | 10, 29, 47 | 6.6 | 18.7 | 25.4 | 2.8 |
| *C. painteri* KASIV | 13, 32, 50 | 9.0 | 22.4 | 31.4 | 2.5 |
| *C. palustris* KASIVa | 2, 21, 38 | 8.6 | 21.6 | 30.4 | 2.5 |
| *C. avigera* KASIVb | 8, 27, 45 | 11.0 | 23.8 | 34.8 | 2.2 |
| *C. procumbens* KASIV | 11, 30, 48 | 8.2 | 25.8 | 34.0 | 3.2 |
| *C. paucipetala* KASIVa | 12, 31, 49 | 8.8 | 29.9 | 39.4 | 3.4 |
| *C. ignea* KASIVa | 15, 34, 52 | 8.6 | 25.8 | 34.4 | 3.0 |
| *C avigera* KASIVa | 14, 33, 51 | 10.0 | 23.0 | 32.9 | 2.3 |
| *C. hookeriana* KASIV | 59, NL, 61 | 14.5 | 27.81 | 42.6 | 3.0 |

The parental strain is a stable microalgal strain expressing the *C. hookeriana* FATB2 under the control of the pH5-compatible PmUAPA1 promoter. The parental strain accumulates 27.8% C8:0-C10:0 with a C10/C8 ratio of 2.6. All transformants are derived from integrations of the KASI transgenes at the pLOOP locus of the parental strain. Means are calculated from at least 19 individual transformants for each KAS transgene (NL=not listed).

As can be seen from Table 8, expression of the following KAS genes significantly increased C8:0-C10:0 levels: *C. avigera* KASIVb (D3287), *C. procumbens* KASIV (D3290), *C. paucipetala* KASIVa (D3291), *C. avigera* KASIVa (D3293), and *C. ignea* KASIVa (D3294). Importantly, expression of the *C. avigera* KASIVb (D3287) augmented the accumulation of both C8:0 and C10:0 fatty acids, while only C10:0 levels were increased upon expression of D3290, D3291, D3293 and D3294. In some cases the sum of C8:0 and C10:0 fatty acids in the fatty acid profile was at least 30%, or at least 35% (area % by FAME-GC-FID). The midchain production far exceeded the negligible amount found in the wild-type oil (see Table 7a).

The mean C8/C10 ratios of Table 8 ranged from 2.2 to 3.4. The sum of mean C8 and C10 ranged from 25.4 to 39.4.

The highest C8:0 producing strain found was D3287, which combined *C. avigera* KASIV with *C. hookeriana*

FATB2. The mean was 11.0% C8:0 with a range of 12.4 to 14.8. Thus, a cell oil with a fatty acid profile of greater than 14% C8 was produced. Furthermore, the C10/C8 ratio was less than 2.5.

Example 3: Identification of KAS Clades and Consensus Sequences

The newly identified sequences of KASI-like genes were compared to those in the ThYme database of thioester-active enzymes maintained by Iowa State University (enzyme.c-birc.iastate.edu) using the blast algorithm and the top hits were extracted. The top 50 BLAST hits were downloaded and a multiple alignment was created using ClustalW alignment algorithm and a phylogenetic tree (FIG. 1) was created using that alignment with the Jukes-Cantor Neighbor-Joining method. The new KASIV genes grouped together with only 4 ThYme KAS genes internal to that group out of the 50 possible. The total ThYme KAS sequences were reduced to 12 because nearly all ThYme KAS grouped away from the new KAS sequences. The ThYme sequences are only 222 residues while the new KASIV are approximately 555 residues in length including the targeting peptide.

Two new clades were identified Clade 1 and Clade 2, characterized by consensus SEQ ID NO: 69 and SEQ ID NO:70, which include transit peptides. The clades can also be characterized by the sequences of the mature consensus proteins SEQ ID NO: 71 and SEQ ID NO: 72, respectively. The KAS genes of Clade 1 are associated with production of elevated C8 and C10 fatty acids based on based on transformations in *P. moriformis* in combination with a FATB acyl-ACP thioesterase as in Example 2. The KAS genes of Clade 2 are associated with production of elevated C10 fatty acids based on transformations in *P. moriformis* in combination with a FATB acyl-ACP thioesterase as in Example 2.

Although the above discussion discloses various exemplary embodiments of the invention, it should be apparent that those skilled in the art can make various modifications that will achieve some of the advantages of the invention without departing from the true scope of the invention.

---

SEQUENCE LISTING

*Cuphea palustris* FATB2 amino acid sequence (Genbank Accession No. AAC49180.1)
SEQ ID NO: 1
MVAAAASAAFFSVATPRTNISPSSLSVPFKPKSNHNGGFQVKANASA

HPKANGSAVSLKSGSLETQEDKTSSSSPPPRTFINQLPVWSMLLSAV

TTVFGVAEKQWPMLDRKSKRPDMLVEPLGVDRIVYDGVSFRQSFSIR

SYEIGADRTASIETLMNMFQETSLNHCKIIGLLNDGFGRTPEMCKRD

LIWVVTKMQIEVNRYPTWGDTIEVNTWVSASGKHGMGRDWLISDCHT

GEILIRATSVWAMMNQKTRRLSKIPYEVRQEIEPQFVDSAPVIVDDR

KFHKLDLKTGDSICNGLTPRWTDLDVNQHVNNVKYIGWILQSVPTEV

FETQELCGLTLEYRRECGRDSVLESVTAMDPSKEGDRSLYQHLLRLE

DGADIVKGRTEWRPKNAGAKGAILTGKTSNGNSIS

Amino acid sequence of the *C. palustris* KASIV (D3145 and D3295, pSZ4312). The algal transit peptide is underlined.
SEQ ID NO: 2
<u>MASAAFTMSACPAMTGRAPGARRSGRPVATRLRGSTFQCLVTSYIDP</u>

CNQFSSSASLSFLGDNGFASLFGSKPFRSNRGHRRLGRASHSGEAMA

VALEPAQEVATKKKPLVKQRRVVVTGMGVVTPLGHEPDVYYNNLLDG

VSGISEIEAFDCTQFPTRIAGEIKSFSTDGWVAPKLSKRMDKFMLYL

LTAGKKALADGGITDDVMKELDKRKCGVLIGSGLGGMKLFSDSIEAL

RISYKKMNPFCVPFATTNMGSAMLAMDLGWMGPNYSISTACATSNFC

ILNSANHIVRGEADMMLCGGSDAVIIPIGLGGFVACRALSQRNNDPT

KASRPWDSNRDGFVMGEGAGVLLLEELEHAKKRGATIYAEFLGGSFT

CDAYHMTEPHPEGAGVILCIEKALAQAGVSREDVNYINAHATSTPAG

DIKEYQALAHCFGQNSELRVNSTKSMIGHLIGAAGGVEAVTVVQAIR

TGWIHPNLNLEDPDKAVDAKVLVGPKKERLNVKVGLSNSFGFGGHNS

SILFAPYN

Amino acid sequence of the *C. camphora* KASIV (D3147, pSZ4338).
SEQ ID NO: 3
<u>MAMMAGSCSNLVIGNRELGGNGPSLLHYNGLRPLENIQTASAVKKPN</u>

<u>GLFASSTARKSKAVR</u>AMVLPTVTAPKREKDPKKRIVITGMGLVSVFG

NDIDTFYSKLLEGESGIGPIDRFDASSFSVRFAGQIHNFSSKGYIDG

KNDRRLDDCWRYCLVAGRRALEDANLGPEVLEKMDRSRIGVLIGTGM

GGLSAFSNGVESLIQKGYKKITPFFIPYSITNMGSALLAIDTGVMGP

NYSISTACATANYCFHAAANHIRRGEAEIMVTGGTEAAVSATGVGGF

IACRALSHRNDEPQTASRPWDKDRDGFVMGEGAGVLVMESLHHARKR

GANIIAEYLGGAVTCDAHHMTDPRADGLGVSSCITKSLEDAGVSPEE

VNYVNAHATSTLAGDLAEVNAIKKVFKDTSEMKMNGTKSMIGHCLGA

AGGLEAIATIKAINTGWLHPTINQFNIEPAVTIDTVPNVKKKHDIHV

GISNSFGFGGHNSVVVFAPFMP

Amino acid sequence of the *C. camphora* KASI (D3148, pSZ4339).
SEQ ID NO: 4
MQILQTPSSSSSSLRMSSMESLSLTPKSLPLKTLLPLRPRPKNLSRR

KSQNPRPISSSSSPERETDPKKRVVITGMGLVSVFGNDVDAYYDRLL

SGESGIAPIDRFDASKFPTRFAGQIRGFTSDGYIDGKNDRRLDDCLR

YCIVSGKKALENAGLGPHLMDGKIDKERAGVLVGTGMGGLTVFSNGV

QTLHEKGYRKMTPFFIPYAITNMGSALLAIELGFMGPNYSISTACAT

SNYCFYAAANHIRRGEADLMLAGGTEAAIIPIGLGGFVACRALSQRN

DDPQTASRPWDKDRDGFVMGEGAGVLVMESLEHAMKRDAPIIAEYLG

GAVNCDAYHMTDPRADGLGVSTCIERSLEDAGVAPEEVNYINAHATS

TLAGDLAEVNAIKKVFTNTSEIKINATKSMIGHCLGAAGGLEAIATI

KAINTGWLHPSINQFNPEPSVEFDTVANKKQQHEVNVAISNSFGFGG

HNSVVVFSAFKP

Amino acid sequence of the *U. californica* KASI (D3150, pSZ4341).
SEQ ID NO: 5
MESLSLTPKSLPLKTLLPFRPRPKNLSRRKSQNPKPISSSSSPERET

DPKKRVVITGMGLVSVFGNDVDAYYDRLLSGESGIAPIDRFDASKFP

SEQUENCE LISTING

TRFAGQIRGFTSDGYIDGKNDRRLDDCLRYCIVSGKKALENAGLGPD
LMDGKIDKERAGVLVGTGMGGLTVFSNGVQTLHEKGYRKMTPFFIPY
AITNMGSALLAIDLGFMGPNYSISTACATSNYCFYAAANHIRRGEAD
VMLAGGTEAAIIPIGLGGFVACRALSQRNDDPQTASRPWDKDRDGFV
MGEGAGVLVMESLEHAMKRDAPIIAEYLGGAVNCDAYHMTDPRADGL
GVSTCIERSLEDAGVAPEEVNYINAHATSTLAGDLAEVNAIKKVFTN
TSEIKINATKSMIGHCLGAAGGLEAIATIKAINTGWLHPSINQFNPE
PSVEFDTVANKKQQHEVNVAISNSFGFGGHNSVVVFSAFKP

Amino acid sequence of the *U. californica* KASIV
(D3152, pSZ4343).
SEQ ID NO: 6
<u>MTQTLICPSSMETLSLTKQSHFRLRLPTPPHIRRGGGHRHPPPFISA</u>
SAAPRRETDPKKRVVITGMGLVSVFGTNVDVYYDRLLAGESGVGTID
RFDASMFPTRFGGQIRRFTSEGYIDGKNDRRLDDYLRYCLVSGKKAI
ESAGFDLHNITNKIDKERAGILVGSGMGGLKVFSDGVESLIEKGYRK
ISPFFIPYMIPNNIGSALLGIDLGFMGPNYSISTACATSNYCIYAAA
NHIRQGDADLMVAGGTEAPIIPIGLGGFVACRALSTRNDDPQTASRP
WDIDRDGFVMGEGAGILVLESLEHAMKRDAPILAEYLGGAVNCDAHH
MTDPRADGLGVSTCIESSLEDAGVAAEEVNYINAHATSTPTGDLAEM
KAIKNVFRNTSEIKINATKSMIGHCLGASGGLEAIATLKAITTGWLH
PTINQFNPEPSVDFDTVAKKKKQHEVNVAISNSFGFGGHNSVLVFSA
FKP Amino acid sequence of the *C. wrightii* KASAI
(D3153, pSZ4379). The algal transit peptide is
underlined.
SEQ ID NO: 7
<u>MASAAFTMSACPAMTGRAPGARRSGRPVATRLRY</u>VFQCLVASCIDPC
DQYRSSASLSFLGDNGFASLFGSKPFMSNRGHRRLRRASHSGEAMAV
ALQPAQEAGTKKKPVIKQRRVVVTGMGVVTPLGHEPDVFYNNLLDGV
SGISEIETFDCTQFPTRIAGEIKSFSTDGWVAPKLSKRMDKFMLYLL
TAGKKALADGGITDEVMKELDKRKCGVLIGSGMGGMKVFNDAIEALR
VSYKKMNPFCVPFATTNMGSAMLAMDLGWMGPNYSISTACATSNFCI
LNAANHIIRGEADMMLCGGSDAVIIPIGLGGFVACRALSQRNSDPTK
ASRPWDSNRDGFVMGEGAGVLLLEELEHAKKRGATIYAEFLGGSFTC
DAYHMTEPHPEGAGVILCIEKALAQAGVSKEDVNYINAHATSTSAGD
IKEYQALARCFGQNSELRVNSTKSMIGHLLGAAGGVEAVTVVQAIRT
GWIHPNLNLEDPDKAVDAKLLVGPKKERLNVKVGLSNSFGFGGHNSS
ILFAPCNV Amino acid sequence of the *C. avigera* KASIVb
(D3287, pSZ4453).
SEQ ID NO: 8
<u>MASAAFTMSACPAMTGRAPGARRSGRPVATRLR</u>GSTFQCYIGDNGFG
SKPPRSNRGHLRLGRTSHSGEVMAVAMQSAQEVSTKEKPATKQRRVV VTGMGVVTALGHDPDVYYNNLLDGVSGISEIENFDCSQLPTRIAGEI
KSFSADGWVAPKFSRRMDKFMLYILTAGKKALVDGGITEDVMKELDK
RKCGVLIGSGLGGMKVFSESIEALRTSYKKISPFCVPFSTTNIVIGS
AILAMDLGWMGPNYSISTACATSNFCILNAANHITKGEADMMLCGGS
DSVILPIGMGGFVACRALSQRNNDPTKASRPWDSNRDGFVMGEGAGV
LLLEELEHAKKRGATIYAEFLGGSFTCDAYHMTEPHPEGAGVILCIE
KALAQSGVSREDVNYINAHATSTPAGDIKEYQALAHCFGQNSELRVN
STKSMIGHLLGGAGGVEAVTVVQAIRTGWIHPNINLDDPDEGVDAKL
LVGPKKEKLKVKVGLSNSFGFGGHNSSILFAPCN Amino acid sequence of the *C. paucipetala*
KASIVb (D3288, pSZ4454).
SEQ ID NO: 9
<u>MASAAFTMSACPAMTGRAPGARRSGRPVATRLR</u>GSTFQCLGDIGFAS
LIGSKPPRSNRNHRRLGRTSHSGEVMAVAMQPAHEASTKNKPVTKQR
RVVVTGMGVATPLGHDPDVYYNNLLDGVSGISQIENFDCTQFPTRIA
GEIKSFSTEGYVIPKFAKRMDKFMLYLLTAGKKALEDGGITEDVMKE
LDKRKCGVLIGSGMGGMKIINDSIAALNVSYKKMTPFCVPFSTTNMG
SAMLAIDLGWMGPNYSISTACATSNYCILNAANHIVRGEADMMLCGG
SDAVIIPVGLGGFVACRALSQRNNDPTKASRPWDSNRDGFVMGEGAG
VLLLEELEHAKKRGATIYAEFLGGSFTCDAYHMTEPHPDGAGVILCI
EKALAQSGVSREDVNYINAHATSTPAGDIKEYQALAHCFGQNSELRV
NSTKSMIGHLLGAAGGVEAVTVVQAIRTGWIHPNINLENPDEAVDAK
LLVGPKKEKLKVKVGLSNSFGFGGHNSSILFAPYN Amino acid sequence of the *C. ignea* KASIVb
(D3289, pSZ4455). The algal transit peptide is
underlined.
SEQ ID NO: 10
<u>MASAAFTMSACPAMTGRAPGARRSGRPVATRLR</u>GSTSQCLVTSYID
PCNKYCSSASLSFLGDNGFASLFGSKPFRSNRGHRRLGRASHSGEA
MAVALQPAQEVTTKKKPVIKQRRVVVTGMGVVTPLGHEPDVYYNNL
LDGVSGISEIETFDCTQFPTRIAGEIKSFSTDGWVAPKLSKRMDKF
MLYLLTAGKKALADGGITDDVMKELDKRKCGVLIGSGMGGMKLFND
SIEALRISYKKMNPFCVPFATTNMGSAMLAMDLGWMGPNYSISTAC
ATSNFCILNASNHIVRGEADMMLCGGSDSVTVPLGVGGFVACRALS
QRNNDPTKASRPWDSNRDGFVMGEGAGVLLLEELEHAKKRGATIYA
EFLGGSFTSDAYHMTEPHPEGAGVILCIEKALAQSGVSREDVNYIN
AHATSTPAGDIKEYQALARCFGQNSELRVNSTKSMIGHLLGAAGGV
EAVAVIQAIRTGWIHPNINLEDPDEAVDPKLLVGPKKEKLKVKVAL
SNSFGFGGHNSSILFAPCN

SEQUENCE LISTING

Amino acid sequence of the *C. procumbens* KASIV (D3290, pSZ4456). The algal transit peptide is underlined.

SEQ ID NO: 11

<u>MASAAFTMSACPAMTGRAPGARRSGRPVATRLRGSTFQCLVTSHND</u>
PCNQYCSSASLSFLGDNGFGSKPFRSNRGHRRLGRASHSGEAMAVA
LQPAQEVATKKKPAMKQRRVVVTGMGVVTPLGHEPDVYYNNLLDGV
SGISEIETFDCTQFPTRIAGEIKSFSTDGWVAPKLSKRMDKFMLYL
LTAGKKALADGGITDDVMKELDKRKCGVLIGSGMGGMKLFNDSIEA
LRVSYKKMNPFCVPFATTNMGSAMLAMDLGWMGPNYSISTACATSN
FCILNAANHIVRGEADMMLCGGSDAVIIPIGLGGFVACRALSQRNN
DPTKASRPWDSNRDGFVMGEGAGVLLLEELEHAKKRGATIYAEFLG
GSFTCDAYHMTEPHPEGAGVILCIEKALAQSGVSREDVNYINAHAT
STPAGDIKEYQALAHCFGQNSELRVNSTKSMIGHLLGAAGGVEAVT
VIQAIRTGWIHPNLNLEDPDKAVDAKFLVGPKKERLNVKVGLSNSF
GFGGHNSSILFAPCN

Amino acid sequence of the *C. paucipetala* KASIVa (D3291, pSZ4457). The algal transit peptide is underlined.

SEQ ID NO: 12

<u>MASAAFTMSACPAMTGRAPGARRSGRPVATRLRGSTFQCLVNSHID</u>
PCNQNVSSASLSFLGDNGFGSNPFRSNRGHRRLGRASHSGEAMAVA
LQPAQEVATKKKPAIKQRRVVVTGMGVVTPLGHEPDVFYNNLLDGV
SGISEIETFDCTQFPTRIAGEIKSFSTDGWVAPKLSKRMDKFMLYL
LTAGKKALADAGITEDVMKELDKRKCGVLIGSGMGGMKLFNDSIEA
LRVSYKKMNPFCVPFATTNMGSAMLAMDLGWMGPNYSISTACATSN
FCILNAANHIIRGEADMMLCGGSDAVIIPIGLGGFVACRALSQRNS
DPTKASRPWDSNRDGFVMGEGAGVLLLEELEHAKKRGATIYAEFLG
GSFTCDAYHMTEPHPDGAGVILCIEKALAQSGVSREDVNYINAHAT
STPAGDIKEYQALAHCFGQNSELRVNSTKSMIGHLLGAAGGVEAVT
VIQAIRTGWIHPNLNLEDPDEAVDAKFLVGPKKERLNVKVGLSNSF
GFGGHNSSILFAPYN

Amino acid sequence of the *C. painteri* KASIV (D3292, pSZ4458). The algal transit peptide is underlined.

SEQ ID NO: 13

<u>MASAAFTMSACPAMTGRAPGARRSGRPVATRLRGSTPQCLDPCNQH</u>
CFLGDNGFASLIGSKPPRSNLGHLRLGRTSHSGEVMAVAQEVSTNK
KHATKQRRVVVTGMGVVTPLGHDPDVYYNNLLEGVSGISEIENFDC
SQLPTRIAGEIKSFSTDGLVAPKLSKRMDKFMLYILTAGKKALADG
GITEDVMKELDKRKCGVLIGSGLGGMKVFSDSVEALRISYKKISPF
CVPFSTTNMGSAMLAMDLGWMGPNYSISTACATSNFCILNAANHIT
KGEADMMLCGGSDAAILPIGMGGFVACRALSQRNNDPTKASRPWDS
NRDGFVMGEGAGVLLLEELEHAKKRGATIYAEFLGGSFTCDAYHMT
EPHPDGAGVILCIEKALAQSGVSREEVNYINAHATSTPAGDIKEYQ
ALAHCFGQNSELRVNSTKSMIGHLLGGAGGVEAVTVVQAIRTGWIH
PNINLEDPDKGVDAKLLVGPKKEKLKVKVGLSNSFGFGGHNSSILF
APCN

Amino acid sequence of the *C. avigera* KASIVa (D3293, pSZ4459). The algal transit peptide is underlined.

SEQ ID NO: 14

<u>MASAAFTMSACPAMTGRAPGARRSGRPVATRLRGSTFQCLVTSYND</u>
PCEQYRSSASLSFLGDNGFASLFGSKPFRSNRGHRRLGRASHSGEA
MAVALQPAQEVGTKKKPVIKQRRVVVTGMGVVTPLGHEPDVYYNNL
LDGVSGISEIETFDCTQFPTRIAGEIKSFSTDGWVAPKLSKRMDKF
MLYLLTAGKKALADGGITDDVMKELDKRKCGVLIGSGLGGMKVFSE
SIEALRTSYKKISPFCVPFSTTNMGSAILAMDLGWMGPNYSISTAC
ATSNFCILNAANHITKGEADMMLCGGSDSVILPIGMGGFVACRALS
QRNNDPTKASRPWDSNRDGFVMGEGAGVLLLEELEHAKKRGATIYA
EFLGGSFTCDAYHMTEPHPEGAGVILCIEKALAQSGVSREDVNYIN
AHATSTPAGDIKEYQALAHCFGQNSELRVNSTKSMIGHLLGGAGGV
EAVTVVQAIRTGWIHPNINLDDPDEGVDAKLLVGPKKEKLKVKVGL
SNSFGFGGHNSSILFAPCN

Amino acid sequence of the *C. ignea* KASIVa (D3294, pSZ4460). The algal transit peptide is underlined.

SEQ ID NO: 15

<u>MASAAFTMSACPAMTGRAPGARRSGRPVATRLRGSTSQCLVTSYID</u>
PCNKYCSSASLSFLGDNGFASLFGSKPFRSNRGHRRLGRASHSGEA
MAVALQPAQEVTTKKKPVIKQRRVVVTGMGVVTPLGHEPDVYYNNL
LDGVSGISEIETFDCTQFPTRIAGEIKSFSTDGWVAPKLSKRMDKF
MLYLLTAGKKALADGGITDDVMKELDKRKCGVLIGSGMGGMKLFND
SIEALRISYKKMNPFCVPFATTNMGSAMLAMDLGWMGPNYSISTAC
ATSNFCILNASNHIVRGEADMMLCGGSDAVIIPIGLGGFVACRALS
QRNNDPTKASRPWDSNRDGFVMGEGAGVLLLEELEHAKKRGATIYA
EFLGGSFTCDAYHMTEPHPEGAGVILCIEKALAQAGVSKEDVNYIN
AHATSTPAGDIKEYQALAQCFGQNSELRVNSTKSMIGHLLGAAGGV
EAVTVVQAIRTGWIHPNLNLEDPDKAVDAKLLVGPKKERLNVKVGL
SNSFGFGGHNSSILFAPYN

Amino acid sequence of the *C. avigera* KASIa (D3342, pSZ4511).

SEQ ID NO: 16

<u>MQSLHSPALRASPLDPLRLKSSANGPSSTAAFRPLRRATLPNIRAA</u>
SPTVSAPKRETDPKKRVVITGMGLVSVFGSDVDAYYEKLLSGESGI
SLIDRFDASKFPTRFGGQIRGFNATGYIDGKNDRRLDDCLRYCIVA
GKKALENSDLGGDSLSKIDKERAGVLVGTGMGGLTVFSDGVQNLIE
KGHRKISPFFIPYAITNMGSALLAIDLGLMGPNYSISTACATSNYC

FYAAANHIRRGEADLMIAGGTEAAIIPIGLGGFVACRALSQRNDDP

QTASRPWDKDRDGFVMGEGAGVLVMESLEHAMKRGAPIIAEYLGGA

VNCDAYHMTDPRADGLGVSSCIESSLEDAGVSPEEVNYINAHATST

LAGDLAEINAIKKVFKNTKDIKINATKSMIGHCLGASGGLEAIATI

KGITTGWLHPSINQFNPEPSVEFDTVANKKQQHEVNVAISNSFGFG

GHNSVVAFSAFKP

Amino acid sequence of the *C. pulcherima* KASI
(D3343, pSZ4512).
SEQ ID NO: 17

<u>MHSLQSPSLRASPLDPFRPKSSTVRPLHRASIPNVR</u>AASPTVSAPK

RETDPKKRVVITGMGLVSVFGSDVDAYYDKLLSGESGIGPIDRFDA

SKFPTRFGGQIRGFNSMGYIDGKNDRRLDDCLRYCIVAGKKSLEDA

DLGADRLSKIDKERAGVLVGTGMGGLTVFSDGVQSLIEKGHRKITP

FFIPYAITNMGSALLAIELGLMGPNYSISTACATSNYCFHAAANHI

RRGEADLMIAGGTEAAIIPIGLGGFVACRALSQRNDDPQTASRPWD

KDRDGFVMGEGAGVLVLESLEHAMKRGAPIIAEYLGGAINCDAYHM

TDPRADGLGVSSCIESSLEDAGVSPEEVNYINAHATSTLAGDLAEI

NAIKKVFKNTKDIKINATKSMIGHCLGASGGLEAIATIKGINTGWL

HPSINQFNPEPSVEFDTVANKKQQHEVNVAISNSFGFGGHNSVVAF

SAFKP

Amino acid sequence of the *C. avigera*
mitochondrial KAS (D3344, pSZ4513).
SEQ ID NO: 18

<u>MVFLPWRKMLCPSQYRFLRPL</u>SSSTTFDPRRVVVTGLGMVTPLGCG

VNTTWKQLIEGKCGIRAISLEDLKMDAFDIDTQAYVFDQLTSKVAA

TVPTGVNPGEFNEDLWFNQKEHRAIARFIAYALCAADEALKDANWE

PTEPEEREMTGVSIGGGTGSISDVLDAGRMICEKKLRRLSPFFIPR

ILINMASGHVSMKYGFQGPNHAAVTACATGAHSIGDAARMIQFGDA

DVMVAGGTESSIDALSIAGFCRSRALTTKYNSCPQEASRPFDTDRD

GFVIGEGSGVLVLEELDHARKRGAKMYAEFCGYGMSGDAHHITQPH

SDGRGAILAMTRALKQSNLHPDQVDYVNAHATSTSLGDAIEAKAIK

TVFSDHAMSGSLALSSTKGAIGHLLGAAGAVEAIFSILAIKNGLAP

LTLNVARPDPVFTERFVPLTASKEMHVRAALSNSFGFGGTNTTLLF

TSPPQN

Amino acid sequence of the *C. avigera* KASIII
(D3345, pSZ4514).
SEQ ID NO: 19

<u>MANAYGFVGSSVPTVGRAAQFQQMGSGFCSVDFISKRVFCC</u>SAVQG

ADKPASGDSRAEYRTPRLVSRGCKLIGSGSAIPTLQVSNDDLAKIV

DTNDEWISVRTGIRNRRVLTGKDSLTNLATEAARKALEMAQVDAED

VDMVLMCTSTPEDLFGSAPQIQKALGCKKNPLSYDITAACSGFVLG

LVSAACHIRGGGFNNVLVIGADSLSRYVDWTDRGTCILFGDAAGAV

LVQSCDAEEDGLFAFDLHSDGDGQRHLRAVITENETDHAVGTNGSV

SDFPPRRSSYSCIQMNGKEVFRFACRSVPQSIELALGKAGLNGSNI

DWLLLHQANQRIIDAVATRLEVPQERVISNLANYGNTSAASIPLAL

DEAVRGGKVKPGHLIATAGFGAGLTWGSAIVRWG

HA Epitope TAG amino acid sequence
SEQ ID NO: 20

TMYPYDVPDYA

*C. palustris* KASIV CDS
SEQ ID NO: 21

ATGGCGGCCGCCGCTTCCATGGTTGCGTCCCCACTCTGTACGTGGC

TCGTAGCCGCTTGCATGTCCACTTCCTTCGACAACGACCCACGTTC

CCCGTCCATCAAGCGTCTCCCCCGCCGGAGGAGGACTCTCTCCCAA

TCCTCCCTCCGCGGCGGATCCACCTTCCAATGCCTCGTCACCTCAT

ACATCGACCCTTGCAATCAGTTCTCCTCCTCCGCCTCCCTTAGCTT

CCTCGGGGATAACGGATTCGCATCCCTTTTCGGATCCAAGCCTTTC

CGGTCCAATCGCGGCCACCGGAGGCTCGGCCGTGCTTCCCATTCCG

GGGAGGCCATGGCCGTGGCTTTGGAACCTGCACAGGAAGTCGCCAC

GAAGAAGAAACCTCTTGTCAAGCAAAGGCGAGTAGTTGTTACAGGA

ATGGGCGTGGTGACTCCTCTAGGCCATGAACCTGATGTTTACTACA

ACAATCTCCTAGATGGAGTAAGCGGCATAAGTGAGATAGAGGCCTT

CGACTGCACTCAGTTTCCCACGAGAATTGCCGGAGAGATCAAGTCT

TTTTCCACAGATGGATGGGTGGCCCCAAAGCTCTCCAAGAGGATGG

ACAAGTTCATGCTTTACTTGTTGACTGCTGGCAAGAAAGCATTAGC

GGATGGTGGAATCACCGATGATGTGATGAAAGAGCTTGATAAAGA

AAGTGTGGAGTTCTCATTGGCTCCGGATTGGGCGGCATGAAGCTGT

TCAGTGATTCCATTGAAGCTCTGAGGATTTCATATAAGAAGATGAA

TCCCTTTTGTGTACCTTTTGCTACTACAAATATGGGATCAGCTATG

CTTGCAATGGACTTGGGATGGATGGGTCCTAACTACTCGATATCAA

CTGCCTGTGCTACAAGTAATTTCTGTATACTGAATTCTGCAAATCA

CATAGTCAGAGGCGAAGCTGACATGATGCTTTGTGGTGGCTCGGAT

GCGGTCATTATACCTATTGGTTTGGGAGGTTTTGTGGCGTGCCGAG

CTTTGTCACAGAGGAATAATGACCCTACCAAAGCTTCGAGACCATG

GGACAGTAATCGTGATGGATTTGTAATGGGCGAAGGAGCTGGAGTG

TTACTTCTCGAGGAGTTAGAGCATGCAAAGAAAAGAGGTGCCACCA

TTTATGCGGAATTTTTAGGGGGCAGTTTCACTTGCGATGCCTACCA

TATGACCGAGCCTCACCCTGAAGGTGCTGGAGTGATCCTCTGCATA

GAGAAGGCCTTGGCTCAGGCCGGAGTCTCTAGAGAAGACGTAAATT

ACATAAATGCGATGCAACTTCCACTCCTGCTGGAGATATCAAGGA

ATACCAAGCTCTCGCACACTGCTTCGGCCAAAACAGTGAGCTGAGA

GTGAATTCCACTAAATCGATGATCGGTCATCTTATTGGAGCAGCTG

GTGGTGTAGAAGCAGTTACCGTAGTTCAGGCGATAAGGACTGGGTG

GATCCATCCAAATCTTAATTTGGAGGACCCGGACAAAGCCGTGGAT

GCAAAAGTGCTCGTAGGACCTAAGAAGGAGAGACTAAATGTCAAGG

TCGGTTTGTCCAATTCATTTGGGTTCGGTGGTCATAACTCGTCCAT

ACTCTTCGCCCCTTACAATTAG

*C. camphora* KASIV CDS

SEQ ID NO: 22

ATGGCAATGATGGCAGGTTCTTGTTCCAATTTGGTGATTGGAAACA

GAGAATTGGGTGGGAATGGGCCTTCTTTGCTTCACTACAATGGCCT

CAGACCATTGGAAAATATTCAAACAGCCTCAGCTGTGAAAAAGCCA

AATGGGTTATTTGCATCTTCTACAGCTCGAAAATCCAAAGCTGTCA

GAGCCATGGTATTGCCCACTGTAACAGCTCCAAAACGCGAAAAAGA

TCCCAAGAAGCGGATTGTAATAACAGGAATGGGCCTGGTTTCCGTC

TTTGGAAATGACATTGATACATTTTATAGTAAACTACTGGAAGGAG

AGAGCGGGATTGGCCCAATCGACAGATTTGATGCTTCTTCCTTCTC

AGTGAGATTTGCTGGTCAGATTCACAATTTCTCATCCAAAGGATAC

ATTGATGGGAAGAATGATCGTCGGCTAGATGACTGCTGGAGGTATT

GCCTTGTGGCTGGAAGAAGAGCCCTTGAAGATGCCAATCTTGGACC

AGAGGTATTGGAAAAAATGGACCGATCTCGAATAGGGGTGCTGATA

GGGACAGGAATGGGTGGGTTGTCAGCCTTTAGCAATGGAGTTGAGT

CTCTGATCCAGAAGGGCTACAAGAAAATCACTCCATTTTTATTCC

TTACTCCATCACCAATATGGGCTCTGCTCTTTTAGCAATCGACACG

GGCGTAATGGGACCAAACTACTCCATTTCAACAGCATGTGCAACCG

CAAACTATTGCTTCCATGCTGCTGCAAATCATATAAGAAGGGGTGA

AGCTGAAATCATGGTGACTGGAGGGACAGAGGCAGCAGTCTCAGCT

ACTGGAGTTGGCGGATTCATAGCATGTAGAGCCTTATCGCACAGGA

ATGATGAGCCCCAGACGGCCTCGAGACCATGGGATAAAGATCGGGA

TGGTTTCGTCATGGGCGAAGGCGCTGGTGTGCTGGTGATGGAGAGC

TTGCATCATGCAAGAAAGAGAGGAGCAAACATAATTGCAGAGTATT

TAGGAGGAGCAGTAACATGTGATGCACATCACATGACAGATCCTCG

AGCTGATGGTCTCGGGGTTTCTTCTTGCATAACCAAGAGCTTAGAA

GATGCAGGAGTCTCCCCAGAAGAGGTGAACTATGTGAATGCTCATG

CAACATCAACACTTGCAGGAGATTTAGCAGAGGTTAATGCCATAAA

GAAGGTCTTCAAGGACACATCTGAAATGAAATGAATGGAACTAAG

TCAATGATTGGACACTGTCTTGGAGCAGCTGGTGGATTAGAAGCCA

TTGCGACCATCAAAGCTATCAATACTGGCTGGCTACATCCAACCAT

CAATCAATTTAACATAGAACCAGCGGTAACTATCGACACGGTCCCA

AATGTGAAGAAAAGCATGATATCCATGTTGGCATCTCTAACTCAT

TTGGCTTTGGTGGGCACAACTCGGTGGTCGTTTTTGCTCCCTTCAT

GCCATGA

*C. camphora* KASI CDS

SEQ ID NO: 23

ATGCAAATCCTCCAAACCCCATCATCATCATCGTCTTCTCTCCGCA

TGTCGTCCATGGAATCTCTCTCTCTCACCCCTAAATCTCTCCCTCT

CAAACCCTTCTTCCCCTTCGTCCTCGCCCTAAAAACCTCTCCAGA

CGCAAATCCCAAAACCCTAGACCCATCTCCTCCTCTTCCTCCCCCG

AGAGAGAGACGGATCCCAAGAAGCGAGTCGTCATCACCGGGATGGG

CCTCGTCTCCGTCTTCGGCAACGATGTCGATGCCTACTACGACCGC

CTCCTCTCGGGAGAGAGCGGCATCGCCCCCATCGATCGCTTCGACG

CCTCCAAGTTCCCCACCAGATTCGCCGGTCAGATCCGAGGGTTCAC

CTCCGACGGCTACATTGACGGGAAGAACGACCGCCGGTTAGACGAT

TGTCTCAGATACTGTATTGTTAGTGGGAAGAAGGCGCTCGAGAATG

CCGGCCTCGGACCCCATCTCATGGACGGAAAGATTGACAAGGAGAG

AGCTGGTGTGCTTGTCGGGACAGGCATGGGTGGTCTTACAGTTTTC

TCTAATGGGGTCCAGACTCTACATGAGAAAGGTTACAGGAAAATGA

CTCCGTTTTTCATCCCTTATGCCATAACAAACATGGGTTCTGCCTT

GCTTGCAATTGAACTTGGTTTTATGGGCCCAAACTATTCTATCTCA

ACTGCATGTGCTACCTCCAATTATTGCTTTTATGCTGCTGCTAACC

ATATACGGAGAGGTGAGGCTGATCTGATGCTTGCTGGTGGAACTGA

AGCTGCAATTATTCCTATTGGATTAGGAGGCTTTGTTGCATGTAGA

GCTTTATCACAGAGAAATGATGACCCCCAGACAGCTTCAAGACCAT

GGGACAAAGATCGAGACGGTTTTGTTATGGGTGAAGGTGCTGGAGT

ATTGGTAATGGAGAGCTTGGAGCATGCTATGAAACGTGATGCACCA

ATTATTGCTGAGTATTTAGGAGGTGCAGTGAACTGTGATGCGTATC

ATATGACGGATCCTAGAGCTGATGGGCTCGGGGTTTCAACATGCAT

AGAAAGAAGTCTTGAAGATGCTGGTGTGGCACCTGAAGAGGTTAAC

TACATAAATGCACATGCAACTTCCACTCTTGCAGGAGACCTGGCTG

AGGTGAATGCGATCAAAAAGGTTTTTACAAACACTTCAGAGATCAA

AATCAATGCAACCAAGTCTATGATAGGGCACTGCCTTGGAGCGGCC

GGGGGGTTAGAAGCCATTGCCACAATCAAAGCAATAAATACTGGTT

GGCTGCACCCTTCTATAAACCAATTTAATCCAGAGCCCTCTGTTGA

GTTTGACACTGTAGCAAATAAAAAGCAGCAGCATGAAGTGAATGTT

GCCATTTCCAACTCTTTCGGGTTTGGCGGACACAACTCAGTCGTGG

TGTTTTCGGCATTCAAGCCTTGA

*Umbellularia californica* KASI CDS

SEQ ID NO: 24

ATGGAATCTCTCTCTCTCACCCCTAAATCTCTCCCTCTCAAACCC

TTCTTCCCCTTCGTCCTCGCCCTAAAAACCTCTCCAGACGCAAATC

CCAAAACCCTAAACCCATCTCCTCCTCTTCCTCCCCGGAGAGAGAG

ACGGATCCCAAGAAGCGAGTCGTCATCACCGGGATGGGCCTCGTCT

SEQUENCE LISTING

CCGTCTTCGGCAACGACGTCGATGCCTACTACGACCGCCTCCTCTC
CGGAGAGAGCGGCATCGCCCCCATCGATCGCTTCGACGCCTCCAAG
TTCCCCACCAGATTCGCCGGTCAGATCCGAGGGTTCACCTCCGACG
GCTACATTGACGGGAAGAACGACCGCCGGTTAGACGATTGTCTCAG
ATACTGTATCGTTAGTGGGAAGAAGGCGCTCGAGAATGCCGGCCTC
GGACCCGATCTCATGGACGGAAAGATTGACAAGGAGCGAGCTGGTG
TGCTTGTCGGGACAGGCATGGGTGGTCTTACAGTTTTCTCTAATGG
GGTTCAGACTCTCCATGAGAAAGGTTACAGGAAAATGACTCCGTTT
TTCATCCCTTATGCCATAACAAACATGGGTTCTGCCTTGCTTGCAA
TTGACCTTGGTTTTATGGGCCCAAACTATTCTATCTCAACTGCATG
TGCTACCTCCAATTATTGCTTTTATGCTGCTGCTAACCATATACGG
AGAGGTGAGGCTGATGTGATGCTTGCTGGTGGAACTGAAGCTGCAA
TTATTCCTATTGGCTTAGGAGGCTTTGTTGCATGTAGAGCTTTATC
ACAGCGAAATGATGACCCCAGACAGCTTCAAGACCATGGGACAAA
GATCGAGACGGTTTTGTTATGGGTGAAGGTGCTGGAGTATTGGTAA
TGGAGAGCTTGGAGCATGCTATGAAACGTGATGCACCAATTATTGC
TGAGTATTTAGGAGGTGCAGTGAACTGTGATGCGTATCATATGACG
GATCCTAGAGCTGATGGGCTCGGGGTTTCAACATGCATAGAAGAA
GTCTTGAAGATGCTGGTGTGGCACCTGAAGAGGTTAACTACATAAA
TGCACATGCAACTTCCACACTTGCAGGTGACCTGGCCGAGGTGAAT
GCCATCAAAAGGTTTTTACAAACACTTCAGAGATCAAAATCAATG
CAACCAAGTCTATGATAGGGCACTGCCTTGGAGCGGCCGGGGGTTT
AGAAGCCATTGCCACAATCAAAGCAATAAATACTGGTTGGCTGCAC
CCTTCTATAAACCAATTTAATCCAGAGCCCTCTGTTGAGTTTGACA
CTGTAGCAAATAAAAGCAGCAGCATGAAGTGAATGTTGCCATTTC
CAACTCTTTCGGGTTTGGTGGACACAACTCGGTCGTGGTGTTTTCG
GCATTCAAGCCTTGA

*Umbellularia californica* KASIV CDS
SEQ ID NO: 25
ATGACGCAAACCCTCATCTGCCCATCCTCCATGGAAACCCTCTCTC
TTACCAAACAATCCCATTTCAGACTCAGGCTACCCACTCCTCCTCA
CATCAGACGCGGCGGCGGCCATCGCCATCCTCCTCCCTTCATCTCC
GCCTCCGCCGCCCCTAGGAGAGAGACCGATCCGAAGAAGAGAGTCG
TCATCACGGGAATGGGCCTCGTCTCCGTCTTCGGCACCAACGTCGA
TGTCTACTACGATCGCCTCCTCGCCGGCGAGAGCGGCGTTGGCACT
ATCGATCGCTTCGACGCGTCGATGTTCCCGACGAGATTCGGCGGCC
AGATCCGGAGGTTCACGTCGGAGGGGTACATCGACGGGAAGAACGA
CCGGCGGCTGGATGACTACCTCCGGTACTGCCTCGTCAGCGGGAAG
AAGGCGATCGAGAGTGCTGGCTTCGATCTCCATAACATCACCAACA
AGATTGACAAGGAGCGAGCTGGGATACTTGTTGGGTCAGGCATGGG

*C. wrightii* KASAI CDS (D3153, pSZ4379)
SEQ ID NO: 26
atggcttccgcggcattcaccatgtcggcgtgccccgcgatgactg
gcagggcccctggggcacgtcgctccggacggccagtcgccacccg
cctgaggtacgtattccagtgcctggtggccagctgcatcgacccc
tgcgaccagtaccgcagcagcgccagcctgagcttcctgggcgaca
acggatcgccagcctgttcggcagcaagccatcatgagcaaccgcg
gccaccgccgcctgcgccgcgccagccacagcggcgaggccatggc
cgtggccctgcagcccgcccaggaggccggcaccaagaagaagccc
gtgatcaagcagcgccgcgtggtggtgaccggcatgggcgtggtga
ccccctgggcacgagcccgacgtgttctacaacaacctgctgga
cggcgtgagcggcatcagcgagatcgagaccttcgactgcacccag
ttccccacccgcatcgccggcgagatcaagagcttcagcaccgacg
gctgggtggcccccaagctgagcaagcgcatggacaagttcatgct
gtacctgctgaccgccggcaagaaggccctggccgacggcggcatc
accgacgaggtgatgaaggagctggacaagcgcaagtgcggcgtgc
tgatcggcagcggcatgggcggcatgaaggtgttcaacgacgccat
cgaggccctgcgcgtgagctacaagaagatgaacccttctgcgtg
cccttcgccaccaccaacatgggcagcgccatgctggccatggacc

SEQUENCE LISTING

```
tgggctggatgggcccccaactacagcatcagcaccgcctgcgccac
cagcaacttctgcatcctgaacgccgccaaccacatcatccgcggc
gaggccgacatgatgctgtgcggcggcagcgacgccgtgatcatcc
ccatcggcctgggcggcttcgtggcctgccgcgcgcctgagccagcg
caacagcgaccccaccaaggccagccgcccctgggacagcaaccgc
gacggcttcgtgatgggcgagggcgccggcgtgctgctgctggagg
agctggagcacgccaagaagcgcggcgccaccatctacgccgagtt
cctgggcggcagatcacctgcgacgcctaccacatgaccgagcccc
accccgagggcgccggcgtgatcctgtgcatcgagaaggccctggc
ccaggccggcgtgagcaaggaggacgtgaactacatcaacgcccac
gccaccagcaccagcgccggcgacatcaaggagtaccaggccctgg
cccgctgatcggccagaacagcgagctgcgcgtgaacagcaccaag
agcatgatcggccacctgctgggcgccgccggcgcggcgtggaggccg
tgaccgtggtgcaggccatccgcaccggctggattcaccccaacct
gaacctggaggaccccgacaaggccgtggacgccaagctgctggtg
ggccccaagaaggagcgcctgaacgtgaaggtgggcctgagcaaca
gatcggatcggcggccacaacagcagcatcctgttcgcccctgca
acgtgtga
```

*C. avigera* KASIVb CDS
SEQ ID NO: 27

```
ATGGCGGCCGCTTCTTGCATGGCTGCGTCCCCTTTCTGTACGTCGC
TCGTGGCTGCATGCATGTCGACTTCATCCGACAACGACCCATGTCC
CCTTTCCCGCCGCGGATCCACCTTCCAATGCTACATCGGGGATAAC
GGATTCGGATCGAAGCCTCCCCGTTCAAATCGTGGCCACCTGAGGC
TCGGCCGCACTTCACATTCCGGAGAGGTGATGGCTGTGGCTATGCA
ATCTGCACAAGAAGTCTCCACAAAGGAGAAACCTGCTACCAAGCAA
AGGCGAGTTGTTGTCACGGGTATGGGTGTGGTGACTGCTCTAGGCC
ATGACCCCGATGTTTACTACAACAATCTCCTAGACGGAGTAAGCGG
CATAAGCGAGATAGAAAACTTTGACTGTTCTCAGCTTCCCACGAGA
ATTGCCGGAGAGATCAAGTCTTTTTCTGCAGATGGGTGGGTGGCCC
CGAAGTTCTCCAGGAGGATGGACAAGTTTATGCTTTACATTCTGAC
TGCAGGCAAGAAAGCATTAGTAGATGGTGGAATCACTGAAGATGTG
ATGAAAGAGCTCGATAAAGAAAGTGTGGAGTTCTCATTGGCTCCG
GATTGGGCGGTATGAAGGTATTTAGCGAGTCCATTGAAGCTCTGAG
GACTTCATATAAGAAGATCAGTCCCTTTTGTGTACCTTTTCTACC
ACGAATATGGGATCCGCTATTCTTGCAATGGACTTGGGATGGATGG
GCCCTAACTATTCGATATCGACTGCCTGTGCAACAAGTAACTTCTG
TATACTGAATGCTGCGAACCACATAACCAAAGGCGAAGCAGACATG
ATGCTTTGTGGTGGCTCGGATTCGGTCATTTTACCTATTGGTATGG
GAGGTTTCGTAGCATGCCGAGCTTTGTCACAGAGGAATAATGACCC
```

TACCAAAGCTTCGAGACCATGGGACAGTAATCGTGATGGATTTGTG
ATGGGAGAAGGTGCTGGAGTTTTACTTCTCGAGGAGTTAGAGCATG
CAAAGAAAAGAGGCGCAACCATTTATGCGGAATTTCTTGGTGGGAG
TTTCACTTGCGATGCCTACCACATGACCGAGCCTCACCCTGAAGGA
GCTGGAGTGATCCTCTGCATAGAGAAGGCCTTGGCTCAGTCCGGAG
TCTCGAGGGAAGACGTAAATTACATAAATGCGCATGCAACTTCCAC
TCCCGCTGGAGATATCAAAGAATACCAAGCTCTCGCCCACTGTTTC
GGCCAAAACAGTGAGTTAAGAGTGAATTCCACCAAGTCGATGATCG
GTCACCTTCTTGGAGGAGCCGGTGGCGTAGAAGCAGTTACAGTCGT
TCAGGCAATAAGGACTGGATGGATCCATCCAAATATTAATTTGGAC
GACCCGGACGAAGGCGTGGATGCAAAACTGCTCGTCGGCCCTAAGA
AGGAGAAACTGAAGGTCAAGGTCGGTTTGTCCAATTCATTCGGGTT
CGGCGGCCATAACTCATCCATACTCTTTGCCCCATGCAATTAG

*C. paucipetala* KASIVb CDS
SEQ ID NO: 28

ATGGCGGCCGCTTCATCAATGGTTGCCTCCCC

SEQUENCE LISTING

```
ATGACCGAGCCTCACCCTGATGGAGCTGGAGTGATCCTCTGCATAG
AGAAGGCTTTGGCACAGTCCGGAGTCTCGAGGGAAGACGTCAATTA
CATAAATGCGCATGCAACTTCTACTCCTGCTGGAGATATCAAGGAA
TACCAAGCTCTCGCCCACTGTTTCGGCCAAAACAGTGAGTTAAGAG
TGAATTCCACCAAATCGATGATCGGTCACCTTCTTGGAGCTGCTGG
TGGCGTAGAAGCAGTTACAGTAGTTCAGGCAATAAGGACTGGGTGG
ATCCATCCAAATATTAATTTGGAAAACCCGGACGAAGCTGTGGATG
CAAAATTGCTCGTCGGCCCTAAGAAGGAGAAACTGAAGGTCAAGGT
CGGTTTGTCCAATTCATTTGGGTTCGGTGGGCATAACTCATCCATA
CTCTTCGCCCCTTACAATTAG
```

*C. ignea* KASIVb CDS

SEQ ID NO: 29

```
ATGGCGGCGGCCGCTTCCATGTTTACGTCCCCACTCTGTACGTGGC
TCGTAGCCTCTTGCATGTCGACTTCCTTCGACAACGACCCACGTTC
GCCGTCCGTCAAGCGTCTCCCCCGCCGGAGGAGGATTCTCTCCCAA
TGCTCCCTCCGCGGATCCACCTCCCAATGCCTCGTCACCTCATACA
TCGACCCTTGCAATAAGTACTGCTCCTCCGCCTCCCTTAGCTTCCT
CGGGGATAACGGATTCGCATCCCTTTTCGGATCTAAGCCATTCCGG
TCCAATCGCGGCCACCGGAGGCTCGGCCGTGCTTCCCATTCCGGGG
AGGCCATGGCTGTGGCTCTGCAACCTGCACAGGAAGTCACCACGAA
GAAGAAACCTGTGATCAAGCAAAGGCGAGTAGTTGTTACAGGAATG
GGCGTGGTGACTCCTCTAGGCCATGAACCTGATGTTTACTACAACA
ATCTCCTAGATGGAGTAAGCGGCATAAGTGAGATAGAGACCTTCGA
CTGCACTCAGTTTCCCACGAGAATCGCCGGAGAGATCAAGTCTTTT
TCCACAGATGGGTGGGTGGCCCCAAAGCTCTCCAAGAGGATGGACA
AGTTCATGCTTTACTTGTTGACTGCTGGCAAGAAAGCATTAGCAGA
TGGTGGAATCACCGATGATGTGATGAAAGAGCTTGATAAAAGAAAG
TGTGGGGTTCTCATTGGCTCTGGAATGGGCGGCATGAAGTTGTTCA
ACGATTCCATTGAAGCTCTGAGGATTTCATATAAAAAGATGAATCC
CTTTTGTGTACCTTTTGCTACCACAAATATGGGATCAGCTATGCTT
GCAATGGACTTGGGATGGATGGGTCCTAACTACTCGATATCAACTG
CCTGTGCAACAAGTAATTTCTGTATACTGAATGCTTCAAACCACAT
AGTCAGAGGCGAAGCTGACATGATGCTTTGTGGTGGCTCGGATTCT
GTCACTGTACCTTTAGGTGTGGGAGGTTTCGTAGCATGCCGAGCTT
TGTCACAGAGGAATAATGACCCTACCAAAGCTTCGAGACCTTGGGA
CAGTAATCGGGATGATTTGTGATGGGAGAAGGAGCTGGAGTGTTA
CTTCTTGAGGAGTTAGAGCATGCAAAGAAAAGAGGTGCAACCATTT
ATGCGGAATTTCTCGGTGGGAGCTTTACTTCTGATGCCTACCACAT
GACCGAGCCTCACCCCGAAGGAGCTGGAGTGATTCTCTGCATTGAG
AAGGCCTTGGCTCAGTCCGGAGTCTCGAGGGAAGACGTGAATTATA
```

```
TAAATGCGCATGCAACTTCCACTCCTGCTGGTGATATAAAGGAATA
CCAAGCTCTCGCCCGCTGTTTCGGCCAAAACAGTGAGTTAAGAGTG
AATTCCACCAAATCGATGATCGGTCACCTTCTTGGAGCAGCTGGTG
GCGTAGAAGCAGTTGCAGTAATTCAGGCAATAAGGACTGGATGGAT
CCATCCAAATATTAATTTGGAAGACCCCGACGAAGCCGTGGATCCA
AAATTGCTCGTCGGCCCTAAGAAGGAGAAACTGAAGGTCAAGGTAG
CTTTGTCCAATTCATTCGGGTTCGGCGGGCATAACTCATCCATACT
CTTTGCCCCTTGCAATTAG
```

*C. procumbens* KASIV CDS

SEQ ID NO: 30

```
ATGGCGGCGGCGCCCTCTTCCCCACTCTGTACGTGGCTCGTAGCCG
CTTGCATGTCCACTTCCTTCGACAACAACCCACGTTCGCCCTCCAT
CAAGCGTCTCCCCCGCCGGAGGAGGGTTCTCTCCCAATGCTCCCTC
CGTGGATCCACCTTCCAATGCCTCGTCACCTCACACAACGACCCTT
GCAATCAGTACTGCTCCTCCGCCTCCCTTAGCTTCCTCGGGGATAA
CGGATTCGGATCCAAGCCATTCCGGTCCAATCGCGGCCACCGGAGG
CTCGGCCGTGCTTCGCATTCCGGGGAGGCCATGGCTGTGGCCTTGC
AACCTGCACAGGAAGTCGCCACGAAGAAGAAACCTGCTATGAAGCA
AAGGCGAGTAGTTGTTACAGGAATGGGCGTGGTGACTCCTCTGGGC
CATGAACCTGATGTTTACTACAACAATCTCCTAGATGGAGTAAGCG
GCATAAGTGAGATAGAGACCTTCGACTGCACTCAGTTTCCCACGAG
AATCGCCGGAGAGATCAAGTCTTTTTCCACAGATGGATGGGTGGCC
CCAAAGCTCTCCAAGAGGATGGACAAGTTCATGCTTTACTTGTTGA
CTGCTGGCAAGAAAGCATTAGCAGATGGTGGAATCACTGATGATGT
GATGAAAGAGCTTGATAAAAGAAAGTGTGGAGTTCTCATTGGCTCT
GGAATGGGCGGCATGAAGTTGTTCAACGATTCCATTGAAGCTCTGA
GAGTTTCATATAAGAAGATGAATCCCTTTTGTGTACCTTTTGCTAC
CACAAATATGGGATCAGCTATGCTTGCAATGGACTTGGGATGGATG
GGTCCTAACTACTCGATATCAACTGCCTGTGCAACAAGTAATTTCT
GTATACTGAATGCTGCAAACCACATAGTCAGAGGCGAAGCTGACAT
GATGCTTTGTGGTGGCTCGGATGCGTCATTATACCTATTGGTTTG
GGAGGTTTTGTGGCGTGCCGAGCTTTGTCACAGAGGAATAATGACC
CTACCAAGGCTTCGAGACCATGGGATAGTAATCGTGATGGATTTGT
AATGGGCGAAGGAGCTGGAGTGTTACTTCTCGAGGAGTTAGAGCAT
GCAAAGAAAAGAGGTGCAACCATTTATGCGGAATTTTTAGGGGGCA
GTTTCACTTGCGATGCCTACCATATGACCGAGCCTCACCCTGAAGG
AGCTGGAGTGATCCTCTGCATAGAGAAGGCCTTGGCTCAGTCCGGA
GTCTCTAGAGAAGACGTAAATTACATAAATGCGCATGCAACTTCCA
CTCCTGCTGGAGATATCAAAGAATACCAAGCTCTCGCCCACTGTTT
```

CGGCCAAAACAGTGAGCTGAGAGTGAATTCCACTAAATCGATGATC

GGTCATCTTCTTGGAGCAGCTGGTGGTGTAGAAGCAGTTACCGTAA

TTCAGGCGATAAGGACTGGGTGGATCCATCCAAATCTTAATTTGGA

AGACCCGGACAAAGCCGTGGATGCAAAATTTCTCGTGGGACCTAAG

AAGGAGAGACTGAATGTCAAGGTCGGTTTGTCCAATTCATTTGGGT

TCGGGGGGCATAACTCATCCATACTCTTTGCCCCTTGCAATTAG

*C. paucipetala* KASIVa CDS

SEQ ID NO: 31

ATGGCGGCGGCGGCCTCTTCCCCACTCTGCACATGGCTCGTAGCCG

CTTGCATGTCCACTTCATTCGACAACAACCCACGTTCGCCCTCCAT

CAAGCGTCTCCCCCGCCGGAGGAGGGTTCTCTCCCAATGCTCCCTC

CGCGGATCCACCTTCCAATGCCTCGTCAACTCACACATCGACCCTT

GCAATCAGAACGTCTCCTCCGCCTCCCTTAGCTTCCTCGGGGATAA

CGGATTCGGATCCAATCCATTCCGGTCCAATCGCGGCCACCGGAGG

CTCGGCCGGGCTTCCCATTCCGGGGAGGCCATGGCTGTTGCTCTGC

AACCTGCACAGGAAGTCGCCACGAAGAAGAAACCTGCTATCAAGCA

AAGGCGAGTAGTTGTTACAGGAATGGGCGTGGTGACTCCTCTAGGC

CATGAGCCTGATGTTTTCTACAACAATCTCCTAGATGGAGTAAGCG

GCATAAGTGAGATAGAGACCTTCGACTGCACTCAGTTTCCCACGAG

AATTGCCGGAGAGATCAAGTCTTTTTCCACAGATGGGTGGGTGGCC

CCAAAGCTCTCCAAGAGGATGGACAAGTTCATGCTTTACTTGTTGA

CTGCTGGCAAGAAAGCATTAGCAGATGCTGGAATTACCGAGGATGT

GATGAAAGAGCTTGATAAAGAAAGTGTGGAGTTCTCATTGGCTCC

GGAATGGGCGGCATGAAGTTGTTCAACGATTCCATTGAAGCTCTGA

GGGTTTCATATAAGAAGATGAATCCCTTTTGTGTACCTTTTGCTAC

CACAAATATGGGATCAGCTATGCTTGCAATGGACTTGGGATGGATG

GGTCCTAACTACTCGATATCGACTGCCTGTGCAACAAGTAATTTCT

GTATACTGAATGCTGCAAACCACATAATCAGAGGCGAAGCTGACAT

GATGCTTTGTGGTGGTTCGGATGCGGTCATTATACCTATTGGTTTG

GGAGGTTTTGTGGCGTGCCGAGCTTTGTCACAGAGGAATAGTGACC

CTACCAAAGCTTCGAGACCATGGGATAGTAATCGTGATGGATTTGT

AATGGGCGAAGGAGCTGGAGTGTTACTTCTCGAGGAGTTAGAGCAT

GCAAAGAAAAGAGGTGCAACCATTTATGCGGAATTTTTAGGGGCA

GCTTCACTTGCGATGCCTACCACATGACCGAGCCTCACCCTGATGG

AGCTGGAGTGATCCTCTGCATAGAGAAGGCTTTGGCACAGTCCGGA

GTCTCGAGGGAAGACGTCAATTACATAAATGCGCATGCAACTTCTA

CTCCTGCTGGAGATATCAAGGAATACCAAGCTCTCGCCCACTGTTT

CGGCCAAAACAGTGAGCTGAGAGTGAATTCCACTAAATCGATGATC

GGTCATCTTCTTGGTGCAGCTGGTGGTGTAGAAGCTGTTACTGTAA

TTCAGGCGATAAGGACTGGGTGGATTCATCCAAATCTTAATTTGGA

AGACCCGGACGAAGCCGTGGATGCAAAATTTCTCGTGGGACCTAAG

AAGGAGAGATTGAATGTCAAGGTCGGTTTGTCCAATTCATTTGGGT

TCGGTGGGCATAACTCATCCATACTCTTCGCCCCTTACAATTAG

*C. painteri* KASIV CDS

SEQ ID NO: 32

ATGGCGGCCTCCTCTTGCATGGTTGCGTCCCCGTTCTGTACGTGGC

TCGTATCCGCATGCATGTCTACTTCATTCGACAACGACCCACGTTC

CCTTTCCCACAAGCGGCTCCGCCTCTCCCGTCGCCGGAGGCCTCTC

TCCTCTCATTGCTCCCTCCGCGGATCCACTCCCCAATGCCTCGACC

CTTGCAATCAGCACTGCTTCCTCGGGGATAACGGATTCGCTTCCCT

CATCGGATCCAAGCCTCCCCGTTCCAATCTCGGCCACCTGAGGCTC

GGCCGCACTTCCCATTCCGGGGAGGTCATGGCTGTGGCACAGGAAG

TCTCCACAAATAAGAAACATGCTACCAAGCAAAGGCGAGTAGTTGT

GACAGGTATGGGCGTGGTGACTCCTCTAGGCCATGACCCCGATGTT

TACTACAACAATCTCCTAGAAGGAGTAAGTGGCATCAGTGAGATAG

AGAACTTCGACTGCTCTCAGCTTCCCACGAGAATTGCCGGAGAGAT

CAAGTCTTTTTCCACAGATGGGTTGGTGGCCCCGAAGCTCTCCAAG

AGGATGGACAAGTTCATGCTTTACATCCTGACTGCAGGCAAGAAAG

CATTAGCAGATGGTGGAATCACTGAAGATGTGATGAAAGAGCTCGA

TAAAAGAAAGTGTGGAGTTCTCATTGGCTCCGGATTGGGCGGTATG

AAGGTATTCAGCGACTCCGTTGAAGCTCTGAGGGATTTCATATAAGA

AGATCAGTCCCTTTTGTGTACCTTTTTCTACCACAAATATGGGATC

CGCTATGCTTGCAATGGACTTGGGATGGATGGGCCCTAACTATTCG

ATATCAACTGCCTGTGCAACAAGTAACTTCTGTATACTGAATGCTG

CGAACCACATAACCAAAGGCGAAGCTGACATGATGCTTTGTGGTGG

CTCGGATGCGGCCATTTTACCTATTGGTATGGGAGGTTTCGTGGCA

TGCCGAGCTTTGTCACAGAGGAATAATGACCCTACCAAAGCTTCGA

GACCATGGGACAGTAATCGTGATGGATTTGTGATGGGAGAAGGAGC

TGGAGTGTTACTTCTCGAGGAGTTAGAGCATGCAAAGAAAAGAGGT

GCAACCATTTATGCGGAATTTCTAGGTGGGAGTTTCACTTGCGATG

CCTACCACATGACCGAGCCTCACCCTGATGGAGCTGGAGTGATCCT

CTGCATAGAGAAGGCCTTGGCTCAGTCCGGAGTCTCGAGGGAAGAA

GTAAATTACATAAATGCGCATGCAACTTCCACTCCTGCTGGAGATA

TCAAGGAATACCAAGCTCTCGCCCATTGTTTCGGCCAAAACAGTGA

GTTAAGAGTGAATTCCACCAAATCGATGATCGGTCACCTTCTTGGA

GGAGCTGGTGGCGTAGAAGCAGTTACAGTAGTTCAGGCAATAAGGA

CTGGATGGATCCATCCAAATATTAATTTGGAAGACCCGGACAAAGG

CGTGGATGCAAAACTGCTCGTCGGCCCTAAGAAGGAGAAACTGAAG

GTCAAGGTCGGTTTGTCCAATTCATTTGGGTTCGGCGGCCATAACT

CATCCATACTCTTTGCCCCATGCAATTAG

C. avigera KASIVa CDS

SEQ ID NO: 33

ATGGCGGCCGCCGCTTCCATGGTTGCGTCCCCATTCTGTACGTGGC

TCGTAGCCGCTTGCATGTCCACTTCCGTCGACAAAGACCCACGTTC

GCCGTCTATCAAGCGTCTCCCCCGCCGGAAGAGGATTCATTCCCAA

TGCTCCCTCCGCGGATCCACCTTCCAATGCCTCGTCACCTCATACA

ACGACCCTTGCAACAATACCGCTCATCCGCCTCCCTTAGCTTCCT

CGGGGATAACGGATTCGCATCCCTTTTCGGATCCAAGCCATTCCGG

TCCAATCGCGGCCACCGGAGGCTCGGCCGTGCTTCCCATTCCGGGG

AGGCCATGGCCGTGGCACTGCAACCTGCACAGGAAGTTGGCACGAA

GAAGAAACCTGTTATCAAGCAAAGGCGAGTAGTTGTTACAGGAATG

GGCGTGGTGACTCCTCTAGGCCATGAACCTGATGTTTACTACAACA

ATCTCCTAGACGGAGTAAGCGGCATAAGTGAGATAGAGACCTTCGA

CTGCACTCAGTTTCCCACGAGAATTGCCGGAGAGATCAAGTCTTTT

TCCACAGATGGGTGGGTGGCTCCAAAGCTCTCTAAGAGGATGGACA

AGTTCATGCTTTACTTGTTGACTGCTGGCAAGAAAGCATTGGCAGA

TGGTGGAATCACCGATGATGTGATGAAAGAGCTTGATAAAAGAAAG

TGTGGAGTTCTCATTGGCTCCGGATTGGGCGGTATGAAGGTATTTA

GCGAGTCCATTGAAGCTCTGAGGACTTCATATAAGAAGATCAGTCC

CTTTTGTGTACCTTTTTCTACCACGAATATGGGATCCGCTATTCTT

GCAATGGACTTGGGATGGATGGGCCCTAACTATTCGATATCGACTG

CCTGTGCAACAAGTAACTTCTGTATACTGAATGCTGCGAACCACAT

AACCAAAGGCGAAGCAGACATGATGCTTTGTGGTGGCTCGGATTCG

GTCATTTTACCTATTGGTATGGGAGGTTTCGTAGCATGCCGAGCTT

TGTCACAGAGGAATAATGACCCTACCAAAGCTTCGAGACCATGGGA

CAGTAATCGTGATGGATTTGTGATGGGAGAAGGTGCTGGAGTTTTA

CTTCTCGAGGAGTTAGAGCATGCAAAGAAAAGAGGCGCAACCATTT

ATGCGGAATTTCTTGGTGGGAGTTTCACTTGCGATGCCTACCACAT

GACCGAGCCTCACCCTGAAGGAGCTGGAGTGATCCTCTGCATAGAG

AAGGCCTTGGCTCAGTCCGGAGTCTCGAGGGAAGACGTAAATTACA

TAAATGCGCATGCAACTTCCACTCCCGCTGGAGATATCAAAGAATA

CCAAGCTCTCGCCCACTGTTTCGGCCAAAACAGTGAGTTAAGAGTG

AATTCCACCAAGTCGATGATCGGTCACCTTCTTGGAGGAGCCGGTG

GCGTAGAAGCAGTTACAGTCGTTCAGGCAATAAGGACTGGATGGAT

CCATCCAAATATTAATTTGGACGACCCGGACGAAGGCGTGGATGCA

AAACTGCTCGTCGGCCCTAAGAAGGAGAAACTGAAGGTCAAGGTCG

GTTTGTCCAATTCATTCGGGTTCGGCGGCCATAACTCATCCATACT

CTTTGCCCCATGCAATTAG

C. ignea KASIVa CDS

SEQ ID NO: 34

ATGGCGGCGGCCGCTTCCATGTTTACGTCCCCACTCTGTACGTGGC

TCGTAGCCTCTTGCATGTCGACTTCCTTCGACAACGACCCACGTTC

GCCGTCCGTCAAGCGTCTCCCCCGCCGGAGGAGGATTCTCTCCCAA

TGCTCCCTCCGCGGATCCACCTCCCAATGCCTCGTCACCTCATACA

TCGACCCTTGCAATAAGTACTGCTCCTCCGCCTCCCTTAGCTTCCT

CGGGGATAACGGATTCGCATCCCTTTTCGGATCTAAGCCATTCCGG

TCCAATCGCGGCCACCGGAGGCTCGGCCGTGCTTCCCATTCCGGGG

AGGCCATGGCTGTGGCTCTGCAACCTGCACAGGAAGTCACCACGAA

GAAGAAACCTGTGATCAAGCAAAGGCGAGTAGTTGTTACAGGAATG

GGCGTGGTGACTCCTCTAGGCCATGAACCTGATGTTTACTACAACA

ATCTCCTAGATGGAGTAAGCGGCATAAGTGAGATAGAGACCTTCGA

CTGCACTCAGTTTCCCACGAGAATCGCCGGAGAGATCAAGTCTTTT

TCCACAGATGGGTGGGTGGCCCCAAAGCTCTCCAAGAGGATGGACA

AGTTCATGCTTTACTTGTTGACTGCTGGCAAGAAAGCATTAGCAGA

TGGTGGAATCACCGATGATGTGATGAAAGAGCTTGATAAAAGAAAG

TGTGGGGTTCTCATTGGCTCTGGAATGGGCGGCATGAAGTTGTTCA

ACGATTCCATTGAAGCTCTGAGGGATTTCATATAAAAAGATGAATCC

CTTTTGTGTACCTTTTGCTACCACAAATATGGGATCAGCTATGCTT

GCAATGGACTTGGGATGGATGGGTCCTAACTACTCGATATCAACTG

CCTGTGCAACAAGTAATTTCTGTATACTGAATGCTTCAAACCACAT

AGTCAGAGGCGAAGCTGACATGATGCTTTGTGGTGGCTCGGATGCG

GTTATTATACCTATTGGTTTGGGAGGTTTTGTGGCGTGCCGAGCTT

TGTCACAGAGGAATAATGACCCTACCAAAGCTTCGAGGCCATGGGA

TAGTAATCGTGATGGATTTGTAATGGGCGAAGGAGCTGGAGTGTTA

CTTCTCGAGGAGTTAGAGCATGCAAAGAAAAGAGGTGCAACCATTT

ATGCGGAATTTTTAGGGGCAGTTTCACTTGCGATGCCTACCACAT

GACCGAGCCTCACCCTGAAGGAGCTGGAGTGATCCTCTGCATAGAG

AAGGCCTTGGCTCAGGCCGGAGTCTCTAAAGAAGATGTAAATTACA

TAAATGCGCATGCAACTTCTACTCCTGCTGGAGATATCAAGGAATA

CCAAGCTCTCGCCCAATGTTTCGGCCAAAACAGTGAGCTGAGAGTG

AATTCCACTAAATCGATGATCGGTCATCTTCTTGGAGCAGCTGGTG

GTGTAGAAGCAGTTACTGTGGTTCAGGCGATAAGGACTGGGTGGAT

CCATCCAAATCTTAATTTGGAAGACCCGGACAAAGCCGTGGATGCA

AAGTTGCTCGTGGGACCTAAGAAGGAGAGACTGAATGTCAAGGTCG

GTTTGTCCAATTCATTTGGGTTCGGTGGGCATAATTCGTCCATACT

CTTCGCCCCTTACAATTAG

C. avigera KASIa CDS

SEQ ID NO: 35

ATGCAATCCCTCCATTCCCCTGCCCTCCGGGCCTCCCCTCTCGACC

CTCTCCGACTCAAATCCTCCGCCAATGGCCCCTCTTCCACCGCCGC
TTTCCGTCCCCTCCGCCGCGCCACCCTCCCCAACATTCGGGCCGCC
TCCCCCACCGTCTCCGCCCCCAAGCGCGAGACCGACCCCAAGAAGC
GTGTCGTCATCACCGGCATGGGCCTCGTCTCCGTCTTCGGCTCCGA
TGTCGACGCTTATTACGAAAAGCTCCTCTCCGGCGAGAGCGGGATC
AGCTTAATCGACCGCTTCGACGCTTCCAAGTTCCCCACGAGGTTCG
GCGGCCAGATCCGGGGATTCAACGCCACGGGATACATCGACGGCAA
AAACGACAGGAGGCTCGACGATTGCCTCCGCTACTGCATTGTCGCC
GGGAAGAAGGCTCTCGAAAATTCCGATCTCGGCGGCGATAGTCTCT
CAAAGATTGATAAGGAGAGAGCTGGAGTGCTAGTTGGAACTGGCAT
GGGTGGCCTAACCGTCTTCTCTGACGGGGTTCAGAATCTAATCGAG
AAAGGTCACCGGAAGATCTCCCCGTTTTTCATTCCATATGCCATTA
CAAACATGGGGTCTGCCCTGCTTGCCATCGATTTGGGTCTGATGGG
CCCAAATTATTCGATTTCAACTGCATGTGCTACTTCCAACTACTGC
TTTTATGCTGCTGCTAATCATATCCGCCGAGGCGAGGCTGACCTCA
TGATTGCTGGAGGAACTGAGGCTGCAATCATTCCAATTGGGTTAGG
AGGATTCGTTGCTTGCAGGGCTTTATCTCAAAGGAATGATGACCCT
CAGACTGCCTCAAGGCCGTGGGATAAGGACCGTGATGGTTTTGTGA
TGGGTGAAGGGGCTGGAGTATTGGTTATGGAGAGCTTAGAACATGC
AATGAAACGAGGAGCGCCGATTATTGCAGAATATTTGGGAGGTGCA
GTCAACTGTGATGCTTATCATATGACTGATCCAAGGGCTGATGGGC
TTGGTGTCTCCTCGTGCATTGAGAGCAGTCTCGAAGATGCCGGGGT
CTCACCTGAAGAGGTCAATTACATAAATGCTCATGCGACTTCTACT
CTTGCTGGGGATCTTGCCGAGATAAATGCCATCAAGAAGGTTTTCA
AGAACACCAAGGATATCAAATCAATGCAACTAAGTCGATGATTGG
ACACTGTCTTGGAGCATCAGGGGGTCTTGAAGCCATTGCGACAATT
AAGGGAATAACCACTGGCTGGCTTCATCCCAGCATAAACCAATTCA
ATCCCGAGCCATCAGTGGAATTTGACACTGTTGCCAACAAGAAGCA
GCAACATGAAGTCAATGTTGCTATCTCAAATTCATTCGGATTCGGA
GGCCACAACTCAGTTGTAGCTTTCTCAGCTTTCAAGCCATGA

*C. pulcherrima* KASI CDS

SEQ ID NO: 36

ATGCATTCCCTCCAGTCACCCTCCCTTCGGGCCTCCCCGCTCGACC
CCTTCCGCCCCAAATCATCCACCGTCCGCCCCCTCCACCGAGCATC
AATTCCCAACGTCCGGGCCGCTTCCCCCACCGTCTCCGCTCCCAAG
CGCGAGACCGACCCCAAGAAGCGCGTCGTGATCACCGGAATGGGCC
TTGTCTCCGTTTTCGGCTCCGACGTCGATGCGTACTACGACAAGCT
CCTGTCAGGCGAGAGCGGGATCGGCCCAATCGACCGCTTCGACGCC
TCCAAGTTCCCCACCAGGTTCGGCGGCCAGATTCGTGGCTTCAACT
CCATGGGATACATTGACGGCAAAAACGACAGGCGGCTTGATGATTG

CCTTCGCTACTGCATTGTCGCCGGGAAGAAGTCTCTTGAGGACGCC
GATCTCGGTGCCGACCGCCTCTCCAAGATCGACAAGGAGAGAGCCG
GAGTGCTGGTTGGGACAGGAATGGGTGGTCTGACTGTCTTCTCTGA
CGGGGTTCAATCTCTTATCGAGAAGGGTCACCGGAAAATCACCCCT
TTCTTCATCCCCTATGCCATTACAAACATGGGGTCTGCCCTGCTCG
CTATTGAACTCGGTCTGATGGGCCCAAACTATTCAATTTCCACTGC
ATGTGCCACTTCCAACTACTGCTTCCATGCTGCTGCTAATCATATC
CGCCGTGGTGAGGCTGATCTTATGATTGCTGGAGGCACTGAGGCCG
CAATCATTCCAATTGGGTTGGGAGGCTTTGTGGCTTGCAGGGCTCT
GTCTCAAAGGAACGATGACCCTCAGACTGCCTCTAGGCCCTGGGAT
AAAGACCGTGATGGTTTTGTGATGGGTGAAGGTGCTGGAGTGTTGG
TGCTGGAGAGCTTGGAACATGCAATGAAACGAGGAGCACCTATTAT
TGCAGAGTATTGGGAGGTGCAATCAACTGTGATGCTTATCACATG
ACTGACCCAAGGGCTGATGGTCTCGGTGTCTCCTCTTGCATTGAGA
GTAGCCTTGAAGATGCTGGCGTCTCACCTGAAGAGGTCAATTACAT
AAATGCTCATGCGACTTCTACTCTAGCTGGGGATCTCGCCGAGATA
AATGCCATCAAGAAGGTTTTCAAGAACACAAAGGATATCAAAATTA
ATGCAACTAAGTCAATGATCGGACACTGTCTTGGAGCCTCTGGAGG
TCTTGAAGCTATAGCGACTATTAAGGGAATAAACACCGGCTGGCTT
CATCCCAGCATTAATCAATTCAATCCTGAGCCATCCGTGGAGTTCG
ACACTGTTGCCAACAAGAAGCAGCAACACGAAGTTAATGTTGCGAT
CTCGAATTCATTTGGATTCGGAGGCCACAACTCAGTCGTGGCTTTC
TCGGCTTTCAAGCCATGA

*C. aviga* mitochondrial KAS CDS

SEQ ID NO: 37

ATGGTGTTTCTTCCTTGGCGAAAAATGCTCTGTCCATCTCAATACC
GTTTTTTGCGGCCCTTATCTTCATCTACAACTTTTGATCCTCGTAG
GGTTGTTGTTACAGGCCTGGGTATGGTGACTCCATTAGGATGCGGG
GTGAACACCACATGGAAACAACTCATAGAGGGGAAATGTGGGATAA
GAGCAATATCCCTTGAAGACCTAAAGATGGATGCTTTTGATATTGA
TACTCAGGCCTATGTATTTGATCAGCTGACCTCGAAGGTCGCTGCC
ACCGTGCCCACCGGAGTGAATCCCGGAGAATTTAATGAAGATTTAT
GGTTCAATCAGAAGGAGCACCGTGCTATTGCAAGGTTCATAGCTTA
TGCACTCTGTGCAGCTGATGAAGCTCTTAAAGATGCAAATTGGGAA
CCTACTGAACCTGAAGAGAGAGAAATGACGGGTGTCTCCATTGGTG
GAGGGACTGGAAGCATTAGCGATGTATTAGATGCTGGTCGGATGAT
TTGTGAGAAGAAATTGCGTCGCCTAAGTCCATTCTTCATTCCACGC
ATATTGATAAATATGGCCTCTGGTCATGTGAGCATGAAATATGGTT
TCCAGGGACCCAACCATGCTGCTGTGACAGCTTGTGCAACAGGGGC

SEQUENCE LISTING

TCATTCGATAGGTGATGCTGCAAGGATGATACAGTTTGGAGATGCA

GATGTCATGGTCGCTGGAGGCACAGAATCTAGCATAGACGCCTTAT

CCATTGCAGGATTTTGCAGGTCAAGGGCTCTTACAACAAAGTATAA

TTCTTGCCCACAAGAAGCTTCACGACCCTTTGATACCGATAGAGAT

GGGTTTGTAATAGGTGAAGGGTCTGGCGTCTTGGTATTGGAGGAAC

TAGATCATGCAAGAAAACGTGGTGCAAAGATGTATGCCGAGTTCTG

TGGATATGGAATGTCTGGTGATGCGCATCATATAACCCAACCTCAT

AGCGATGGAAGAGGTGCCATTTTAGCAATGACCCGTGCATTGAAGC

AGTCAAATCTACATCCGGATCAGGTGGATTATGTAAATGCTCACGC

TACGTCTACTTCTTTAGGTGATGCAATTGAAGCTAAGGCGATTAAA

ACAGTTTTCTCGGATCATGCGATGTCAGGTTCGCTCGCCCTTTCCT

CCACCAAGGGAGCTATTGGGCATCTCCTCGGAGCAGCGGGTGCTGT

GGAAGCCATTTTCTCCATTCTGGCTATAAAAAACGGACTTGCGCCT

TTGACGCTAAATGTCGCAAGACCAGACCCTGTGTTTACCGAGCGGT

TTGTGCCTTTGACTGCTTCAAAAGAGATGCATGTAAGGGCGGCGTT

GTCAAACTCTTTTGGCTTTGGAGGTACAAATACTACACTTCTTTTC

ACTTCACCTCCTCAAAACTAA

Cuphea palustris KAS IV codon optimized for Prototheca with cloning sequence and tags. Nucleotide sequence of the C. palustris KASIV expression vector (D3145 and D3295, pSZ4312). The 5' and 3' homology arms enabling targeted integration into the pLOOP locus are noted with lowercase; the PmHXT1-2 promoter is noted in uppercase italic which drives expression of the ScMelibiase selection marker noted with lowercase italic followed by the PmPGK 3'UTR terminator highlighted in uppercase. The PmACP promoter (noted in bold text) drives the expression of the codon optimized Cpal KASIV (noted with lowercase bold text) and is terminated with the CvNR 3'UTR noted in underlined, lower case bold. Restriction cloning sites and spacer DNA fragments are noted as underlined, uppercase plain lettering.

SEQ ID NO: 38 aacggaggtctgtcaccaaatggacccgtctattgcgggaaacca cggcgatggcacgtttcaaaacttgatgaaatacaatattcagtat gtcgcgggcggcgacggcgggagctgatgtcgcgctgggtattga taatcgccagatcgcccccgtatggcgcgaggcgtgaacaagccga ccgatgtgcacgagcaaatcctgacactagaaggctgactcgccc ggcacggctgaattacacaggcttgcaaaaataccagaatttgcac gcaccgtattcgcggtattttgttggacagtgaatagcgatgcggc aatggcttgtggcgttagaaggtgcgacgaaggtggtgccaccact gtgccagccagtcctggcggctcccagggccccgatcaagagccag gacatccaaactacccacagcatcaacgccccggcctatactcgaa ccccacttgcactctgcaatggtatgggaaccacggggcagtcttg tgtgggtcgcgcctatcgcggtcggcgaagaccgggaaGGTACCCC

GCTCCCGTCTGGTCCTCACGTTCGTGTACGGCCTGGATCCCGGAAA

GGGCGGATGCACGTGGTGTTGCCCCGCCATTGGCGCCCACGTTTCA

AAGTCCCCGGCCAGAAATGCACAGGACCGGCCCGGCTCGCACAGGC

CATGACGAATGCCCAGATTTCGACAGCAAAACAATCTGGAATAATC

GCAACCATTCGCGTTTTGAACGAAACGAAAAGACGCTGTTTAGCAC

GTTTCCGATATCGTGGGGGCCGAAGCATGATTGGGGGGAGGAAAGC

GTGGCCCCAAGGTAGCCCATTCTGTGCCACACGCCGACGAGGACCA

ATCCCCGGCATCAGCCTTCATCGACGGCTGCGCCGCACATATAAAG

CCGGACGCCTTCCCGACACGTTCAAACAGTTTTATTTCCTCCACTT

CCTGAATCAAACAAATCTTCAAGGAAGATCCTGCTCTTGAGCA<u>ACT</u>

<u>AGT</u>atgttcgcgttctacttcctgacggcctgcatctccctgaagg gcgtgttcggcgtctcccccctcctacaacggcctgggcctgacgcc ccagatgggctgggacaactggaacacgttcgcctgcgacgtctcc gagcagctgctgctggacacggccgaccgcatctccgacctgggcc tgaaggacatgggctacaagtacatcatcctggacgactgctggtc ctccggccgcgactccgacggcttcctggtcgccgacgagcagaag ttccccaacgcatgggccacgtcgccgaccacctgcacaacaact ccttcctgttcggcatgtactcctccgcgggcgagtacacgtgcgc cggctaccccggctccctgggccgcgaggaggaggacgccagttc ttcgcgaacaaccgcgtggactacctgaagtacgacaactgctaca acaagggccagttcggcacgcccgagatctcctaccaccgctacaa ggccatgtccgacgccctgaacaagacgggccgcccccatcttctac tccctgtgcaactggggccaggacctgaccttctactggggctccg gcatcgcgaactcctggcgcatgtccggcgacgtcacggcggagtt cacgcgccccgactcccgctgccctgcgacggcgacgagtacgac tgcaagtacgccggcttccactgctccatcatgaacatcctgaaca aggccgcccccatgggccagaacgcgggcgtcggcggctggaacga cctggacaacctggaggtcggcgtcggcaacctgacggacgacgag gagaaggcgcacttctccatgtgggccatggtgaagtcccccctga tcatcggcgcgaacgtgaacaacctgaaggcctcctcctactccat ctactcccaggcgtccgtcatcgccatcaaccaggactccaacggc atccccgccacgcgcgtctgcgcgctactacgtgtccgacacggacg agtacgccagggcgagatccagatgtggtccggcccccctggacaa cggcgaccaggtcgtggcgctgctgaacggcggctccgtgtcccgc cccatgaacacgacccggaggagatcttcttcgactccaacctgg gctccaagaagctgacctccacctgggacatctacgacctgtgggc gaaccgcgtcgacaactccacggcgtccgccatcctgggccgcaac aagaccgccaccggcatcctgtacaacgccaccgagcagtcctaca aggacggcctgtccaagaacgacacccgcctgttcggccagaagat cggctccctgtccccaacgcgatcctgaacacgaccgtccccgcc cacggcatcgcgttctaccgcctgcgcccctcctcctgaTACAACT

TATTACGTATTCTGACCGGCGCTGATGTGGCGCGGACGCCGTCGTA

CTCTTTCAGACTTTACTCTTGAGGAATTGAACCTTTCTCGCTTGCT

GGCATGTAAACATTGGCGCAATTAATTGTGTGATGAAGAAAGGGTG

GCACAAGATGGATCGCGAATGTACGAGATCGACAACGATGGTGATT

GTTATGAGGGGCCAAACCTGGCTCAATCTTGTCGCATGTCCGGCGC

AATGTGATCCAGCGGCGTGACTCTCGCAACCTGGTAGTGTGTGCGC

ACCGGGTCGCTTTGATTAAAACTGATCGCATTGCCATCCCGTCAAC

TCACAAGCCTACTCTAGCTCCCATTGCGCACTCGGGCGCCCGGCTC

GATCAATGTTCTGAGCGGAGGGCGAAGCGTCAGGAAATCGTCTCGG

CAGCTGGAAGCGCATGGAATGCGGAGCGGAGATCGAATCAGGATCC

CGCGTCTCGAACAGAGCGCGCAGAGGAACGCTGAAGGTCTCGCCTC

TGTCGCACCTCAGCGCGGCATACACCACAATAACCACCTGACGAAT

GCGCTTGGTTCTTCGTCCATTAGCGAAGCGTCCGGTTCACACACGT

GCCACGTTGGCGAGGTGGCAGGTGACAATGATCGGTGGAGCTGATG

GTCGAAACGTTCACAGCCTAGGGATATCGCCTGCTCAAGCGGGCGC

TCAACATGCAGAGCGTCAGCGAGACGGGCTGTGGCGATCGCGAGAC

GGACGAGGCCGCCTCTGCCCTGTTTGAACTGAGCGTCAGCGCTGGC

TAAGGGGAGGGAGACTCATCCCCAGGCTCGCGCCAGGGCTCTGATC

CCGTCTCGGGCGGTGATCGGCGCGCATGACTACGACCCAACGACGT

ACGAGACTGATGTCGGTCCCGACGAGGAGCGCCGCGAGGCACTCCC

GGGCCACCGACCATGTTTACACCGACCGAAAGCACTCGCTCGTATC

CATTCCGTGCGCCCGCACATGCATCATCTTTTGGTACCGACTTCGG

TCTTGTTTTACCCCTACGACCTGCCTTCCAAGGTGTGAGCAACTCG

CCCGGACATGACCGAGGGTGATCATCCGGATCCCCAGGCCCCAGCA

GCCCCTGCCAGAATGGCTCGCGCTTTCCAGCCTGCAGGCCCGTCTC

CCAGGTCGACGCAACCTACATGACCACCCCAATCTGTCCCAGACCC

CAAACACCCTCCTTCCCTGCTTCTCTGTGATCGCTGATCAGCAACA

CATatggcttccgcggcattcaccatgtcggcgtgccccgcgatga ctggcagggccctggggcacgtcgctccggacggccagtcgccac ccgcctgaggggctccaccttccagtgcctggtgacctcctacatc gaccctgcaaccagttctcctcctccgcctccctgtccttcctgg gcgacaacggcttcgcctcctgttcggctccaagccttccgctc caaccgcggccaccgccgctgggccgcgcctcccactccggcgag gccatgccgtggccctggagcccgcccaggaggtggccaccaaga agaagccctggtgaagcagcgccgcgtggtggtgaccggcatggg cgtggtgaccccctgggccacgagcccgacgtgtactacaacaac ctgctggacggcgtgtccggcatctccgagatcgaggccttcgact gcacccagttccccacccgcatcgccggcgagatcaagtccttctc caccgacggctgggtggccccaagctgtccaagcgcatggacaag ttcatgctgtacctgctgaccgccggcaagaaggccctggccgacg gcggcatcaccgacgacgtgatgaaggagctggacaagcgcaagtg cggcgtgctgatcggctccggcctgggcggcatgaagctgttctcc gactccatcgaggccctgcgcatctcctacaagaagatgaacccct tctgcgtgcccttcgccaccaacatgggctccgccatgctggc catggacctgggctggatgggccccaactactccatctccaccgcc tgcgccacctccaacttctgcatcctgaactccgccaaccacatcg tgcgcggcgaggccgacatgatgctgtgcggcggctccgacgccgt gatcatccccatcggcctgggcggcttcgtggcctgccgcgccctg tcccagcgcaacaacgaccccaccaaggcctcccgccctgggact ccaaccgcgacggcttcgtgatgggcgagggcgccggcgtgctgct gctggaggagctggagcacgccaagaagcgcggcgccaccatctac gccgagttcctgggcggctccttcacctgcgacgcctaccacatga ccgagcccacccgagggcgccggcgtgatcctgtgcatcgagaa ggccctggcccaggccggcgtgtcccgcgaggacgtgaactacatc aacgcccacgccacctccaccccgccggcgacatcaaggagtacc aggccctggcccactgcttcggccagaactccgagctgcgcgtgaa ctccaccaagtccatgatcggccacctgatcggcgccgccggcggc gtggaggccgtgaccgtggtgcaggccatccgcaccggctggatcc accccaacctgaacctggaggaccccgacaaggccgtggacgccaa ggtgctggtgggccccaagaaggagcgcctgaacgtgaaggtgggc ctgtccaactcctcggcttcggcggccacaactcctccatcctgt tcgcccctacaacaccatgtaccccatacgacgtgcccgactacgc ctgaTATCGAGgcagcagcagctcggatagtatcgacacactctgg acgctggtcgtgtgatggactgttgccgccacacttgctgccttga cctgtgaatatccctgccgcttttatcaaacagcctcagtgtcttg atcttgtgtgtacgcgcttttgcgagttgctagctgcttgtgctat ttgcgaataccaccccagcatcccttccctcgtttcatatcgct tgcatcccaaccgcaacttatctacgctgtcctgctatccctcagc gctgctcctgctcctgctcactgcccctcgcacagccttggtttgg gctccgcctgtattctcctggtactgcaacctgtaaaccagcactg caatgctgatgcacgggaagtagtgggatgggaacacaaatggaAA GCTTGAGCTCagcggcgacggtcctgctaccgtacgacgttgggca cgcccatgaaagtttgtataccgagcttgttgagcgaactgcaagc gcggctcaaggatacttgaactcctggattgatatcggtccaataa

SEQUENCE LISTING tggatggaaaatccgaacctcgtgcaagaactgagcaaacctcgtt acatggatgcacagtcgccagtccaatgaacattgaagtgagcgaa ctgttcgcttcggtggcagtactactcaaagaatgagctgctgtta aaaatgcactctcgttctctcaagtgagtggcagatgagtgctcac gccttgcacttcgctgcccgtgtcatgccctgcgccccaaaatttg aaaaaagggatgagattattgggcaatggacgacgtcgtcgctccg ggagtcaggaccggcggaaaataagaggcaacacactccgcttctt a

*Cuphea palustris* KAS IV codon optimized for
Prototheca

SEQ ID NO: 39 atggcttccgcggcattcaccatgtcggcgtgccccgcgatgactg gcagggcccctggggcacgtcgctccggacggccagtcgccacccg cctgaggggctccaccttccagtgcctggtgacctcctacatcgac ccctgcaaccagttctcctcctccgcctcccgtccttcctgggcg acaacggcttcgcctccctgttcggctccaagcccttccgctccaa ccgcggccaccgccgctgggccgcgcctcccactccggcgaggcc atggccgtggccctggagcccgcccaggaggtggccaccaagaaga agcccctggtgaagcagcgccgcgtggtggtgaccggcatgggcgt ggtgacccccctgggccacgagcccgacgtgtactacaacaacctg ctggacggcgtgtccgcatctccgagatcgaggccttcgactgca cccagttccccaccccgcatcgccggcgagatcaagtccttctccac cgacggctgggtggccccaagctgtccaagcgcatggacaagttc atgctgtacctgctgaccgccggcaagaaggccctggccgacggcg gcatcaccgacgacgtgatgaaggagctggacaagcgcaagtgcgg cgtgctgatcggctccggcctgggcggcatgaagctgttctccgac tccatcgaggccctgcgcatctcctacaagaagatgaacccttct gcgtgcccttcgccaccaccaacatgggctccgccatgctggccat ggacctgggctggatgggcccaactactccatctccaccgcctgc gccacctccaacttctgcatcctgaactccgccaaccacatcgtgc gcggcgaggccgacatgatgctgtgcggcggctccgacgccgtgat catccccatcggcctgggcggcttcgtggcctgccgcgcctgtcc cagcgcaacaacgaccccaccaaggcctcccgccctgggactcca accgcgacggcttcgtgatgggcgagggcgccggcgtgctgctgct ggaggagctggagcacgccaagaagcgcggcgccaccatctacgcc gagttcctgggcggctccttcacctgcgacgcctaccacatgaccg agccccacccgagggcgccggcgtgatcctgtgcatcgagaaggc cctggcccaggccggcgtgtccgcgaggacgtgaactacatcaac gcccacgccacctcaccccgccggcgacatcaaggagtaccagg ccctggcccactgatcggcagaactccgagctgcgcgtgaactcc accaagtccatgatcggccacctgatcggcgccgccggcggcgtgg aggccgtgaccgtggtgcaggccatccgcaccggctggatccaccc caacctgaacctggaggacccccgacaaggccgtggacgccaaggtg ctggtgggccccaagaaggagcgcctgaacgtgaaggtgggcctgt ccaactccttcggatcggcggccacaactcctccatcctgttcgcc ccctacaacaccatgtaccctacgacgtgcccgactacgcctga

*C. camphora* KASIV codon optimized for
Prototheca. Nucleotide sequence from the
*C. camphora* KASIV (D3147, pSZ4338) expression
vector. Only the codon optimized *C. camphora*
KASIV sequence is shown, the promoter, 3'UTR,
selection marker and targeting arms are the
same as in SEQ ID NO: 38.

SEQ ID NO: 40 atggccatgatggccggctcctgctccaacctggtgatcggcaacc gcgagctgggcggcaacgccccctccctgctgcactacaacggcct gcgcccctggagaacatccagaccgcctccgccgtgaagaagccc aacggcctgttcgcctcctccaccgcccgcaagtccaaggccgtgc gcgccatggtgctgcccaccgtgaccgccccaagcgcgagaagga ccccaagaagcgcatcgtgatcaccggcatgggcctggtgtccgtg ttcggcaacgacatcgacaccttctactccaagctgctggagggcg agtccggcatcggccccatcgaccgcttcgacgcctcctccttctc cgtgcgcttcgccggccagatccacaacttctcctccaagggctac atcgacggcaagaacgaccgccgcctggacgactgctggcgctact gcctggtggccggccgccgcgccctggaggacgccaacctgggccc cgaggtgctggagaagatggaccgctcccgcatcggcgtgctgatc ggcaccggcatgggcggcctgtccgccttctccaacggcgtggagt ccctgatccagaagggctacaagaagatcacccccttcttcatccc ctactccatcaccaacatgggctccgccctgctggccatcgacacc ggcgtgatgggccccaactactccatctccaccgcctgcgccaccg ccaactactgcttccacgccgccgccaaccacatccgccgcggcga ggccgagatcatggtgaccggcggcaccgaggccgccgtgtccgcc accggcgtgggcggcttcatcgcctgccgcgcctgtcccaccgca acgacgagccccagaccgcctcccgccctgggacaaggaccgcga cggcttcgtgatgggcgagggcgccggcgtgctggtgatggagtcc ctgccaccacgcccgcaagcgcggcgccaacatcatcgccgagtacc tgggcggcgccgtgacctgcgacgccaccacatgaccgaccccg cgccgacggcctgggcgtgtcctcctgcatcaccaagtccctggag gacgccggcgtgtcccccgaggaggtgaactacgtgaacgcccacg ccacctccaccctggccggcgacctggccgaggtgaacgccatcaa gaaggtgttcaaggacacctccgagatgaagatgaacgccaccaag tccatgatcggccactgcctgggcgccgccggcggcctggaggcca tcgccaccatcaaggccatcaacaccggctggctgcacccaccat

SEQUENCE LISTING caaccagttcaacatcgagcccgccgtgaccatcgacaccgtgccc aacgtgaagaagaagcacgacatccacgtgggcatctccaactcct tcggcttcggcggccacaactccgtggtggtgttcgccccttcat gcccaccatgtaccctacgacgtgcccgactacgcctga C. camphora KASI (D3148, pSZ4339) codon
optimized for Prototheca

SEQ ID NO: 41 atgcagatcctgcagaccccctcctcctcctcctccctgcgca tgtcctccatggagtccctgtccctgaccccaagtccctgccct gaagaccctgctgcccctgcgccccgccccaagaacctgtcccgc cgcaagtcccagaaccccgcccatctcctcctcctcctccccg agcgcgagaccgaccccaagaagcgcgtggtgatcaccggcatggg cctggtgtccgtgttcggcaacgacgtggacgcctactacgaccgc ctgctgtccggcgagtccggcatcgcccccatcgaccgcttcgacg cctccaagttccccacccgcttcgccggccagatccgcggcttcac ctccgacggctacatcgacggcaagaacgaccgccgcctggacgac tgcctgcgctactgcatcgtgtccggcaagaaggccctggagaacg ccggcctgggccccacctgatggacggcaagatcgacaaggagcg cgccggcgtgctggtgggcaccggcatgggcggcctgaccgtgttc tccaacggcgtgcagaccctgcacgagaagggctaccgcaagatga ccccccttcttcatcccctacgccatcaccaacatgggctccgccct gctggccatcgagctgggcttcatgggccccaactactccatctcc accgcctgcgccacctccaactactgcttctacgccgccgccaacc acatccgcgcggcgaggccgacctgatgctggccggcggcaccga ggccgccatcatccccatcggcctgggcggcttcgtggcctgccgc gccctgtcccagcgcaacgacgaccccagaccgcctcccgcccct gggacaaggaccgcgacggcttcgtgatgggcgagggcgccggcgt gctggtgatggagtccctggagcacgccatgaagcgcgacgccccc atcatcgccgagtacctgggcggcgccgtgaactgcgacgcctacc acatgaccgaccccgcgccgacggcctgggcgtgtccacctgcat cgagcgctcctggaggacgccggcgtggcccccgaggaggtgaac tacatcaacgcccacgccacctccaccctggccggcgacctggccg aggtgaacgccatcaaggaaggtgttcaccaacacctccgagatcaa gatcaacgccaccaagtccatgatcggccactgcctgggcgccgcc ggcggcctggaggccatcgccaccatcaaggccatcaacaccggct ggctgcacccctccatcaaccagttcaaccccgagccctccgtgga gttcgacaccgtggccaacaagaagcagcagcacgaggtgaacgtg gccatctccaactcctcggcttcggcggccacaactccgtggtgg tgttctccgccttcaagccaccatgtaccctacgacgtgcccga ctacgcctga U. californica KASI
U. californica KASI (D3150, pSZ4341) codon
optimized for Prototheca

SEQ ID NO: 42 atggagtccctgtccctgaccccaagtccctgccctgaagaccc tgctgcccttccgccccgccccaagaacctgtcccgccgcaagtc ccagaaccccaagcccatctcctcctcctcctccccgagcgcgag accgaccccaagaagcgcgtggtgatcaccggcatgggcctggtgt ccgtgttcggcaacgacgtggacgcctactacgaccgcctgctgtc cggcgagtccggcatcgcccccatcgaccgcttcgacgcctccaag ttccccacccgcttcgccggccagatccgcggcttcacctccgacg gctacatcgacggcaagaacgaccgccgcctggacgactgcctgcg ctactgcatcgtgtccggcaagaaggccctggagaacgccggcctg ggccccgacctgatggacggcaagatcgacaaggagcgcgccggcg tgctggtgggcaccggcatgggcggcctgaccgtgttctccaacgg cgtgcagaccctgcacgagaagggctaccgcaagatgaccccccttc ttcatcccctacgccatcaccaacatgggctccgccctgctggcca tcgacctgggcttcatgggccccaactactccatctccaccgcctg cgccacctccaactactgcttctacgccgccgccaaccacatccgc cgcggcgaggccgacgtgatgctggccggcggcaccgaggccgcca tcatccccatcggcctgggcggcttcgtggcctgccgcgccctgtc ccagcgcaacgacgaccccagaccgcctcccgcccctgggacaag gaccgcgacggcttcgtgatgggcgagggcgccggcgtgctggtga tggagtccctggagcacgccatgaagcgcgacgcccccatcatcgc cgagtacctgggcggcgccgtgaactgcgacgcctaccacatgacc gaccccgcgccgacggcctgggcgtgtccacctgcatcgagcgct ccctggaggacgccggcgtggcccccgaggaggtgaactacatcaa cgcccacgccacctccaccctggccggcgacctggccgaggtgaac gccatcaagaaggtgttcaccaacacctccgagatcaagatcaacg ccaccaagtccatgatcggccactgcctgggcgccgccggcggcct ggaggccatcgccaccatcaaggccatcaacaccggctggctgcac ccctccatcaaccagttcaaccccgagccctccgtggagttcgaca ccgtggccaacaagaagcagcagcacgaggtgaacgtggccatctc caactcctcggcttcggcggccacaactccgtggtggtgttctcc gccttcaagccaccatgtaccctacgacgtgcccgactacgcct ga U. californica KASIV (D3152, pSZ4343) codon
optimized for Prototheca

SEQ ID NO: 43 atgacccagaccctgatctgccccctcctccatggagaccctgtccc tgaccaagcagtcccacttccgcctgcgcctgcccacccccccca catccgccgcggcggcggccaccgccaccccccccccttcatctcc

SEQUENCE LISTING gcctccgccgcccccgccgcgagaccgaccccaagaagcgcgtgg tgatcaccggcatgggcctggtgtccgtgttcggcaccaacgtgga cgtgtactacgaccgctgctggccggcgagtccggcgtgggcacc atcgaccgcttcgacgcctccatgttccccacccgcttcggcggcc agatccgccgcttcacctccgagggctacatcgacgcgcaagaacga ccgccgcctggacgactacctgcgctactgcctggtgtccggcaag aaggccatcgagtccgccggcttcgacctgcacaacatcaccaaca agatcgacaaggagcgcgccggcatcctggtgggctccggcatggg cggcctgaaggtgttctccgacggcgtggagtccctgatcgagaag ggctaccgcaagatctccccccttcttcatcccctacatgatcccca acatgggctccgccctgctgggcatcgacctgggcttcatgggccc caactactccatctccaccgcctgcgccacctccaactactgcatc tacgccgccgccaaccacatccgccagggcgacgccgacctgatgg tggccggcggcaccgaggcccccatcatccccatcggcctgggcgg atcgtggcctgccgcgccctgtccacccgcaacgacgaccccaga ccgcctcccgcccctgggacatcgaccgcgacggcttcgtgatggg cgagggcgccggcatcctggtgctggagtccctggagcacgccatg aagcgcgacgccccccatcctggccgagtacctgggcggcgccgtga actgcgacgccaccacatgaccgaccccgcgccgacggcctggg cgtgtccacctgcatcgagtcctccctggaggacgccggcgtggcc gccgaggaggtgaactacatcaacgcccacgccacctccacccccca ccggcgacctggccgagatgaaggccatcaagaacgtgttccgcaa cacctccgagatcaagatcaacgccaccaagtccatgatcggccac tgcctgggcgcctccggcggcctggaggccatcgccacccctgaagg ccatcaccaccggctgctgcaccccaccatcaaccagttcaaccc cgagccctccgtggacttcgacaccgtggccaagaagaagaagcag cacgaggtgaacgtggccatctccaactccttcggcttcggcggcc acaactccgtgctggtgttctccgccttcaagcccaccatgtaccc ctacgacgtgcccgactacgcctga

*C. wrightii* KASAI (D3153, pSZ4379) codon optimized for Prototheca

SEQ ID NO: 44 atggcttccgcggcattcaccatgtcggcgtgccccgcgatgactg gcagggcccctggggcacgtcgctccggacggccagtcgccacccg cctgaggtacgtattccag

SEQUENCE LISTING tctcccgccgcatggacaagttcatgctgtacatcctgaccgccgg caagaaggccctggtggacggcggcatcaccgaggacgtgatgaag gagctggacaagcgcaagtgcggcgtgctgatcggctccggcctgg gcggcatgaaggtgttctccgagtccatcgaggccctgcgcacctc ctacaagaagatctccccttctgcgtgcccttctccaccaccaac atgggctccgccatcctggccatggacctgggctggatgggcccca actactccatctccaccgcctgcgccacctccaacttctgcatcct gaacgccgccaaccacatcaccaagggcgaggccgacatgatgctg tgcggcggctccgactccgtgatcctgcccatcggcatgggcggct tcgtggcctgccgcgccctgtcccagcgcaacaacgaccccaccaa ggcctcccgcccctgggactccaaccgcgacggcttcgtgatgggc gagggcgccggcgtgctgctgctggaggagctggagcacgccaaga agcgcggcgccaccatctacgccgagttcctgggcggctccttcac ctgcgacgcctaccacatgaccgagccccaccccgagggcgccggc gtgatcctgtgcatcgagaaggccctggcccagtccggcgtgtccc gcgaggacgtgaactacatcaacgcccacgccacctccacccccgc cggcgacatcaaggagtaccaggccctggcccactgatcggccaga actccgagctgcgcgtgaactccaccaagtccatgatcggccacct gctgggcggcgccggcggcgtggaggccgtgaccgtggtgcaggcc atccgcaccggctggatccaccccaacatcaacctggacgaccccg acgagggcgtggacgccaagctgctggtgggccccaagaaggagaa gctgaaggtgaaggtgggcctgtccaactccttcggcttcggcggc cacaactcctccatcctgttcgccccctgcaacaccatgtacccct acgacgtgcccgactacgcctga

*C. paucipetala* KASIVb codon optimized for Prototheca

SEQ ID NO: 46 atggcttccgcggcattcaccatgtcggcgtgccccgcgatgactg gcagggcccctggggcacgtcgctccggacggccagtcgccacccg cctgaggggctccaccttccagtgcctgggcgacatcggcttcgcc tccctgatcggctccaagcccccccgctccaaccgcaaccaccgcc gcctgggccgcacctcccactccggcgaggtgatggccgtggccat gcagcccgcccacgaggcctccaccaagaacaagcccgtgaccaag cagcgccgcgtggtggtgaccggcatgggcgtggccacccccctgg gccacgaccccgacgtgtactacaacaacctgctggacggcgtgtc cggcatctcccagatcgagaacttcgactgcacccagttccccacc cgcatcgccggcgagatcaagtccttctccaccgagggctacgtga tccccaagttcgccaagcgcatggacaagttcatgctgtacctgct gaccgccggcaagaaggccctggaggacggcggcatcaccgaggac gtgatgaaggagctggacaagcgcaagtgcggcgtgctgatcggct

SEQUENCE LISTING ccggcatgggcggcatgaagatcatcaacgactccatcgccgccct gaacgtgtcctacaagaagatgacccccttctgcgtgcccttctcc accaccaacatgggctccgccatgctggccatcgacctgggctgga tgggccccaactactccatctccaccgcctgcgccacctccaacta ctgcatcctgaacgccgccaaccacatcgtgcgcggcgaggccgac atgatgctgtgcggcggctccgacgccgtgatcatccccgtgggcc tgggcggcttcgtggcctgccgcgccctgtcccagcgcaacaacga ccccaccaaggcctcccgcccctgggactccaaccgcgacggcttc gtgatgggcgagggcgccggcgtgctgctgctggaggagctggagc acgccaagaagcgcggcgccaccatctacgccgagttcctgggcgg ctccttcacctgcgacgcctaccacatgaccgagccccaccccgac ggcgccggcgtgatcctgtgcatcgagaaggccctggcccagtccg gcgtgtcccgcgaggacgtgaactacatcaacgcccacgccacctc cacccccgccggcgacatcaaggagtaccaggccctggcccactgc ttcggccagaactccgagctgcgcgtgaactccaccaagtccatga tcggccacctgctgggcgccgccggcggcgtggaggccgtgaccgt ggtgcaggccatccgcaccggctggatccaccccaacatcaacctg gagaaccccgacgaggccgtggacgccaagctgctggtgggcccca agaaggagaagctgaaggtgaaggtgggcctgtccaactccttcgg cttcggcggccacaactcctccatcctgttcgcccccctacaacacc atgtacccctacgacgtgcccgactacgcctga

*C. ignea* KASIVb (D3289, pSZ4455) codon optimized for Prototheca

SEQ ID NO: 47 atggcttccgcggcattcaccatgtcggcgtgccccgcgatgactg gcagggcccctggggcacgtcgctccggacggccagtcgccacccg cctgaggggctccacctcccagtgcctggtgacctcctacatcgac ccctgcaacaagtactgctcctccgcctccctgtccttcctgggcg acaacggcttcgcctccctgttcggctccaagcccttccgctccaa ccgcggccaccgccgcctgggccgcgcctcccactccggcgaggcc atggccgtggccctgcagcccgcccaggaggtgaccaccaagaaga agcccgtgatcaagcagcgccgcgtggtggtgaccggcatgggcgt ggtgacccccctgggccacgagcccgacgtgtactacaacaacctg ctggacggcgtgtccggcatctccgagatcgagaccttcgactgca cccagttccccacccgcatcgccggcgagatcaagtccttctccac cgacggctgggtggcccccaagctgtccaagcgcatggacaagttc atgctgtacctgctgaccgccggcaagaaggccctggccgacggcg gcatcaccgacgacgtgatgaaggagctggacaagcgcaagtgcgg cgtgctgatcggctccggcatgggcggcatgaagctgttcaacgac tccatcgaggccctgcgcatctcctacaagaagatgaaccccttct gcgtgcccttcgccaccaccaacatgggctccgccatgctggccat
ggacctgggctggatgggccccaactactccatctccaccgcctgc
gccacctccaacttctgcatcctgaacgcctccaaccacatcgtgc
gcggcgaggccgacatgatgctgtgcggcggctccgactccgtgac
cgtgcccctgggcgtgggcggcttcgtggcctgccgcgccctgtcc
cagcgcaacaacgaccccaccaaggcctcccgcccctgggactcca
accgcgacggcttcgtgatgggcgagggcgccggcgtgctgctgct
ggaggagctggagcacgccaagaagcgcggcgccaccatctacgcc
gagttcctgggcggctccttcacctgcgacgcctaccacatgaccg
agcccccaccccgagggcgccggcgtgatcctgtgcatcgagaaggc
cctggcccagtccggcgtgtcccgcgaggacgtgaactacatcaac
gcccacgccacctccaccccgccggcgacatcaaggagtaccagg
ccctggcccgctgcttcggccagaactccgagctgcgcgtgaactc
caccaagtccatgatcggccacctgctgggcgccgccggcggcgtg
gaggccgtggccgtgatccaggccatccgcaccggctggatccacc
ccaacatcaacctggaggaccccgacgaggccgtggaccccaagct
gctggtgggccccaagaaggagaagctgaaggtgaaggtggccctg
tccaactccttcggcttcggcggccacaactcctccatcctgttcg
cccccctgcaacaccatgtaccctacgacgtgcccgactacgcctg
a

*Cuphea procumbens* KASIV (D3290, pSZ4456) codon optimized for Prototheca

SEQ ID NO: 48 atggcttccgcggcattcaccatgtcggcgtgccccgcgatgactg
gcagggcccctggggcacgtcgctccggacggccagtcgccacccg
cctgaggggctccaccttccagtgcctggtgacctcccacaacgac
ccctgcaaccagtactgctcctccgcctcccgtccttcctgggcg
acaacggcttcggctccaagcccttccgctccaaccgcggccaccg
ccgcctgggccgcgcctcccactccggcgaggccatggccgtggcc
ctgcagcccgcccaggaggtggccaccaagaagaagcccgccatga
agcagccgcgtggtggtgaccggcatgggcgtggtgacccccct
gggccacgagcccgacgtgtactacaacaacctgctggacggcgtg
tccggcatctccgagatcgagaccttcgactgcacccagttcccca
cccgcatcgccggcgagatcaagtccttctccaccgacggctgggt
ggcccccaagctgtccaagcgcatggacaagttcatgctgtacctg
ctgaccgccggcaagaaggccctggccgacgccgcatcaccgacg
acgtgatgaaggagctggacaagcaagtgcggcgtgctgatcgg
ctccggcatgggcggcatgaagctgttcaacgactccatcgaggcc
ctgcgcgtgtcctacaagaagatgaaccccttctgcgtgcccttcg
ccaccaccaacatgggctccgccatgctggccatggacctgggctg gatgggccccaactactccatctccaccgcctgcgccacctccaac
ttctgcatcctgaacgccgccaaccacatcgtgcgcggcgaggccg
acatgatgctgtgcggcggctccgacgccgtgatcatccccatcgg
cctgggcggcttcgtggcctgccgcgccctgtcccagcgcaacaac
gaccccaccaaggcctcccgcccctgggactccaaccgcgacggct
tcgtgatgggcgagggcgccggcgtgctgctgctggaggagctgga
gcacgccaagaagcgcggcgccaccatctacgccgagttcctgggc
ggctccttcacctgcgacgcctaccacatgaccgagcccccacccg
agggcgccggcgtgatcctgtgcatcgagaaggccctggcccagtc
cggcgtgtcccgcgaggacgtgaactacatcaacgcccacgccacc
tccacccccgccggcgacatcaaggagtaccaggccctggcccact
gcttcggccagaactccgagctgcgcgtgaactccaccaagtccat
gatcggccacctgctgggcgccgccggcggcgtggaggccgtgacc
gtgatccaggccatccgcaccggctggatccaccccaacctgaacc
tggaggaccccgacaaggccgtggacgccaagttcctggtgggccc
caagaaggagcgcctgaacgtgaaggtgggcctgtccaactccttc
ggcttcggcggccacaactcctccatcctgttcgcccccctgcaaca
ccatgtaccctacgacgtgcccgactacgcctga

*C paucipetala* KASIVa (D3291, pSZ4457) codon optimized for Prototheca

SEQ ID NO: 49 atggcttccgcggcattcaccatgtcggcgtgccccgcgatgactg
gcagggcccctggggcacgtcgctccggacggccagtcgccacccg
cctgaggggctccaccttccagtgcctggtgaactcccacatcgac
ccctgcaaccagaacgtgcctccgcctcccgtccttcctgggcg
acaacggcttcggctccaacccttccgctccaaccgcggccaccg
ccgcctgggccgcgcctcccactccggcgaggccatggccgtggcc
ctgcagcccgcccaggaggtggccaccaagaagaagcccgccatca
agcagccgcgtggtggtgaccggcatgggcgtggtgacccccct
gggccacgagcccgacgtgttctacaacaacctgctggacggcgtg
tccggcatctccgagatcgagaccttcgactgcacccagttcccca
cccgcatcgccggcgagatcaagtccttctccaccgacggctgggt
ggcccccaagctgtccaagcgcatggacaagttcatgctgtacctg
ctgaccgccggcaagaaggccctggccgacgccggcatcaccgagg
acgtgatgaaggagctggacaagcaagtgcggcgtgctgatcgg
ctccggcatgggcggcatgaagctgttcaacgactccatcgaggcc
ctgcgcgtgtcctacaagaagatgaaccccttctgcgtgcccttcg
ccaccaccaacatgggctccgccatgctggccatggacctgggctg
gatgggccccaactactccatctccaccgcctgcgccacctccaac
ttctgcatcctgaacgccgccaaccacatcatccgcggcgaggccg

```
acatgatgctgtgcggcggctccgacgccgtgatcatccccatcgg
cctgggcggcttcgtggcctgccgcgccctgtcccagcgcaactcc
gaccccaccaaggcctcccgcccctgggactccaaccgcgacggct
tcgtgatgggcgagggcgccggcgtgctgctgctggaggagctgga
gcacgccaagaagcgcggcgccaccatctacgccgagttcctgggc
ggctccttcacctgcgacgcctaccacatgaccgagccccaccccg
acggcgccggcgtgatcctgtgcatcgagaaggccctggcccagtc
cggcgtgtcccgcgaggacgtgaactacatcaacgcccacgccacc
tccaccccgccggcgacatcaaggagtaccaggccctggcccact
gcttcggccagaactccgagctgcgcgtgaactccaccaagtccat
gatcggccacctgctgggcgccgccggcggcgtggaggccgtgacc
gtgatccaggccatccgcaccggctggatccaccccaacctgaacc
tggaggaccccgacgaggccgtggacgccaagttcctggtgggccc
caagaaggagcgcctgaacgtgaaggtgggcctgtccaactccttc
ggcttcggcggccacaactcctccatcctgttcgcccccctacaaca
ccatgtaccctacgacgtgcccgactacgcctga
```

*Cuphea painteri* KASIV (D3292, pSZ4458) codon
optimized for Prototheca
SEQ ID NO: 50
```
atggcttccgcggcattcaccatgtcggcgtgccccgcgatgactg
cagggcccctggggcacgtcgctccggacggccagtcgccacccg
cctgaggggctccaccccccagtgcctggaccccctgcaaccagcac
tgcttcctgggcgacaacggcttcgcctccctgatcggctccaagc
cccccgctccaacctgggccacctgcgcctgggccgcacctccca
ctccggcgaggtgatggccgtggcccaggaggtgtccaccaacaag
aagcacgccaccaagcagcgccgcgtggtggtgaccggcatgggcg
tggtgaccccctgggccacgaccccgacgtgtactacaacaacct
gctggagggcgtgtccggcatctccgagatcgagaacttcgactgc
tcccagctgcccacccgcatcgccggcgagatcaagtccttctcca
ccgacggcctggtggcccccaagctgtccaagcgcatggacaagtt
catgctgtacatcctgaccgccggcaagaaggccctggccgacggc
ggcatcaccgaggacgtgatgaaggagctggacaagcgcaagtgcg
gcgtgctgatcggctccggcctgggcggcatgaaggtgttctccga
ctccgtggaggcctgcgcatctcctacaagaagatctcccccttc
tgcgtgcccttctccaccaccaacatgggctccgccatgctggcca
tggacctgggctggatgggcccccaactactccatctccaccgcctg
cgccacctccaacttctgcatcctgaacgccgccaaccacatcacc
aagggcgaggccgacatgatgctgtgcggcggctccgacgccgcca
tcctgcccatcggcatgggcggcttcgtggcctgccgcgccctgtcc
cagcgcaacaacgaccccaccaaggcctcccgcccctgggactcca
```

```
aaccgcgacggcttcgtgatgggcgagggcgccggcgtgctgctgc
tggaggagctggagcacgccaagaagcgcggcgccaccatctacgc
cgagttcctgggcggctccttcacctgcgacgcctaccacatgacc
gagccccaccccgacggcgccggcgtgatcctgtgcatcgagaagg
ccctggcccagtccggcgtgtcccgcgaggaggtgaactacatcaa
cgcccacgccacctccaccccgccggcgacatcaaggagtaccag
gccctggcccactgcttcggccagaactccgagctgcgcgtgaact
ccaccaagtccatgatcggccacctgctgggcggcgccggcggcgt
ggaggccgtgaccgtggtgcaggccatccgcaccggctggatccac
cccaacatcaacctggaggaccccgacaagggcgtggacgccaagc
tgctggtgggccccaagaaggagaagctgaaggtgaaggtgggcct
gtccaactccttcggcttcggcggccacaactcctccatcctgttc
gccccctgcaacaccatgtaccctacgacgtgcccgactacgcct
ga
```

*C. avigera* KASIVa (D3293, pSZ4459) codon
optimized for Prototheca
SEQ ID NO: 51
```
atggcttccgcggcattcaccatgtcggcgtgccccgcgatgactg
gcagggcccctggggcacgtcgctccggacggccagtcgccacccg
cctgaggggctccaccttccagtgcctggtgacctcctacaacgac
ccctgcgagcagtaccgctcctccgcctcccgtccttcctgggcg
acaacggcttcgcctccctgttcggctccaagcccttccgctccaa
ccgcggccaccgccgctgggccgcgcctcccactccggcgaggcc
atggccgtggccctgcagcccgcccaggaggtgggcaccaagaaga
agcccgtgatcaagcagcgccgcgtggtggtgaccggcatgggcgt
ggtgaccccctgggccacgagcccgacgtgtactacaacaacctg
ctggacggcgtgtccggcatctccgagatcgagaccttcgactgca
cccagttccccacccgcatcgccggcgagatcaagtccttctccac
cgacggctgggtggcccccaagctgtccaagcgcatggacaagttc
atgctgtacctgctgaccgccggcaagaaggccctggccgacggcg
gcatcaccgacgacgtgatgaaggagctggacaagcgcaagtgcgg
cgtgctgatcggctccggcctgggcggcatgaaggtgttctccgag
tccatcgaggcctgcgcacctcctacaagaagatctcccccttct
gcgtgcccttctccaccaccaacatgggctccgccatcctggccat
ggacctgggctggatgggccccaactactccatctccaccgcctgc
gccacctccaacttctgcatcctgaacgccgccaaccacatcacca
agggcgaggccgacatgatgctgtgcggcggctccgactccgtgat
cctgcccatcggcatgggcggcttcgtggcctgccgcgccctgtcc
cagcgcaacaacgaccccaccaaggcctcccgcccctgggactcca
accgcgacggcttcgtgatgggcgagggcgccggcgtgctgctgct
``` ggaggagctggagcacgccaagaagcgcggcgccaccatctacgcc
gagttcctgggcggctccttcacctgcgacgcctaccacatgaccg
agccccaccccgagggcgccggcgtgatcctgtgcatcgagaaggc
cctggcccagtccggcgtgtcccgcgaggacgtgaactacatcaac
gcccacgccacctccaccccgccggcgacatcaaggagtaccagg
ccctggcccactgcttcggccagaactccgagctgcgcgtgaactc
caccaagtccatgatcggccacctgctgggcggcgccggcggcgtg
gaggccgtgaccgtggtgcaggccatccgcaccggctggatccacc
caacatcaacctggacgaccccgacgagggcgtggacgccaagct
gctggtgggccccaagaaggagaagctgaaggtgaaggtgggcctg
tccaactccttcggcttcggcggccacaactcctccatcctgttcg
cccccctgcaacaccatgtaccccatgacgtgcccgactacgcctg
a

*C ignea* KASIVa (D3294, pSZ4460) codon
optimized for Prototheca

SEQ ID NO: 52 atggcttccgcggcattcaccatgtcggcgtgccccgcgatgact agaacaccaaggacatcaagatcaacgccaccaagtccatgatcgg ccactgcctgggcgcctccggcggcctggaggccatcgccaccatc aagggcatcaccaccggctggctgcacccctccatcaaccagttca accccgagccctccgtggagttcgacaccgtggccaacaagaagca gcagcacgaggtgaacgtggccatctccaactccttcggcttcggc ggccacaactccgtggtggccttctccgccttcaagcccaccatgt accccctacgacgtgcccgactacgcctga

*C. pulcherrima* KASI (D3343, pSZ4512) codon
optimized for Prototheca
SEQ ID NO: 54 atgcactccctgcagtccccctccctgcgcgcctccccctggacc ccttccgccccaagtcctccaccgtgcgcccctgcaccgcgcctc catccccaacgtgcgcgccgcctccccaccgtgtccgcccccaag cgcgagaccgaccccaagaagcgcgtggtgatcaccggcatgggcc tggtgtccgtgttcggctccgacgtggacgcctactacgacaagct gctgtccggcgagtccggcatcggccccatcgaccgcttcgacgcc tccaagttccccaccccgcttcggcggcagatccgcggcttcaact ccatgggctacatcgacggcaagaacgaccgccgcctggacgactg cctgcgctactgcatcgtggccggcaagaagtccctggaggacgcc gacctgggcgccgaccgcctgtccaagatcgacaaggagcgcgccg gcgtgctggtgggcaccggcatgggcggcctgaccgtgttctccga cggcgtgcagtccctgatcgagaagggccaccgcaagatcaccccc ttcttcatcccctacgccatcaccaacatgggctccgccctgctgg ccatcgagctgggcctgatgggccccaactactccatctccaccgc ctgcgccacctccaactactgcttccacgccgccgccaaccacatc cgccgcggcgaggccgacctgatgatcgccggcggcaccgaggccg ccatcatccccatcggcctgggcggcttcgtggcctgccgcgccct gtcccagcgcaacgacgaccccagaccgcctcccgcccctgggac aaggaccgcgacggcttcgtgatgggcgagggcgccggcgtgctgg tgctggagtccctggagcacgccatgaagcgcggcgcccccatcat cgccgagtacctgggcggcgccatcaactgcgacgcctaccacatg accgaccccgcgccgacgcctgggcgtgtcctcctgcatcgagt cctccctggaggacgccggcgtgtccccgaggaggtgaactacat caacgcccacgccacctccaccctggccggcgacctggccgagatc aacgccatcaagaaggtgttcaagaacaccaaggacatcaagatca cgccaccaagtccatgatcggccactgcctgggcgcctccggcgg cctggaggccatcgccaccatcaagggcatcaacaccggctggctg cacccctccatcaaccagttcaaccccgagccctccgtggagttcg acaccgtggccaacaagaagcagcagcacgaggtgaacgtggccat ctccaactccttcggcttcggcggccacaactccgtggtggccttc tccgccttcaagcccaccatgtaccccctacgacgtgcccgactacg cctga

*C. avigera* mitochondrial KAS (D3344, pSZ4513)
codon optimized for Prototheca
SEQ ID NO: 55 atggtgttcctgccctggcgcaagatgctgtgccccctcccagtacc gcttcctgcgcccccgtcctcctccaccaccttcgaccccgccg cgtggtggtgaccggcctgggcatggtgaccccctgggctgcgg gtgaacaccacctggaagcagctgatcgagggcaagtgcggcatcc gcgccatctccctggaggacctgaagatggacgccttcgacatcga cacccaggcctacgtgttcgaccagctgacctccaaggtggccgcc accgtgcccaccggcgtgaaccccggcgagttcaacgaggacctgt ggttcaaccagaaggagcaccgcgccatcgcccgcttcatcgccta cgccctgtgcgccgccgacgaggccctgaaggacgccaactgggag cccaccgagcccgaggagcgcgagatgaccgcgtgtccatcggcg gcggcaccggctccatctccgacgtgctggacgccggccgcatgat ctgcgagaagaagctgcgccgcctgtccccttcttcatccccgc atcctgatcaacatggcctccggccacgtgtccatgaagtacggct tccaggccccaaccacgccgccgtgaccgcctgcgccaccggcgc ccactccatcggcgacgccgccgcatgatccagttcggcgacgcc gacgtgatggtggccggcggcaccgagtcctccatcgacgccctgt ccatcgccggcttctgccgctccgcgccctgaccaccaagtacaa ctcctgccccaggaggcctcccgccccttcgacaccgaccgcgac ggcttcgtgatcggcgagggctccggcgtgctggtgctggaggagc tggaccacgcccgcaagcgcggcgccaagatgtacgccgagttctg cggctacggcatgtccggcgacgccaccacatcacccagcccac tccgacggccgcggcgccatcctggccatgacccgcgccctgaagc agtccaacctgcaccccgaccaggtggactacgtgaacgccacgc cacctccacctccctgggcgacgccatcgaggccaaggccatcaag accgtgttctccgaccacgccatgtccggctccctggccctgtcct ccaccaagggcgccatcggccacctgctgggcgccgccggcgccgt ggaggccatcttctccatcctggccatcaagaacggcctggcccc ctgaccctgaacgtggcccgccccgaccccgtgttcaccgagcgct tcgtgcccctgaccgcctccaaggagatgcacgtgcgcgccgccct gtccaactccttcggcttcggcggcaccaacaccaccctgctgttc acctcccccccagaacaccatgtaccccctacgacgtgcccgact acgcctga

*C. avigera* KASIII (D3345, pSZ4514) Codon
optimized for Prototheca.
SEQ ID NO: 56 atggccaacgcctacggcttcgtgggctcctccgtgcccaccgtgg gccgcgccgcccagttccagcagatgggctccggcttctgctccgt ggacttcatctccaagcgcgtgttctgctgctccgccgtgcagggc gccgacaagcccgcctccggcgactccgcgccgagtaccgcaccc cccgcctggtgtcccgcggctgcaagctgatcggctccggctccgc catcccaccctgcaggtgtccaacgacgacctggccaagatcgtg gacaccaacgacgagtggatctccgtgcgcaccggcatccgcaacc gccgcgtgctgaccggcaaggactccctgaccaacctggccaccga ggccgcccgcaaggccctggagatggcccaggtggacgccgaggac gtggacatggtgctgatgtgcacctccaccccgaggacctgttcg gctccgcccccagatccagaaggccctgggctgcaagaagaaccc cctgtcctacgacatcaccgccgcctgctccggcttcgtgctgggc ctggtgtccgccgcctgccacatccgcggcggcggcttcaacaacg tgctggtgatcggcgccgactccctgtcccgctacgtggactggac cgaccgcggcacctgcatcctgttcggcgacgccgccggcgccgtg ctggtgcagtcctgcgacgccgaggaggacggcctgttcgccttcg acctgcactccgacggcgacggccagcgccacctgcgcgccgtgat caccgagaacgagaccgaccacgccgtgggccaccaacggctccgtg tccgacttcccccccgccgctcctcctactcctgcatccagatga acggcaaggaggtgttccgcttcgcctgccgctccgtgccccagtc catcgagctggccctgggcaaggccggcctgaacggctccaacatc gactggctgctgctgcaccaggccaaccagcgcatcatcgacgccg tggccaccgcctggaggtgcccaggagcgcgtgatctccaacct ggccaactacggcaacacctccgccgcctccatcccctggccctg gacgaggccgtgcgcggcggcaaggtgaagcccggccacctgatcg ccaccgccggcttcggcgccggcctgacctggggctccgccatcgt gcgctggggcaccatgtaccctacgacgtgcccgactacgcctga C. hookeriana FATB2 ("Ch FATB2")
SEQ ID NO: 57
MVAAAASSAFFPVPAPGASPKPGKFGNWPSSLSPSFKPKSIPNGGF

QVKANDSAHPKANGSAVSLKSGSLNTQEDTSSSPPPRTFLHQLPDW

SRLLTAITTVFVKSKRPDMHDRKSKRPDMLVDSFGLESTVQDGLVF

RQSFSIRSYEIGTDRTASIETLMNHLQETSLNHCKSTGILLDGFGR

TLEMCKRDLIWVVIKMQIKVNRYPAWGDTVEINTRFSRLGKIGMGR

DWLISDCNTGEILVRATSAYAMMNQKTRRLSKLPYEVHQEIVPLFV

DSPVIEDSDLKVHKEKVKTGDSIQKGLTPGWNDLDVNQHVSNVKYI

GWILESMPTEVLETQELCSLALEYRRECGRDSVLESVTAMDPSKVG

VRSQYQHLLRLEDGTAIVNGATEWRPKNAGANGAISTGKTSNGNSV

S 23S rRNA for UTEX 1439, UTEX 1441, UTEX 1435,
UTEX 1437 Prototheca moriformis
SEQ ID NO: 58
TGTTGAAGAATGAGCCGGCGACTTAAAATAAATGGCAGGCTAAGAG

AATTAATAACTCGAAACCTAAGCGAAAGCAAGTCTTAATAGGGCGC

TAATTTAACAAAACATTAAATAAAATCTAAAGTCATTTATTTTAGA

CCCGAACCTGAGTGATCTAACCATGGTCAGGATGAAACTTGGGTGA

CACCAAGTGGAAGTCCGAACCGACCGATGTTGAAAAATCGGCGGAT

GAACTGTGGTTAGTGGTGAAATACCAGTCGAACTCAGAGCTAGCTG

GTTCTCCCCGAAATGCGTTGAGGCGCAGCAATATATCTCGTCTATC

TAGGGGTAAAGCACTGTTTCGGTGCGGGCTATGAAAATGGTACCAA

ATCGTGGCAAACTCTGAATACTAGAAATGACGATATATTAGTGAGA

CTATGGGGGATAAGCTCCATAGTCGAGAGGGAAACAGCCCAGACCA

CCAGTTAAGGCCCCAAAATGATAATGAAGTGGTAAAGGAGGTGAAA

ATGCAAATACAACCAGGAGGTTGGCTTAGAAGCAGCCATCCTTTAA

AGAGTGCGTAATAGCTCACTG

Amino acid sequence of the C. hookeriana KASIV
(D3668, pSZ4756). The algal transit
peptide is underlined.
SEQ ID NO: 59
<u>MASAAFTMSACPAMTGRAPGARRSGRPVATRLRGSTFQCLDPCNQQ</u>

<u>RFLGDNGFASLFGSKPLRSNRGHLRLGRTSHSGEVMAVAMQPAQEV</u>

STNKKPATKQRRVVVTGMGVVTPLGHDPDVYYNNLLDGISGISEIE

NFDCSQFPTRIAGEIKSFSTDGWVAPKFSERMDKFMLYMLTAGKKA

LADGGITEDAMKELNKRKCGVLIGSGLGGMKVFSDSIEALRTSYKK

ISPFCVPFSTTNMGSAILAMDLGWMGPNYSISTACATSNFCILNAA

NHIIKGEADMMLCGGSDAAVLPVGLGGFVACRALSQRNNDPTKASR

PWDSNRDGFVMGEGAGVLLLEELEHAKKRGATIYAEFLGGSFTCDA

YHMTEPHPEGAGVILCIEKALAQSGVSREDVNYINAHATSTPAGDI

KEYQALAHCFGQNSELRVNSTKSMIGHLLGGAGGVEAVAVVQAIRT

GWIHPNINLEDPDEGVDAKLLVGPKKEKLKVKVGLSNSFGFGGHNS

SILFAPCN

Nucleotide sequence of the C. hookeriana KASIV
(D3668, pSZ4756) expression vector. The 5' and
3' homology arms enabling targeted integration
into the SAD2-1 locus are noted with
lowercase. The endogenous SAD2-1 promoter
(present within the 5' homology targeting arm)
drives the expression of the codon optimized
Ch KASIV (noted with lowercase bold text) and
is terminated with the PmHSP90 3'UTR noted in
underlined, lower case bold. The PmHXT1-2
promoter is noted in uppercase italic which
drives expression of the ScMelibiase
selection marker noted with lowercase italic
followed by the PmPGK 3'UTR terminator
highlighted in uppercase. Restriction cloning
sites and spacer DNA fragments are noted as
underlined, uppercase plain lettering.

SEQUENCE LISTING

SEQ ID NO: 60
gccggtcaccacccgcatgctcgtactacagcgcacgcaccgcttc
gtgatccaccgggtgaacgtagtcctcgacggaaacatctggttcg
ggcctcctgcttgcactcccgccatgccgacaacctttctgctgt
taccacgacccacaatgcaacgcgacacgaccgtgtgggactgatc
ggttcactgcacctgcatgcaattgtcacaagcgcttactccaatt
gtattcgtttgttttctgggagcagttgctcgaccgcccgcgtccc
gcaggcagcgatgacgtgtgcgtggcctgggtgtttcgtcgaaagg
ccagcaaccctaaatcgcaggcgatccggagattgggatctgatcc
gagtttggaccagatccgcccgatgcggcacgggaactgcatcga
ctcggcgcggaacccagctttcgtaaatgccagattggtgtccgat
acctggatttgccatcagcgaaacaagacttcagcagcgagcgtat
ttggcgggcgtgctaccaggggttgcatacattgcccatttctgtct
ggaccgctttactggcgcagagggtgagttgatggggttggcaggc
atcgaaacgcgcgtgcatggtgtgcgtgtctgttttcggctgcacg
aattcaatagtcggatgggcgacggtagaattgggtgtggcgctcg
cgtgcatgcctcgcccgtcgggtgtcatgacccgggactggaatcc
ccctcgcgaccatcttgctaacgctcccgactctcccgaccgcgc
gcaggatagactcttgttcaaccaatcgaca<u>GGTACC</u>atggcttcc
gcggcattcaccatgtcggcgtgcccgcgatgactggcagggccc
ctggggcacgtcgctccggacggccagtcgccacccgcctgagggg
cagcaccttccagtgcctggacccctgcaaccagcagcgcttcctg
ggcgacaacggcttcgcgtcgctgttcggctccaagcccctgcgca
gcaaccgcggccacctgcgcctgggccgcacctcgcactccggcga
ggtgatggccgtcgcgatgcagcccgccaggaggtgagcaccaac
aagaagcccgcgaccaagcagcgccgcgtggtcgtgaccggcatgg
gcgtcgtgacccctgggccacgaccccgacgtgtattataacaa
cctgctggacggcatctcgggcatctccgagatcgagaacttcgac
tgcagccagttcccaccgcatcgccggcgagatcaagtcgttct
ccaccgacggctgggtcgcgcccaagttcagcgagcgcatggacaa
gttcatgctgtatgctgaccgccggcaagaaggcgctggccgac
ggcggcatcaccgaggacgcgatgaaggagctgaacaagcgcaagt
gcggcgtgctgatcggctcgggcctgggcggcatgaaggtcttctc
cgacagcatcgaggccctgcgcacctcgtataagaagatctccccc
ttctgcgtgcccttcagcaccaccaacatgggctcggcgatcctgg
cgatggacctgggctggatgggccccaactattccatcagcaccgc
gtgcgccacctcgaacttctgcatcctgaacgcggccaaccacatc
atcaagggcgaggcggacatgatgctgtgcggcggctccgacgcg
cggtgctgcccgtcggcctgggcggcttcgtggcctgccgcgcgct gagccagcgcaacaacgaccccaccaaggcctcgcgccctgggac
tccaaccgcgacggcttcgtcatgggcgagggcgcgggcgtgctgc
tgctggaggagctggagcacgccaagaagcgcggcgcgaccatcta
tgccgagttcctgggcggcagcttcacctgcgacgcgtatcacatg
accgagcccaccccgagggcgccggcgtcatcctgtgcatcgaga
aggcgctggcccagtcgggcgtgtcccgcgaggacgtgaactatat
caacgcgcacgccaccagcaccccgcgggcgacatcaaggagtat
caggccctggcgcactgcttcggccagaactcggagctgcgcgtca
actccaccaagagcatgatcggccacctgctgggcggcgccggcgg
cgtggaggcggtcgccgtggtccaggcgatccgcaccggctggatc
caccccaacatcaacctggaggacccgacgagggcgtggacgcca
agctgctggtcggccccaagaaggagaagctgaaggtgaaggtcgg
cctgtcgaactccttcggcttcggcggccacaacagctcgatcctg
ttcgcgccctgcaactga<u>CTCGAG</u>acagacgaccttggcaggcgtc
gggtagggaggtggtggtgatggcgtctcgatgccatcgcacgcat
ccaacgaccgtatacgcatcgtccaatgaccgtcggtgtcctctct
gcctccgttttgtgagatgtctcaggcttggtgcatcctcgggtgg
ccagccacgttgcgcgtcgtgctgcttgcctctcttgcgcctctgt
ggtactggaaaatatcatcgaggcccgtttttttgctcccatttcc
tttccgctacatcttgaaagcaaacgacaaacgaagcagcaagcaa
agagcacgaggacggtgaacaagtctgtcacctgtatacatctatt
tccccgcgggtgcacctactctctctcctgcccggcagagtcagc
tgccttacgtgacCCTAGGTGCGGTGAGAATCGAAAATGCATCGTT
TCTAGGTTCGGAGACGGTCAATTCCCTGCTCCGGCGAATCTGTCGG
TCAAGCTGGCCAGTGGACAATGTTGCTATGGCAGCCCGCGCACATG
GGCCTCCCGACGCGGCCATCAGGAGCCCAAACAGCGTGTCAGGGTA
TGTGAAACTCAAGAGGTCCCTGCTGGGCACTCCGGCCCCACTCCGG
GGGCGGACGCCAGGCATTCGCGGTCGGTCCCGCGCGACGAGCGAA
ATGATGATTCGGTTACGAGACCAGGACGTCGTCGAGGTCGAGAGGC
AGCCTCGGACACGTCTCGCTAGGGCAACGCCCCGAGTCCCCGCGAG
GGCCGTAAACATTGTTTCTGGGTGTCGGAGTGGGCATTTTGGGCCC
GATCCAATCGCCTCATGCCGCTCTCGTCGGTCCTCACGTTCGCGT
ACGGCCTGGATCCCGGAAAGGGCGGATGCACGTGGTGTTGCCCCGC
CATTGGCGCCCACGTTTCAAAGTCCCCGGCCAGAAATGCACAGGAC
CGGCCCGGCTCGCACAGGCCATGCTGAACGCCCAGATTTCGACAGC
AACACCATCTAGAATAATCGCAACCATCCGCGTTTTGAACGAAACG
AAACGGCGCTGTTTAGCATGTTTCCGACATCGTGGGGGCCGAAGCA
TGCTCCGGGGGAGGAAAGCGTGGCACAGCGGTAGCCCATTCTGTG
CCACACGCCGACGAGGACCAATCCCCGGCATCAGCCTTCATCGACG

SEQUENCE LISTING

GCTGCGCCGCACATATAAAGCCGGACGCCTAACCGGTTTCGTGGTT

ATG<u>ACTAGT</u>atgttcgcgttctacttcctgacggcctgcatctccc tgaagggcgtgttcggcgtctcccctcctacaacgcctgggcct gacgccccagatgggctgggacaactggaacacgttcgcctgcgac gtctccgagcagctgctgctggacacggccgaccgcatctccgacc tgggcctgaaggacatgggctacaagtacatcatcctggacgactg ctggtcctccgccgcgactccgacggcttcctggtcgccgacgag cagaagttccccaacggcatgggccacgtcgccgaccacctgcaca acaactccttcctgttcggcatgtactcctccgcgggcgagtacac gtgcgccggctaccccggctccctgggccgcgaggaggaggacgcc cagttcttcgcgaacaaccgcgtggactacctgaagtacgacaact gctacaacaagggccagttcggcacgcccgagatctcctaccaccg ctacaaggccatgtccgacgccctgaacaagacgggccgccccatc ttctactccctgtgcaactggggccaggacctgaccttctactggg gctccggcatcgcgaactcctggcgcatgtccggcgacgtcacggc ggagttcacgcgccccgactccgctgcccctgcgacggcgacgag tacgactgcaagtacgccggcttccactgctccatcatgaacatcc tgaacaaggccgcccccatgggccagaacgcgggcgtcggcggctg gaacgacctggacaacctggaggtcggcgtcggcaacctgacggac gacgaggagaaggcgcacttctccatgtgggccatggtgaagtccc ccctgatcatcggcgcgaacgtgaacaacctgaaggcctcctccta ctccatctactcccaggcgtccgtcatcgccatcaaccaggactcc aacggcatccccgccacgcgcgtctggcgctactacgtgtccgaca cggacgagtacggccagggcgagatccagatgtggtccgcccccct ggacaacggcgaccaggtcgtggcgctgctgaacggcggctccgtg tcccgccccatgaacacgaccctggaggagatcttcttcgactcca acctgggctccaagaagctgacctccacctgggacatctacgacct gtgggcgaaccgcgtcgacaactccacggcgtccgccatcctgggc cgcaacaagaccgccaccggcatcctgtacaacgccaccgagcagt cctacaaggacggcctgtccaagaacgacacccgcctgttcggcca gaagatcggctccctgtccccaacgcgatcctgaacacgaccgtc cccgcccacggcatcgcgttctaccgcctgcgcccctcctcctgAT

ACAACTTATTACGTATTCTGACCGGCGCTGATGTGGCGCGGACGCC

GTCGTACTCTTTCAGACTTTACTCTTGAGGAATTGAACCTTTCTCG

CTTGCTGGCATGTAAACATTGGCGCAATTAATTGTGTGATGAAGAA

AGGGTGGCACAAGATGGATCGCGAATGTACGAGATCGACAACGATG

GTGATTGTTATGAGGGGCCAAACCTGGCTCAATCTTGTCGCATGTC

CGGCGCAATGTGATCCAGCGGCGTGACTCTCGCAACCTGGTAGTGT

GTGCGCACCGGGTCGCTTTGATTAAAACTGATCGCATTGCCATCCC

GTCAACTCACAAGCCTACTCTAGCTCCCATTGCGCACTCGGGCGCC

CGGCTCGATCAATGTTCTGAGCGGAGGGCGAAGCGTCAGGAAATCG

TCTCGGCAGCTGGAAGCGCATGGAATGCGGAGCGGAGATCGAATCA

<u>GATATCAAGCTCCATCGAGCTC</u>cagccacggcaacaccgcgcgcct tgcggccgagcacggcgacaagaacctgagcaagatctgcgggctg atcgccagcgacgagggccggcacgagatcgcctacacgcgcatcg tggacgagttcttccgcctcgaccccgagggcgccgtcgccgccta cgccaacatgatgcgcaagcagatcaccatgcccgcgcacctcatg gacgacatgggccacggcgaggccaacccgggccgcaacctcttcg ccgacttctccgcggtcgccgagaagatcgacgtctacgacgccga ggactactgccgcatcctggagcacctcaacgcgcgctggaaggtg gacgagcgccaggtcagcggccaggccgccgcggaccaggagtacg tcctgggcctgccccagcgcttccggaaactcgccgagaagaccgc cgccaagcgcaagcgcgtcgcgcgcaggcccgtcgccttctcctgg atctccggggcgcgagatcatggtctagggagcgacgagtgtgcgtg cggggctggcgggagtgggacgccctcctcgctcctctctgttctg aacggaacaatcggccaccccgcgctacgcgccacgcatcgagcaa cgaagaaaaccccccgatgataggttgcggtggctgccgggatata gatccggccgcacatcaaagggcccctccgccagagaagaagctcc tttcccagcagactcct Nucleotide sequence of the *C. hookeriana* KASIV
CDS codon optimized for *P. moriformis*.

SEQ ID NO: 61 atggcttccgcggcattcaccatgtcggcgtgccccgcgatgactg gcagggcccctggggcacgtcgctccggacggccagtcgccacccg cctgaggggcagcaccttccagtgcctggacccctgcaaccagcag cgcttcctgggcgacaacggcttcgcgtcgctgttcggctccaagc ccctgcgcagcaaccgcggccacctgcgcctgggccgcacctcgca ctccggcgaggtgatggccgtcgcgatgcagcccgcccaggaggtg agcaccaacaagaagcccgcgaccaagcagcgccgcgtggtcgtga ccggcatgggcgtcgtgacccccctgggccacgaccccgacgtgta ttataacaacctgctggacggcatctcgggcatctccgagatcgag aacttcgactgcgccagttccccaccccgcatcgccggcgagatca agtcgttctccaccgacggctgggtcgcgcccaagttcagcgagcg catggacaagttcatgctgtatatgctgaccgccggcaagaaggcg ctggccgacggcggcatcaccgaggacgcgatgaaggagctgaaca agcgcaagtgcggcgtgctgatcggctcgggcctgggcggcatgaa ggtcttctccgacagcatcgaggcctgcgcacctcgtataagaag atctccccccttctgcgtgcccttcagcaccaccaacatgggctcgg

SEQUENCE LISTING

```
cgatcctggcgatggacctgggctggatgggcccaactattccat
cagcaccgcgtgcgccacctcgaacttctgcatcctgaacgcggcc
aaccacatcatcaagggcgaggcggacatgatgctgtgcggcggct
ccgacgccgcggtgctgcccgtcggcctgggcggcttcgtggcctg
ccgcgcgctgagccagcgcaacaacgaccccaccaaggcctcgcgc
ccctgggactccaaccgcgacggcttcgtcatgggcgagggcgcgg
gcgtgctgctgctggaggagctggagcacgccaagaagcgcggcgc
gaccatctatgccgagttcctgggcggcagcttcacctgcgacgcg
tatcacatgaccgagccccaccccgagggcgccggcgtcatcctgt
gcatcgagaaggcgctggcccagtcggcgtgtcccgcgaggacgt
gaactatatcaacgcgcaccaccagcaccccgcgggcgacatc
aaggagtatcaggccctggcgcactgcttcggccagaactcggagc
tgcgcgtcaactccaccaagagcatgatcggccacctgctgggcgg
cgccggcggcgtggaggcggtcgccgtggtccaggcgatccgcacc
ggctggatccaccccaacatcaacctggaggaccccgacgagggcg
tggacgccaagctgctggtcggccccaagaaggagaagctgaaggt
gaaggtcggcctgtcgaactccttcggcttcggcggccacaacagc
tcgatcctgttcgcgccctgcaactga
```

Amino acid sequence of the *C. aequipetala* KASIV. The algal transit peptide is underlined.
*C aeque* KASIV
SEQ ID NO: 62

<u>MAAAASMVASPLCTWLVAACMSTSFDNDPRSPSIKRIPRRRRILSQ</u>
SSLRGSTFQCLVTSYIDPCNQFSSSASLSFLGDNGFASLFGSKPFR
SIRGHRRLGRASHSGEAMAVALEPAQEVATKKKPVVKQRRVVVTGM
GVVTPLGHEPDVYYNNLLDGVSGISEIETFDCNQFPTRIAGEIKSF
STDGWVAPKLSKRMDKFMLYLLTAGKKALADGGITDDVMKELDKRK
CGVLIGSGLGGMKLFSDSIEALRISYKKMNPFCVPFATTNMGSAML
AMDLGWMGPNYSISTACATSNFCILNSANHIVRGEADMMLCGGSDA
VIIPIGLGGFVACRALSQRNNDPTKASRPWDSNRDGFVMGEGAGVL
LLEELEHAKKRGATIYAEFLGGSFTCDAYHMTEPHPEGAGVILCIE
KALAQAGVSREDVNYINAHATSTPAGDIKEYQALAHCFGHNSELRV
NSTKSMIGHLIGAAGGVEAVTVVQAIRTGWIHPNLNLEDPDKAVDA
KLLVGPKKERLNVKVGLSNSFGFGGHNSSILFAPYN

Amino acid sequence of the *C. glassostoma* KASIV. The algal transit peptide is underlined.
S07_Cg_Locus_4548_Transcript_4/9_translation
SEQ ID NO: 63
MAAAASSQLCTWLVAACMSTSFDNNPRSPSIKRLPRRRRVLSHCSL
RGSTFQCLVTSYIDPCNQYCSSASLSFLGDNGFTPLIGSKPFRSNR
GHPRLGRASHSGEAMAVALQPAQEVATKKKPAMKQRRVVVTGMGVV
TPLGHEPDVYYNNLLDGVSGISEIETFDCTQFPTRIAGEIKSFSTD GWVAPKLSKRMDKFMLYLLTAGKKALADGGITDDVMKELDKRKCGV
LIGSGMGGMKLFNDSIEALRVSYKKMNPFCVPFATTNMGSAMLAMD
LGWMGPNYSISTACATSNFCILNAANHIVRGEADMMLCGGSDAVII
PIGLGGFVACRALSQRNNDPTKASRPWDSNRDGFVMGEGAGVLLLE
ELEHAKKRGATIYAEFLGGSFTCDAYHMTEPHPEGAGVILCIEKAL
AQAGVSREDVNYINAHATSTPAGDIKEYQALAHCFGQNSELRVNST
KSMIGHLLGAAGGVEAVTVIQAIRTGWIHPNLNLDDPDKAVDAKFL
VGPKKERLNVKVGLSNSFGFGGHNSSILFAPYN Amino acid sequence of the *C. hookeriana* KASIV. The algal transit peptide is underlined.
S26_ChookKASIV_trinity_43853-translation
SEQ ID NO: 64
<u>MAASSCMVGSPFCTWLVSACMSTSFDNDPRSLSHKRLRLSRRRRTL
SSHC</u>SLRGSTPQCLDPCNQHCFLGDNGFASLFGSKPPRSDLGHLRL
GRTSHSGEVMAVAQEVSTNKKPATKQRRVVVTGMGVVTPLGHDPDV
YYNNLLDGVSGISEIETFDCTQFPTRIAGEIKSFSTDGLVAPKLSK
RMDKFMLYILTAGKKALADGGITEDVMKELDKRKCGVLIGSGLGGM
KVFSDSVEALRISYKKISPFCVPFSTTNMGSAILAMDLGWMGPNYS
ISTACATSNFCILNAANHITKGEADMMLCGGSDAAILPIGMGGFVA
CRALSQRNNDPTKASRPWDSNRDGFVMGEGAGVLLLEELEHAKKRG
ATIYAEFLGGSFTCDAYHMTEPHPEGAGVILCIEKALAQAGVSRED
VNYINAHATSTPAGDIKEYQALAHCFGQNSELRVNSTKSMIGHLIG
AAGGVEAVTVIQAIRTGWIHPNLNLENPDKAVDAKLLVGPKKERLD
VKVGLSNSFGFGGHNSSILFAPYN Amino acid sequence of the *C. glassostoma* KASIV. The algal transit peptide is underlined
S07_Cg_Locus_3059_Transcript_2/2_translation
SEQ ID NO: 65
<u>MAAASSMVASSFSTSLVAACMSTSFDNDPRFLSHKRIRLSLRRGST
FQCL</u>GDNGFASLIGSKPPRSNHGHRRLGRTSHSGEAMAVAMQPAQE
ASTKNKHVTKQRRVVVTGMGVVTPLGHDPDVYYNNLLDGVSGISEI
ENFDCSQFPTRIAGEIKSFSTEGYVIPKFAKRMDKFMLYLLTAGKK
ALEDGGITEDVMKELDKRKCGVLIGSGMGGMKIINDSIAALNVSYK
KMTPFCVPFSTTNMGSAMLAIDLGWMGPNYSISTACATSNYCILNA
ANHIIRGEANMMLCGGSDAVVIPVGLGGFVACRALSQRNNDPTKAS
RPWDSNRDGFVMGEGAGVLLLEELEHAKKRGATIYAEFLGGSFTCD
AYHMTEPHPDGAGVILCIEKALAQSGVSREDVNYINAHATSTPAGD
IKEYQALAHCFGQNSELRVNSTKSMIGHLLGAAGGVEAVSVVQAIR
TGWIHPNINLEDPEAVDAKLLVGPKKEKLKVKVGLSNSFGFGGHN
SSILFAPCN

SEQUENCE LISTING

Amino acid sequence of the *C. carthagenesis* KASIV. The algal transit peptide is underlined
S05_CcrKASIV_17190_Seq_7/7_translation
SEQ ID NO: 66

MAAAAAFASPFCTWLVAACMSSASRHDPLPSPSSKPRLRRKILFQC
AGRGSSAGSGSSFHSLVTSYLGCLEPCHEYYTSSSSLGFSSLFGST
PGRTSRRQRRLHRASHSGEAMAVALQPAQEVTTKKKPSIKQRRVVV
TGMGVVTPLGHDPDVFYNNLLDGASGISEIETFDCAQFPTRIAGEI
KSFSTDGWVAPKLSKRMDKFMLYMLTAGKKALADGGISEDVMKELD
KRKCGVLIGSAMGGMKVFNDAIEALRISYKKMNPFCVPFATTNMGS
AMLAMDLGWMGPNYSISTACATSNFCILNAANHITRGEADMMLCGG
SDAVIIPIGLGGFVACRALSQRNNDPTKASRPWDSNRDGFVMGEGA
GVLLLEELEHAKKRGATIYAEFLGGSFTCDAYHMTEPHPKGAGVIL
CIERALAQSGVSREDVNYINAHATSTPAGDIKEYQALAHCFGQNSE
LRVNSTKSMIGHLLGAAGGVEAVTVVQAIRTGWVHPNINLENPDEG
VDAKLLVGPKKEKLKVKVGLSNSFGFGGHNSSILFAPYN

Amino acid sequence of the *C. carthagenesis* KASIV. The algal transit peptide is underlined
S05_CcrKASIV_17190_Seq_6/7_translation
SEQ ID NO: 67

MAAAASVVASPFCTWLVAACMSASFDNEPRSLSPKRRRSLSRSSSA
SLRFLGGNGFASLFGSDPLRPNRGHRRLRHASHSGEAMAVALQPAQ
EVSTKKKPVTKQRRVVVTGMGVVTPLGHDPDVYYNNLLDGVSGISE
IETFDCTQFPTRIAGEIKSFSTDGWVAPKLSKRMDKFMLYMLTAGK
KALADGGITEEVMKELDKRKCGVLIGSGMGGMKLFNDSIEALRISY
KKMNPFCVPFATTNMGSAMLAMDLGWMGPNYSISTACATSNFCILN
AANHITRGEADMMLCGGSDAVIIPIGLGGFVACRALSQRNNDPTKA
SRPWDSNRDGFVMGEGAGVLLLEELEHAKKRGATIYAEFLGGSFTC
DAYHMTEPHPKGAGVILCIERALAQSGVSREDVNYINAHATSTPAG
DIKEYQALAHCFGQNSELRVNSTKSMIGHLLGAAGGVEAVTVVQAI
RTGWVHPNINLENPDEGVDAKLLVGPKKEKLKVKVGLSNSFGFGGH
NSSILFAPYN

Amino acid sequence of the *C. pulcherrima* KASIV. The algal transit peptide is underlined
pSZ2181-CpulcKASIV
SEQ ID NO: 68

MPAASSLLASPLCTWLLAACMSTSFHPSDPLPPSISSPRRRLSRRR
ILSQCAPLPSASSALRGSSFHTLVTSYLACFEPCHDYYTSASLFGS
RPIRTTRRHRRLNRASPSREAMAVALQPEQEVTTKKKPSIKQRRVV
VTGMGVVTPLGHDPDVFYNNLLDGTSGISEIETFDCAQFPTRIAGE
IKSFSTDGWVAPKLSKRMDKFMLYMLTAGKKALTDGGITEDVMKEL
DKRKCGVLIGSAMGGMKVFNDAIEALRISYKKMNPFCVPFATTNMG
SAMLAMDLGWMGPNYSISTACATSNFCIMNAANHIIRGEADVMLCG

GSDAVIIPIGMGGFVACRALSQRNSDPTKASRPWDSNRDGFVMGEG
AGVLLLEELEHAKKRGATIYAEFLGGSFTCDAYHMTEPHPDGAGVI
LCIEKALAQSGVSREDVNYINAHATSTPAGDIKEYQALIHCFGQNR
ELKVNSTKSMIGHLLGAAGGVEAVSVVQAIRTGWIHPNINLENPDE
GVDTKLLVGPKKERLNVKVGLSNSFGFGGHNSSILFAPYI

Clade 1 KASIV consensus C8 and C10
SEQ ID NO: 69

MAAASCMVASPFCTWLVAACMSTSXDNDPRSLSHKRLRLSRRRRTL
SSHCSLRGSTFQCLDPCNQHCFLGDNGFASLFGSKPPRSNRGHLRL
GRTSHSGEVMAVAXQXAQEVSTNKKPATKQRRVVVTGMGVVTPLGH
DPDVYYNNLLDGVSGISEIENFDCSQFPTRIAGEIKSFSTDGWVAP
KLSKRMDKFMLYILTAGKKALADGGITEDVMKELDKRKCGVLIGSG
LGGMKVFSDSIEALRTSYKKISPFCVPFSTTNMGSAILAMDLGWMG
PNYSISTACATSNFCILNAANHITKGEADMMLCGGSDAAILPIGMG
GFVACRALSQRNNDPTKASRPWDSNRDGFVMGEGAGVLLLEELEHA
KKRGATIYAEFLGGSFTCDAYHMTEPHPEGAGVILCIEKALAQSGV
SREDVNYINAHATSTPAGDIKEYQALAHCFGQNSELRVNSTKSMIG
HLLGAAGGVEAVTVVQAIRTGWIHPNINLEDPDEGVDAKLLVGPKK
EKLKVKVGLSNSFGFGGHNSSILFAPCN

Clade 2 KASIV consensus C10 only
SEQ ID NO: 70

MAAAASMXXSPLCTWLVAACMSTSFDNDPRSPSIKRLPRRRRVLSQ
CSLRGSTFQCLVTSYIDPCNQYCSSASLSFLGDNGFASLFGSKPFR
SNRGHRRLGRASHSGEAMAVALQPAQEVATKKKPVIKQRRVVVTGM
GVVTPLGHEPDVYYNNLLDGVSGISEIETFDCTQFPTRIAGEIKSF
STDGWVAPKLSKRMDKFMLYLLTAGKKALADGGITDDVMKELDKRK
CGVLIGSGMGGMKLFNDSIEALRXSYKKMNPFCVPFATTNMGSAML
AMDLGWMGPNYSISTACATSNFCILNAANHIVRGEADMMLCGGSDA
VIIPIGLGGFVACRALSQRNNDPTKASRPWDSNRDGFVMGEGAGVL
LLEELEHAKKRGATIYAEFLGGSFTCDAYHMTEPHPEGAGVILCIE
KALAQAGVSREDVNYINAHATSTPAGDIKEYQALAHCFGQNSELRV
NSTKSMIGHLLGAAGGVEAVTVXQAIRTGWIHPNLNLEDPDKAVDA
KLLVGPKKERLNVKVGLSNSFGFGGHNSSILFAPYNV

Clade 1 KASIV consensus mature protein
SEQ ID NO: 71

KQRRVVVTGMGVVTPLGHDPDVYYNNLLDGVSGISEIENFDCSQFP
TRIAGEIKSFSTDGWVAPKLSKRMDKFMLYILTAGKKALADGGITE
DVMKELDKRKCGVLIGSGLGGMKVFSDSIEALRTSYKKISPFCVPF
STTNMGSAILAMDLGWMGPNYSISTACATSNFCILNAANHITKGEA
DMMLCGGSDAAILPIGMGGFVACRALSQRNNDPTKASRPWDSNRDG
FVMGEGAGVLLLEELEHAKKRGATIYAEFLGGSFTCDAYHMTEPHP

SEQUENCE LISTING

EGAGVILCIEKALAQSGVSREDVNYINAHATSTPAGDIKEYQALAH

CFGQNSELRVNSTKSMIGHLLGGAGGVEAVTVVQAIRTGWIHPNIN

LEDPDEGVDAKLLVGPKKEKLKVKVGLSNSFGFGGHNSSILFAPCN

Clade 2 KASIV consensus mature protein

SEQ ID NO: 72

KQRRVVVTGMGVVTPLGHEPDVYYNNLLDGVSGISEIETFDCTQFP

TRIAGEIKSFSTDGWVAPKLSKRMDKFMLYLLTAGKKALADGGITD

DVMKELDKRKCGVLIGSGMGGMKLFNDSIEALRXSYKKMNPFCVPF

ATTNMGSAMLAMDLGWMGPNYSISTACATSNFCILNAANHIVRGEA

DMMLCGGSDAVIIPIGLGGFVACRALSQRNNDPTKASRPWDSNRDG

FVMGEGAGVLLLEELEHAKKRGATIYAEFLGGSFTCDAYHMTEPHP

EGAGVILCIEKALAQAGVSREDVNYINAHATSTPAGDIKEYQALAH

CFGQNSELRVNSTKSMIGHLLGAAGGVEAVTVXQAIRTGWIHPNLN

LEDPDKAVDAKLLVGPKKERLNVKVGLSNSFGFGGHNSSILFAPYN

V

What is claimed is:

1. A recombinant polynucleotide or a complement thereof encoding a polypeptide having at least 94% sequence identity to amino acids 34 to 502 of SEQ ID NO: 8 or 92% sequence identity to amino acids 34 to 525 of SEQ ID NO: 14 wherein said polypeptide has β-keto-acyl ACP synthase (KASIV) activity.

2. A transformation vector comprising the polynucleotide of claim 1.

3. The vector of claim 2, comprising promoter and 3'UTR sequences in operable linkage to the polynucleotide, and optionally a flanking sequence for homologous recombination.

4. A host cell comprising the vector of claim 2.

5. The host cell of claim 4, wherein the host cell is a plastidic oleaginous cell having a type II fatty acid biosynthesis pathway.

6. The host cell of claim 5, wherein the host cell is a microalga.

7. The host cell of claim 6, wherein the host cell is of Trebouxiophyceae, and optionally of the genus *Chlorella* or *Prototheca*.

8. The host cell of claim 7, wherein the microalga is of the species *Prototheca moriformis*.

9. A method for making a cell-oil, the method comprising cultivating a host cell of any one of claim 4, so as produce the cell-oil, wherein the oil comprises triglcyerides and microalgal sterols.

10. The method of claim 9, wherein the cell oil comprises sterols characterized by a sterol profile and the sterol profile has an excess of ergosterol over β-sitosterol and/or the presence of 22, 23-dihydrobrassicasterol, poriferasterol or clionasterol.

11. A host cell comprising
a recombinant polynucleotide or a complement thereof encoding a polypeptide having at least 94% sequence identity to amino acids 34 to 502 of SEQ ID NO: 8 or 92% sequence identity to amino acids 34 to 525 of SEQ ID NO: 14 wherein said polypeptide has β-keto-acyl ACP synthase (KASIV) activity.

12. The host cell of claim 11, further comprising a polynucleotide encoding a fatty acyl-ACP thioesterase (FATB) polypeptide, wherein the FATB polypeptide has at least 90% amino acid sequence identity to SEQ ID NO: 1 or SEQ ID NO: 57.

13. The host cell of claim 12, wherein the host cell produces a cell oil characterized by a fatty acid profile with (i) at least 30, 40, 50, or 55% C14:0, (ii) at least 7, 8, 9, 10, 11, 12, 13, or 14% C8:0, (ii) at least 10, 15, 20, 25, 30, or 35 area % for the sum of C8:0 and C10:0, or (iii) a C8/C10 ratio in the range of 2.2-2.5, 2.5-3.0, or 3.0-3.4.

14. The host cell of any one of claim 11, wherein the host cell is a plastidic oleaginous cell having a type II fatty acid biosynthesis pathway.

15. The host cell of claim 14, wherein the host cell is a microalga.

16. The host cell of claim 15, wherein the host cell is of Trebouxiophyceae, and optionally of the genus *Chlorella* or *Prototheca*.

17. The host cell of claim 16, wherein the microalga is of the species *Prototheca moriformis*.

18. The host cell of claim 11, wherein one or more of the polynucleotides is codon-optimized for expression in the host cell such that the polynucleotide's coding sequence contains the most or second most preferred codon for at least 60% of the codons of the coding sequence such that the codon-optimized sequence is more efficiently translated in the host cell relative to a non-optimized sequence.

19. The host cell of claim 18, wherein the coding sequence comprises the most preferred codon for at least 80% of the codons of the coding sequence.

20. A method for making a cell-oil, the method comprising cultivating a host cell of claim 11, so as produce the cell-oil, wherein the oil comprises triglcyerides and microalgal sterols.

21. The recombinant polynucleotide of claim 1, wherein the polynucleotide is codon-optimized for expression in microalgae.

22. The recombinant polynucleotide of claim 21, wherein the polynucleotide's coding sequence comprises the most or second most preferred codon for at least 60% of the codons.

23. The recombinant polynucleotide of claim 22, wherein the coding sequence comprises the most preferred codon for at least 80% of the codons.

24. The recombinant polynucleotide of claim 1, wherein the polynucleotide comprises nucleic acids 105 to 1515 of SEQ ID NO: 27 or nucleic acids 150 to 1629 of SEQ ID NO: 33.

25. The recombinant polynucleotide of claim 22, wherein the polynucleotide comprises nucleic acids 102 to 1542 of SEQ ID NO: 45 or nucleic acids 100 to 1611 of SEQ ID NO: 51.

* * * * *